(12) United States Patent
Narayanan et al.

(10) Patent No.: US 9,814,698 B2
(45) Date of Patent: Nov. 14, 2017

(54) SELECTIVE ANDROGEN RECEPTOR DEGRADER (SARD) LIGANDS AND METHODS OF USE THEREOF

(71) Applicants: GTx, Inc., Memphis, TN (US); University of Tennessee Research Foundation, Knoxville, TN (US)

(72) Inventors: Ramesh Narayanan, Cordova, TN (US); Duane D. Miller, Collierville, TN (US); Thamarai Ponnusamy, Memphis, TN (US); Dong-Jin Hwang, Arlington, TN (US); Jayaprakash Pagadala, Boca Raton, FL (US); Charles B. Duke, Memphis, TN (US); Christopher C. Coss, Upper Arlington, OH (US); James T. Dalton, Ann Arbor, MI (US); Yali He, Germantown, TN (US)

(73) Assignees: UNIVERSITY OF TENNESSEE RESEARCH FOUNDATION, Knoxville, TN (US); GTX, INC., Memphis, TN (US)

(*) Notice: Subject to any disclaimer, the term of this patent is extended or adjusted under 35 U.S.C. 154(b) by 0 days.

(21) Appl. No.: 15/135,334

(22) Filed: Apr. 21, 2016

(65) Prior Publication Data
US 2017/0095446 A1   Apr. 6, 2017

Related U.S. Application Data

(60) Provisional application No. 62/150,763, filed on Apr. 21, 2015, provisional application No. 62/220,057, filed on Sep. 17, 2015, provisional application No. 62/220,187, filed on Sep. 17, 2015, provisional application No. 62/219,859, filed on Sep. 17, 2015, provisional application No. 62/241,532, filed on Oct. 14, 2015.

(51) Int. Cl.
```
A61K 31/404    (2006.01)
A61K 9/00      (2006.01)
A61K 31/437    (2006.01)
A61K 31/4184   (2006.01)
A61K 31/47     (2006.01)
A61K 31/472    (2006.01)
A61K 31/403    (2006.01)
A61K 31/416    (2006.01)
```
(52) U.S. Cl.
CPC ......... *A61K 31/404* (2013.01); *A61K 9/0014* (2013.01); *A61K 31/403* (2013.01); *A61K 31/416* (2013.01); *A61K 31/4184* (2013.01); *A61K 31/437* (2013.01); *A61K 31/47* (2013.01); *A61K 31/472* (2013.01)

(58) Field of Classification Search
CPC ............... A61K 31/404; A61K 31/437; A61K 31/4187; A61K 31/47; A61K 31/472; A61K 31/403; A61K 31/416; A61K 9/0014
See application file for complete search history.

(56) References Cited

U.S. PATENT DOCUMENTS

| | | | |
|---|---|---|---|
| 5,480,656 A | 1/1996 | Okada et al. | |
| 5,575,987 A | 11/1996 | Kamei et al. | |
| 5,631,020 A | 5/1997 | Okada et al. | |
| 5,643,607 A | 7/1997 | Okada et al. | |
| 5,716,640 A | 2/1998 | Kamei et al. | |
| 5,814,342 A | 9/1998 | Okada et al. | |
| 6,036,976 A | 3/2000 | Takechi et al. | |
| 7,022,870 B2 | 4/2006 | Dalton et al. | |
| 7,118,552 B2 | 10/2006 | Shaw et al. | |
| 7,220,247 B2 | 5/2007 | Shaw et al. | |
| 7,500,964 B2 | 3/2009 | Shaw et al. | |
| 7,741,371 B2 | 6/2010 | Dalton | |
| 8,735,440 B2 | 5/2014 | McKnight et al. | |
| 9,550,742 B2* | 1/2017 | Marugan | C07D 417/12 |
| 2006/0142387 A1 | 6/2006 | Cadilla et al. | |

(Continued)

FOREIGN PATENT DOCUMENTS

| | | |
|---|---|---|
| CN | 1597662 A | 3/2005 |
| EP | 100172 A1 | 2/2004 |

(Continued)

OTHER PUBLICATIONS

Andersen et al. "Regression of castrate-recurrent prostate cancer by a small-molecule inhibitor of the amino-terminus domain of the androgen receptor" Cancer cell. Jun. 15, 2010;17(6):535-46.
Antonarakis et al. "AR-V7 and resistance to enzalutamide and abiraterone in prostate cancer" New England Journal of Medicine. Sep. 11, 2014;371(11):1028-38.
Attard et al. "Selective inhibition of CYP17 with abiraterone acetate is highly active in the treatment of castration-resistant prostate cancer" Journal of clinical oncology. May 26, 2009;27(23):3742-8.
Baek et al. "Ligand-specific allosteric regulation of coactivator functions of androgen receptor in prostate cancer cells" Proceedings of the National Academy of Sciences of the United States of America. Feb. 28, 2006;103(9):3100-5.

(Continued)

*Primary Examiner* — D M Seaman
(74) *Attorney, Agent, or Firm* — Mark S. Cohen; Pearl Cohen Zedek Latzer Baratz LLP

(57) ABSTRACT

This invention provides novel indole, indazole, benzimidazole, indoline, quinolone, isoquinoline, and carbazole selective androgen receptor degrader (SARD) compounds, pharmaceutical compositions and uses thereof in treating prostate cancer, advanced prostate cancer, castration resistant prostate cancer, androgenic alopecia or other hyper androgenic dermal diseases, Kennedy's disease, amyotrophic lateral sclerosis (ALS), and uterine fibroids, and to methods for reducing the levels of androgen receptor-full length (AR-FL) including pathogenic and/or resistance mutations, AR-splice variants (AR-SV), and pathogenic polyglutamine (polyQ) polymorphisms of AR in a subject.

47 Claims, 53 Drawing Sheets

(56) References Cited

U.S. PATENT DOCUMENTS

| | | | |
|---|---|---|---|
| 2006/0173037 | A1 | 8/2006 | Schlienger et al. |
| 2006/0241180 | A1 | 10/2006 | Dalton et al. |
| 2007/0049629 | A1 | 3/2007 | Scanlan et al. |
| 2007/0123563 | A1 | 5/2007 | Dalton et al. |
| 2007/0173546 | A1 | 7/2007 | Dalton et al. |
| 2008/0293766 | A1 | 11/2008 | Diamond et al. |
| 2009/0042844 | A1 | 2/2009 | Labrie et al. |
| 2009/0060873 | A1 | 3/2009 | Sporn et al. |
| 2009/0142323 | A1 | 6/2009 | Quarles et al. |
| 2011/0028719 | A1 | 2/2011 | Slon-Usakiewicz |
| 2014/0018433 | A1 | 1/2014 | Dalton et al. |
| 2014/0094474 | A1 | 4/2014 | Törmakängas et al. |

FOREIGN PATENT DOCUMENTS

| | | | |
|---|---|---|---|
| WO | WO 2002/016310 | A1 | 2/2002 |
| WO | WO 2002/046164 | A1 | 6/2002 |
| WO | WO 2003/106401 | A1 | 12/2003 |
| WO | WO 2005000794 | A1 | 1/2005 |
| WO | WO 2007/005887 | A2 | 1/2007 |
| WO | WO 2007/126988 | A2 | 11/2007 |
| WO | WO 2008/011072 | A2 | 1/2008 |
| WO | WO 2008/124000 | A2 | 10/2008 |
| WO | WO 2009/010480 | A1 | 1/2009 |
| WO | WO 2009/069736 | A1 | 6/2009 |
| WO | WO 2009/082437 | A2 | 7/2009 |
| WO | WO 2012/007644 | A1 | 1/2012 |
| WO | WO 2014/113260 | A1 | 7/2014 |
| WO | WO 2015/042297 | A1 | 3/2015 |

OTHER PUBLICATIONS

Berrevoets et al. "Effects of antiandrogens on transformation and transcription activation of wild-type and mutated (LNCaP) androgen receptors" The Journal of steroid biochemistry and molecular biology. Dec. 31, 1993;46(6):731-6.

Bohl et al. "Structural basis for antagonism and resistance of bicalutamide in prostate cancer" Proceedings of the National Academy of Sciences. Apr. 26, 2005;102(17):6201-6.

Bohl et al. "A ligand-based approach to identify quantitative structure—activity relationships for the androgen receptor" Journal of medicinal chemistry. Jul. 15, 2004;47(15):3765.

Bohl et al. "Structural basis for accommodation of nonsteroidal ligands in the androgen receptor" Journal of Biological Chemistry. Nov. 11, 2005;280(45):37747-54.

Claessens et al. "Diverse roles of androgen receptor (AR) domains in AR-mediated signaling" Nuclear receptor signaling. Jun. 27, 2008;6:e008.

Clegg et al. "ARN-509: a novel antiandrogen for prostate cancer treatment" Cancer research. Mar. 15, 2012;72(6):1494-503.

Danquah et al. "Combination therapy of antiandrogen and XIAP inhibitor for treating advanced prostate cancer" Pharmaceutical research. Aug. 1, 2012;29(8):2079-91.

De Bono et al. "Abiraterone and increased survival in metastatic prostate cancer" New England Journal of Medicine. May 26, 2011;364(21):1995-2005.

Dehm et al. "Alternatively spliced androgen receptor variants" Endocrine-related cancer. Oct. 1, 2011;18(5):R183-96.

Dehm et al. "Splicing of a novel androgen receptor exon generates a constitutively active androgen receptor that mediates prostate cancer therapy resistance" Cancer research. Jul. 1, 2008;68(13):5469-77.

Duke III, Charles B., et al. "Synthesis and biological studies of androgen receptor ligands: Towards mutation-resistant nonsteroidal antagonism." Abstracts of Papers of the American Chemical Society. vol. 240. 1155 16th St, NW, Washington, DC 20036 USA: Amer Chemical Soc, 2010.

Hu et al. "Distinct transcriptional programs mediated by the ligand-dependent full-length androgen receptor and its splice variants in castration-resistant prostate cancer" Cancer research. Jul. 15, 2012;72(14):3457-62.

Hwang et al. "Arylisothiocyanato selective androgen receptor modulators (SARMs) for prostate cancer" Bioorganic & medicinal chemistry. Oct. 1, 2006;14(19):6525-38.

International Search Report for PCT Application No. PCTUS1628674 dated Sep. 6, 2016.

Kim et al. "Ribosomal proteins as unrevealed caretakers for cellular stress and genomic instability" Oncotaraet. Feb. 1, 2014;5(4):860-71.

Klotz L. "Maximal androgen blockade for advanced prostate cancer" Best Practice & Research Clinical Endocrinology & Metabolism. Apr. 30, 2008;22(2):331-40.

Li et al. "Androgen receptor splice variants mediate enzalutamide resistance in castration-resistant prostate cancer cell lines" Cancer research. Jan. 15, 2013;73(2):483-9.

MaClean et al. "Spinal and bulbar muscular atrophy: androgen receptor dysfunction caused by a trinucleotide repeat expansion" Journal of the neurological sciences. Feb. 29, 1996;135(2):149-57.

Marhefka et al. "Homology modeling using multiple molecular dynamics simulations and docking studies of the human androgen receptor ligand binding domain bound to testosterone and nonsteroidal ligands" Journal of medicinal chemistry. May 24, 2001;44(11):1729-40.

Marhefka et al. "Design, synthesis, and biological characterization of metabolically stable selective androgen receptor modulators" Journal of medicinal chemistry. Feb. 12, 2004;47(4):993.

McGinley et al. "Circumventing anti-androgen resistance by molecular design" Journal of the American Chemical Society. Apr. 4, 2007;129(13):3822-3.

Mitsiades N. "A road map to comprehensive androgen receptor axis targeting for castration-resistant prostate cancer" Cancer research. Aug. 1, 2013;73(15):4599-605.

Monge et al. "Unfaithfulness and promiscuity of a mutant androgen receptor in a hormone-refractory prostate cancer" Cellular and molecular life sciences. Feb. 1, 2006;63(4):487-97.

Nazareth et al. "Activation of the human androgen receptor through a protein kinase A signaling pathway" Journal of Biological Chemistry. Aug. 16, 1996;271(33):19900-7.

Nyquist et al. "TALEN-engineered AR gene rearrangements reveal endocrine uncoupling of androgen receptor in prostate cancer" Proceedings of the National Academy of Sciences. Oct. 22, 2013;110(43):17492-7.

Sadar MD. "Androgen-independent induction of prostate-specific antigen gene expression via cross-talk between the androgen receptor and protein kinase A signal transduction pathways" Journal of Biological Chemistry. Mar. 19, 1999;274(12):7777-83.

Sadar et al. "Ligand-independent activation of the androgen receptor by the differentiation agent butyrate in human prostate cancer cells" Cancer research. Oct. 15, 2000;60(20):5825-31.

Sartor et al. "Androgen receptor variant-7: an important predictive biomarker in castrate resistant prostate cancer" Asian journal of andrology. May 2015;17(3):439.

Scher et al. "Increased survival with enzalutamide in prostate cancer after chemotherapy" New England Journal of Medicine. Sep. 27, 2012;367(13):1187-97.

Sieber PR. "Treatment of bicalutamide-induced breast events" Expert review of anticancer therapy. Dec. 1, 2007;7(12):1773-9.

Siegel et al. "Cancer statistics" CA Cancer. J. Clin. 2014;64:9-29.

Tran et al. "Development of a second-generation antiandrogen for treatment of advanced prostate cancer" Science. May 8, 2009;324(5928):787-90.

Ueda et al. Ligand-independent activation of the androgen receptor by interleukin-6 and the role of steroid receptor coactivator-1 in prostate cancer cells: Journal of Biological Chemistry. Oct. 11, 2002;277(41):38087-94.

Weiner LP. "Possible role of androgen receptors in amyotrophic lateral sclerosis: a hypothesis" Archives of neurology. Mar. 1, 1980;37(3):129-31.

Wen et al. "LHRH-conjugated micelles for targeted delivery of antiandrogen to treat advanced prostate cancer" Pharmaceutical research. Oct. 1, 2014;31(10):2784-95.

Xu et al. "hSSB1 binds and protects p21 from ubiquitin-mediated degradation and positively correlates with p21 in human hepatocellular carcinomas" Oncogene. May 12, 2011;30(19):2219-29.

(56) References Cited

OTHER PUBLICATIONS

Yamashita et al. "ASC-J9 suppresses castration-resistant prostate cancer growth through degradation of full-length and splice variant androgen receptors" Neoplasia. Jan. 1, 2012;14(1):74IN9-83IN12.
Yoshida et al. "Antiandrogen bicalutamide promotes tumor growth in a novel androgen-dependent prostate cancer xenograft model derived from a bicalutamide-treated patient" Cancer Research. Nov. 1, 2005;65(21):9611-6.
Zhou et al. "Study of the impact of the T877A mutation on ligand-induced helix-12 positioning of the androgen receptor resulted in design and synthesis of novel antiandrogens" Proteins: Structure, Function, and Bioinformatics. Feb. 15, 2010;78(3):623-37.

\* cited by examiner

22RV-1 Western

All these data were generated in LNCaP cells

All these data were generated in 22RV-1 cells

All experiments in this figure were done in LNCaP cells.

This experiment was done in 22RV-1 cells.

All experiments in this figure were done in LNCaP cells.

All experiments in this figure were done in 22RV-1 cells.

LNCaP

40

205

LNCaP

22RV1

SELECTIVE ANDROGEN RECEPTOR DEGRADER (SARD) LIGANDS AND METHODS OF USE THEREOF

CROSS REFERENCE TO RELATED APPLICATIONS

This application claims the benefit of U.S. Ser. No. 62/150,763, filed on 21 Apr. 2015, U.S. Ser. No. 62/220,057, filed 17 Sep. 2015, U.S. Ser. No. 62/241,532, filed on 14 Oct. 2015, U.S. Ser. No. 62/220,187, filed on 17 Sep. 2015, and U.S. Ser. No. 62/219,859, filed on 17 Sep. 2015 which are incorporated in their entirety herein by reference.

FIELD OF THE INVENTION

This invention is directed to novel indole, indazole, benzimidazole, indoline, quinolone, isoquinoline, and carbazole selective androgen receptor degrader (SARD) compounds, pharmaceutical compositions and uses thereof in treating prostate cancer, advanced prostate cancer, castration resistant prostate cancer, androgenic alopecia or other hyper androgenic dermal diseases, Kennedy's disease, amyotrophic lateral sclerosis (ALS), and uterine fibroids, and to methods for reducing the levels of androgen receptor-full length (AR-FL) including pathogenic and/or resistance mutations, AR-splice variants (AR-SV), and pathogenic polyglutamine (polyQ) polymorphisms of AR in a subject.

BACKGROUND OF THE INVENTION

Prostate cancer (PCa) is one of the most frequently diagnosed noncutaneous cancers among men in the US and is the second most common cause of cancer deaths with more than 200,000 new cases and over 30,000 deaths each year in the United States. PCa therapeutics market is growing at an annual rate of 15-20% globally.

Androgen-deprivation therapy (ADT) is the standard of treatment for advanced PCa. Patients with advanced prostate cancer undergo ADT, either by luteinizing hormone releasing hormone (LHRH) agonists, LHRH antagonists or by bilateral orchidectomy. Despite initial response to ADT, disease progression is inevitable and the cancer emerges as castration-resistant prostate cancer (CRPC). Up to 30% of patients with prostate cancer that undergo primary treatment by radiation or surgery will develop metastatic disease within 10 years of the primary treatment. Approximately 50,000 patients a year will develop metastatic disease, which is termed metastatic CRPC (mCRPC).

Patients with CRPC have a median survival of 12-18 months. Though castration-resistant, CRPC is still dependent on the androgen receptor (AR) signaling axis for continued growth. The primary reason for CRPC re-emergence is re-activation of AR by alternate mechanisms such as 1) intracrine androgen synthesis, 2) AR splice variants (AR-SV) that lack ligand binding domain (LBD), 3) AR-LBD mutations with potential to resist AR antagonists (i.e., mutants that are not sensitive to inhibition by AR antagonists, and in some cases AR antagonists act as agonists of the AR bearing these LBD mutations); and 4) amplications of the AR gene within the tumor.

A critical barrier to progress in treating CRPC is that AR signaling inhibitors such as enzalutamide, flutamide, bicalutamide, and abiraterone, acting through the LBD, fail to inhibit growth driven by the N-terminal domain (NTD)-dependent constitutively active AR-SV. Recent high-impact clinical trials with enzalutamide and abiraterone in CRPC patients demonstrated that 0% of AR-V7 (the predominant AR-SV) expressing patients responded to either of the treatments, indicating the requirement for next generation AR antagonists that target AR-SVs. In addition, a significant number of CRPC patients are becoming refractory to abiraterone or enzalutamide, emphasizing the need for next generation AR antagonists.

Current evidences demonstrate that CRPC growth is dependent on constitutively active AR including AR-SV's that lack the LBD such as AR-V7 and therefore cannot be inhibited by conventional antagonists. AR inhibition and degradation through binding to a domain that is distinct from the AR LBD provides alternate strategies to manage CRPC.

Molecules that degrade the AR prevent any inadvertent AR activation through growth factors or signaling pathways, or promiscuous ligand-dependent AR activation. In addition, molecules that inhibit the constitutive activation of AR-SVs are extremely important to provide extended benefit to CRPC patients.

Currently only a few chemotypes are known to degrade AR which include the SARDs AZD-3514, ARN-509 and ASC-J9. However, these molecules degrade AR indirectly at much higher concentrations than their binding coefficient and they fail to degrade the AR-SVs that have become in recent years the primary reason for resurgence of treatment-resistant CRPC.

This invention describes novel AR antagonists with unique pharmacology that strongly (high potency and efficacy) and selectively bind AR (better than known antagonists), antagonize AR, and degrade AR full length (AR-FL) and AR-SV. Selective androgen receptor degrader (SARD) compounds possess dual degradation and AR-SV inhibitory functions and hence are distinct from any available CRPC therapeutics. These novel selective androgen receptor degrader (SARD) compounds inhibit the growth of PCa cells and tumors that are dependent on AR-FL and AR-SV for proliferation.

SARDs have the potential to evolve as new therapeutics to treat CRPCs that are untreatable with any other antagonists. This unique property of degrading AR-SV has extremely important health consequences for prostate cancer. Till date only one molecule (EPI-001) is reported to bind to AR-NTD and inhibit AR function and PCa cell growth, albeit at lower affinity and it has an inability to degrade the receptor. The SARDs of this invention also bind AR-NTD and inhibit NTD-driven (i.e., ligand independent) AR activity.

The positive correlation between AR and PCa and the lack of a fail-safe AR antagonist, emphasizes the need for molecules that inhibit AR function through novel or alternate mechanisms and/or binding sites, and that can elicit antagonistic activities within an altered cellular environment.

Traditional antiandrogens such as bicalutamide and flutamide were approved for use in prostate cancer. Subsequent studies have demonstrated the utility of antiandrogens (e.g., flutamide, spironolactone, cyproterone acetate, finasteride and chlormadinone acetate) in androgen-dependent dermatological conditions such as androgenic alopecia (male pattern baldness), acne vulgaris, and hirsutism. Prepubertal castration prevents sebum production and androgenic alopecia but this can be reversed by use of testosterone, suggesting its androgen-dependence.

The AR gene has a polymorphism of glutamine repeats (polyQ) within exon 1 which when shortened may augment AR transactivation (i.e., hyperandrogenism). It has been found that shortened polyQ polymorphisms are more common in people with alopecia, hirsutism, and acne. Classic antiandrogens are undesirable for these purposes because they are ineffective through dermal dosing and their long-term systemic use raises the risks of untoward sexual effects such as gynecomastia and impotence. Further, similar to CRPC discussed above, inhibition of ligand-dependent AR activity alone may not be sufficient as AR can be activated by various cellular factors other than the endogeneous androgens testosterone (T) and dihydrotestosterone (DHT), such as growth factors, kinases, co-activator overexpression and/or promiscuous activation by other hormones (e.g., estrogens or glucocorticoids). Consequently, blocking the binding of T and DHT to AR with a classical antiandrogen may not be sufficient to have the desired efficacy.

An emerging concept is the topical application of a SARD to destroy the AR localized to the affected areas of the skin or other tissue(s) without exerting any systemic antiandrogenism. For this use, a SARD that does not penetrate the skin or is rapidly metabolized would be preferable.

Supporting this approach is the observation that cutaneous wound healing has been demonstrated to be suppressed by androgens. Castration of mice accelerates cutaneous wound healing while attenuating the inflammation in the wounds. The negative correlation between androgen levels and cutaneous healing and inflammation, in part, explains another mechanism by which high levels of endogenous androgens exacerbate hyperandrogenic dermatological conditions such those described herein. Further, it provides a rationale for the treatment of wounds such as diabetic ulcers or even trauma, or skin disorders with an inflammatory component such as acne or psoriasis, with a topical SARD.

Androgenic alopecia occurs in ~50% of Caucasian males by midlife and up to 90% by 80 years old. Minoxidil (a topical vasodilator) and finasteride (a systemic 5-alpha reductase type II inhibitor) are FDA approved for alopecia but require 4-12 months of treatment to produce a therapeutic effect and only arrest hair loss in most with mild to moderate hair regrowth in 30-60%. Since currently available treatments have slow and limited efficacy that vary widely between individuals, and produce unwanted sexual side effects, it is important to find a novel approach to treat androgenic alopecia and other hyperandrogenic dermatologic diseases.

Amyotrophic lateral sclerosis (ALS) is a fatal neurodegenerative disease. Patients with ALS are characterized by extended AR polyglutamine repeats. Riluzole is an available drug for ALS treatment, however, only provides short-term effects. There is an urgent need for drugs that extend the survival of ALS patients. Transgenic animals of ALS were shown to survive longer upon castration and reduction in AR levels compared to castration+nandrolone (agonist) supplementation. Castration reduces the AR level, which may be the reason for extended survival.

Androgens promote uterine proliferation. Higher testosterone levels increase the risk of uterine fibroids. Treatment of uterine fibroids with SARDs would help prevent or treat uterine fibroids.

Here we describe indole, indazole, benzimidazole, indoline, quinolone, isoquinoline, and carbazole SARDs that bind to LBD and an alternate binding and degradation domain (BDD; located outside the LBD, probably in the NTD), antagonize AR, and degrade AR thereby blocking ligand-dependent and ligand-independent AR activities. This novel mechanism produces improved efficacy when dosed systemically (e.g., for prostate cancer) or topically (e.g., dermatological diseases).

X-linked spinal-bulbar muscular atrophy (SBMA—also known as Kennedy's disease) is a muscular atrophy that arises from a defect in the androgen receptor gene on the X chromosome. Proximal limb and bulbar muscle weakness results in physical limitations including dependence on a wheelchair in some cases. The mutation results in a protracted polyglutamine tract added to the N-terminal domain of the androgen receptor (polyQ AR). Binding and activation of this lengthened polyQ AR by endogeneous androgens (testosterone and DHT) results in unfolding and nuclear translocation of the mutant androgen receptor. These steps are required for pathogenesis and result in partial loss of the transactivation function (i.e., an androgen insensitivity) and a poorly understood neuromuscular degeneration. Currently there are no disease-modifying treatments but rather only symptom directed treatments. Efforts to target the polyQ AR of Kennedy's disease as the proximal mediator of toxicity by harnessing cellular machinery to promote its degradation, i.e., through the use of a SARD, hold promise for therapeutic intervention. Selective androgen receptor degraders such as those reported herein bind to and degrade a variety of androgen receptors (full length, splice variant, antiandrogen resistance mutants, and are likely to degrade polyQ AR polymorphisms as well), indicating that they are promising leads for treatment of SBMA.

SUMMARY OF THE INVENTION

In one embodiment, this invention provides a selective androgen receptor degrader (SARD) compound represented by the structure of formula I:

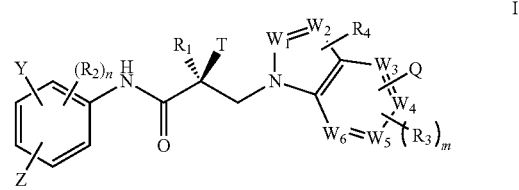

wherein $W_1$ and $W_2$ are each independently selected from N or CH;

$W_3$, $W_4$, $W_5$ and $W_6$ are each independently selected from CH or N;

wherein if any one of $W_1$, $W_2$, $W_3$, $W_4$, $W_5$, and $W_6$ is CH, then the H is optionally replaced with $R_4$, Q or $R_3$ in the respective position, and if any one of $W_1$, $W_2$, $W_3$, $W_4$, $W_5$, and $W_6$ is not CH, then the respective position is unsubstituted;

T is OH, OR, —NHCOCH$_3$, NHCOR or

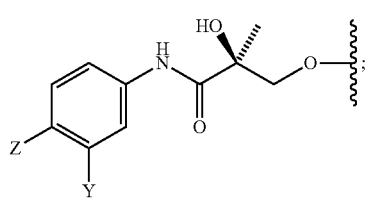

Z is NO$_2$, CN, COOH, COR, NHCOR or CONHR;
Y is CF$_3$, F, I, Br, Cl, CN or C(R)$_3$;
R is alkyl, haloalkyl, dihaloalkyl, trihaloalkyl, CH$_2$F, CHF$_2$, CF$_3$, CF$_2$CF$_3$, aryl, phenyl, F, Cl, Br, I, alkenyl or OH;
R$_1$ is CH$_3$, CH$_2$F, CHF$_2$, CF$_3$, CH$_2$CH$_3$, or CF$_2$CF$_3$;

$R_2$ is hydrogen, halogen, CN, $NO_2$, COOH, COOR, COR, NHCOR, CONHR, OH, OR, SH, SR, $NH_2$, NHR, $NR_2$, $C_1$-$C_{12}$-alkyl, $C_1$-$C_{12}$-haloalkyl, O—$C_1$-$C_{12}$-alkyl, O—$C_1$-$C_{12}$-haloalkyl, —$SO_2$-aryl, —$SO_2$-phenyl, —CO-aryl, arylalkyl, benzyl, aryl, or $C_3$-$C_7$-cycloalkyl;

Q is hydrogen, F, Cl, Br, I, $CF_3$, CN, $NO_2$, COOH, COOR, alkoxy, haloalkyl, optionally substituted linear or branched alkyl, optionally substituted linear or branched heteroalkyl, optionally substituted aryl, optionally substituted phenyl, optionally substituted cycloalkyl, optionally substituted heterocycloalkyl, optionally substituted arylalkyl, $C(R)_3$, $N(R)_2$, $NHCOCH_3$, $NHCOCF_3$, NHCOR, NHCONHR, NHCOOR, OCONHR, CONHR, $NHCSCH_3$, $NHCSCF_3$, NHCSR, $NHSO_2CH_3$, $NHSO_2R$, OR, COR, OCOR, $OSO_2R$, $SO_2R$, SR, NCS, SCN, NCO, or OCN;

$R_3$ is hydrogen, F, Cl, Br, I, $CF_3$, CN, $NO_2$, $NH_2$, SH, COOH, COOR, alkoxy, haloalkyl, optionally substituted linear or branched alkyl, optionally substituted linear or branched heteroalkyl, optionally substituted aryl, optionally substituted phenyl, optionally substituted cycloalkyl, optionally substituted heterocycloalkyl, optionally substituted arylalkyl, $C(R)_3$, $N(R)_2$, $NHCOCH_3$, $NHCOCF_3$, NHCOR, NHCONHR, NHCOOR, OCONHR, CONHR, $NHCSCH_3$, $NHCSCF_3$, NHCSR, $NHSO_2CH_3$, $NHSO_2R$, OR, COR, OCOR, $OSO_2R$, $SO_2R$, SR, NCS, SCN, NCO or OCN;

$R_4$ is hydrogen, F, Cl, Br, I, $CF_3$, CN, $NO_2$, $NH_2$, SH, COOH, COOR, alkoxy, haloalkyl, optionally substituted linear or branched alkyl, optionally substituted linear or branched heteroalkyl, optionally substituted aryl, optionally substituted phenyl, optionally substituted cycloalkyl, optionally substituted heterocycloalkyl, optionally substituted arylalkyl, $C(R)_3$, $N(R)_2$, $NHCOCH_3$, $NHCOCF_3$, NHCOR, NHCONHR, NHCOOR, OCONHR, CONHR, $NHCSCH_3$, $NHCSCF_3$, NHCSR, $NHSO_2CH_3$, $NHSO_2R$, OR, COR, OCOR, $OSO_2R$, $SO_2R$, SR, NCS, SCN, NCO or OCN;

n is an integer between 1-3; and
m is an integer between 1-3.

In another embodiment, $W_1$, $W_2$, $W_3$, $W_4$, $W_5$, and $W_6$ are CH. In another embodiment, $W_2$ is N and $W_1$, $W_3$, $W_4$, $W_5$, and $W_6$ are CH. In another embodiment, $W_3$ is N and $W_1$, $W_2$, $W_4$, $W_5$, and $W_6$ are CH. In another embodiment, $W_1$ is N and $W_2$, $W_3$, $W_4$, $W_5$, and $W_6$ are CH.

In another embodiment, the selective androgen receptor degrader (SARD) compound is represented by the structure of formula III:

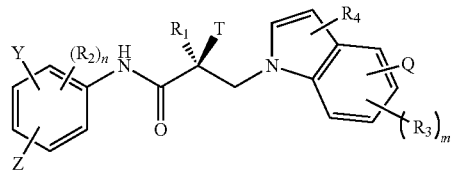

III wherein
T is OH, OR, —$NHCOCH_3$, NHCOR or

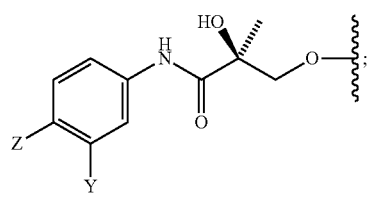

Z is $NO_2$, CN, COOH, COR, NHCOR or CONHR;
Y is $CF_3$, F, I, Br, Cl, CN or $C(R)_3$;
R is alkyl, haloalkyl, dihaloalkyl, trihaloalkyl, $CH_2F$, $CHF_2$, $CF_3$, $CF_2CF_3$, aryl, phenyl, F, Cl, Br, I, alkenyl or OH;

$R_1$ is $CH_3$, $CH_2F$, $CHF_2$, $CF_3$, $CH_2CH_3$, or $CF_2CF_3$;

$R_2$ is hydrogen, halogen, CN, $NO_2$, COOH, COOR, COR, NHCOR, CONHR, OH, OR, SH, SR, $NH_2$, NHR, $NR_2$, $C_1$-$C_{12}$-alkyl, $C_1$-$C_{12}$-haloalkyl, O—$C_1$-$C_{12}$-alkyl, O—$C_1$-$C_{12}$-haloalkyl, —$SO_2$-aryl, —$SO_2$-phenyl, —CO-aryl, arylalkyl, benzyl, aryl, or $C_3$-$C_7$-cycloalkyl;

Q is hydrogen, F, Cl, Br, I, $CF_3$, CN, $NO_2$, COOH, COOR, alkoxy, haloalkyl, optionally substituted linear or branched alkyl, optionally substituted linear or branched heteroalkyl, optionally substituted aryl, optionally substituted phenyl, optionally substituted cycloalkyl, optionally substituted heterocycloalkyl, optionally substituted arylalkyl, $C(R)_3$, $N(R)_2$, $NHCOCH_3$, $NHCOCF_3$, NHCOR, NHCONHR, NHCOOR, OCONHR, CONHR, $NHCSCH_3$, $NHCSCF_3$, NHCSR, $NHSO_2CH_3$, $NHSO_2R$, OR, COR, OCOR, $OSO_2R$, $SO_2R$, SR, NCS, SCN, NCO or OCN;

$R_3$ is hydrogen, F, Cl, Br, I, $CF_3$, CN, $NO_2$, $NH_2$, SH, COOH, COOR, alkoxy, haloalkyl, optionally substituted linear or branched alkyl, optionally substituted linear or branched heteroalkyl, optionally substituted aryl, optionally substituted phenyl, optionally substituted cycloalkyl, optionally substituted heterocycloalkyl, optionally substituted arylalkyl, $C(R)_3$, $N(R)_2$, $NHCOCH_3$, $NHCOCF_3$, NHCOR, NHCONHR, NHCOOR, OCONHR, CONHR, $NHCSCH_3$, $NHCSCF_3$, NHCSR, $NHSO_2CH_3$, $NHSO_2R$, OR, COR, OCOR, $OSO_2R$, $SO_2R$, SR, NCS, SCN, NCO or OCN;

$R_4$ is hydrogen, F, Cl, Br, I, $CF_3$, CN, $NO_2$, $NH_2$, SH, COOH, COOR, alkoxy, haloalkyl, optionally substituted linear or branched alkyl, optionally substituted linear or branched heteroalkyl, optionally substituted aryl, optionally substituted phenyl, optionally substituted cycloalkyl, optionally substituted heterocycloalkyl, optionally substituted arylalkyl, $C(R)_3$, $N(R)_2$, $NHCOCH_3$, $NHCOCF_3$, NHCOR, NHCONHR, NHCOOR, OCONHR, CONHR, $NHCSCH_3$, $NHCSCF_3$, NHCSR, $NHSO_2CH_3$, $NHSO_2R$, OR, COR, OCOR, $OSO_2R$, $SO_2R$, SR, NCS, SCN, NCO or OCN;

n is an integer between 1-3; and
m is an integer between 1-3.

In another embodiment, the selective androgen receptor degrader (SARD) compound is represented by the structure of formula V:

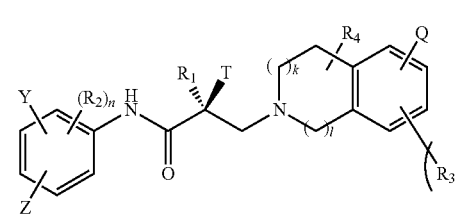

V wherein Z, Y, R, Q, $R_1$, $R_2$, $R_3$, $R_4$, T, m and n are as described in the structure of formula III; and l is 0 or 1; and k is 0, 1 or 2.

In another embodiment, the selective androgen receptor degrader (SARD) compound is represented by the structure of formula VI:

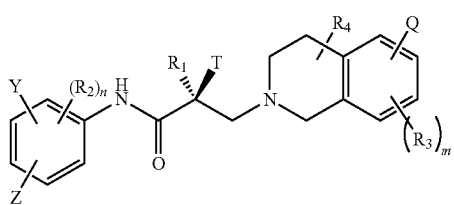

VI wherein Z, Y, R, Q, $R_1$, $R_2$, $R_3$, $R_4$, T, m and n are as described in the structure of formula III.

In another embodiment, the selective androgen receptor degrader (SARD) compound is represented by the structure of formula VII:

VII wherein Z, Y, R, Q, $R_1$, $R_2$, $R_3$, $R_4$, T, m and n are as described in the structure of formula III.

In another embodiment, the selective androgen receptor degrader (SARD) compound is represented by the structure of formula IV:

IV

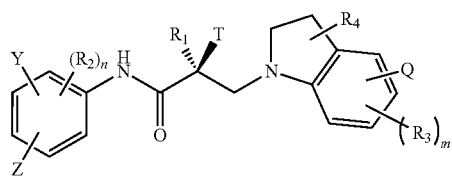

wherein Z, Y, R, Q, $R_1$, $R_2$, $R_3$, $R_4$, T, m and n are as described in the structure of formula III.

In another embodiment, the SARD compound of this invention is represented by the structure of any one of the following compounds:

Indoles:

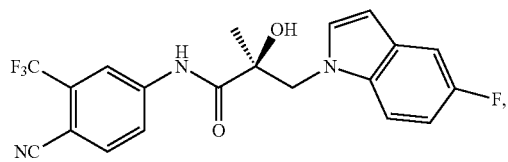
11

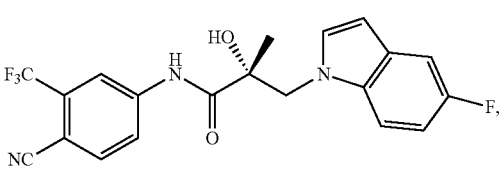
11R

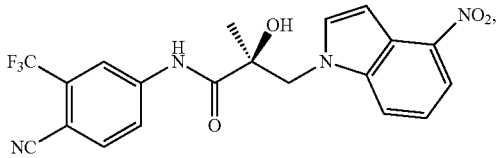
12

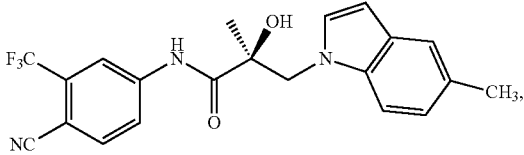
13

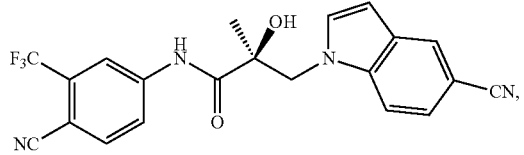
14

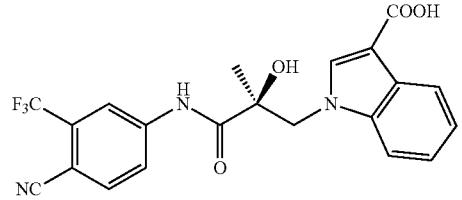
15

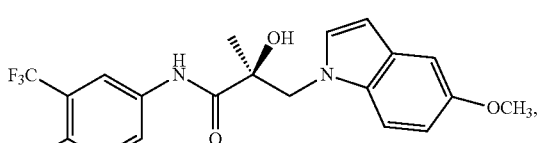
16

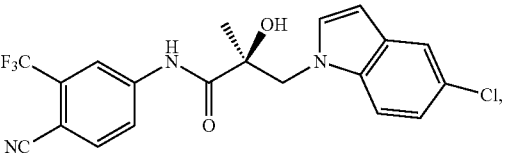
17

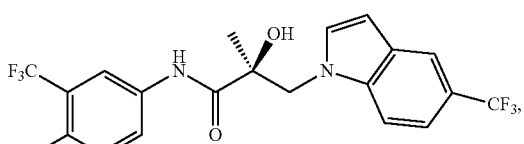
19

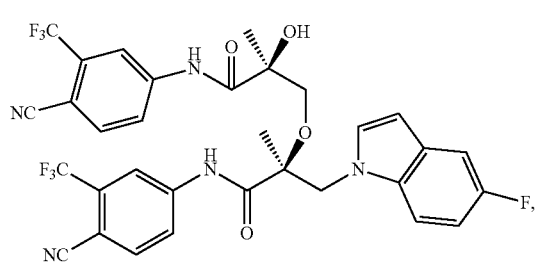
19

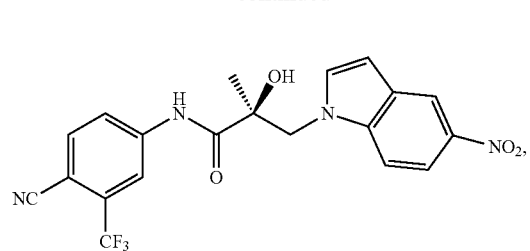
20
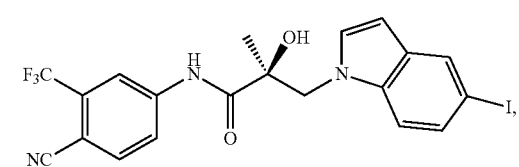
21
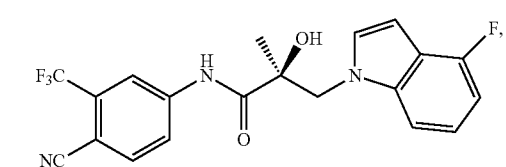
22
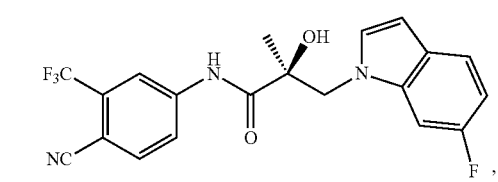
23
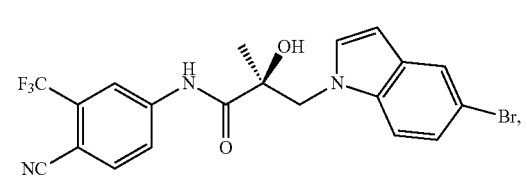
24
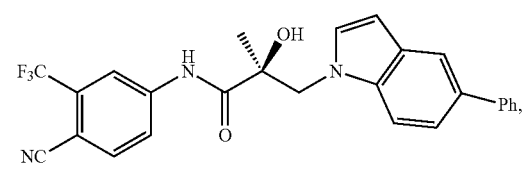
25
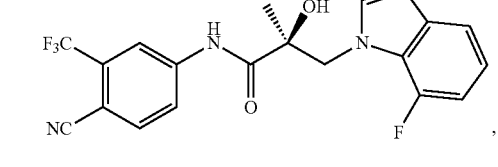
26
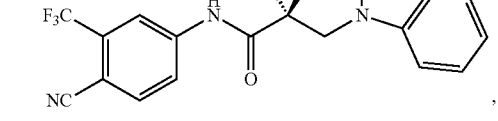
27
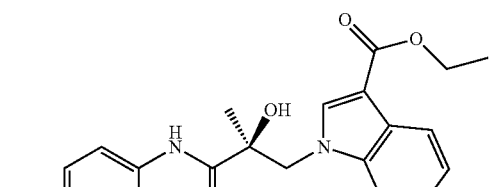
30
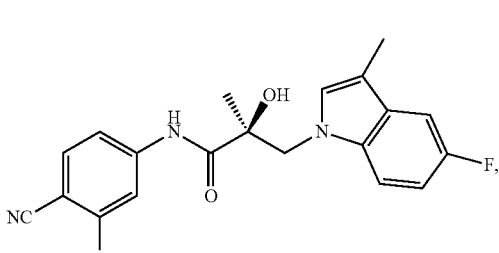
31
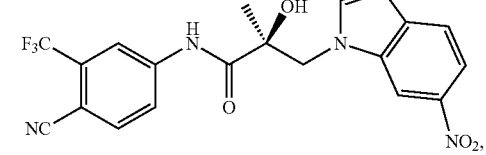
32
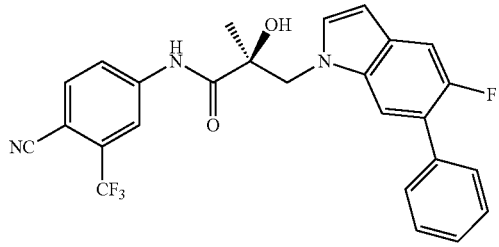
33
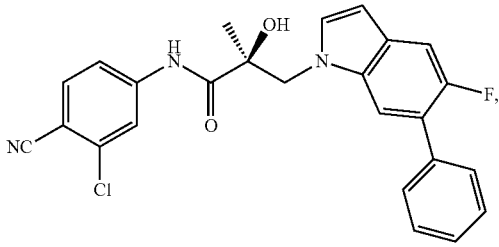
34
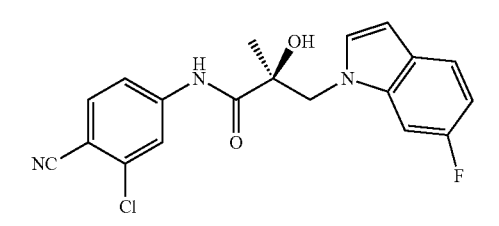
35

-continued
36
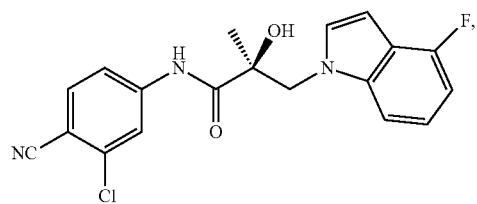
37
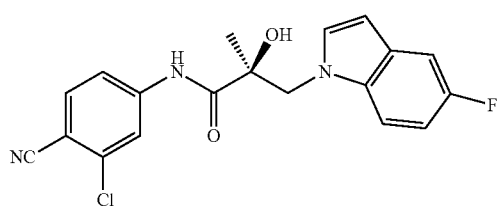
38
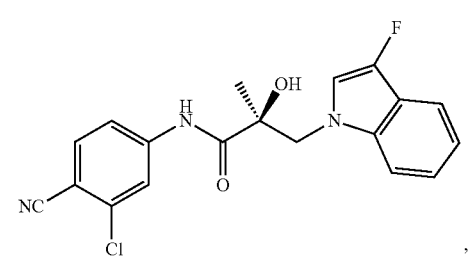
39
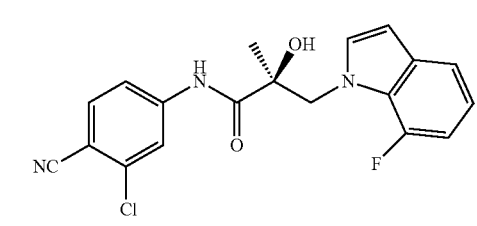
40
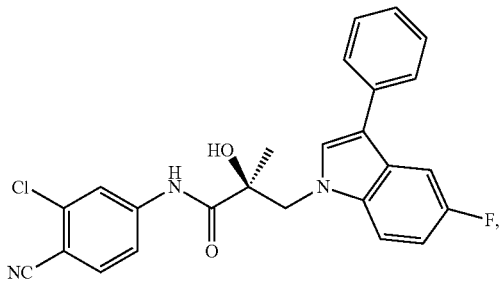
41
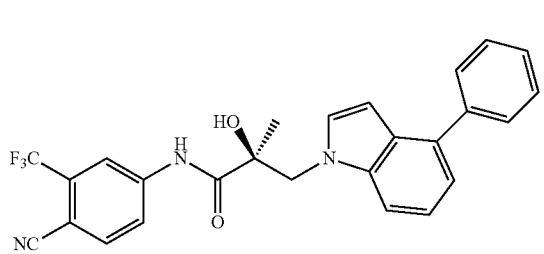
42
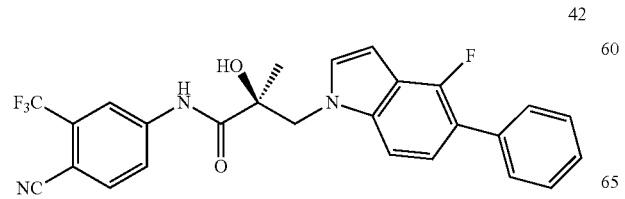
Benzimidazoles:
70
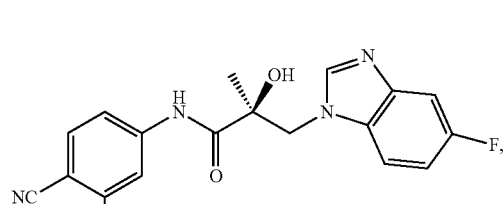
71
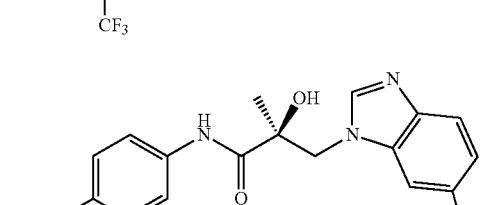
72
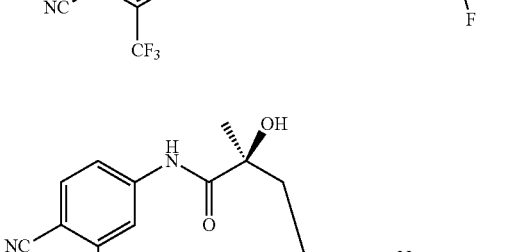
73
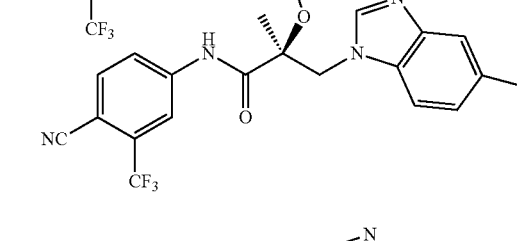
74
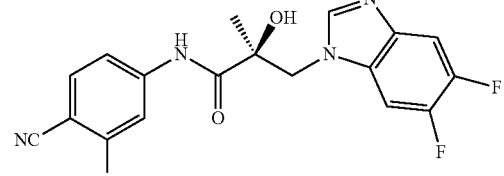
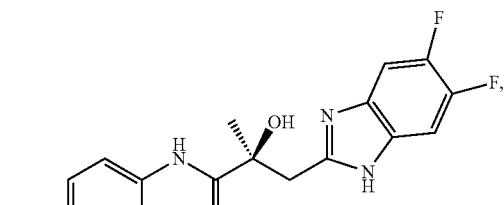
75
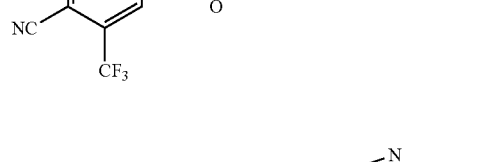
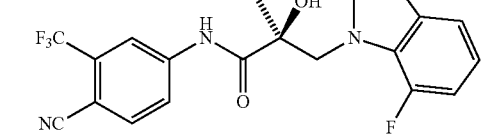

Pyrrolo-Pyridine:
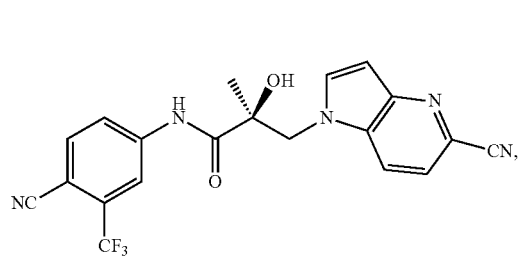
80
Indazoles:
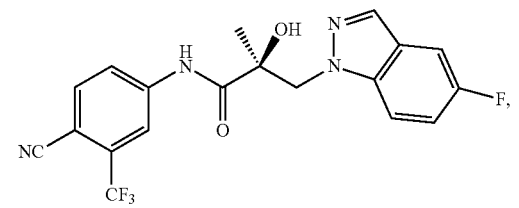
90
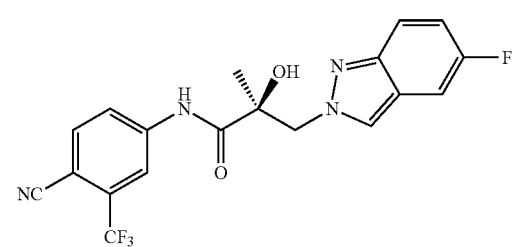
91
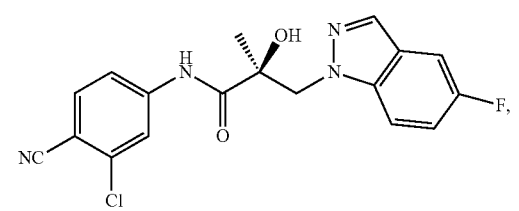
92
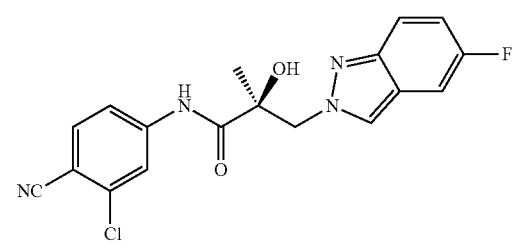
93
Indolines:
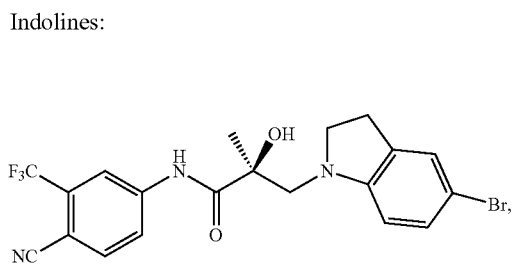
100
-continued
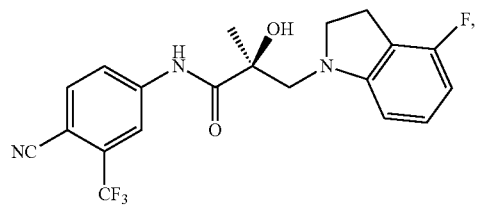
101
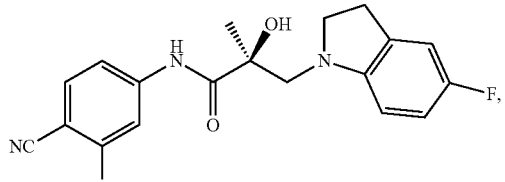
102
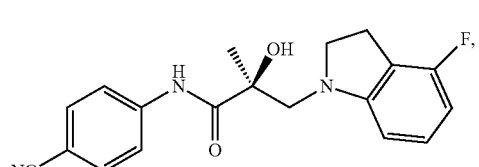
103
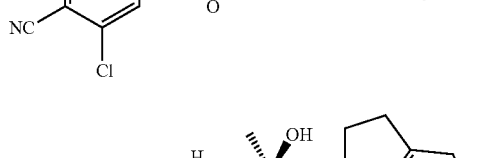
104
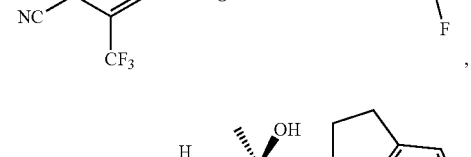
105
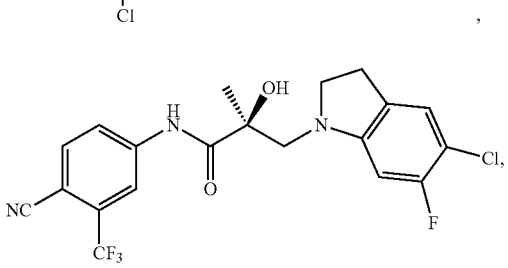
106, 107

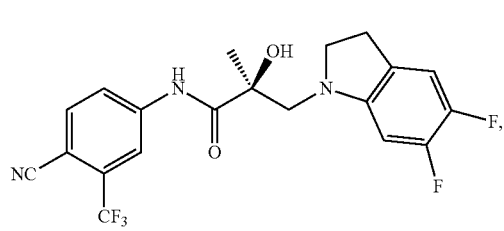
108
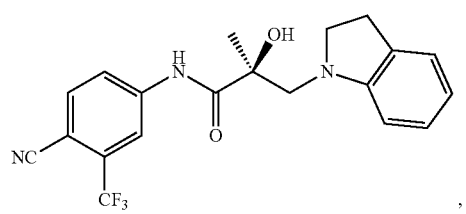
109
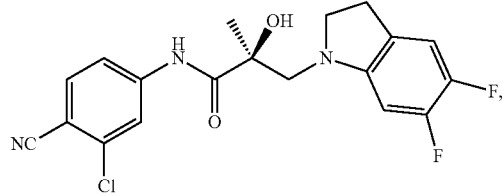
110
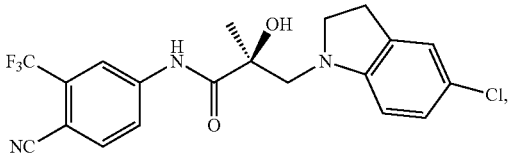
111
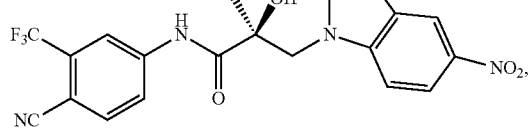
112
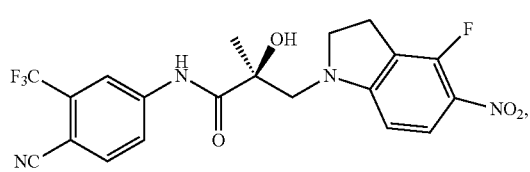
113
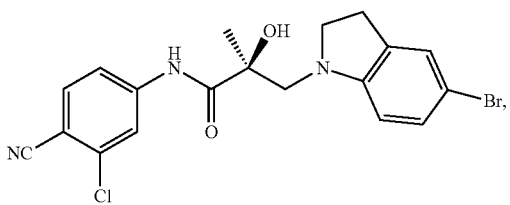
114
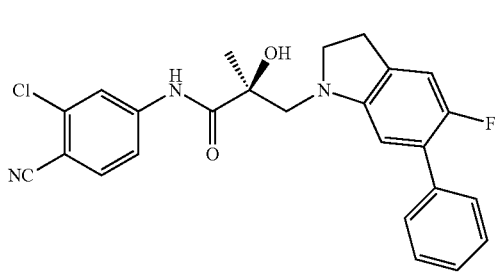
115
Isoquinolines and Quinolines:
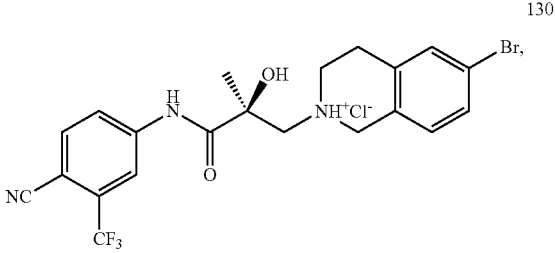
130
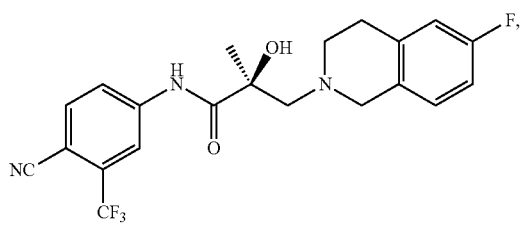
131
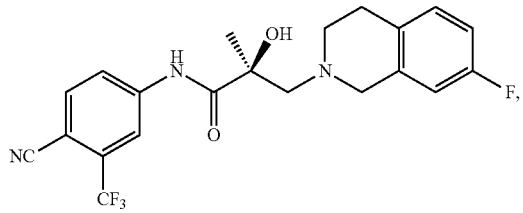
132
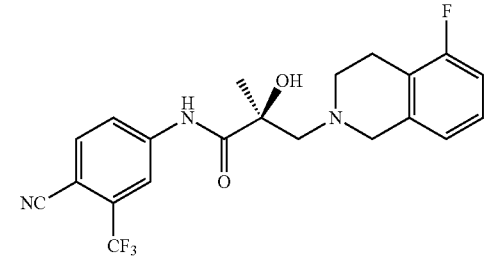
133
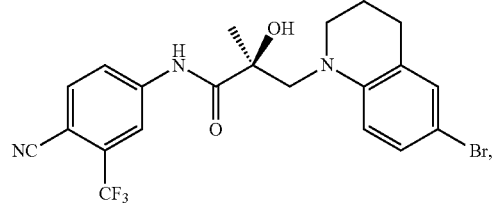
134

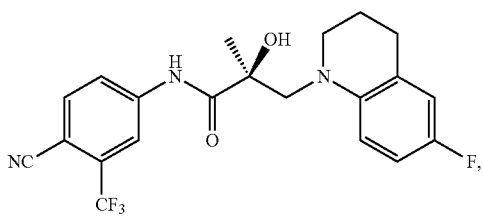

135


136 , or

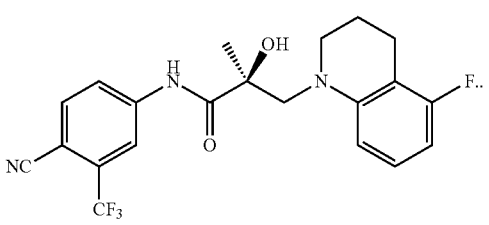

137

In another embodiment, the compound of this invention binds to the AR through an alternate binding and degradation domain (BDD). In another embodiment, some of the compounds of this invention further bind the AR ligand binding domain (LBD). In another embodiment, the compound exhibits AR-splice variant (AR-SV) degradation activity. In another embodiment, the compound further exhibits AR-full length (AR-FL) degradation activity. In another embodiment, the compound exhibits AR-SV inhibitory activity (i.e., is an AR-SV antagonist). In another embodiment, the compound further exhibits AR-FL inhibitory activity (i.e., is an AR-FL antagonist). In another embodiment, the compound possesses dual AR-SV degradation and AR-SV inhibitory functions. In another embodiment, the compound further possesses dual AR-FL degradation and AR-FL inhibitory functions.

In one embodiment, this invention is directed to a pharmaceutical composition comprising a SARD compound according to this invention, or its isomer, pharmaceutically acceptable salt, pharmaceutical product, polymorph, hydrate or any combination thereof, and a pharmaceutically acceptable carrier. In another embodiment, the pharmaceutical composition is formulated for topical use. In another embodiment, the pharmaceutical composition is in the form of a solution, lotion, salve, cream, ointment, liposome, spray, gel, foam, roller stick, cleansing soaps or bars, emulsion, mousse, aerosol, shampoo, or any combination thereof.

In one embodiment, this invention is directed to a method of treating, suppressing, reducing the incidence, reducing the severity, or inhibiting the progression of prostate cancer (PCa) and its symptoms, or increasing the survival of a male subject suffering from prostate cancer comprising administering to said subject a therapeutically effective amount of a compound according to this invention, or its isomer, pharmaceutically acceptable salt, pharmaceutical product, polymorph, hydrate or any combination thereof. In another embodiment, the prostate cancer is advanced prostate cancer, castration resistant prostate cancer (CRPC), metastatic CRPC (mCRPC), non-metastatic CRPC (nmCRPC), high-risk nmCRPC or any combination thereof.

In one embodiment, this invention is directed to a method of treating, suppressing, reducing the incidence, reducing the severity, or inhibiting the progression of advanced prostate cancer and its symptoms, or increasing the survival of a male subject suffering from advanced prostate cancer comprising administering to said subject a therapeutically effective amount of a compound of this invention, or its isomer, pharmaceutically acceptable salt, pharmaceutical product, polymorph, hydrate or any combination thereof.

In one embodiment, this invention is directed to a method of treating, suppressing, reducing the incidence, reducing the severity, or inhibiting the progression of castration resistant prostate cancer (CRPC) and its symptoms, or increasing the survival of a male subject suffering from castration resistant prostate cancer comprising administering to said subject a therapeutically effective amount of a compound of this invention, or its isomer, pharmaceutically acceptable salt, pharmaceutical product, polymorph, hydrate or any combination thereof.

In another embodiment, the prostate cancer depends on AR-SV for proliferation. In another embodiment, the prostate cancer further depends on AR-FL for proliferation. In another embodiment, the AR-SV is AR-V7 or ARv567es. In another embodiment, the prostate cancer depends on AR that contains the W741L mutation or T877A mutation or other antiandrogen resistance-conferring AR-LBD mutations, or any combination thereof. In another embodiment, the prostate cancer depends on amplications of the AR gene within the tumor. In another embodiment, there may be a heterogenous expression of AR such that the prostate cancer may depend on multiple AR variations and/or amplifications within a single patient. In another embodiment, the subject further receives androgen deprivation therapy (ADT). In another embodiment, the subject has failed androgen deprivation therapy (ADT). In another embodiment, the cancer is resistant to treatment with an androgen receptor antagonist. In another embodiment, the androgen receptor antagonist is enzalutamide, flutamide, bicalutamide, abiraterone, ARN-509, AZD-3514, galeterone, ASC-J9, flutamide, hydroxyflutamide, nilutamide, cyproterone acetate, ketoconazole, spironolactone, or any combination thereof. In another embodiment, the administering of the compound reduces the levels of AR, AR-full length (AR-FL), AR-FL with antiandrogen resistance-conferring AR-LBD mutations, AR-splice variant (AR-SV), gene-amplified AR, or any combination thereof, in said subject.

In one embodiment, this invention is directed to a method of reducing the levels of AR-splice variants in a subject, comprising administering to said subject a therapeutically effective amount of a compound of this invention, or its isomer, pharmaceutically acceptable salt, pharmaceutical product, polymorph, hydrate or any combination thereof. In another embodiment, the method further reduces the levels of AR-full length in said subject. In another embodiment, the reduction is achieved by degradation, inhibition, or dual degradation and inhibitory function of AR-splice variants (AR-SV) or AR-FL variations including antiandrogen resistance mutants such as W741L and T877A. In another embodiment, the reduction is further achieved by degradation, inhibition, or dual degradation and inhibitory function of AR-FL. In another embodiment, the reduction is further achieved by degradation or inhibition of AR from amplified AR gene within the tumor.

In one embodiment, this invention is directed to a method of treating, suppressing, reducing the incidence, reducing the severity, or inhibiting the progression of the Kennedy's disease in a subject, comprising administering to said subject a compound of this invention.

In one embodiment, this invention is directed to a method of reducing the levels of polyglutamine (polyQ) AR polymorphs in a subject comprising administering a compound according to this invention. In another embodiment, the reduction is achieved by degradation, inhibition, or dual degradation and inhibitory function of said polyglutamine (polyQ) AR polymorphs (polyQ-AR). In another embodiment, the polyQ-AR is a short polyQ polymorph or a long polyQ polymorph. In another embodiment, the polyQ-AR is a short polyQ polymorph, and the method further treats dermal disease. In another embodiment the polyQ-AR is a long polyQ polymorph, and said method further treats Kennedy's disease.

In one embodiment, this invention is directed to a method of treating, suppressing, reducing the incidence, reducing the severity, or inhibiting the progression of amyotrophic lateral sclerosis (ALS) in a subject, comprising administering a therapeutically effective amount of the compound of this invention, or its isomer, pharmaceutically acceptable salt, pharmaceutical product, polymorph, hydrate or any combination thereof; or a pharmaceutical composition thereof.

In one embodiment, this invention is directed to a method of treating, suppressing, reducing the incidence, reducing the severity, or inhibiting the progression of uterine fibroids in a subject, comprising administering a therapeutically effective amount of the compound of this invention, or its isomer, pharmaceutically acceptable salt, pharmaceutical product, polymorph, hydrate or any combination thereof; or a pharmaceutical composition thereof.

In one embodiment, this invention is directed to a method of: (a) treating, suppressing, reducing the incidence, reducing the severity, or inhibiting the progression of acne in a subject; (b) decreasing sebum production in a subject; (c) treating, suppressing, reducing the incidence, reducing the severity, or inhibiting the progression of hirsutism in a subject; (d) treating, suppressing, reducing the incidence, reducing the severity, or inhibiting the progression of alopecia in a subject; (e) treating, suppressing, reducing the incidence, reducing the severity, or inhibiting the progression of a hormonal condition in female; (f) treating, suppressing, reducing the incidence, reducing the severity, or inhibiting the progression of sexual perversion, hypersexuality, or paraphilias in a subject; (g) treating, suppressing, reducing the incidence, reducing the severity, or inhibiting the progression of androgen psychosis in a subject; (h) treating, suppressing, reducing the incidence, reducing the severity, or inhibiting the progression of virilization in a subject; (i) treating, suppressing, reducing the incidence, reducing the severity, or inhibiting the progression of androgen insensitivity syndrome in a subject; (j) increasing, modulating, or improving ovulation in an animal; (k) treating, suppressing, reducing the incidence, reducing the severity, or inhibiting the progression of cancer in a subject; (l) treating, suppressing, reducing the incidence, reducing the severity, or inhibiting the progression of amyotrophic lateral sclerosis (ALS); (m) treating, suppressing, reducing the incidence, reducing the severity, or inhibiting the progression of uterine fibroids or any combination thereof, comprising administering a compound of this invention or a pharmaceutical composition thereof.

BRIEF DESCRIPTION OF THE DRAWINGS

The subject matter regarded as the invention is particularly pointed out and distinctly claimed in the concluding portion of the specification. The invention, however, both as to organization and method of operation, together with objects, features, and advantages thereof, may best be understood by reference to the following detailed description when read with the accompanying drawings in which:

(FIG. 1A) 14, 18, and 20; (FIG. 1B) 11 and 12; and (FIG. 1C) 1123 and 27; of this invention.

(FIG. 7A) AR A/BCD increases GRE-LUC reporter activity. AR A/BCD construct that lacks the ligand binding domain or empty vector was transfected into HEK-293 cells along with GRE-LUC and CMV-renilla LUC. Forty eight hours after transfection cells were harvested and luciferase assay performed. (FIG. 7B) AR A/BCD activity was inhibited by 11. The A/BCD AR construct that lacks the ligand binding domain (LBD) was transfected along with GRE-LUC and CMV-LUC. Cells were treated 24 hrs after transfection as indicated in the figure and luciferase assay performed 48 hrs after transfection. 11 (a SARD) inhibited the activity of construct lacking LBD confirming the binding to an alternate site in addition to the LBD. (FIG. 7C) and (FIG. 7D) Non-SARD antagonists ARN-509 and enzalutamide did not inhibit the activity of this AR construct lacking the LBD, suggesting that of the compounds tested, only SARDs of this invention have the ability to inhibit ligand independent AR activity.

(FIG. 8A) 11, 12, and 14, galeterone, EPI-001, and enzalutamide; and (FIG. 8B) 11, galeterone, and enzaluatamide. SARDs of this invention more potently inhibited (AR-FL) transaction.

(FIG. 9A) 11 significantly reduced tumor volume and (FIG. 9B) tumor weight in a 22RV-1 xenograft tumor study, whereas AR antagonist enzalutamide did not have any effect compared to vehicle. (FIG. 9C) shows tumor expressed levels of AR-FL and AR-V7 were decreased by 11 but not enzalutamide, demonstrating that in vivo activity correlated with AR degradation in the tumors; and (FIG. 9D) demonstrates an in vivo antiandrogenic tone in gene expression as the serum PSA in these animals was decreased by 11 but not enzalutamide in this 22RV-1 xenograft study.

(FIG. 17A) and (FIG. 17B) A dose-dependent shift in the fluorescence intensity, i.e., fluorescent quenching, was observed with 11 when incubated with AR AF-1. The fluorescence shoulder observed at 307 nm, which corresponds to tyrosine residues in the AF-1, is shifted by 11. The overall fluorescence is also markedly altered by 11. (FIG. 17C) Data shown was plotted as difference in fluorescence between control and 11 treated samples (fluorescence in the absence of compound—fluorescence in the presence of compound), a dose dependent increase was observed in the presence of 11. Cumulatively, these data suggest a direct interaction between 11 and AR AF-1.

(FIG. 29A) presents transactivation data for 42 ($IC_{50}$=1015 nM) and binding (Ki=86.1 nM). (FIG. 29O) presents (1) transactivation data for 34 ($IC_{50}$=nM) and binding (Ki=nM); (2) AR full length degradation; and (3) AR splice variant degradation.

(FIG. 30A) and (FIG. 30D) SARDs demonstrated various degrees of decreased seminal vesicles weight, (FIG. 30B) increased in body weight, and (FIG. 30C) decreased prostate weight. This behavior is consistent with an in vivo antiandrogenic effect exerted by SARDs of this invention.

Figure 1A:
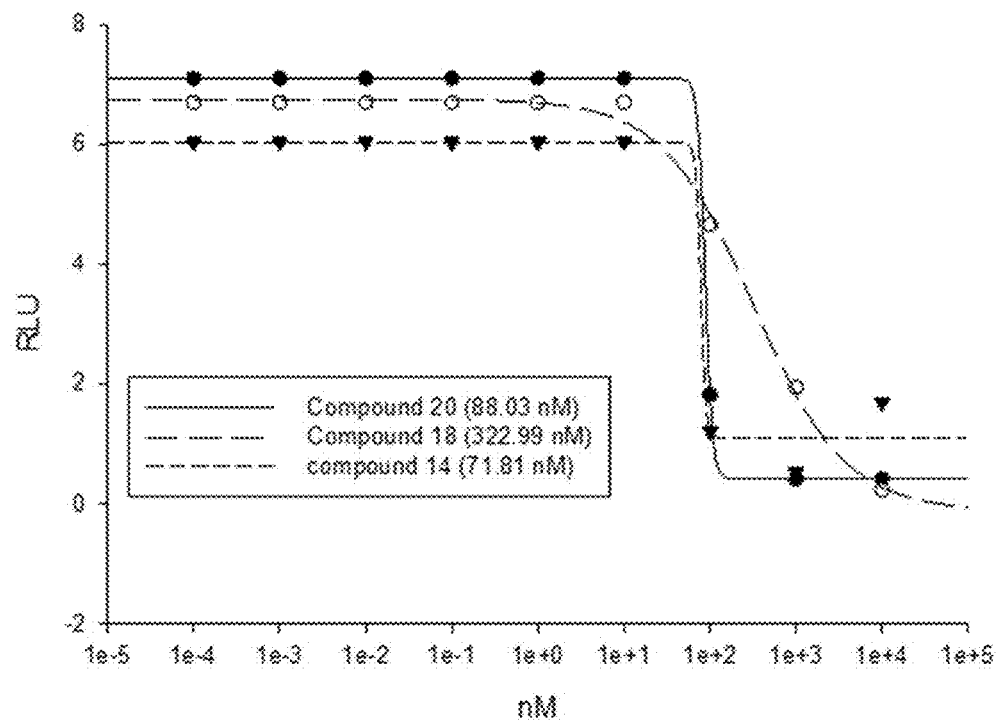
FIG. 1A-FIG. 1C presents inhibition of AR transactivation for the SARD compounds.
Figure 1A:
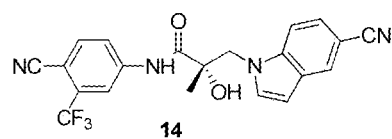
Figure 1A:
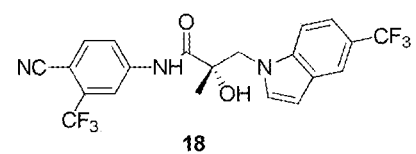
Figure 1A:
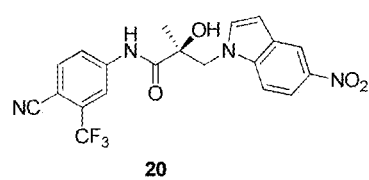

It will be appreciated that for simplicity and clarity of illustration, elements shown in the figures have not necessarily been drawn to scale. For example, the dimensions of some of the elements may be exaggerated relative to other elements for clarity. Further, where considered appropriate, reference numerals may be repeated among the figures to indicate corresponding or analogous elements.

DETAILED DESCRIPTION OF THE PRESENT INVENTION

In the following detailed description, numerous specific details are set forth in order to provide a thorough understanding of the invention. However, it will be understood by those skilled in the art that the present invention may be practiced without these specific details. In other instances, well-known methods, procedures, and components have not been described in detail so as not to obscure the present invention.

Androgens act in cells by binding to the AR, a member of the steroid receptor superfamily of transcription factors. As the growth and maintenance of prostate cancer (PCa) is largely controlled by circulating androgens, treatment of PCa heavily relies on therapies that target AR. Treatment with AR antagonists such as enzalutamide, flutamide, bicalutamide or hydroxyflutamide to disrupt receptor activation has been successfully used in the past to reduce PCa growth. All currently available AR antagonists competitively bind AR and recruit corepressors such as NCoR and SMRT to repress transcription of target genes. However, altered intracellular signaling, AR mutations, and increased expression of coactivators lead to functional impairment of antagonists or even transformation of antagonists into agonists. Studies have demonstrated that mutation of W741 and T877 within AR converts bicalutamide and hydroxyflutamide, respectively, to agonists. Similarly, increased intracellular cytokines recruit coactivators instead of corepressors to AR-responsive promoters subsequently converting bicalutamide to an agonist.

Despite initial response to androgen deprivation therapy (ADT), PCa disease progression is inevitable and the cancer emerges as castration resistant prostate cancer (CRPC). The primary reason for castration resistant prostate cancer (CRPC) re-emergence is re-activation of androgen receptor (AR) by alternate mechanisms such as:

(a) intracrine androgen synthesis;
(b) expression of AR splice variants (AR-SV) that lack ligand binding domain (LBD);
(c) AR-LBD mutations with potential to resist antagonists;
(d) hyper-sensitization of AR to low androgen levels, e.g., due to AR gene amplification or AR mutation;
(e) amplification of the AR gene within the tumor; and
(f) over expression of coactivators.

In one embodiment, this invention is directed to novel selective androgen receptor degrader (SARD) compounds, which inhibit the growth of prostate cancer (PCa) cells and tumors that are dependent on AR full length (AR-FL) including pathogenic and resistance-conferring mutation and/or wildtype, and/or AR splice variants (AR-SV) for proliferation.

According to this invention, a "selective androgen receptor degrader" (SARD) compound is an androgen receptor antagonist that is capable of inhibiting the growth of PCa cells and tumors that are dependent on AR-full length (AR-FL) and/or AR splice variants (AR-SV) for proliferation. In another embodiment, the SARD compound does not bind to the ligand binding domain (LBD). In another embodiment, the SARD compound binds to the N-terminal domain (NTD) of the AR. In another embodiment, the SARD compound binds to an alternate binding and degradation domain (BDD) of the AR. In another embodiment, the SARD compound binds both to the AR ligand binding domain (LBD) and to an alternate binding and degradation domain (BDD). In another embodiment, the SARD compound binds both to the N-terminal domain (NTD) and to the ligand binding domain (LBD) of the AR. In another embodiment, the SARD compound is capable of inhibiting growth driven by the N-terminal domain (NTD)-dependent constitutively active AR-SV. In another embodiment, the SARD compound inhibits the AR through binding to a domain that is distinct from the AR LBD. In another embodiment, the SARD compound is a strong (i.e., highly potent and highly efficacious) selective androgen receptor antagonist, which antagonizes the AR stronger than other known AR antagonists (e.g., enzalutamide, flutamide, bicalutamide and abiraterone). In another embodiment, the SARD compound is a selective androgen receptor antagonist, which targets AR-SVs, which cannot be inhibited by conventional antagonists. In another embodiment, the SARD compound exhibits AR-splice variant (AR-SV) degradation activity. In another embodiment, the SARD compound further exhibits AR-full length (AR-FL) degradation activity. In another embodiment, the SARD compound exhibits AR-splice variant (AR-SV) inhibitory activity (i.e., is an AR-SV antagonist). In another embodiment, the SARD compound further exhibits AR-full length (AR-FL) inhibitory activity (i.e., is an AR-FL antagonist). In another embodiment, the SARD compound possesses dual AR-SV degradation and AR-SV inhibitory functions. In another embodiment, the SARD compound further possesses dual AR-FL degradation and AR-FL inhibitory functions. In another embodiment, the SARD compound is a selective androgen receptor antagonist, which targets AR-SVs. In another embodiment, the SARD compound further targets AR-FLs. In another embodiment, the SARD compound inhibits the constitutive activation of AR-SVs. In another embodiment, the SARD compound further inhibits the constitutive activation of AR-FLs. In another embodiment, the SARD compound is a selective androgen receptor antagonist, which degrades AR-full length (AR-FL) and AR splice variants (AR-SV). In another embodiment, the SARD compound degrades the AR through binding to a domain that is distinct from the AR LBD. In another embodiment, the SARD compound possesses dual degradation and AR-SV inhibitory functions, that are distinct from any available CRPC therapeutics. In another embodiment, the SARD compound inhibits the re-activation of the AR by alternate mechanisms such as: intracrine androgen synthesis, expression of AR splice variants (AR-SV) that lack ligand binding domain (LBD) and AR-LBD mutations with potential to resist antagonists. In another embodiment, the SARD compound inhibits re-activated androgen receptors present in pathogenically altered cellular environments.

Nonlimiting examples of AR-splice variants (AR-SVs) are: AR-V7 and ARv567es (a.k.a. AR-V12). Nonlimiting examples of AR mutations conferring antiandrogen resistance are: W741L mutation and T877A mutation. AR-V7 is a splice variant of AR that lacks the LBD. It is constitutively active and has been demonstrated to be responsible for aggressive PCa and resistance to endocrine therapy.

In one embodiment, this invention is directed to novel selective androgen receptor degrader (SARD) compounds, which bind to the AR through an alternate binding and degradation domain (BDD). In another embodiment, the SARD further binds the AR ligand binding domain (LBD).

In one embodiment, this invention is directed to novel selective androgen receptor degrader (SARD) compounds, which exhibit AR-splice variant (AR-SV) inhibitory activity (i.e., is an AR-SV antagonist). In another embodiment, the novel selective androgen receptor degrader (SARD) compounds, further exhibit AR-full length (AR-FL) inhibitory activity (i.e., is an AR-FL antagonist).

In one embodiment, this invention is directed to novel selective androgen receptor degrader (SARD) compounds, which exhibit AR-splice variant (AR-SV) degradation activity. In another embodiment, the novel selective androgen receptor degrader (SARD) compounds, further exhibit AR-full length (AR-FL) degradation activity.

In one embodiment, this invention is directed to novel selective androgen receptor degrader (SARD) compounds, which possess dual AR-SV degradation and AR-SV inhibitory functions. In another embodiment, the SARDs further possess dual AR-FL degradation and AR-FL inhibitory functions. In another embodiment, this invention is directed to novel selective androgen receptor degrader (SARD) compounds, which possess dual AR-SV and AR-FL degradation, and AR-SV and AR-FL inhibitory functions.

In one embodiment, this invention is directed to novel selective androgen receptor degrader (SARD) compounds, for use in treating CRPC that cannot be treated with any other antagonist.

In one embodiment, this invention is directed to selective androgen receptor degrader (SARD) compounds, for use in treating CRPC, by degrading AR-SVs.

In one embodiment, the novel SARD compounds according to this invention maintain their antagonistic activity in AR mutants that normally convert AR antagonists to agonists. In another embodiment, the SARD compounds maintain their antagonistic activity to AR mutants W741 and T877. In another embodiment, the SARD compounds elicit antagonistic activity within an altered cellular environment in which LBD-targeted agents are not effective. In another embodiment, the SARD compounds elicit antagonistic activity within an altered cellular environment in which NTD-dependent AR activity is constitutively active.

Selective Androgen Receptor Degrader (SARD) Compounds

In one embodiment, this invention is directed to a selective androgen receptor degrader (SARD) compound represented by the structure of formula I:

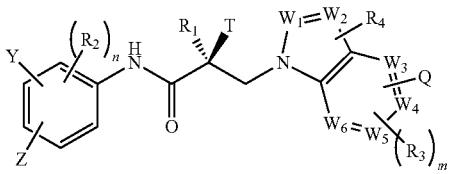

I wherein
W$_1$ and W$_2$ are each independently selected from N or CH;
W$_3$, W$_4$, W$_5$ and W$_6$ are each independently selected from CH or N;
wherein if any one of W$_1$, W$_2$, W$_3$, W$_4$, W$_5$, and W$_6$ is CH, then the H is optionally replaced with R$_4$, Q or R$_3$ in the respective position, and if any one of W$_1$, W$_2$, W$_3$, W$_4$, W$_5$, and W$_6$ is not CH, then the respective position is unsubstituted;
T is OH, OR, —NHCOCH$_3$, NHCOR or

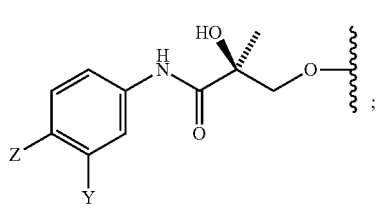

;

Z is NO$_2$, CN, COOH, COR, NHCOR or CONHR;
Y is CF$_3$, F, I, Br, Cl, CN or C(R)$_3$;
R is alkyl, haloalkyl, dihaloalkyl, trihaloalkyl, CH$_2$F, CHF$_2$, CF$_3$, CF$_2$CF$_3$, aryl, phenyl, F, Cl, Br, I, alkenyl or OH;
R$_1$ is CH$_3$, CH$_2$F, CHF$_2$, CF$_3$, CH$_2$CH$_3$, or CF$_2$CF$_3$;
R$_2$ is hydrogen, halogen, CN, NO$_2$, COOH, COOR, COR, NHCOR, CONHR, OH, OR, SH, SR, NH$_2$, NHR, NR$_2$, C$_1$-C$_{12}$-alkyl, C$_1$-C$_{12}$-haloalkyl, O—C$_1$-C$_{12}$-alkyl, O—C$_1$-C$_{12}$-haloalkyl, —SO$_2$-aryl, —SO$_2$-phenyl, —CO-aryl, arylalkyl, benzyl, aryl, or C$_3$-C$_7$-cycloalkyl;
Q is hydrogen, F, Cl, Br, I, CF$_3$, CN, NO$_2$, COOH, COOR, alkoxy, haloalkyl, optionally substituted linear or branched alkyl, optionally substituted linear or branched heteroalkyl, optionally substituted aryl, optionally substituted phenyl, optionally substituted cycloalkyl, optionally substituted heterocycloalkyl, optionally substituted arylalkyl, C(R)$_3$, N(R)$_2$, NHCOCH$_3$, NHCOCF$_3$, NHCOR, NHCONHR, NHCOOR, OCONHR, CONHR, NHCSCH$_3$, NHCSCF$_3$, NHCSR, NHSO$_2$CH$_3$, NHSO$_2$R, OR, COR, OCOR, OSO$_2$R, SO$_2$R, SR, NCS, SCN, NCO or OCN;
R$_3$ and R$_4$ are independently selected from hydrogen, F, Cl, Br, I, CF$_3$, CN, NO$_2$, NH$_2$, SH, COOH, COOR, alkoxy, haloalkyl, optionally substituted linear or branched alkyl, optionally substituted linear or branched heteroalkyl, optionally substituted aryl, optionally substituted phenyl, optionally substituted cycloalkyl, optionally substituted heterocycloalkyl, optionally substituted arylalkyl, C(R)$_3$, N(R)$_2$, NHCOCH$_3$, NHCOCF$_3$, NHCOR, NHCONHR, NHCOOR, OCONHR, CONHR, NHCSCH$_3$, NHCSCF$_3$, NHCSR, NHSO$_2$CH$_3$, NHSO$_2$R, OR, COR, OCOR, OSO$_2$R, SO$_2$R, SR, NCS, SCN, NCO or OCN;
n is an integer between 1-3; and
m is an integer between 1-3.

In another embodiment, W$_1$, W$_2$, W$_3$, W$_4$, W$_5$, and W$_6$ of formula I are each independently CH. In another embodiment, W$_1$ is N. In another embodiment, W$_2$ is N. In another embodiment, W$_1$ is CH. In another embodiment, W$_2$ is CH. In another embodiment, W$_3$ is N. In another embodiment, W$_4$ is N. In another embodiment, W$_5$ is N. In another embodiment, W$_6$ is N.

In another embodiment, W$_1$ is N and W$_1$, W$_3$, W$_4$, W$_5$, and W$_6$ are CH. In another embodiment, W$_2$ is N and W$_1$, W$_3$, W$_4$, W$_5$, and W$_6$ are CH. In another embodiment, W$_3$ is N and W$_1$, W$_2$, W$_4$, W$_5$, and W$_6$ are CH. In another embodiment, W$_4$ is N and W$_1$, W$_2$, W$_3$, W$_5$, and W$_6$ are CH. In another embodiment, W$_5$ is N and W$_1$, W$_2$, W$_3$, W$_4$, and W$_6$ are CH. In another embodiment, W$_6$ is N and W$_1$, W$_2$, W$_3$, W$_4$, and W$_5$ are CH.

In one embodiment, this invention is directed to a selective androgen receptor degrader (SARD) compound represented by the structure of formula II:

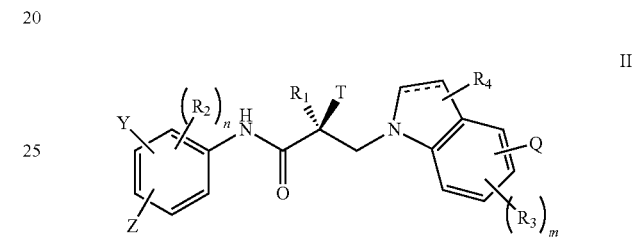

II wherein ≈≈≈ is a single or double bond;
T is OH, OR, —NHCOCH$_3$, NHCOR or

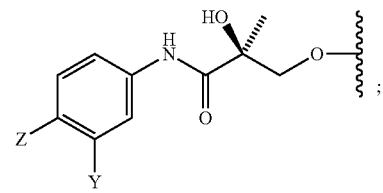

;

Z is NO$_2$, CN, COOH, COR, NHCOR or CONHR;
Y is CF$_3$, F, I, Br, Cl, CN or C(R)$_3$;
R is alkyl, haloalkyl, dihaloalkyl, trihaloalkyl, CH$_2$F, CHF$_2$, CF$_3$, CF$_2$CF$_3$, aryl, phenyl, F, Cl, Br, I, alkenyl or OH;
R$_1$ is CH$_3$, CH$_2$F, CHF$_2$, CF$_3$, CH$_2$CH$_3$, or CF$_2$CF$_3$;
R$_2$ is hydrogen, halogen, CN, NO$_2$, COOH, COOR, COR, NHCOR, CONHR, OH, OR, SH, SR, NH$_2$, NHR, NR$_2$, C$_1$-C$_{12}$-alkyl, C$_1$-C$_{12}$-haloalkyl, O—C$_1$-C$_{12}$-alkyl, O—C$_1$-C$_{12}$-haloalkyl, —SO$_2$-aryl, —SO$_2$-phenyl, —CO-aryl, arylalkyl, benzyl, aryl, or C$_3$-C$_7$-cycloalkyl;
Q is hydrogen, F, Cl, Br, I, CF$_3$, CN, NO$_2$, COOH, COOR, alkoxy, haloalkyl, optionally substituted linear or branched alkyl, optionally substituted linear or branched heteroalkyl, optionally substituted aryl, optionally substituted phenyl, optionally substituted cycloalkyl, optionally substituted heterocycloalkyl, optionally substituted arylalkyl, C(R)$_3$, N(R)$_2$, NHCOCH$_3$, NHCOCF$_3$, NHCOR, NHCONHR, NHCOOR, OCONHR, CONHR, NHCSCH$_3$, NHCSCF$_3$, NHCSR, NHSO$_2$CH$_3$, NHSO$_2$R, OR, COR, OCOR, OSO$_2$R, SO$_2$R, SR, NCS, SCN, NCO or OCN;
R$_3$ is hydrogen, F, Cl, Br, I, CF$_3$, CN, NO$_2$, NH$_2$, SH, COOH, COOR, alkoxy, haloalkyl, optionally substituted linear or branched alkyl, optionally substituted linear or branched heteroalkyl, optionally substituted aryl, optionally substituted phenyl, optionally substituted cycloalkyl, optionally substituted heterocycloalkyl, optionally substituted arylalkyl, $C(R)_3$, $N(R)_2$, $NHCOCH_3$, $NHCOCF_3$, NHCOR, NHCONHR, NHCOOR, OCONHR, CONHR, $NHCSCH_3$, $NHCSCF_3$, NHCSR, $NHSO_2CH_3$, $NHSO_2R$, OR, COR, OCOR, $OSO_2R$, $SO_2R$, SR, NCS, SCN, NCO or OCN;

$R_4$ is hydrogen, F, Cl, Br, I, $CF_3$, CN, $NO_2$, $NH_2$, SH, COOH, COOR, alkoxy, haloalkyl, optionally substituted linear or branched alkyl, optionally substituted linear or branched heteroalkyl, optionally substituted aryl, optionally substituted phenyl, optionally substituted cycloalkyl, optionally substituted heterocycloalkyl, optionally substituted arylalkyl, $C(R)_3$, $N(R)_2$, $NHCOCH_3$, $NHCOCF_3$, NHCOR, NHCONHR, NHCOOR, OCONHR, CONHR, $NHCSCH_3$, $NHCSCF_3$, NHCSR, $NHSO_2CH_3$, $NHSO_2R$, OR, COR, OCOR, $OSO_2R$, $SO_2R$, SR, NCS, SCN, NCO or OCN;

n is an integer between 1-3; and m is an integer between 1-3.

In one embodiment, this invention is directed to a selective androgen receptor degrader (SARD) compound represented by the structure of formula III:

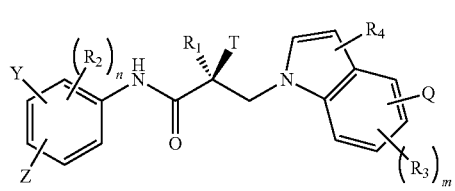

III wherein

T is OH, OR, —$NHCOCH_3$, NHCOR or

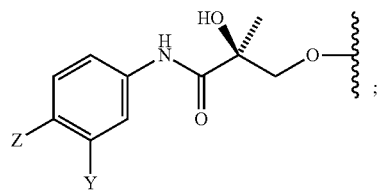

;

Z is $NO_2$, CN, COOH, COR, NHCOR or CONHR;

Y is $CF_3$, F, I, Br, Cl, CN or $C(R)_3$;

R is alkyl, haloalkyl, dihaloalkyl, trihaloalkyl, $CH_2F$, $CHF_2$, $CF_3$, $CF_2CF_3$, aryl, phenyl, F, Cl, Br, I, alkenyl or OH;

$R_1$ is $CH_3$, $CH_2F$, $CHF_2$, $CF_3$, $CH_2CH_3$, or $CF_2CF_3$;

$R_2$ is hydrogen, halogen, CN, $NO_2$, COOH, COOR, COR, NHCOR, CONHR, OH, OR, SH, SR, $NH_2$, NHR, $NR_2$, $C_1$-$C_{12}$-alkyl, $C_1$-$C_{12}$-haloalkyl, O—$C_1$-$C_{12}$-alkyl, O—$C_1$-$C_{12}$-haloalkyl, —$SO_2$-aryl, —$SO_2$-phenyl, —CO-aryl, arylalkyl, benzyl, aryl, or $C_3$-$C_7$-cycloalkyl;

Q is hydrogen, F, Cl, Br, I, $CF_3$, CN, $NO_2$, COOH, COOR, alkoxy, haloalkyl, optionally substituted linear or branched alkyl, optionally substituted linear or branched heteroalkyl, optionally substituted aryl, optionally substituted phenyl, optionally substituted cycloalkyl, optionally substituted heterocycloalkyl, optionally substituted arylalkyl, $C(R)_3$, $N(R)_2$, $NHCOCH_3$, $NHCOCF_3$, NHCOR, NHCONHR, NHCOOR, OCONHR, CONHR, $NHCSCH_3$, $NHCSCF_3$, NHCSR, $NHSO_2CH_3$, $NHSO_2R$, OR, COR, OCOR, $OSO_2R$, $SO_2R$, SR, NCS, SCN, NCO or OCN;

$R_3$ is hydrogen, F, Cl, Br, I, $CF_3$, CN, $NO_2$, $NH_2$, SH, COOH, COOR, alkoxy, haloalkyl, optionally substituted linear or branched alkyl, optionally substituted linear or branched heteroalkyl, optionally substituted aryl, optionally substituted phenyl, optionally substituted cycloalkyl, optionally substituted heterocycloalkyl, optionally substituted arylalkyl, $C(R)_3$, $N(R)_2$, $NHCOCH_3$, $NHCOCF_3$, NHCOR, NHCONHR, NHCOOR, OCONHR, CONHR, $NHCSCH_3$, $NHCSCF_3$, NHCSR, $NHSO_2CH_3$, $NHSO_2R$, OR, COR, OCOR, $OSO_2R$, $SO_2R$, SR, NCS, SCN, NCO or OCN;

$R_4$ is hydrogen, F, Cl, Br, I, $CF_3$, CN, $NO_2$, $NH_2$, SH, COOH, COOR, alkoxy, haloalkyl, optionally substituted linear or branched alkyl, optionally substituted linear or branched heteroalkyl, optionally substituted aryl, optionally substituted phenyl, optionally substituted cycloalkyl, optionally substituted heterocycloalkyl, optionally substituted arylalkyl, $C(R)_3$, $N(R)_2$, $NHCOCH_3$, $NHCOCF_3$, NHCOR, NHCONHR, NHCOOR, OCONHR, CONHR, $NHCSCH_3$, $NHCSCF_3$, NHCSR, $NHSO_2CH_3$, $NHSO_2R$, OR, COR, OCOR, $OSO_2R$, $SO_2R$, SR, NCS, SCN, NCO or OCN;

n is an integer between 1-3; and m is an integer between 1-3.

In one embodiment, this invention is directed to a selective androgen receptor degrader (SARD) compound represented by the structure of formula IV:

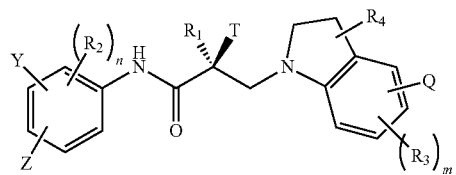

IV wherein

T is OH, OR, —$NHCOCH_3$, NHCOR or

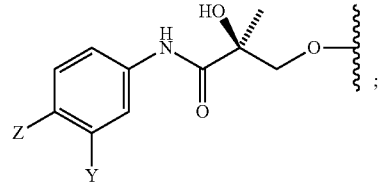

;

Z is $NO_2$, CN, COOH, COR, NHCOR or CONHR;

Y is $CF_3$, F, I, Br, Cl, CN or $C(R)_3$;

R is alkyl, haloalkyl, dihaloalkyl, trihaloalkyl, $CH_2F$, $CHF_2$, $CF_3$, $CF_2CF_3$, aryl, phenyl, F, Cl, Br, I, alkenyl or OH;

$R_1$ is $CH_3$, $CH_2F$, $CHF_2$, $CF_3$, $CH_2CH_3$, or $CF_2CF_3$;

$R_2$ is hydrogen, halogen, CN, $NO_2$, COOH, COOR, COR, NHCOR, CONHR, OH, OR, SH, SR, $NH_2$, NHR, $NR_2$, $C_1$-$C_{12}$-alkyl, $C_1$-$C_{12}$-haloalkyl, O—$C_1$-$C_{12}$-alkyl, O—$C_1$-$C_{12}$-haloalkyl, —$SO_2$-aryl, —$SO_2$-phenyl, —CO-aryl, arylalkyl, benzyl, aryl, or $C_3$-$C_7$-cycloalkyl;

Q is hydrogen, F, Cl, Br, I, $CF_3$, CN, $NO_2$, COOH, COOR, alkoxy, haloalkyl, optionally substituted linear or branched alkyl, optionally substituted linear or branched heteroalkyl, optionally substituted aryl, optionally substituted phenyl, optionally substituted cycloalkyl, optionally substituted heterocycloalkyl, optionally substituted arylalkyl, C(R)$_3$, N(R)$_2$, NHCOCH$_3$, NHCOCF$_3$, NHCOR, NHCONHR, NHCOOR, OCONHR, CONHR, NHCSCH$_3$, NHCSCF$_3$, NHCSR, NHSO$_2$CH$_3$, NHSO$_2$R, OR, COR, OCOR, OSO$_2$R, SO$_2$R, SR, NCS, SCN, NCO or OCN;

R$_3$ is hydrogen, F, Cl, Br, I, CF$_3$, CN, NO$_2$, NH$_2$, SH, COOH, COOR, alkoxy, haloalkyl, optionally substituted linear or branched alkyl, optionally substituted linear or branched heteroalkyl, optionally substituted aryl, optionally substituted phenyl, optionally substituted cycloalkyl, optionally substituted heterocycloalkyl, optionally substituted arylalkyl, C(R)$_3$, N(R)$_2$, NHCOCH$_3$, NHCOCF$_3$, NHCOR, NHCONHR, NHCOOR, OCONHR, CONHR, NHCSCH$_3$, NHCSCF$_3$, NHCSR, NHSO$_2$CH$_3$, NHSO$_2$R, OR, COR, OCOR, OSO$_2$R, SO$_2$R, SR, NCS, SCN, NCO or OCN;

R$_4$ is hydrogen, F, Cl, Br, I, CF$_3$, CN, NO$_2$, NH$_2$, SH, COOH, COOR, alkoxy, haloalkyl, optionally substituted linear or branched alkyl, optionally substituted linear or branched heteroalkyl, optionally substituted aryl, optionally substituted phenyl, optionally substituted cycloalkyl, optionally substituted heterocycloalkyl, optionally substituted arylalkyl, C(R)$_3$, N(R)$_2$, NHCOCH$_3$, NHCOCF$_3$, NHCOR, NHCONHR, NHCOOR, OCONHR, CONHR, NHCSCH$_3$, NHCSCF$_3$, NHCSR, NHSO$_2$CH$_3$, NHSO$_2$R, OR, COR, OCOR, OSO$_2$R, SO$_2$R, SR, NCS, SCN, NCO or OCN;

n is an integer between 1-3; and
m is an integer between 1-3.

In one embodiment, this invention is directed to a selective androgen receptor degrader (SARD) compound represented by the structure of formula V:

wherein
T is OH, OR, —NHCOCH$_3$, NHCOR or

Z is NO$_2$, CN, COOH, COR, NHCOR or CONHR;
Y is CF$_3$, F, I, Br, Cl, CN or C(R)$_3$;
R is alkyl, haloalkyl, dihaloalkyl, trihaloalkyl, CH$_2$F, CHF$_2$, CF$_3$, CF$_2$CF$_3$, aryl, phenyl, F, Cl, Br, I, alkenyl or OH;
R$_1$ is CH$_3$, CH$_2$F, CHF$_2$, CF$_3$, CH$_2$CH$_3$, or CF$_2$CF$_3$;
R$_2$ is hydrogen, halogen, CN, NO$_2$, COOH, COOR, COR, NHCOR, CONHR, OH, OR, SH, SR, NH$_2$, NHR, NR$_2$, C$_1$-C$_{12}$-alkyl, C$_1$-C$_{12}$-haloalkyl, O—C$_1$-C$_{12}$-alkyl, O—C$_1$-C$_{12}$-haloalkyl, —SO$_2$-aryl, —SO$_2$-phenyl, —CO-aryl, arylalkyl, benzyl, aryl, or C$_3$-C$_7$-cycloalkyl;
Q is hydrogen, F, Cl, Br, I, CF$_3$, CN, NO$_2$, COOH, COOR, alkoxy, haloalkyl, optionally substituted linear or branched alkyl, optionally substituted linear or branched heteroalkyl, optionally substituted aryl, optionally substituted phenyl, optionally substituted cycloalkyl, optionally substituted heterocycloalkyl, optionally substituted arylalkyl, C(R)$_3$, N(R)$_2$, NHCOCH$_3$, NHCOCF$_3$, NHCOR, NHCONHR, NHCOOR, OCONHR, CONHR, NHCSCH$_3$, NHCSCF$_3$, NHCSR, NHSO$_2$CH$_3$, NHSO$_2$R, OR, COR, OCOR, OSO$_2$R, SO$_2$R, SR, NCS, SCN, NCO or OCN;

R$_3$ is hydrogen, F, Cl, Br, I, CF$_3$, CN, NO$_2$, NH$_2$, SH, COOH, COOR, alkoxy, haloalkyl, optionally substituted linear or branched alkyl, optionally substituted linear or branched heteroalkyl, optionally substituted aryl, optionally substituted phenyl, optionally substituted cycloalkyl, optionally substituted heterocycloalkyl, optionally substituted arylalkyl, C(R)$_3$, N(R)$_2$, NHCOCH$_3$, NHCOCF$_3$, NHCOR, NHCONHR, NHCOOR, OCONHR, CONHR, NHCSCH$_3$, NHCSCF$_3$, NHCSR, NHSO$_2$CH$_3$, NHSO$_2$R, OR, COR, OCOR, OSO$_2$R, SO$_2$R, SR, NCS, SCN, NCO or OCN;

R$_4$ is hydrogen, F, Cl, Br, I, CF$_3$, CN, NO$_2$, NH$_2$, SH, COOH, COOR, keto (=O), alkoxy, haloalkyl, optionally substituted linear or branched alkyl, optionally substituted linear or branched heteroalkyl, optionally substituted aryl, optionally substituted phenyl, optionally substituted cycloalkyl, optionally substituted heterocycloalkyl, optionally substituted arylalkyl, C(R)$_3$, N(R)$_2$, NHCOCH$_3$, NHCOCF$_3$, NHCOR, NHCONHR, NHCOOR, OCONHR, CONHR, NHCSCH$_3$, NHCSCF$_3$, NHCSR, NHSO$_2$CH$_3$, NHSO$_2$R, OR, COR, OCOR, OSO$_2$R, SO$_2$R, SR, NCS, SCN, NCO or OCN;

n is an integer between 1-3;
m is an integer between 1-3;
l is 0 or 1; and
k is 0, 1 or 2.

In one embodiment, this invention is directed to a selective androgen receptor degrader (SARD) compound represented by the structure of formula VI:

wherein
T is OH, OR, —NHCOCH$_3$, NHCOR or

Z is NO$_2$, CN, COOH, COR, NHCOR or CONHR;
Y is CF$_3$, F, I, Br, Cl, CN or C(R)$_3$;
R is alkyl, haloalkyl, dihaloalkyl, trihaloalkyl, CH$_2$F, CHF$_2$, CF$_3$, CF$_2$CF$_3$, aryl, phenyl, F, Cl, Br, I, alkenyl or OH;

$R_1$ is $CH_3$, $CH_2F$, $CHF_2$, $CF_3$, $CH_2CH_3$, or $CF_2CF_3$;

$R_2$ is hydrogen, halogen, CN, $NO_2$, COOH, COOR, COR, NHCOR, CONHR, OH, OR, SH, SR, $NH_2$, NHR, $NR_2$, $C_1$-$C_{12}$-alkyl, $C_1$-$C_{12}$-haloalkyl, O—$C_1$-$C_{12}$-alkyl, O—$C_1$-$C_{12}$-haloalkyl, —$SO_2$-aryl, —$SO_2$-phenyl, —CO-aryl, arylalkyl, benzyl, aryl, or $C_3$-$C_7$-cycloalkyl;

Q is hydrogen, F, Cl, Br, I, $CF_3$, CN, $NO_2$, COOH, COOR, alkoxy, haloalkyl, optionally substituted linear or branched alkyl, optionally substituted linear or branched heteroalkyl, optionally substituted aryl, optionally substituted phenyl, optionally substituted cycloalkyl, optionally substituted heterocycloalkyl, optionally substituted arylalkyl, $C(R)_3$, $N(R)_2$, $NHCOCH_3$, $NHCOCF_3$, NHCOR, NHCONHR, NHCOOR, OCONHR, CONHR, $NHCSCH_3$, $NHCSCF_3$, NHCSR, $NHSO_2CH_3$, $NHSO_2R$, OR, COR, OCOR, $OSO_2R$, $SO_2R$, SR, NCS, SCN, NCO or OCN;

$R_3$ is hydrogen, F, Cl, Br, I, $CF_3$, CN, $NO_2$, $NH_2$, SH, COOH, COOR, alkoxy, haloalkyl, optionally substituted linear or branched alkyl, optionally substituted linear or branched heteroalkyl, optionally substituted aryl, optionally substituted phenyl, optionally substituted cycloalkyl, optionally substituted heterocycloalkyl, optionally substituted arylalkyl, $C(R)_3$, $N(R)_2$, $NHCOCH_3$, $NHCOCF_3$, NHCOR, NHCONHR, NHCOOR, OCONHR, CONHR, $NHCSCH_3$, $NHCSCF_3$, NHCSR, $NHSO_2CH_3$, $NHSO_2R$, OR, COR, OCOR, $OSO_2R$, $SO_2R$, SR, NCS, SCN, NCO or OCN;

$R_4$ is hydrogen, F, Cl, Br, I, $CF_3$, CN, $NO_2$, $NH_2$, SH, COOH, COOR, keto (=O), alkoxy, haloalkyl, optionally substituted linear or branched alkyl, optionally substituted linear or branched heteroalkyl, optionally substituted aryl, optionally substituted phenyl, optionally substituted cycloalkyl, optionally substituted heterocycloalkyl, optionally substituted arylalkyl, $C(R)_3$, $N(R)_2$, $NHCOCH_3$, $NHCOCF_3$, NHCOR, NHCONHR, NHCOOR, OCONHR, CONHR, $NHCSCH_3$, $NHCSCF_3$, NHCSR, $NHSO_2CH_3$, $NHSO_2R$, OR, COR, OCOR, $OSO_2R$, $SO_2R$, SR, NCS, SCN, NCO or OCN;

n is an integer between 1-3; and m is an integer between 1-3.

In one embodiment, this invention is directed to a selective androgen receptor degrader (SARD) compound represented by the structure of formula VII:

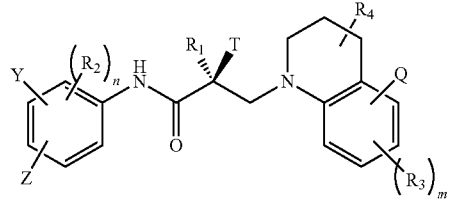

VII wherein

T is OH, OR, —$NHCOCH_3$, NHCOR or Y

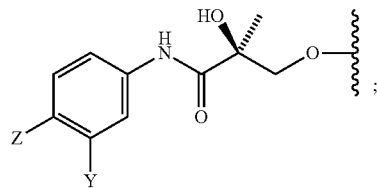

Z is $NO_2$, CN, COOH, COR, NHCOR or CONHR;

Y is $CF_3$, F, I, Br, Cl, CN or $C(R)_3$;

R is alkyl, haloalkyl, dihaloalkyl, trihaloalkyl, $CH_2F$, $CHF_2$, $CF_3$, $CF_2CF_3$, aryl, phenyl, F, Cl, Br, I, alkenyl or OH;

$R_1$ is $CH_3$, $CH_2F$, $CHF_2$, $CF_3$, $CH_2CH_3$, or $CF_2CF_3$;

$R_2$ is hydrogen, halogen, CN, $NO_2$, COOH, COOR, COR, NHCOR, CONHR, OH, OR, SH, SR, $NH_2$, NHR, $NR_2$, $C_1$-$C_{12}$-alkyl, $C_1$-$C_{12}$-haloalkyl, O—$C_1$-$C_{12}$-alkyl, O—$C_1$-$C_{12}$-haloalkyl, —$SO_2$-aryl, —$SO_2$-phenyl, —CO-aryl, arylalkyl, benzyl, aryl, or $C_3$-$C_7$-cycloalkyl;

Q is hydrogen, F, Cl, Br, I, $CF_3$, CN, $NO_2$, COOH, COOR, alkoxy, haloalkyl, optionally substituted linear or branched alkyl, optionally substituted linear or branched heteroalkyl, optionally substituted aryl, optionally substituted phenyl, optionally substituted cycloalkyl, optionally substituted heterocycloalkyl, optionally substituted arylalkyl, $C(R)_3$, $N(R)_2$, $NHCOCH_3$, $NHCOCF_3$, NHCOR, NHCONHR, NHCOOR, OCONHR, CONHR, $NHCSCH_3$, $NHCSCF_3$, NHCSR, $NHSO_2CH_3$, $NHSO_2R$, OR, COR, OCOR, $OSO_2R$, $SO_2R$, SR, NCS, SCN, NCO or OCN;

$R_3$ is hydrogen, F, Cl, Br, I, $CF_3$, CN, $NO_2$, $NH_2$, SH, COOH, COOR, alkoxy, haloalkyl, optionally substituted linear or branched alkyl, optionally substituted linear or branched heteroalkyl, optionally substituted aryl, optionally substituted phenyl, optionally substituted cycloalkyl, optionally substituted heterocycloalkyl, optionally substituted arylalkyl, $C(R)_3$, $N(R)_2$, $NHCOCH_3$, $NHCOCF_3$, NHCOR, NHCONHR, NHCOOR, OCONHR, CONHR, $NHCSCH_3$, $NHCSCF_3$, NHCSR, $NHSO_2CH_3$, $NHSO_2R$, OR, COR, OCOR, $OSO_2R$, $SO_2R$, SR, NCS, SCN, NCO or OCN;

$R_4$ is hydrogen, F, Cl, Br, I, $CF_3$, CN, $NO_2$, $NH_2$, SH, COOH, COOR, keto (=O), alkoxy, haloalkyl, optionally substituted linear or branched alkyl, optionally substituted linear or branched heteroalkyl, optionally substituted aryl, optionally substituted phenyl, optionally substituted cycloalkyl, optionally substituted heterocycloalkyl, optionally substituted arylalkyl, $C(R)_3$, $N(R)_2$, $NHCOCH_3$, $NHCOCF_3$, NHCOR, NHCONHR, NHCOOR, OCONHR, CONHR, $NHCSCH_3$, $NHCSCF_3$, NHCSR, $NHSO_2CH_3$, $NHSO_2R$, OR, COR, OCOR, $OSO_2R$, $SO_2R$, SR, NCS, SCN, NCO or OCN;

n is an integer between 1-3; and m is an integer between 1-3.

In one embodiment, this invention is directed to a selective androgen receptor degrader (SARD) compound represented by the structure of formula VIII:

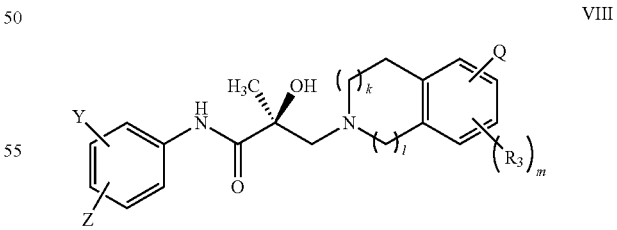

VIII wherein

Z is $NO_2$, CN, COOH, COR, NHCOR or CONHR;

Y is $CF_3$, F, I, Br, Cl, CN or $C(R)_3$;

R is alkyl, haloalkyl, dihaloalkyl, trihaloalkyl, $CH_2F$, $CHF_2$, $CF_3$, $CF_2CF_3$, aryl, phenyl, F, Cl, Br, I, alkenyl or OH;

Q is hydrogen, F, Cl, Br, I, $CF_3$, CN, $NO_2$, COOH, COOR, alkoxy, haloalkyl, optionally substituted linear or branched alkyl, optionally substituted linear or branched heteroalkyl, optionally substituted aryl, optionally substituted phenyl, optionally substituted cycloalkyl, optionally substituted heterocycloalkyl, optionally substituted arylalkyl, C(R)$_3$, N(R)$_2$, NHCOCH$_3$, NHCOCF$_3$, NHCOR, NHCONHR, NHCOOR, OCONHR, CONHR, NHCSCH$_3$, NHCSCF$_3$, NHCSR, NHSO$_2$CH$_3$, NHSO$_2$R, OR, COR, OCOR, OSO$_2$R, SO$_2$R, SR, NCS, SCN, NCO or OCN;

R$_3$ is hydrogen, F, Cl, Br, I, CF$_3$, CN, NO$_2$, NH$_2$, SH, COOH, COOR, alkoxy, haloalkyl, optionally substituted linear or branched alkyl, optionally substituted linear or branched heteroalkyl, optionally substituted aryl, optionally substituted phenyl, optionally substituted cycloalkyl, optionally substituted heterocycloalkyl, optionally substituted arylalkyl, C(R)$_3$, N(R)$_2$, NHCOCH$_3$, NHCOCF$_3$, NHCOR, NHCONHR, NHCOOR, OCONHR, CONHR, NHCSCH$_3$, NHCSCF$_3$, NHCSR, NHSO$_2$CH$_3$, NHSO$_2$R, OR, COR, OCOR, OSO$_2$R, SO$_2$R, SR, NCS, SCN, NCO or OCN;

m is an integer between 1-3;
l is 0 or 1; and
k is 0, 1 or 2.

In one embodiment, this invention is directed to a selective androgen receptor degrader (SARD) compound represented by the structure of formula IXa, IXb, IXc or IXd:

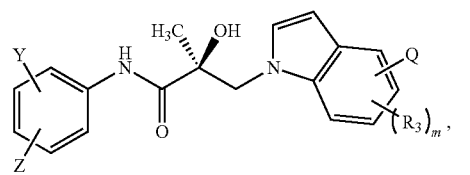

IXa

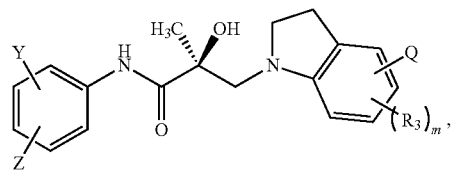

IXb

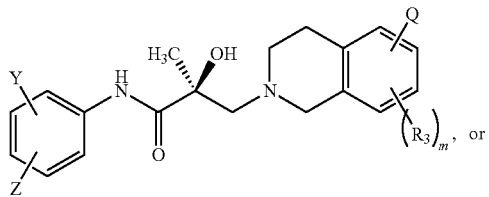

IXc

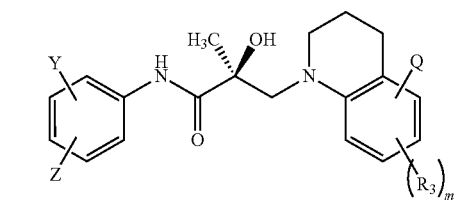

IXd wherein
Z is NO$_2$, CN, COOH, COR, NHCOR or CONHR;
Y is CF$_3$, F, I, Br, Cl, CN or C(R)$_3$;
R is alkyl, haloalkyl, dihaloalkyl, trihaloalkyl, CH$_2$F, CHF$_2$, CF$_3$, CF$_2$CF$_3$, aryl, phenyl, F, Cl, Br, I, alkenyl or OH;
Q is hydrogen, F, Cl, Br, I, CF$_3$, CN, NO$_2$, COOH, COOR, alkoxy, haloalkyl, optionally substituted linear or branched alkyl, optionally substituted linear or branched heteroalkyl, optionally substituted aryl, optionally substituted phenyl, optionally substituted cycloalkyl, optionally substituted heterocycloalkyl, optionally substituted arylalkyl, C(R)$_3$, N(R)$_2$, NHCOCH$_3$, NHCOCF$_3$, NHCOR, NHCONHR, NHCOOR, OCONHR, CONHR, NHCSCH$_3$, NHCSCF$_3$, NHCSR, NHSO$_2$CH$_3$, NHSO$_2$R, OR, COR, OCOR, OSO$_2$R, SO$_2$R, SR, NCS, SCN, NCO or OCN;

R$_3$ is hydrogen, F, Cl, Br, I, CF$_3$, CN, NO$_2$, NH$_2$, SH, COOH, COOR, alkoxy, haloalkyl, optionally substituted linear or branched alkyl, optionally substituted linear or branched heteroalkyl, optionally substituted aryl, optionally substituted phenyl, optionally substituted cycloalkyl, optionally substituted heterocycloalkyl, optionally substituted arylalkyl, C(R)$_3$, N(R)$_2$, NHCOCH$_3$, NHCOCF$_3$, NHCOR, NHCONHR, NHCOOR, OCONHR, CONHR, NHCSCH$_3$, NHCSCF$_3$, NHCSR, NHSO$_2$CH$_3$, NHSO$_2$R, OR, COR, OCOR, OSO$_2$R, SO$_2$R, SR, NCS, SCN, NCO or OCN; and m is an integer between 1-3.

In one embodiment, this invention is directed to a selective androgen receptor degrader (SARD) compound represented by the structure of formula X:

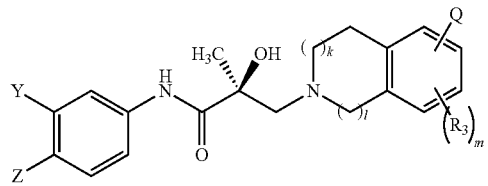

X wherein
Z is NO$_2$, CN, COOH, COR, NHCOR or CONHR;
Y is CF$_3$, F, I, Br, Cl, CN or C(R)$_3$;
R is alkyl, haloalkyl, dihaloalkyl, trihaloalkyl, CH$_2$F, CHF$_2$, CF$_3$, CF$_2$CF$_3$, aryl, phenyl, F, Cl, Br, I, alkenyl or OH;
Q is hydrogen, F, Cl, Br, I, CF$_3$, CN, NO$_2$, COOH, COOR, alkoxy, haloalkyl, optionally substituted linear or branched alkyl, optionally substituted linear or branched heteroalkyl, optionally substituted aryl, optionally substituted phenyl, optionally substituted cycloalkyl, optionally substituted heterocycloalkyl, optionally substituted arylalkyl, C(R)$_3$, N(R)$_2$, NHCOCH$_3$, NHCOCF$_3$, NHCOR, NHCONHR, NHCOOR, OCONHR, CONHR, NHCSCH$_3$, NHCSCF$_3$, NHCSR, NHSO$_2$CH$_3$, NHSO$_2$R, OR, COR, OCOR, OSO$_2$R, SO$_2$R, SR, NCS, SCN, NCO or OCN;

R$_3$ is hydrogen, F, Cl, Br, I, CF$_3$, CN, NO$_2$, NH$_2$, SH, COOH, COOR, alkoxy, haloalkyl, optionally substituted linear or branched alkyl, optionally substituted linear or branched heteroalkyl, optionally substituted aryl, optionally substituted phenyl, optionally substituted cycloalkyl, optionally substituted heterocycloalkyl, optionally substituted arylalkyl, C(R)$_3$, N(R)$_2$, NHCOCH$_3$, NHCOCF$_3$, NHCOR, NHCONHR, NHCOOR, OCONHR, CONHR, NHCSCH$_3$, NHCSCF$_3$, NHCSR, NHSO$_2$CH$_3$, NHSO$_2$R, OR, COR, OCOR, OSO$_2$R, SO$_2$R, SR, NCS, SCN, NCO or OCN;

m is an integer between 1-3;
l is 0 or 1; and
k is 0, 1 or 2.

In one embodiment, this invention is directed to a selective androgen receptor degrader (SARD) compound represented by the structure of formula XIa, XIb, XIc or XId:

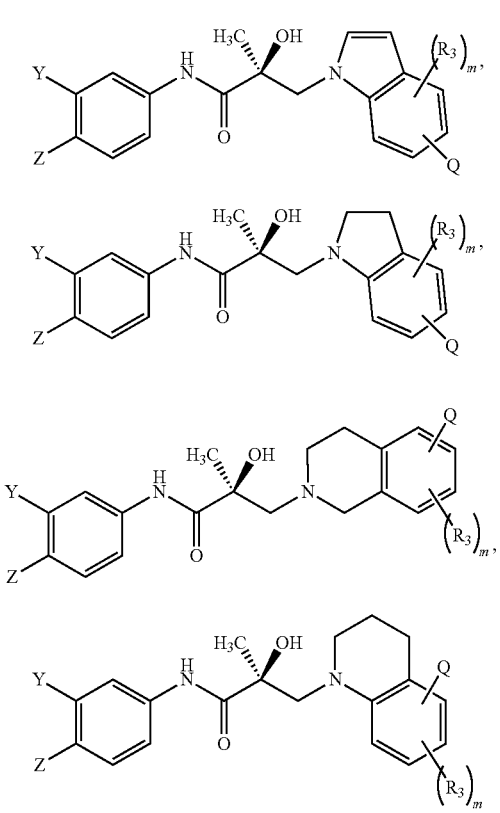

wherein

Z is NO₂, CN, COOH, COR, NHCOR or CONHR;

Y is CF₃, F, I, Br, Cl, CN or C(R)₃;

R is alkyl, haloalkyl, dihaloalkyl, trihaloalkyl, CH₂F, CHF₂, CF₃, CF₂CF₃, aryl, phenyl, F, Cl, Br, I, alkenyl or OH;

Q is hydrogen, F, Cl, Br, I, CF₃, CN, NO₂, COOH, COOR, alkoxy, haloalkyl, optionally substituted linear or branched alkyl, optionally substituted linear or branched heteroalkyl, optionally substituted aryl, optionally substituted phenyl, optionally substituted cycloalkyl, optionally substituted heterocycloalkyl, optionally substituted arylalkyl, C(R)₃, N(R)₂, NHCOCH₃, NHCOCF₃, NHCOR, NHCONHR, NHCOOR, OCONHR, CONHR, NHCSCH₃, NHCSCF₃, NHCSR, NHSO₂CH₃, NHSO₂R, OR, COR, OCOR, OSO₂R, SO₂R, SR, NCS, SCN, NCO or OCN;

R₃ is hydrogen, F, Cl, Br, I, CF₃, CN, NO₂, NH₂, SH, COOH, COOR, alkoxy, haloalkyl, optionally substituted linear or branched alkyl, optionally substituted linear or branched heteroalkyl, optionally substituted aryl, optionally substituted phenyl, optionally substituted cycloalkyl, optionally substituted heterocycloalkyl, optionally substituted arylalkyl, C(R)₃, N(R)₂, NHCOCH₃, NHCOCF₃, NHCOR, NHCONHR, NHCOOR, OCONHR, CONHR, NHCSCH₃, NHCSCF₃, NHCSR, NHSO₂CH₃, NHSO₂R, OR, COR, OCOR, OSO₂R, SO₂R, SR, NCS, SCN, NCO or OCN; and m is an integer between 1-3.

In one embodiment, this invention is directed to a selective androgen receptor degrader (SARD) compound represented by the structure of formula XII:

wherein

Z is NO₂, CN, COOH, COR, NHCOR or CONHR;

Y is CF₃, F, I, Br, Cl, CN or C(R)₃;

R is alkyl, haloalkyl, dihaloalkyl, trihaloalkyl, CH₂F, CHF₂, CF₃, CF₂CF₃, aryl, phenyl, F, Cl, Br, I, alkenyl or OH;

Q is hydrogen, F, Cl, Br, I, CF₃, CN, NO₂, COOH, COOR, alkoxy, haloalkyl, optionally substituted linear or branched alkyl, optionally substituted linear or branched heteroalkyl, optionally substituted aryl, optionally substituted phenyl, optionally substituted cycloalkyl, optionally substituted heterocycloalkyl, optionally substituted arylalkyl, C(R)₃, N(R)₂, NHCOCH₃, NHCOCF₃, NHCOR, NHCONHR, NHCOOR, OCONHR, CONHR, NHCSCH₃, NHCSCF₃, NHCSR, NHSO₂CH₃, NHSO₂R, OR, COR, OCOR, OSO₂R, SO₂R, SR, NCS, SCN, NCO or OCN;

l is 0 or 1; and k is 0, 1 or 2.

In one embodiment, this invention is directed to a selective androgen receptor degrader (SARD) compound represented by the structure of formula XIIIa, XIIIb, XIIIc or IIId:

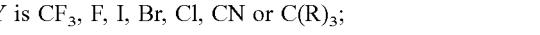

wherein

Z is NO₂, CN, COOH, COR, NHCOR or CONHR;

Y is CF₃, F, I, Br, Cl, CN or C(R)₃;

R is alkyl, haloalkyl, dihaloalkyl, trihaloalkyl, $CH_2F$, $CHF_2$, $CF_3$, $CF_2CF_3$, aryl, phenyl, F, Cl, Br, I, alkenyl or OH; and Q is hydrogen, F, Cl, Br, I, $CF_3$, CN, $NO_2$, COOH, COOR, alkoxy, haloalkyl, optionally substituted linear or branched alkyl, optionally substituted linear or branched heteroalkyl, optionally substituted aryl, optionally substituted phenyl, optionally substituted cycloalkyl, optionally substituted heterocycloalkyl, optionally substituted arylalkyl, $C(R)_3$, $N(R)_2$, $NHCOCH_3$, $NHCOCF_3$, NHCOR, NHCONHR, NHCOOR, OCONHR, CONHR, $NHCSCH_3$, $NHCSCF_3$, NHCSR, $NHSO_2CH_3$, $NHSO_2R$, OR, COR, OCOR, $OSO_2R$, $SO_2R$, SR, NCS, SCN, NCO or OCN.

In one embodiment, this invention is directed to a selective androgen receptor degrader (SARD) compound represented by the structure of formula XIV:

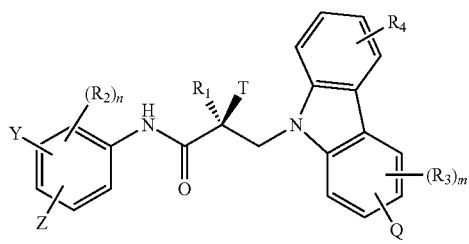

XIV wherein
T is OH, OR, —$NHCOCH_3$, or NHCOR;
Z is $NO_2$, CN, COOH, COR, NHCOR or CONHR;
Y is $CF_3$, F, I, Br, Cl, CN or $C(R)_3$;
R is alkyl, haloalkyl, dihaloalkyl, trihaloalkyl, $CH_2F$, $CHF_2$, $CF_3$, $CF_2CF_3$, aryl, phenyl, F, Cl, Br, I, alkenyl or OH;
$R_1$ is $CH_3$, $CH_2F$, $CHF_2$, $CF_3$, $CH_2CH_3$, or $CF_2CF_3$;
$R_2$ is hydrogen, halogen, CN, $NO_2$, COOH, COOR, COR, NHCOR, CONHR, OH, OR, SH, SR, $NH_2$, NHR, $NR_2$, $C_1$-$C_{12}$-alkyl, $C_1$-$C_{12}$-haloalkyl, O—$C_1$-$C_{12}$-alkyl, O—$C_1$-$C_{12}$-haloalkyl, —$SO_2$-aryl, —$SO_2$-phenyl, —CO-aryl, arylalkyl, benzyl, aryl, or $C_3$-$C_7$-cycloalkyl;
Q is hydrogen, F, Cl, Br, I, $CF_3$, CN, $NO_2$, COOH, COOR, alkoxy, haloalkyl, optionally substituted linear or branched alkyl, optionally substituted linear or branched heteroalkyl, optionally substituted aryl, optionally substituted phenyl, optionally substituted cycloalkyl, optionally substituted heterocycloalkyl, optionally substituted arylalkyl, $C(R)_3$, $N(R)_2$, $NHCOCH_3$, $NHCOCF_3$, NHCOR, NHCONHR, NHCOOR, OCONHR, CONHR, $NHCSCH_3$, $NHCSCF_3$, NHCSR, $NHSO_2CH_3$, $NHSO_2R$, OR, COR, OCOR, $OSO_2R$, $SO_2R$, SR, NCS, SCN, NCO or OCN;
$R_3$ is hydrogen, F, Cl, Br, I, $CF_3$, CN, $NO_2$, $NH_2$, SH, COOH, COOR, alkoxy, haloalkyl, optionally substituted linear or branched alkyl, optionally substituted linear or branched heteroalkyl, optionally substituted aryl, optionally substituted phenyl, optionally substituted cycloalkyl, optionally substituted heterocycloalkyl, optionally substituted arylalkyl, $C(R)_3$, $N(R)_2$, $NHCOCH_3$, $NHCOCF_3$, NHCOR, NHCONHR, NHCOOR, OCONHR, CONHR, $NHCSCH_3$, $NHCSCF_3$, NHCSR, $NHSO_2CH_3$, $NHSO_2R$, OR, COR, OCOR, $OSO_2R$, $SO_2R$, SR, NCS, SCN, NCO or OCN;
$R_4$ is hydrogen, F, Cl, Br, I, $CF_3$, CN, $NO_2$, $NH_2$, SH, COOH, COOR, alkoxy, haloalkyl, optionally substituted linear or branched alkyl, optionally substituted linear or branched heteroalkyl, optionally substituted aryl, optionally substituted phenyl, optionally substituted cycloalkyl, optionally substituted heterocycloalkyl, optionally substituted arylalkyl, $C(R)_3$, $N(R)_2$, $NHCOCH_3$, $NHCOCF_3$, NHCOR, NHCONHR, NHCOOR, OCONHR, CONHR, $NHCSCH_3$, $NHCSCF_3$, NHCSR, $NHSO_2CH_3$, $NHSO_2R$, OR, COR, OCOR, $OSO_2R$, $SO_2R$, SR, NCS, SCN, NCO or OCN;
n is an integer between 1-3; and
m is an integer between 1-3.

In one embodiment, this invention is directed to a selective androgen receptor degrader (SARD) compound represented by the structure of formula XV:

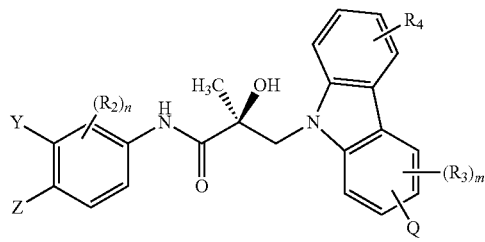

XV wherein
Z is $NO_2$, CN, COOH, COR, NHCOR or CONHR;
Y is $CF_3$, F, I, Br, Cl, CN or $C(R)_3$;
R is alkyl, haloalkyl, dihaloalkyl, trihaloalkyl, $CH_2F$, $CHF_2$, $CF_3$, $CF_2CF_3$, aryl, phenyl, F, Cl, Br, I, alkenyl or OH;
$R_2$ is hydrogen, halogen, CN, $NO_2$, COOH, COOR, COR, NHCOR, CONHR, OH, OR, SH, SR, $NH_2$, NHR, $NR_2$, $C_1$-$C_{12}$-alkyl, $C_1$-$C_{12}$-haloalkyl, O—$C_1$-$C_{12}$-alkyl, O—$C_1$-$C_{12}$-haloalkyl, —$SO_2$-aryl, —$SO_2$-phenyl, —CO-aryl, arylalkyl, benzyl, aryl, or $C_3$-$C_7$-cycloalkyl;
Q is hydrogen, F, Cl, Br, I, $CF_3$, CN, $NO_2$, COOH, COOR, alkoxy, haloalkyl, optionally substituted linear or branched alkyl, optionally substituted linear or branched heteroalkyl, optionally substituted aryl, optionally substituted phenyl, optionally substituted cycloalkyl, optionally substituted heterocycloalkyl, optionally substituted arylalkyl, $C(R)_3$, $N(R)_2$, $NHCOCH_3$, $NHCOCF_3$, NHCOR, NHCONHR, NHCOOR, OCONHR, CONHR, $NHCSCH_3$, $NHCSCF_3$, NHCSR, $NHSO_2CH_3$, $NHSO_2R$, OR, COR, OCOR, $OSO_2R$, $SO_2R$, SR, NCS, SCN, NCO or OCN;
$R_3$ is hydrogen, F, Cl, Br, I, $CF_3$, CN, $NO_2$, $NH_2$, SH, COOH, COOR, alkoxy, haloalkyl, optionally substituted linear or branched alkyl, optionally substituted linear or branched heteroalkyl, optionally substituted aryl, optionally substituted phenyl, optionally substituted cycloalkyl, optionally substituted heterocycloalkyl, optionally substituted arylalkyl, $C(R)_3$, $N(R)_2$, $NHCOCH_3$, $NHCOCF_3$, NHCOR, NHCONHR, NHCOOR, OCONHR, CONHR, $NHCSCH_3$, $NHCSCF_3$, NHCSR, $NHSO_2CH_3$, $NHSO_2R$, OR, COR, OCOR, $OSO_2R$, $SO_2R$, SR, NCS, SCN, NCO or OCN;
$R_4$ is hydrogen, F, Cl, Br, I, $CF_3$, CN, $NO_2$, $NH_2$, SH, COOH, COOR, alkoxy, haloalkyl, optionally substituted linear or branched alkyl, optionally substituted linear or branched heteroalkyl, optionally substituted aryl, optionally substituted phenyl, optionally substituted cycloalkyl, optionally substituted heterocycloalkyl, optionally substituted arylalkyl, $C(R)_3$, $N(R)_2$, $NHCOCH_3$, $NHCOCF_3$, NHCOR, NHCONHR, NHCOOR, OCONHR, CONHR, $NHCSCH_3$, $NHCSCF_3$, NHCSR, $NHSO_2CH_3$, $NHSO_2R$, OR, COR, OCOR, $OSO_2R$, $SO_2R$, SR, NCS, SCN, NCO or OCN;
n is an integer between 1-3; and
m is an integer between 1-3.

In one embodiment, Q of compound of formulas I-VIII, IXa-IXd, X, XIa-XId, XII, XIIIa-XIIId, XIV and XV is hydrogen. In one embodiment, Q of compound of formulas I-VIII, IXa-IXd, X, XIa-XId, XII, XIIIa-XIIId, XIV and XV is halogen. In one embodiment, Q of compound of formulas I-VIII, IXa-IXd, X, XIa-XId, XII, XIIIa-XIIId, XIV and XV is F. In one embodiment, Q of compound of formulas I-VIII, IXa-IXd, X, XIa-XId, XII, XIIIa-XIIId, XIV and XV is Br. In one embodiment, Q of compound of formulas I-VIII, IXa-IXd, X, XIa-XId, XII, XIIIa-XIIId, XIV and XV is Cl. In one embodiment, Q of compound of formulas I-VIII, IXa-IXd, X, XIa-XId, XII, XIIIa-XIIId, XIV and XV is I. In one embodiment, Q of compound of formulas I-VIII, IXa-IXd, X, XIa-XId, XII, XIIIa-XIIId, XIV and XV is CN. In one embodiment, Q of compound of formulas I-VIII, IXa-IXd, X, XIa-XId, XII, XIIIa-XIIId, XIV and XV is $NO_2$. In one embodiment, Q of compound of formulas I-VIII, IXa-IXd, X, XIa-XId, XII, XIIIa-XIIId, XIV and XV is optionally substituted linear or branched alkyl. In one embodiment, Q of compound of formulas I-VIII, IXa-IXd, X, XIa-XId, XII, XIIIa-XIIId, XIV and XV is $CH_3$. In one embodiment, Q of compound of formulas I-VIII, IXa-IXd, X, XIa-XId, XII, XIIIa-XIIId, XIV and XV is alkoxy. In one embodiment, Q of compound of formulas I-VI is $OCH_3$. In one embodiment, Q of compound of formulas I-VIII, IXa-IXd, X, XIa-XId, XII, XIIIa-XIIId, XIV and XV is $CF_3$. In one embodiment, Q of compound of formulas I-VIII, IXa-IXd, X, XIa-XId, XII, XIIIa-XIIId, XIV and XV is optionally substituted phenyl. In one embodiment, Q of compound of formulas I-VIII, IXa-IXd, X, XIa-XId, XII, XIIIa-XIIId, XIV and XV is unsubstituted phenyl.

In one embodiment, $R_3$ of compound of formulas I-VIII, IXa-IXd, X, XIa-XId, XIV and XV is hydrogen. In one embodiment, $R_3$ of compound of formulas I-VIII, IXa-IXd, X, XIa-XId, XIV and XV is halogen. In one embodiment, $R_3$ of compound of formulas I-VIII, IXa-IXd, X, XIa-XId, XIV and XV is F. In one embodiment, $R_3$ of compound of formulas I-VIII, IXa-IXd, X, XIa-XId, XIV and XV is Cl. In one embodiment, $R_3$ of compound of formulas I-VIII, IXa-IXd, X, XIa-XId, XIV and XV is Br. In one embodiment, $R_3$ of compound of formulas I-VIII, IXa-IXd, X, XIa-XId, XIV and XV is I. In one embodiment, $R_3$ of compound of formulas I-VIII, IXa-IXd, X, XIa-XId, XIV and XV is CN. In one embodiment, $R_3$ of compound of formulas I-VIII, IXa-IXd, X, XIa-XId, XIV and XV is COOH. In one embodiment, $R_3$ of compound of formulas I-VIII, IXa-IXd, X, XIa-XId, XIV and XV is $NO_2$. In one embodiment, $R_3$ of compound of formulas I-VIII, IXa-IXd, X, XIa-XId, XIV and XV is $CF_3$.

In one embodiment, $R_4$ of compound of formulas I-VII, XIV, XV is hydrogen. In one embodiment, $R_4$ of compound of formulas I-VII, XIV, XV is halogen. In one embodiment, $R_4$ of compound of formulas I-VII, XIV, XV is F. In one embodiment, $R_4$ of compound of formulas I-VII, XIV, XV is Cl. In one embodiment, $R_4$ of compound of formulas I-VII, XIV, XV is Br. In one embodiment, $R_4$ of compound of formulas I-VII, XIV, XV is I. In one embodiment, $R_4$ of compound of formulas I-III is CN. In one embodiment, $R_4$ of compound of formulas I-VII, XIV, XV is COOH. In one embodiment, $R_4$ of compound of formulas I-III is $NO_2$. In one embodiment, $R_4$ of compound of formulas I-III is $CF_3$. In one embodiment, $R_4$ of compound of formulas I-VII, XIV, XV is methyl. In one embodiment, $R_4$ of compound of formulas I-VII, XIV, XV is COOR.

In one embodiment, Z of compound of formulas I-VIII, IXa-IXd, X, XIa-XId, XII, XIIIa-XIIId, XIV and XV is CN. In another embodiment, Z of compound of formulas I-VIII, IXa-IXd, X, XIa-XId, XII, XIIIa-XIIId, XIV and XV is $NO_2$. In another embodiment, Z of compound of formulas I-VIII, IXa-IXd, X, XIa-XId, XII, XIIIa-XIIId, XIV and XV is COOH. In another embodiment, Z of compound of formulas I-VIII, IXa-IXd, X, XIa-XId, XII, XIIIa-XIIId, XIV and XV is COR. In another embodiment, Z of compound of formulas I-VIII, IXa-IXd, X, XIa-XId, XII, XIIIa-XIIId, XIV and XV is NHCOR. In another embodiment, Z of compound of formulas I-VIII, IXa-IXd, X, XIa-XId, XII, XIIIa-XIIId, XIV and XV is CONHR. In another embodiment, Z of compound of formulas I-VIII, IXa-IXd, X, XIa-XId, XII, XIIIa-XIIId, XIV and XV is in the para position.

In one embodiment, Y of compound of formulas I-VIII, IXa-IXd, X, XIa-XId, XII, XIIIa-XIIId, XIV and XV is $CF_3$. In another embodiment, Y of compound of formulas I-VIII, IXa-IXd, X, XIa-XId, XII, XIIIa-XIIId, XIV and XV is F. In another embodiment, Y of compound of formulas I-VIII, IXa-IXd, X, XIa-XId, XII, XIIIa-XIIId, XIV and XV is I. In another embodiment, Y of compound of formulas I-VIII, IXa-IXd, X, XIa-XId, XII, XIIIa-XIIId, XIV and XV is Br. In another embodiment, Y of compound of formulas I-VIII, IXa-IXd, X, XIa-XId, XII, XIIIa-XIIId, XIV and XV is Cl. In another embodiment, Y of compound of formulas I-VIII, IXa-IXd, X, XIa-XId, XII, XIIIa-XIIId, XIV and XV is CN. In another embodiment, Y of compound of formulas I-VIII, IXa-IXd, X, XIa-XId, XII, XIIIa-XIIId, XIV and XV is $C(R)_3$. In another embodiment, Y of compound of formulas I-VIII, IXa-IXd, X, XIa-XId, XII, XIIIa-XIIId, XIV and XV is in the meta position.

In one embodiment, Z of compound of formulas I-VIII, IXa-IXd, X, XIa-XId, XII, XIIIa-XIIId, XIV and XV is CN and Y is $CF_3$. In another embodiment, Z is $NO_2$ and Y is $CF_3$. In another embodiment, Z is $NO_2$ and Y is halogen. In another embodiment, Z is CN and Y is halogen. In another embodiment, Z of compound of formulas I-VIII, IXa-IXd, X, XIa-XId, XII, XIIIa-XIIId, XIV and XV is in the para position and Y is in the meta position.

In one embodiment, $R_2$ of compound of formulas I-VII, XIV and XV is hydrogen. In one embodiment, $R_2$ of compound of formulas I-VII, XIV and XV is halogen. In one embodiment, $R_2$ of compound of formulas I-VII, XIV and XV is CN. In one embodiment, $R_2$ of compound of formulas I-VII, XIV and XV is $NO_2$. In one embodiment, $R_2$ of compound of formulas I-VII, XIV and XV is $C_1$-$C_{12}$-alkyl. In one embodiment, $R_2$ of compound of formulas I-VII, XIV and XV is aryl. In one embodiment, $R_2$ of compound of formulas I-VII, XIV and XV is phenyl. In one embodiment, $R_2$ of compound of formulas I-VII, XIV and XV is COOH. In one embodiment, $R_2$ of compound of formulas I-VII, XIV and XV is COOR. In one embodiment, $R_2$ of compound of formulas I-VII, XIV and XV is COR. In one embodiment, $R_2$ of compound of formulas I-VII, XIV and XV is NHCOR. In one embodiment, $R_2$ of compound of formulas I-VII, XIV and XV is CONHR. In one embodiment, $R_2$ of compound of formulas I-VII, XIV and XV is OH. In one embodiment, $R_2$ of compound of formulas I-VII, XIV and XV is OR. In one embodiment, $R_2$ of compound of formulas I-VII, XIV and XV is SH. In one embodiment, $R_2$ of compound of formulas I-VII, XIV and XV is SR. In one embodiment, $R_2$ of compound of formulas I-VII, XIV and XV is $NH_2$. In one embodiment, $R_2$ of compound of formulas I-VII, XIV and XV is NHR. In one embodiment, $R_2$ of compound of formulas I-VII, XIV and XV is $N(R)_2$. In one embodiment, $R_2$ of compound of formulas I-VII, XIV and XV is $C_1$-$C_{12}$-haloalkyl. In one embodiment, $R_2$ of compound of formulas I-VII, XIV and XV is O—$C_1$-$C_{12}$-alkyl. In one embodiment, R₂ of compound of formulas I-VII, XIV and XV is O—C₁-C₁₂-haloalkyl. In one embodiment, R₂ of compound of formulas I-III is —SO₂-aryl. In one embodiment, R₂ of compound of formulas I-VII, XIV and XV is —SO₂-phenyl. In one embodiment, R₂ of compound of formulas I-VII, XIV and XV is —CO-aryl. In one embodiment, R₂ of compound of formulas I-VII, XIV and XV is arylalkyl. In one embodiment, R₂ of compound of formulas I-VII, XIV and XV is benzyl. In one embodiment, R₂ of compound of formulas I-VII, XIV and XV is C₃-C₇-cycloalkyl.

In one embodiment, R₁ of compound of formulas I-VII and XIV is CH₃. In another embodiment, R₁ of compound of formulas I-VII and XIV is CF₃.

In one embodiment, T of compound of formulas I-VII and XIV is OH. In another embodiment, T of compound of formulas I-VII and XIV is OCH₃. In another embodiment, T of compound of formulas I-VII and XIV is

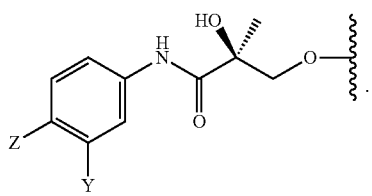

In one embodiment, R of compound of formulas I-VIII, IXa-IXd, X, XIa-XId, XII, XIIIa-XIIId, XIV and XV is alkyl. In another embodiment, R is haloalkyl. In another embodiment, R is dihaloalkyl. In another embodiment, R is trihaloalkyl. In another embodiment, R is CH₂F. In another embodiment, R is CHF₂. In another embodiment, R is CF₃. In another embodiment, R is CF₂CF₃. In another embodiment, R is aryl. In another embodiment, R is phenyl. In another embodiment, R is F. In another embodiment, R is Cl. In another embodiment, R is Br. In another embodiment, R is I. In another embodiment, R is alkenyl. In another embodiment, R is hydroxyl (OH).

In one embodiment, m of compound of formulas I-VIII, IXa-IXd, X, XIa-XId, XIV and XV is 1. In one embodiment, m of compound of formulas I-VIII, IXa-IXd, X, XIa-XId, XIV and XV is 2. In one embodiment, m of compound of formulas I-VIII, IXa-IXd, X, XIa-XId, XIV and XV is 3.

In one embodiment, n of compound of formulas I-VII, XIV and XV is 1. In one embodiment, n of compound of formulas I-VII, XIV and XV is 2. In one embodiment, m of compound of formulas I-VII, XIV and XV is 3.

In one embodiment, this invention is directed to a selective androgen receptor degrader (SARD) compound selected from the following structures:

Indoles:

11

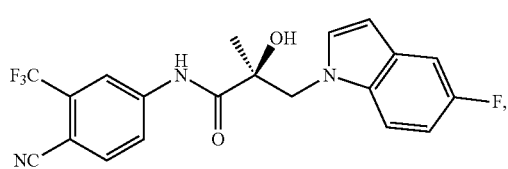

11R

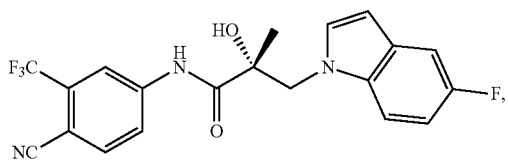

12

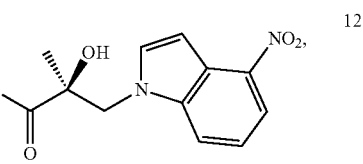

13

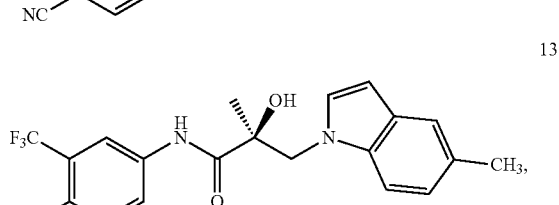

14

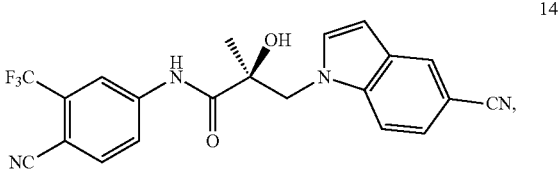

15

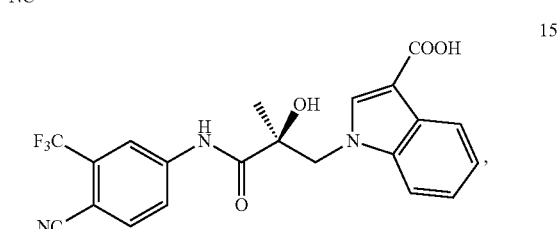

16

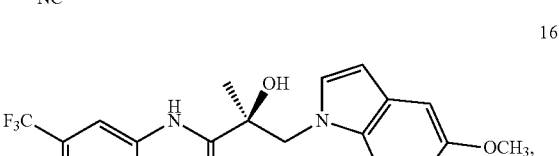

17

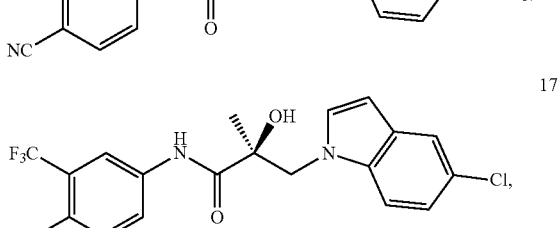

18

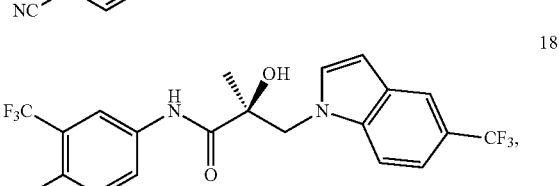

19

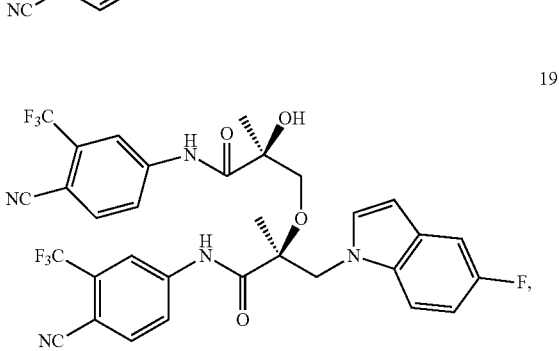

20
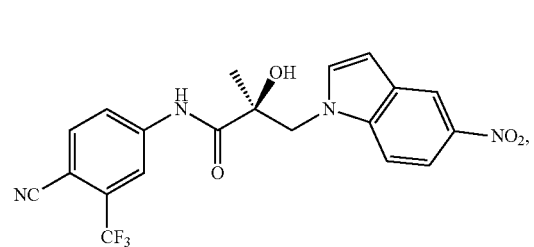
21
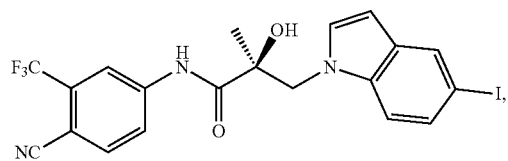
22
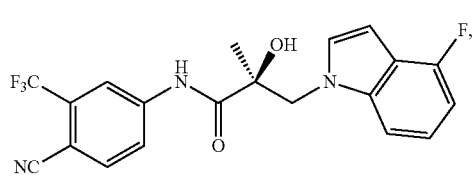
23
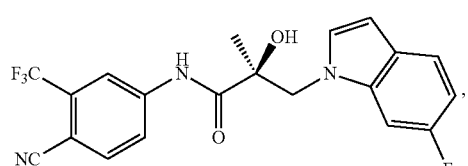
24
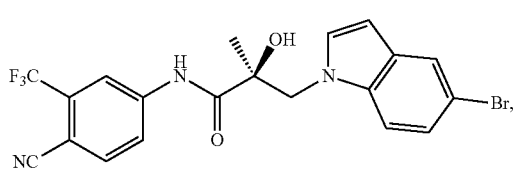
25
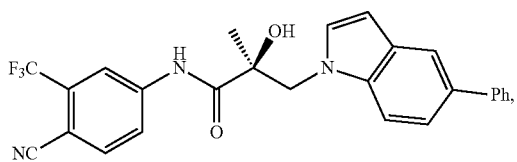
26
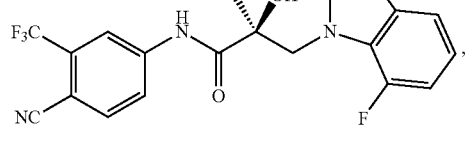
27
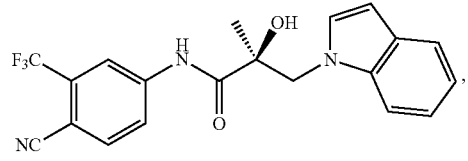
30
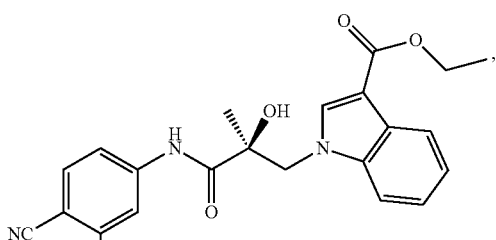
31
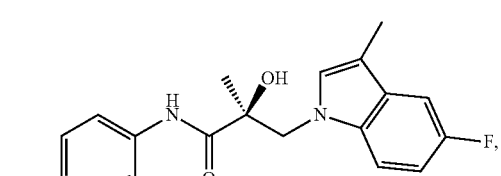
32
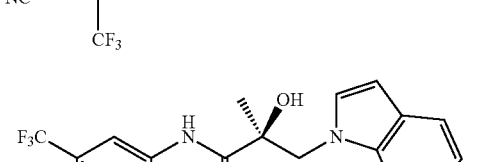
33
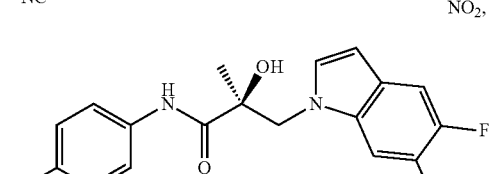
34
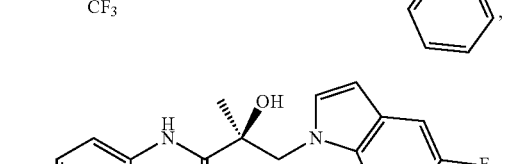
35
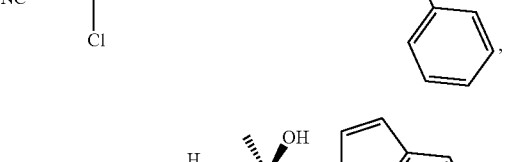
36
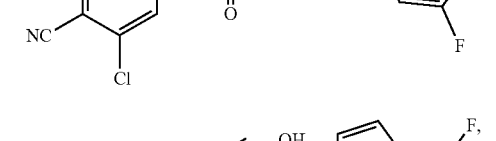
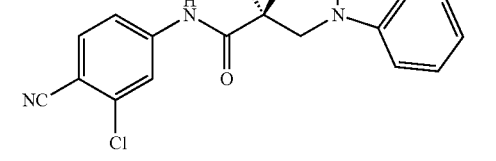

-continued
37
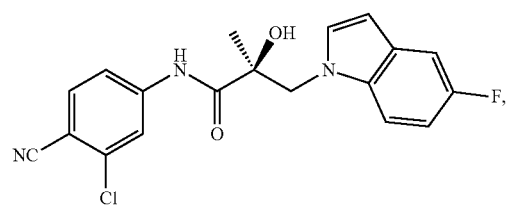
38
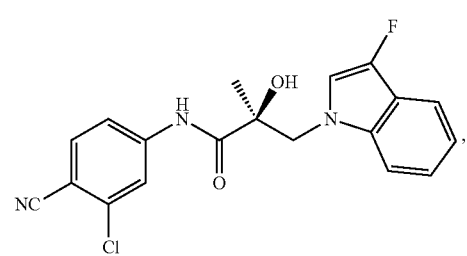
39
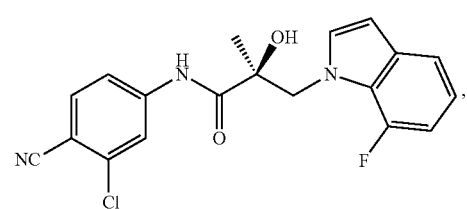
40
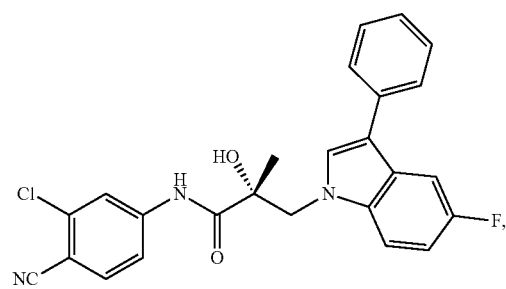
41
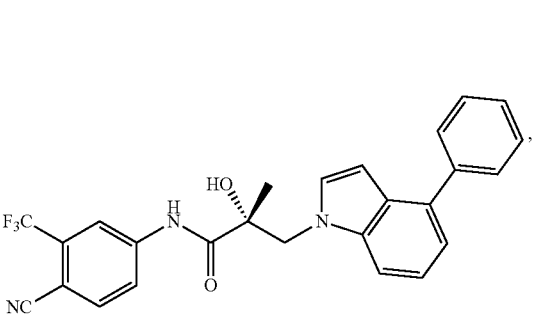
42
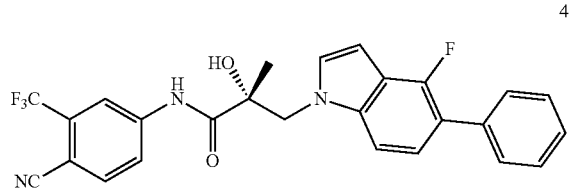
Benzimidazoles:
70
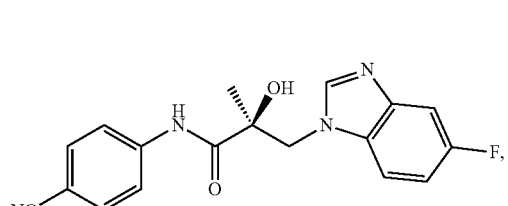
71
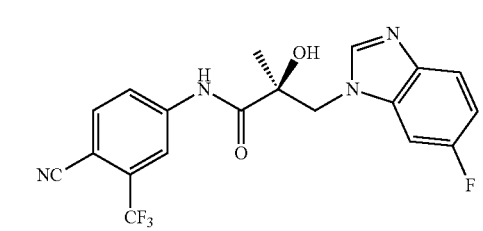
72
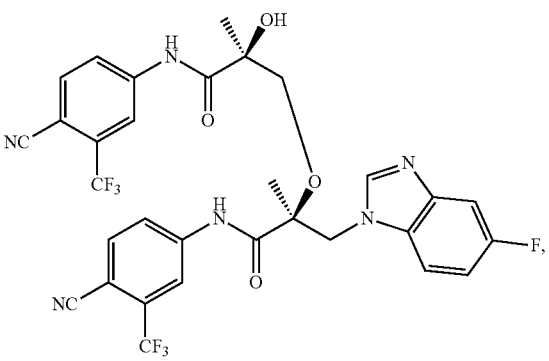
73
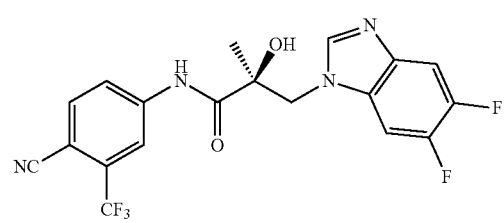
74
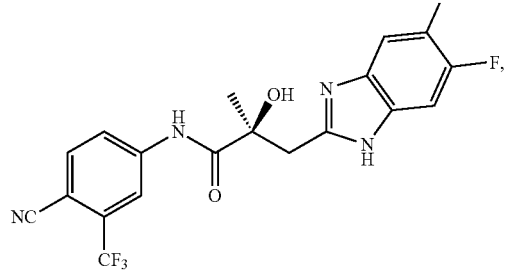
75
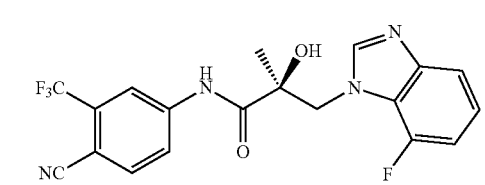

Pyrrolo-Pyridine:
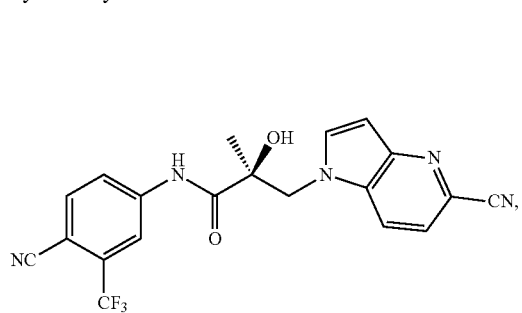 80
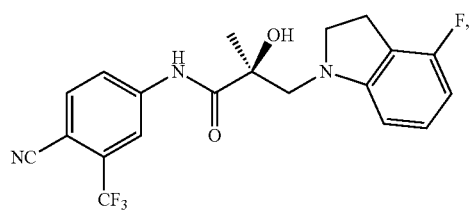 101
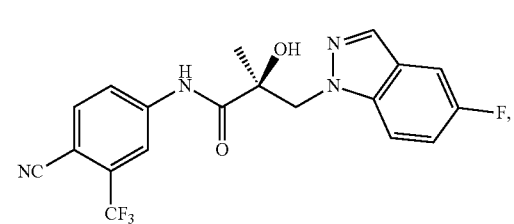 90
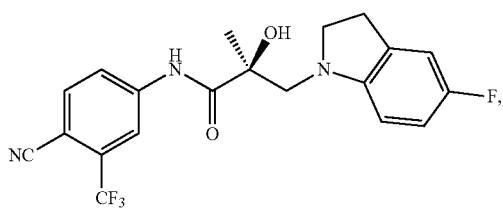 102
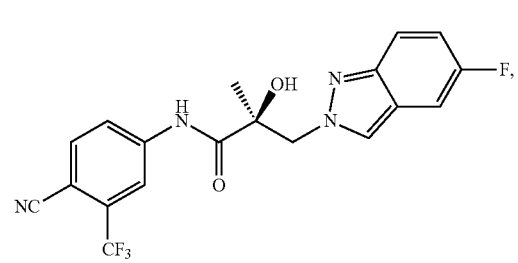 91
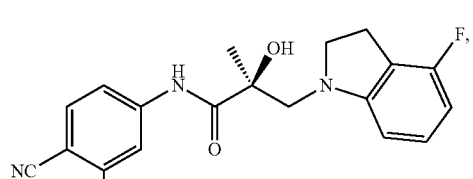 103
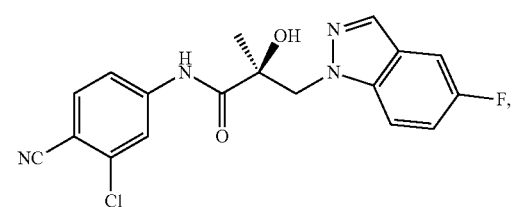 92
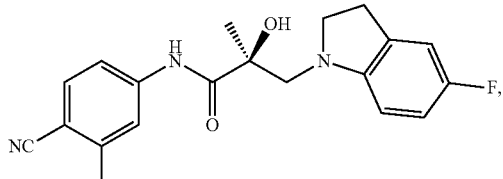 104
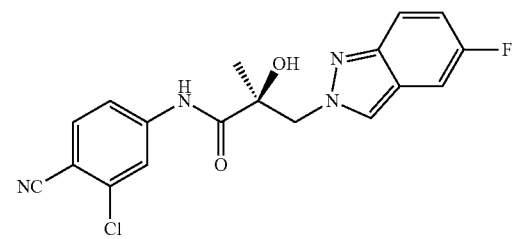 93
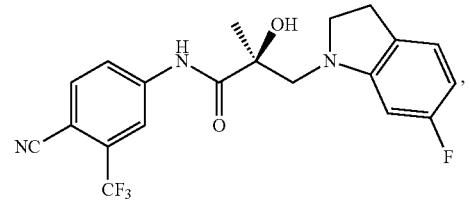 105
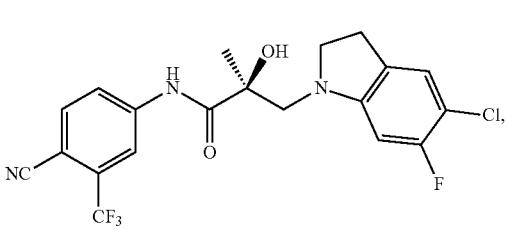 106
Indolines:
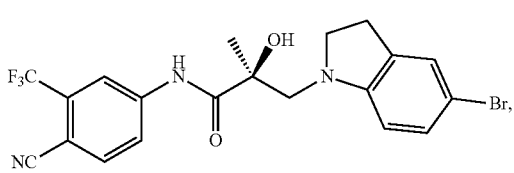 100
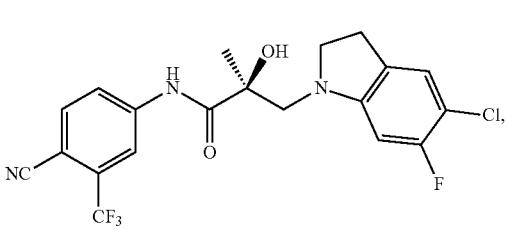 107

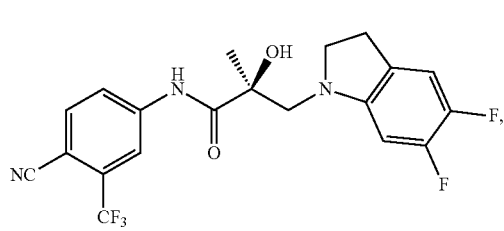
108
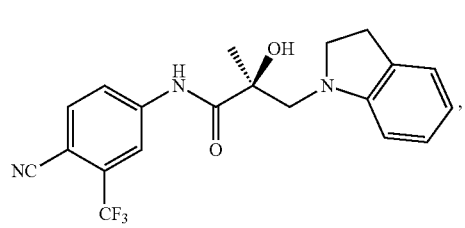
109
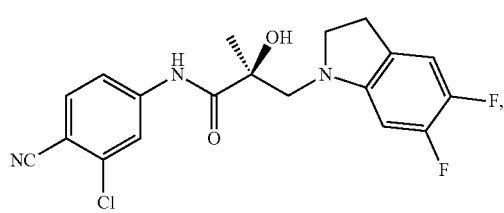
110
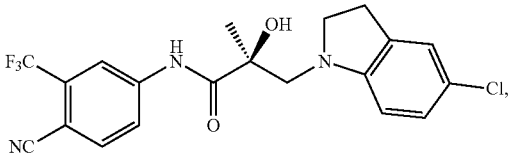
111
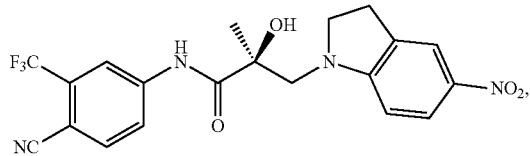
112
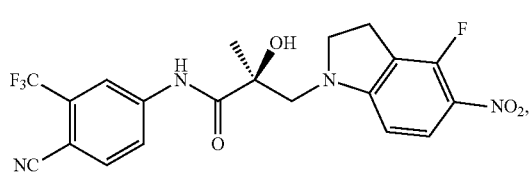
113
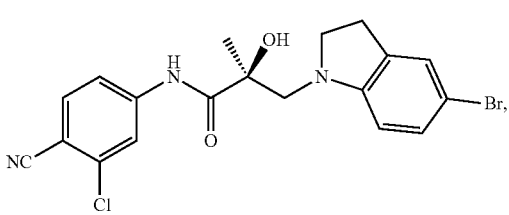
114
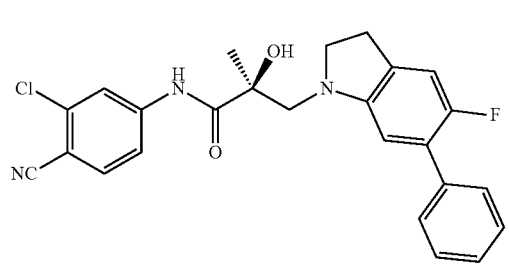
115
Isoquinolines and Quinolines:
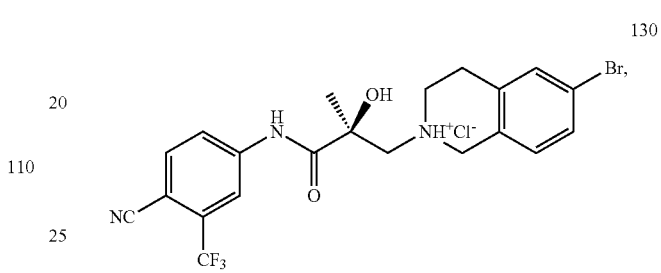
130
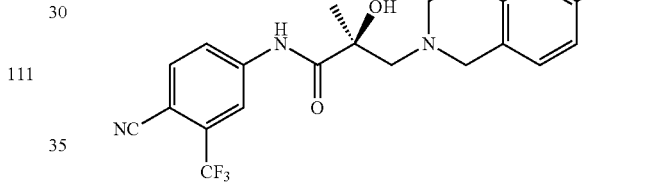
131
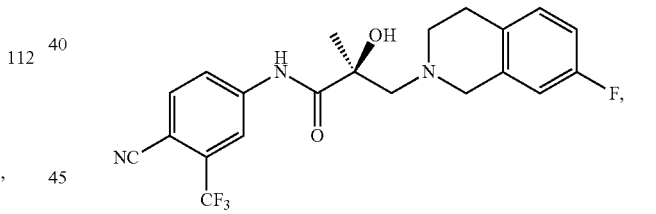
132
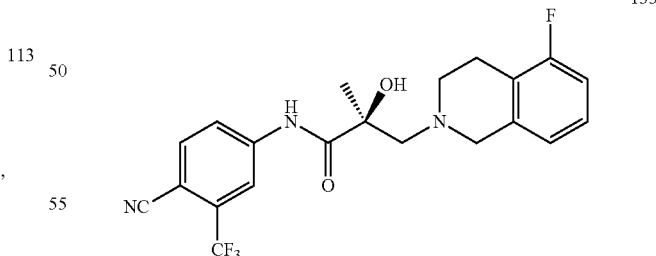
133
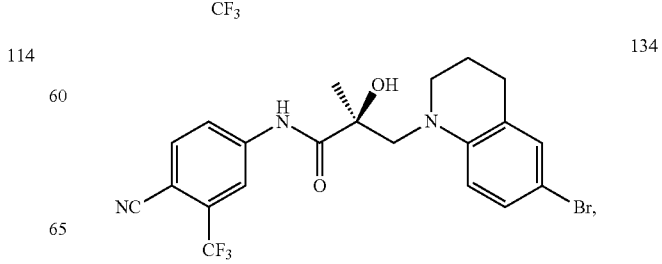
134

53
-continued

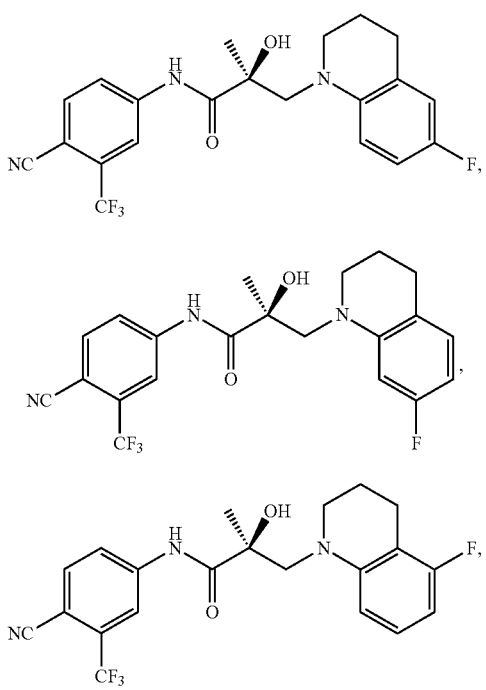

Carbazoles:

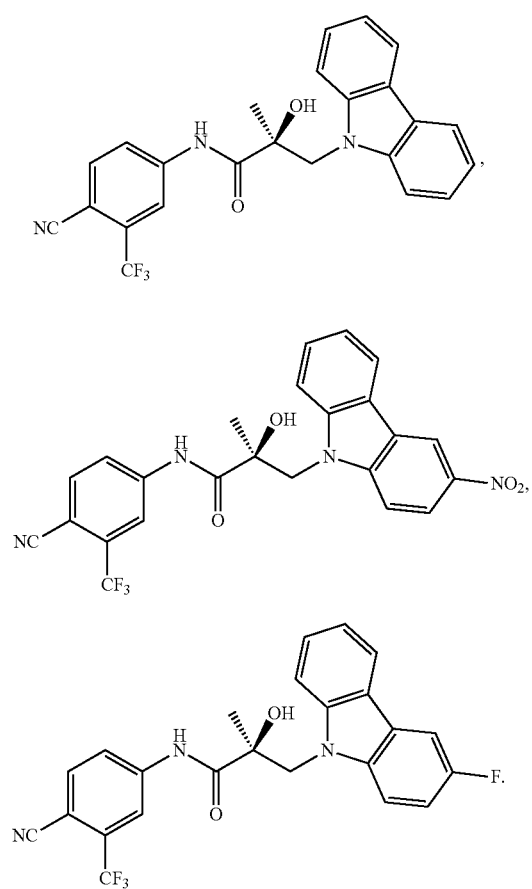

54
-continued

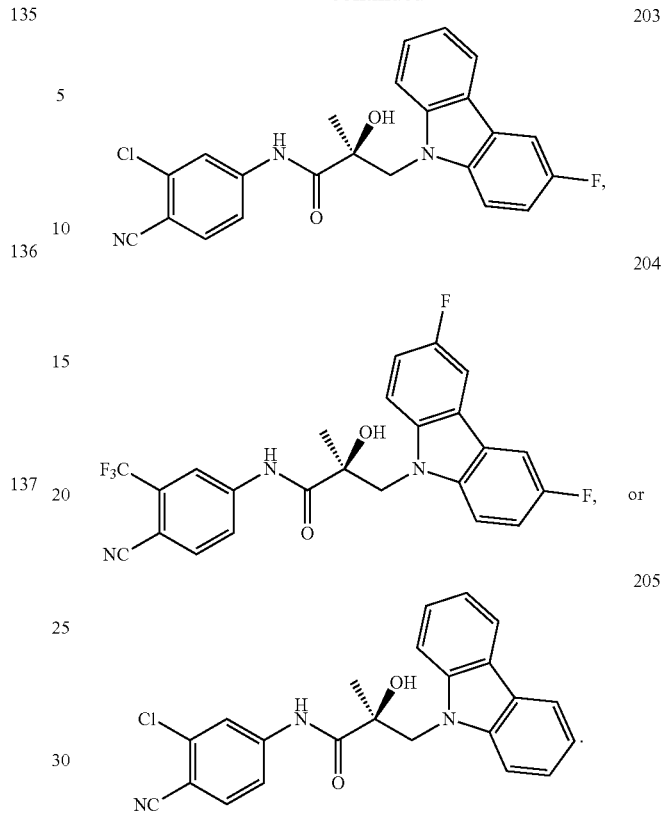

The term "heterocycloalkyl" group refers, in one embodiment, to a cycloalkyl structure comprising in addition to carbon atoms, sulfur, oxygen, nitrogen or any combination thereof, as part of the ring. In another embodiment, the heterocycloalkyl is a 3-12 membered ring. In another embodiment, the heterocycloalkyl is a 6 membered ring. In another embodiment, the heterocycloalkyl is a 5-7 membered ring. In another embodiment, the heterocycloalkyl is a 4-8 membered ring. In another embodiment, the heterocycloalkyl group may be unsubstituted or substituted by a halogen, haloalkyl, hydroxyl, alkoxy, carbonyl, amido, alkylamido, dialkylamido, cyano, nitro, $CO_2H$, amino, alkylamino, dialkylamino, carboxyl, thio and/or thioalkyl. In another embodiment, the heterocycloalkyl ring may be fused to another saturated or unsaturated cycloalkyl or heterocyclic 3-8 membered ring. In another embodiment, the heterocyclic ring is a saturated ring. In another embodiment, the heterocyclic ring is an unsaturated ring. In another embodiment, the heterocycloalkyl is piperidine, tetrahydrofuran, morpholine, pyrrolidine, or piperazine.

The term "cycloalkyl" refers to a non-aromatic, monocyclic or polycyclic ring comprising carbon and hydrogen atoms. A cycloalkyl group can have one or more carbon-carbon double bonds in the ring so long as the ring is not rendered aromatic by their presence. Examples of cycloalkyl groups include, but are not limited to, ($C_3$-$C_7$) cycloalkyl groups, such as cyclopropyl, cyclobutyl, cyclopentyl, cyclohexyl, and cycloheptyl, and saturated cyclic and bicyclic terpenes and ($C_3$-$C_7$) cycloalkenyl groups, such as cyclopropenyl, cyclobutenyl, cyclopentenyl, cyclohexenyl, and cycloheptenyl, and unsaturated cyclic and bicyclic terpenes. A cycloalkyl group can be unsubstituted or substituted by one or two substituents. Preferably, the cycloalkyl group is a monocyclic ring or bicyclic ring.

The term "alkyl" refers, in one embodiment, to a saturated aliphatic hydrocarbon, including straight-chain, branched-chain and cyclic alkyl groups. In one embodiment, the alkyl group has 1-12 carbons. In another embodiment, the alkyl group has 1-7 carbons. In another embodiment, the alkyl group has 1-6 carbons. In another embodiment, the alkyl group has 1-4 carbons. In another embodiment, the cyclic alkyl group has 3-8 carbons. In another embodiment, the cyclic alkyl group has 3-12 carbons. In another embodiment, the branched alkyl is an alkyl substituted by alkyl side chains of 1 to 5 carbons. In another embodiment, the branched alkyl is an alkyl substituted by haloalkyl side chains of 1 to 5 carbons. The alkyl group may be unsubstituted or substituted by a halogen, haloalkyl, hydroxyl, alkoxy carbonyl, amido, alkylamido, dialkylamido, nitro, amino, alkylamino, dialkylamino, carboxyl, thio and/or thioalkyl.

The term "heteroalkyl" refers to any alkyl as defined above wherein one or more of the carbons are being replaced by oxygen, nitrogen, sulfur, phosphorous or combination thereof.

An "arylalkyl" group refers to an alkyl bound to an aryl, wherein alkyl and aryl are as defined above. An example of an arylalkyl group is a benzyl group.

An "alkenyl" group refers, in another embodiment, to an unsaturated hydrocarbon, including straight chain, branched chain and cyclic groups having one or more double bonds. The alkenyl group may have one double bond, two double bonds, three double bonds, etc. In another embodiment, the alkenyl group has 2-12 carbons. In another embodiment, the alkenyl group has 2-6 carbons. In another embodiment, the alkenyl group has 2-4 carbons. Examples of alkenyl groups are ethenyl, propenyl, butenyl, cyclohexenyl, etc. The alkenyl group may be unsubstituted or substituted by a halogen, hydroxy, alkoxy carbonyl, amido, alkylamido, dialkylamido, nitro, amino, alkylamino, dialkylamino, carboxyl, thio and/or thioalkyl.

An "aryl" group refers to an aromatic group having at least one carbocyclic aromatic group or heterocyclic aromatic group, which may be unsubstituted or substituted by one or more groups selected from halogen, haloalkyl, hydroxy, alkoxy carbonyl, amido, alkylamido, dialkylamido, nitro, amino, alkylamino, dialkylamino, carboxy or thio or thioalkyl. Nonlimiting examples of aryl rings are phenyl, naphthyl, pyranyl, pyrrolyl, pyrazinyl, pyrimidinyl, pyrazolyl, pyridinyl, furanyl, thiophenyl, thiazolyl, imidazolyl, isoxazolyl, and the like. In one embodiment, the aryl group is a 4-8 membered ring. In another embodiment, the aryl group is a 4-12 membered ring(s). In another embodiment, the aryl group is a 6 membered ring. In another embodiment, the aryl group is a 5 membered ring. In another embodiment, the aryl group is 2-4 fused ring system. In another embodiment, the aryl is phenyl.

A "haloalkyl" group refers, in another embodiment, to an alkyl group as defined above, which is substituted by one or more halogen atoms, e.g. by F, Cl, Br or I.

A "hydroxyl" group refers, in another embodiment, to an OH group. It is understood by a person skilled in the art that when T, Q, $R_2$ $R_3$ or $R_4$ in the compounds of the present invention is OR, then the corresponding R is not OH.

In one embodiment, the term "halogen" or "halo" refers to a halogen, such as F, Cl, Br or I.

In one embodiment, this invention provides for the use of a compound as herein described and/or, its derivative, isomer, metabolite, pharmaceutically acceptable salt, pharmaceutical product, hydrate, N-oxide, prodrug, polymorph, crystal or combinations thereof.

In one embodiment, the methods of this invention make use of "pharmaceutically acceptable salts" of the compounds, which may be produced, by reaction of a compound of this invention with an acid or base.

Suitable pharmaceutically acceptable salts of amines of the compounds of the methods of this invention may be prepared from an inorganic acid or from an organic acid. In one embodiment, examples of inorganic salts of amines are bisulfates, borates, bromides, chlorides, hemisulfates, hydrobromates, hydrochlorates, 2-hydroxyethylsulfonates (hydroxyethanesulfonates), iodates, iodides, isothionates, nitrates, persulfates, phosphate, sulfates, sulfamates, sulfanilates, sulfonic acids (alkylsulfonates, arylsulfonates, halogen substituted alkylsulfonates, halogen substituted arylsulfonates), sulfonates and thiocyanates.

In one embodiment, examples of organic salts of amines may be selected from aliphatic, cycloaliphatic, aromatic, araliphatic, heterocyclic, carboxylic and sulfonic classes of organic acids, examples of which are acetates, arginines, aspartates, ascorbates, adipates, anthranilates, algenates, alkane carboxylates, substituted alkane carboxylates, alginates, benzenesulfonates, benzoates, bisulfates, butyrates, bicarbonates, bitartrates, carboxylates, citrates, camphorates, camphorsulfonates, cyclohexylsulfamates, cyclopentanepropionates, calcium edetates, camsylates, carbonates, clavulanates, cinnamates, dicarboxylates, digluconates, dodecylsulfonates, dihydrochlorides, decanoates, enanthuates, ethanesulfonates, edetates, edisylates, estolates, esylates, fumarates, formates, fluorides, galacturonates, gluconates, glutamates, glycolates, glucorates, glucoheptanoates, glycerophosphates, gluceptates, glycollylarsanilates, glutarates, glutamates, heptanoates, hexanoates, hydroxymaleates, hydroxycarboxlic acids, hexylresorcinates, hydroxybenzoates, hydroxynaphthoates, hydrofluorates, lactates, lactobionates, laurates, malates, maleates, methylenebis(beta-oxynaphthoate), malonates, mandelates, mesylates, methane sulfonates, methylbromides, methylnitrates, methylsulfonates, monopotassium maleates, mucates, monocarboxylates, nitrates, naphthalenesulfonates, 2-naphthalenesulfonates, nicotinates, napsylates, N-methylglucamines, oxalates, octanoates, oleates, pamoates, phenylacetates, picrates, phenylbenzoates, pivalates, propionates, phthalates, pectinates, phenylpropionates, palmitates, pantothenates, polygalacturates, pyruvates, quinates, salicylates, succinates, stearates, sulfanilates, subacetates, tartarates, theophyllineacetates, p-toluenesulfonates (tosylates), trifluoroacetates, terephthalates, tannates, teoclates, trihaloacetates, triethiodide, tricarboxylates, undecanoates and valerates.

In one embodiment, examples of inorganic salts of carboxylic acids or phenols may be selected from ammonium, alkali metals to include lithium, sodium, potassium, cesium; alkaline earth metals to include calcium, magnesium, aluminium; zinc, barium, cholines, quaternary ammoniums.

In another embodiment, examples of organic salts of carboxylic acids or phenols may be selected from arginine, organic amines to include aliphatic organic amines, alicyclic organic amines, aromatic organic amines, benzathines, t-butylamines, benethamines (N-benzylphenethylamine), dicyclohexylamines, dimethylamines, diethanolamines, ethanolamines, ethylenediamines, hydrabamines, imidazoles, lysines, methylamines, meglamines, N-methyl-D-glucamines, N,N'-dibenzylethylenediamines, nicotinamides, organic amines, ornithines, pyridines, picolies, piperazines, procaine, tris(hydroxymethyl)methylamines, triethylamines, triethanolamines, trimethylamines, tromethamines and ureas.

In one embodiment, the salts may be formed by conventional means, such as by reacting the free base or free acid form of the product with one or more equivalents of the appropriate acid or base in a solvent or medium in which the salt is insoluble or in a solvent such as water, which is removed in vacuo or by freeze drying or by exchanging the ions of a existing salt for another ion or suitable ion-exchange resin.

In one embodiment, the methods of this invention make use of a pharmaceutically acceptable salt of the compounds of this invention. In one embodiment, the methods of this invention make use of a pharmaceutically acceptable salt of compounds of formulas I-VIII, IXa-IXd, X, XIa-XId, XII, XIIIa-XIIId, XIV and XV. In one embodiment, the methods of this invention make use of a salt of an amine of the compounds of formulas I-VIII, IXa-IXd, X, XIa-XId, XII, XIIIa-XIIId, XIV and XV of this invention. In one embodiment, the methods of this invention make use of a salt of a phenol of the compounds of formulas I-VIII, IXa-IXd, X, XIa-XId, XII, XIIIa-XIIId, XIV and XV of this invention.

In one embodiment, the methods of this invention make use of a free base, free acid, non charged or non-complexed compounds of formulas I-VIII, IXa-IXd, X, XIa-XId, XII, XIIIa-XIIId, XIV and XV and/or its isomer, pharmaceutical product, hydrate, polymorph, or combinations thereof.

In one embodiment, the methods of this invention make use of an isomer of a compound of formulas I-VIII, IXa-IXd, X, XIa-XId, XII, XIIIa-XIIId, XIV and XV. In one embodiment, the methods of this invention make use of a pharmaceutical product of a compound of formulas I-VIII, IXa-IXd, X, XIa-XId, XII, XIIIa-XIIId, XIV and XV. In one embodiment, the methods of this invention make use of a hydrate of a compound of formulas I-VIII, IXa-IXd, X, XIa-XId, XII, XIIIa-XIIId, XIV and XV. In one embodiment, the methods of this invention make use of a polymorph of a compound of formulas I-VIII, IXa-IXd, X, XIa-XId, XII, XIIIa-XIIId, XIV and XV. In one embodiment, the methods of this invention make use of a metabolite of a compound of formulas I-VIII, IXa-IXd, X, XIa-XId, XII, XIIIa-XIIId, XIV and XV. In another embodiment, the methods of this invention make use of a composition comprising a compound of formulas I-VIII, IXa-IXd, X, XIa-XId, XII, XIIIa-XIIId, XIV and XV, as described herein, or, in another embodiment, a combination of isomer, metabolite, pharmaceutical product, hydrate, polymorph of a compound of formulas I-VIII, IXa-IXd, X, XIa-XId, XII, XIIIa-XIIId, XIV and XV.

In one embodiment, the term "isomer" includes, but is not limited to, optical isomers and analogs, structural isomers and analogs, conformational isomers and analogs, and the like.

In one embodiment, the term "isomer" is meant to encompass optical isomers of the SARD compound. It will be appreciated by those skilled in the art that the SARDs of the present invention contain at least one chiral center. Accordingly, the SARDs used in the methods of the present invention may exist in, and be isolated in, optically-active or racemic forms. Some compounds may also exhibit polymorphism. It is to be understood that the present invention encompasses any racemic, optically-active, polymorphic, or stereoisomeric form, or mixtures thereof, which form possesses properties useful in the treatment of androgen-related conditions described herein. In one embodiment, the SARDs are the pure (R)-isomers. In another embodiment, the SARDs are the pure (S)-isomers. In another embodiment, the SARDs are a mixture of the (R) and the (S) isomers. In another embodiment, the SARDs are a racemic mixture comprising an equal amount of the (R) and the (S) isomers. It is well known in the art how to prepare optically-active forms (for example, by resolution of the racemic form by recrystallization techniques, by synthesis from optically-active starting materials, by chiral synthesis, or by chromatographic separation using a chiral stationary phase).

In another embodiment, this invention further includes hydrates of the compounds. The invention also includes use of N-oxides of the amino substituents of the compounds described herein.

In one embodiment, the term "hydrate" refers to hemihydrate, monohydrate, dihydrate, trihydrate or others, as known in the art.

This invention provides, in other embodiments, use of metabolites of the compounds as herein described. In one embodiment, "metabolite" means any substance produced from another substance by metabolism or a metabolic process.

In one embodiment, the compounds of this invention are prepared according to Examples 1-4.

Biological Activity of Selective Androgen Receptor Degraders

In one embodiment, this invention provides a method of treating, suppressing, reducing the incidence, reducing the severity, or inhibiting the progression of prostate cancer (PCa) and its symptoms, or increasing the survival of a male subject suffering from prostate cancer comprising administering to said subject a therapeutically effective amount of a compound or its isomer, pharmaceutically acceptable salt, pharmaceutical product, polymorph, hydrate or any combination thereof, represented by the structure of formula I-VIII, IXa-IXd, X, XIa-XId, XII, XIIIa-XIIId, XIV or XV as described above, pharmaceutically acceptable saltpharmaceutically acceptable saltpharmaceutically acceptable saltpharmaceutically acceptable saltpharmaceutically acceptable salt In another embodiment, the prostate cancer is advanced prostate cancer, castration resistant prostate cancer (CRPC), metastatic CRPC (mCRPC), non-metastatic CRPC (nmCRPC), high-risk nmCRPC or any combination thereof. In another embodiment, the prostate cancer depends on AR-FL and/or AR-SV for proliferation. In another embodiment, the subject further receives androgen deprivation therapy (ADT). In another embodiment, the subject has failed androgen deprivation therapy (ADT). In another embodiment, the cancer is resistant to treatment with an androgen receptor antagonist. In another embodiment, the cancer is resistant to treatment with enzalutamide, flutamide, bicalutamide, abiraterone, ARN-509, AZD-3514, galeterone, ASC-J9, flutamide, hydroxyflutamide, nilutamide, cyproterone acetate, ketoconazole, spironolactone, or any combination thereof. In another embodiment, administering the compound to a subject reduces the levels of AR, AR-full length (AR-FL), AR-FL with antiandrogen resistance-conferring AR-LBD mutations, AR-splice variant (AR-SV), gene-amplified AR, or any combination thereof, in said subject.

In one embodiment, this invention provides a method of treating, suppressing, reducing the incidence, reducing the severity, or inhibiting the progression of prostate cancer (PCa) and its symptoms, or increasing the survival of a male subject suffering from prostate cancer comprising administering to said subject a therapeutically effective amount of a compound or its isomer, pharmaceutically acceptable salt, pharmaceutical product, polymorph, hydrate or any combination thereof, selected from the following structures:

Indoles:
11
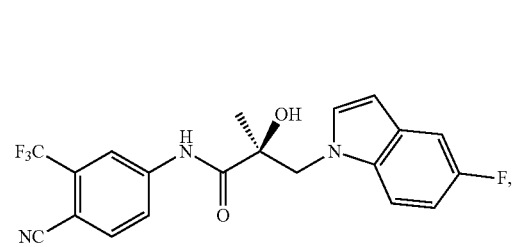
11R
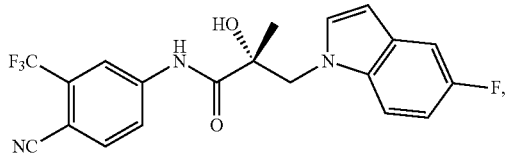
12
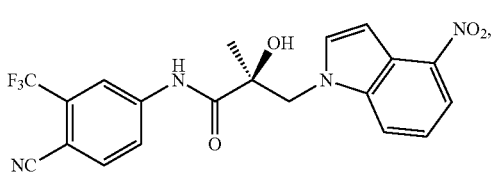
13
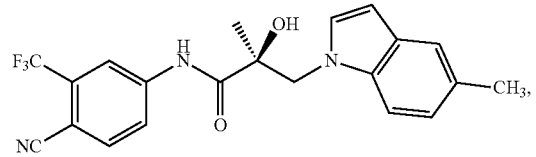
14
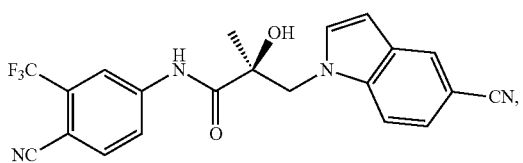
15
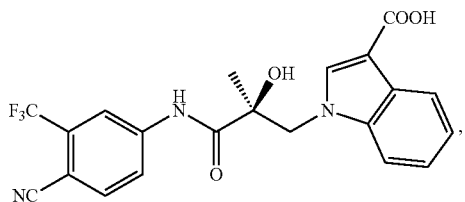
16
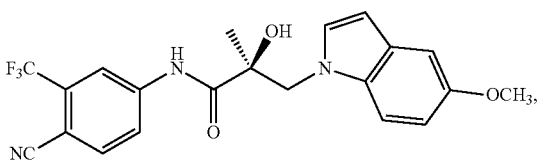
17
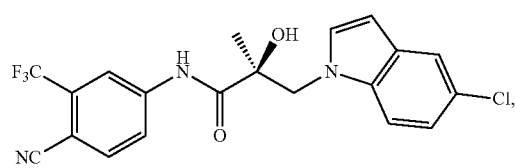
-continued
18
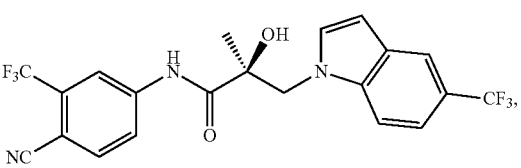
19
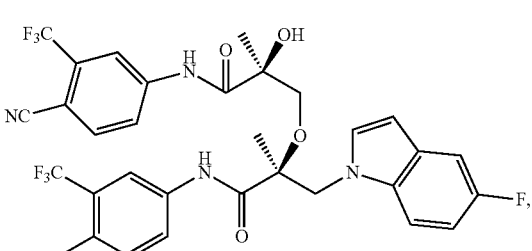
20
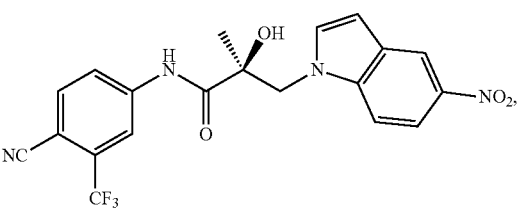
21
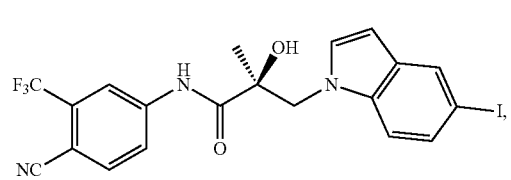
22
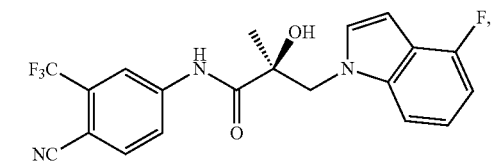
23
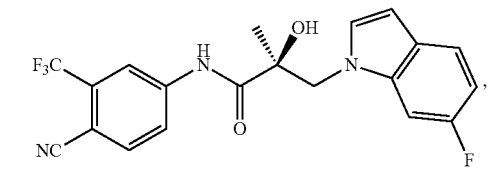
24
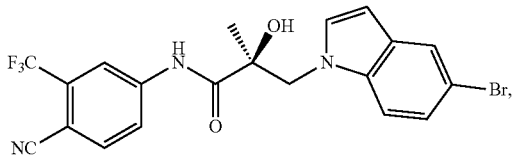
25

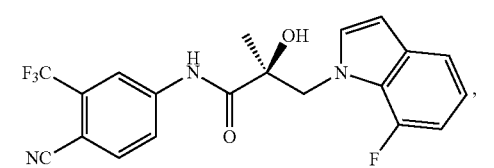
26
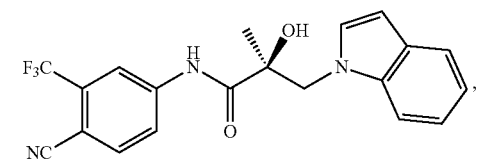
27
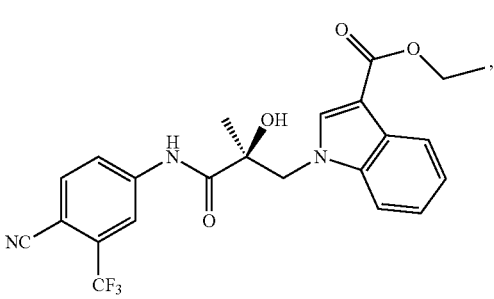
30
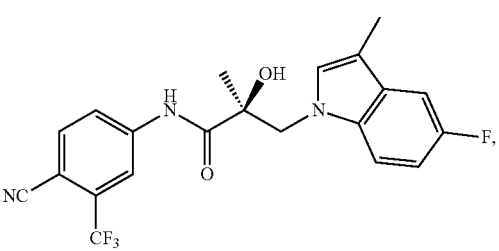
31
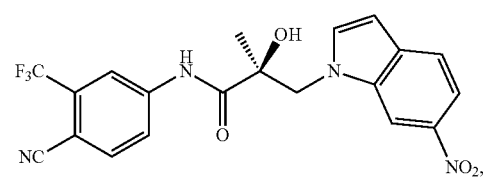
32
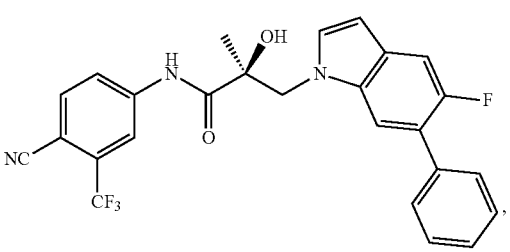
33
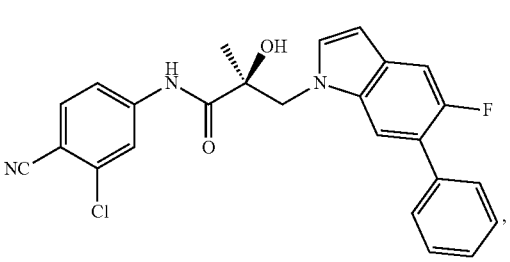
34
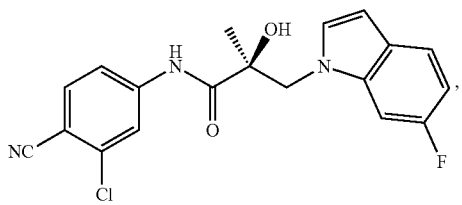
35
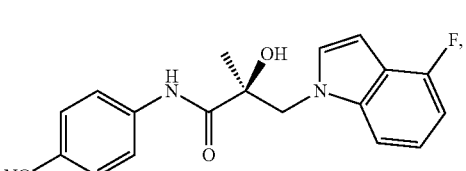
36
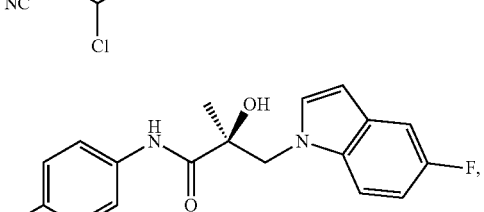
37
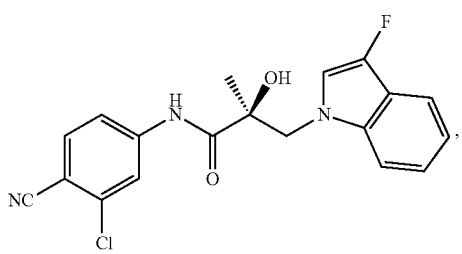
38
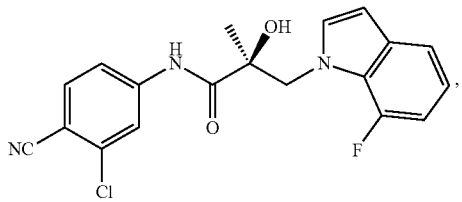
39
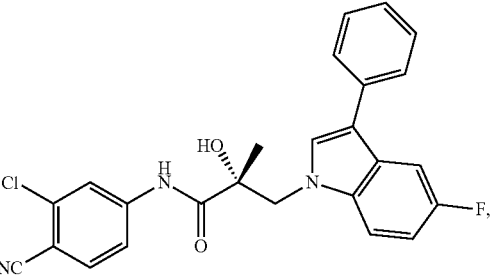
40
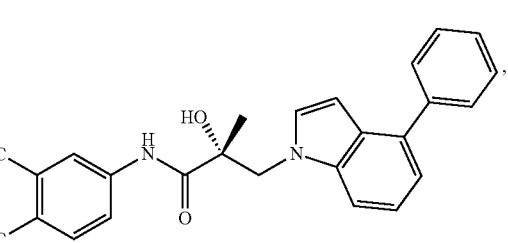
41

Benzimidazoles:

Pyrrolo-Pyridine:

Indazoles:

Indolines:
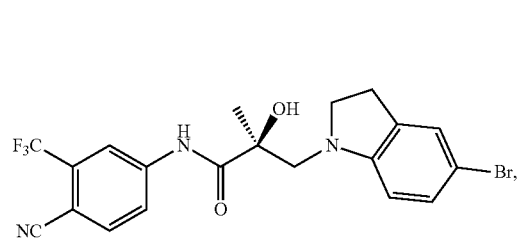 100
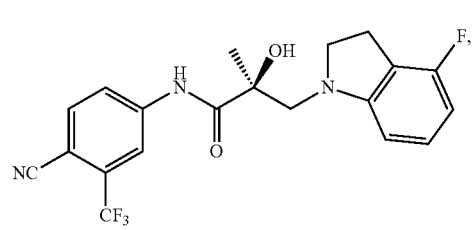 101
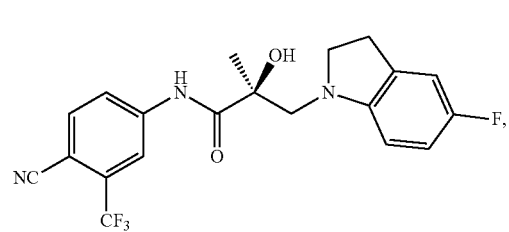 102
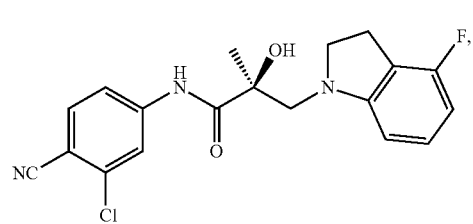 103
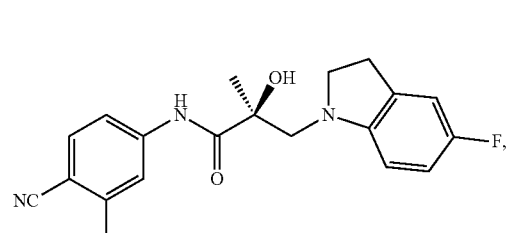 104
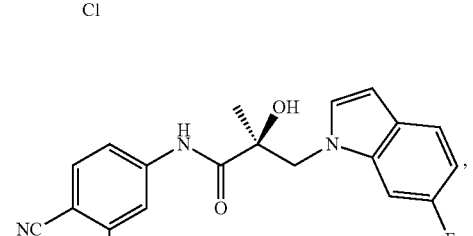 105
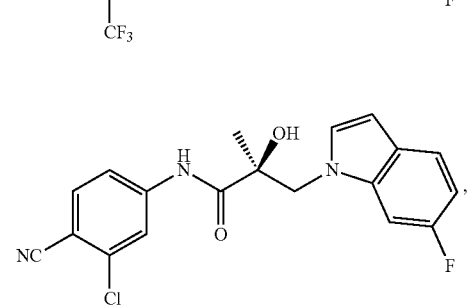 106
-continued
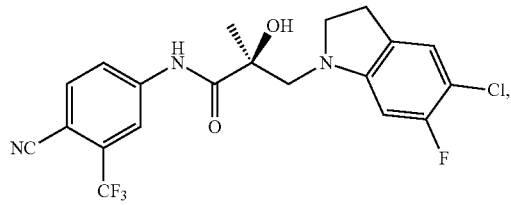 107
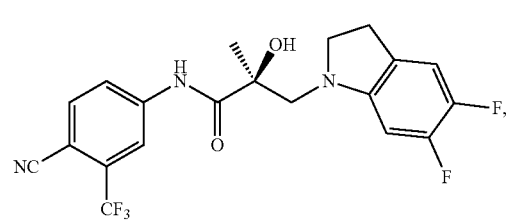 108
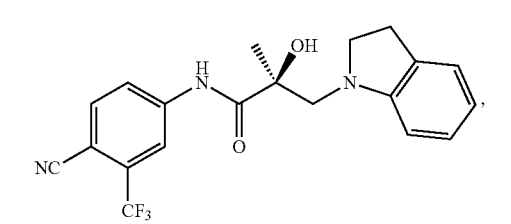 109
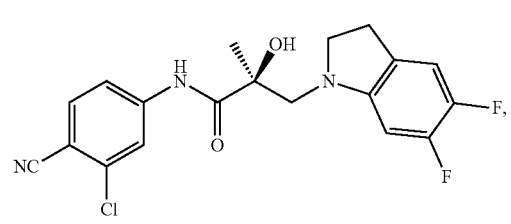 110
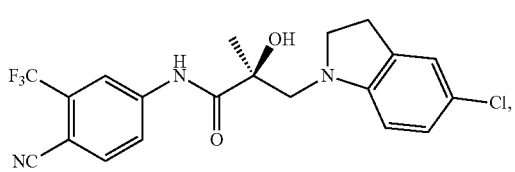 111
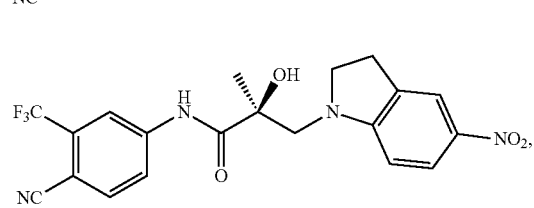 112
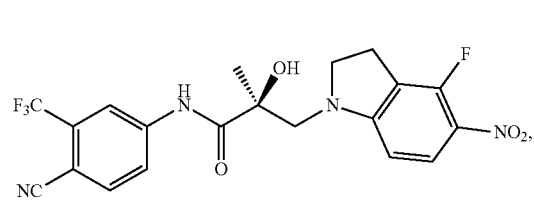 113
114

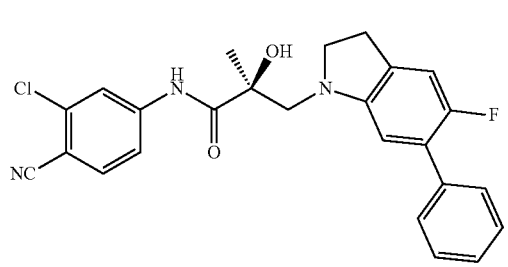
115
Isoquinolines and Quinolines:
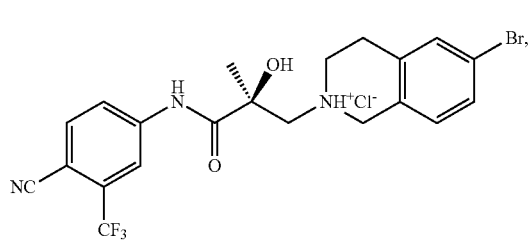
130
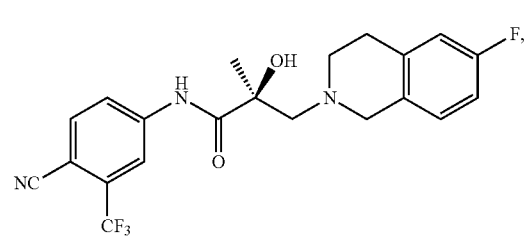
131
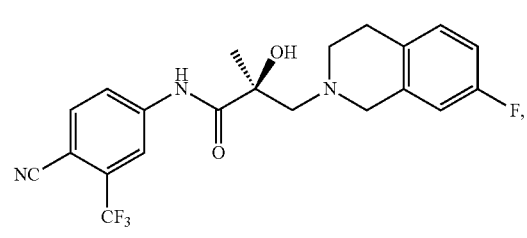
132
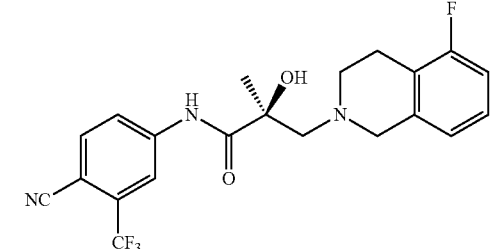
133
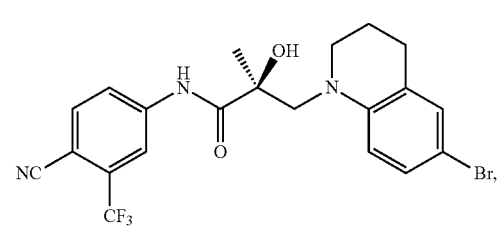
134
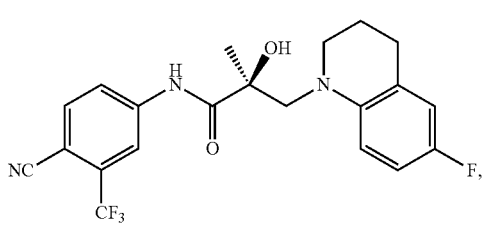
135
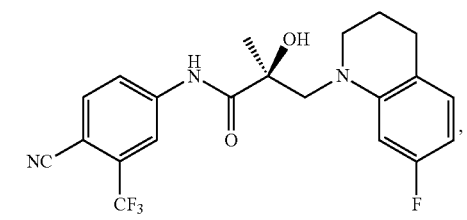
136
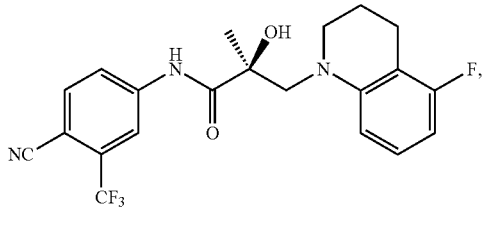
137
Carbazoles:
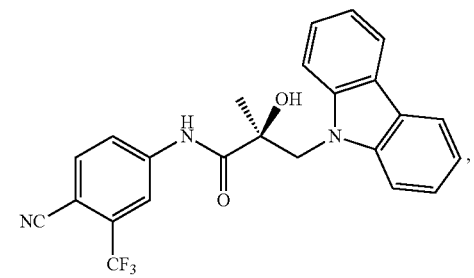
200
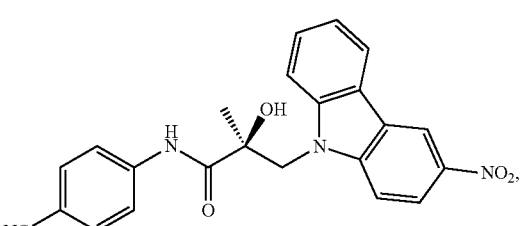
201
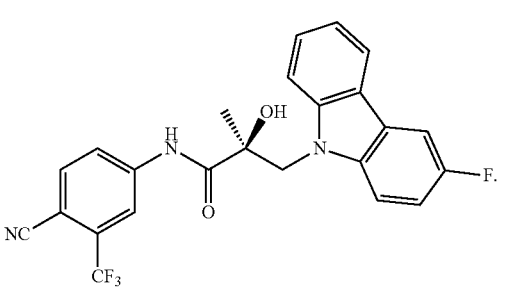
202

-continued

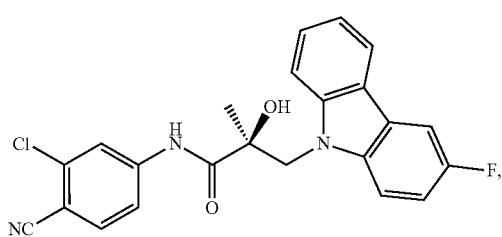
203

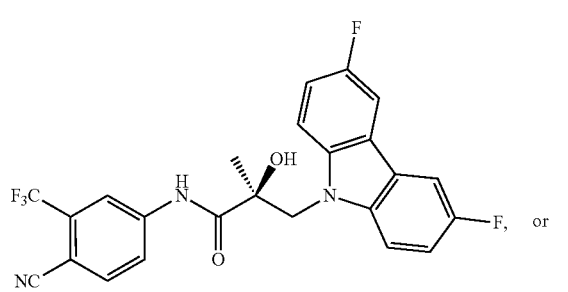
204

, or

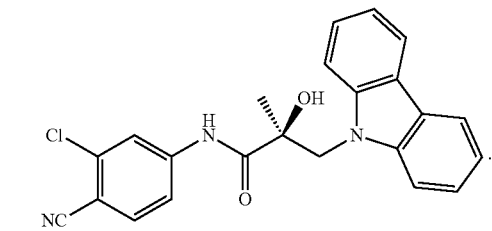
205

In another embodiment, the prostate cancer is advanced prostate cancer, castration resistant prostate cancer (CRPC), metastatic CRPC (mCRPC), non-metastatic CRPC (nm-CRPC), high-risk nmCRPC or any combination thereof. In another embodiment, the prostate cancer depends on AR-FL and/or AR-SV for proliferation. In another embodiment, the subject further receives androgen deprivation therapy (ADT). In another embodiment, the subject has failed androgen deprivation therapy (ADT). In another embodiment, the cancer is resistant to treatment with an androgen receptor antagonist. In another embodiment, the cancer is resistant to treatment with enzalutamide, flutamide, bicalutamide, abiraterone, ARN-509, AZD-3514, galeterone, ASC-J9, flutamide, hydroxyflutamide, nilutamide, cyproterone acetate, ketoconazole, spironolactone, or any combination thereof. In another embodiment, administering the compound to a subject reduces the levels of AR, AR-full length (AR-FL), AR-FL with antiandrogen resistance-conferring AR-LBD mutations, AR-splice variant (AR-SV), gene-amplified AR, or any combination thereof, in said subject.

In one embodiment, the methods of this invention are directed to treating, suppressing, reducing the incidence, reducing the severity, inhibiting, providing palliative care, or increasing the survival of a subject suffering from prostate cancer. In one embodiment, the methods of this invention are directed to methods of treating, suppressing, reducing the incidence, reducing the severity, inhibiting, providing palliative care, or increasing the survival of advanced prostate cancer in a subject. In one embodiment, the methods of this invention are directed to treating, suppressing, reducing the incidence, reducing the severity, inhibiting, providing palliative care, or increasing the survival of a subject suffering from castration resistant prostate cancer (CRPC). In one embodiment, the methods of this invention are directed to treating, suppressing, reducing the incidence, reducing the severity, inhibiting, providing palliative care, or increasing the survival of a subject suffering from metastatic castration resistant prostate cancer (mCRPC). In one embodiment, the methods of this invention are directed to treating, suppressing, reducing the incidence, reducing the severity, inhibiting, providing palliative care, or increasing the survival of a subject suffering from non-metastatic castration resistant prostate cancer (nmCRPC). In one embodiment, the nmCRPC is high-risk nmCRPC. In another embodiment, the subject has high or increasing prostate specific antigen (PSA) levels.

In one embodiment, this invention provides a method of treating, suppressing, reducing the incidence, reducing the severity, or inhibiting the progression of prostate cancer (PCa) and its symptoms, or increasing the survival of a male subject suffering from prostate cancer comprising administering to said subject a therapeutically effective amount of a SARD compound or its isomer, pharmaceutically acceptable salt, pharmaceutical product, polymorph, hydrate or any combination thereof, said compound is represented by a compound of formulas I-VIII, IXa-IXd, X, XIa-XId, XII, XIIIa-XIIId, XIV or XV or any one of compounds 11-27, 30-42, 11R, 70-75, 80, 90-93, 100-115, 130-137, or 200-205.

In one embodiment, this invention provides a method of treating, suppressing, reducing the incidence, reducing the severity, or inhibiting the progression of advanced prostate cancer and its symptoms, or increasing the survival of a male subject suffering from advanced prostate cancer comprising administering to said subject a therapeutically effective amount of a SARD compound or its isomer, pharmaceutically acceptable salt, pharmaceutical product, polymorph, hydrate or any combination thereof, said compound is represented by a compound of formulas I-VIII, IXa-IXd, X, XIa-XId, XII, XIIIa-XIIId, XIV or XV or any one of compounds 11-27, 30-42, 11R, 70-75, 80, 90-93, 100-115, 130-137, or 200-205.

In one embodiment, this invention provides a method of treating, suppressing, reducing the incidence, reducing the severity, or inhibiting the progression of metastatic prostate cancer and its symptoms, or increasing the survival of a male subject suffering from metastatic prostate cancer comprising administering to said subject a therapeutically effective amount of a SARD compound or its isomer, pharmaceutically acceptable salt, pharmaceutical product, polymorph, hydrate or any combination thereof, said compound is represented by a compound of formulas I-VIII, IXa-IXd, X, XIa-XId, XII, XIIIa-XIIId, XIV or XV or any one of compounds 11-27, 30-42, 11R, 70-75, 80, 90-93, 100-115, 130-137, or 200-205.

In one embodiment, this invention provides a method of treating, suppressing, reducing the incidence, reducing the severity, or inhibiting the progression of castration resistant prostate cancer (CRPC) and its symptoms, or increasing the survival of a male subject suffering from castration resistant prostate cancer (CRPC) comprising administering to said subject a therapeutically effective amount of a SARD compound or its isomer, pharmaceutically acceptable salt, pharmaceutical product, polymorph, hydrate or any combination thereof, said compound is represented by a compound of formulas I-VIII, IXa-IXd, X, XIa-XId, XII, XIIIa-XIIId, XIV or XV or any one of compounds 11-27, 30-42, 11R, 70-75, 80, 90-93, 100-115, 130-137, or 200-205.

In one embodiment, the SARD compounds as described herein and/or compositions comprising the same may be used for treating, suppressing, reducing the incidence, reducing the severity, or inhibiting the progression of castration resistant prostate cancer (CRPC) and its symptoms, or increasing the survival of men with castration resistant prostate cancer. In another embodiment, the CRPC is metastatic CRPC (mCRPC). In another embodiment, the CRPC is non-metastatic CRPC (nmCRPC). In one embodiment, the nmCRPC is high-risk nmCRPC. In another embodiment, the subject further receives androgen deprivation therapy.

As used herein, the terms "increase" and "prolong" may be used interchangeably having all the same meanings and qualities, wherein these terms may in one embodiment refer to a lengthening of time. In another embodiment, as used herein, the terms "increase", increasing" "increased" may be used interchangeably and refer to an entity becoming progressively greater (as in size, amount, number, or intensity), wherein for example the entity is sex hormone-binding globulin (SHBG) or prostate-specific antigen (PSA).

In one embodiment, the compounds as described herein and/or compositions comprising the same may be used for increasing metastasis-free survival (MFS) in a subject suffering from non-metastatic prostate cancer. In one embodiment, the non-metastatic prostate cancer is non-metastatic advanced prostate cancer. In another embodiment, the non-metastatic prostate cancer is non-metastatic CRPC (nmCRPC). In one embodiment, the nmCRPC is high-risk nmCRPC.

In one embodiment, the SARD compounds as described herein and/or compositions comprising the same may be used to provide a dual action, for example treating prostate cancer and preventing metastases. In one embodiment, the prostate cancer being treated is advanced prostate cancer. In one embodiment, the prostate cancer being treated is castration resistant prostate cancer (CRPC). In one embodiment, the prostate cancer being treated is metastatic CRPC (mCRPC). In one embodiment, the prostate cancer being treated is non-metastatic CRPC (nmCRPC). In one embodiment, the nmCRPC is high-risk nmCRPC.

Men with advanced prostate cancer who are at high risk for progression to castration resistant prostate cancer (CRPC), in one embodiment, are men on ADT with serum total testosterone concentrations greater than 20 ng/dL or in another embodiment, men with advanced prostate cancer who at the time of starting ADT had either (1) confirmed Gleason pattern 4 or 5 prostate cancer, (2) metastatic prostate cancer, (3) a PSA doubling time <3 months, (4) a PSA ≥20 ng/mL, or (5) a PSA relapse in <3 years after definitive local therapy (radical prostatectomy or radiation therapy).

Men with high risk non-metastatic castration resistant prostate cancer (high-risk nmCRPC) may include those with rapid PSA doubling times, having an expected progression-free survival of approximately 18 months or less (Miller K, Moul J W, Gleave M, et al. 2013. Phase III, randomized, placebo-controlled study of once-daily oral zibotentan (ZD4054) in patients with non-metastatic castration-resistant prostate cancer. *Prostate Canc Prost Dis.* February; 16:187-192). This relatively rapid progression of their disease underscores the importance of novel therapies for these individuals. In one embodiment, the PSA levels are greater than 8 ng/mL in a subject suffering from high-risk nmCRPC. In one embodiment, the PSA doubling time is less than 8 months in a subject suffering from high-risk nmCRPC. In another embodiment, the PSA doubling time is less than 10 months in a subject suffering from high-risk nmCRPC. In one embodiment, the total serum testosterone levels are greater than 20 ng/mL in a subject suffering from high-risk nmCRPC. In one embodiment, the serum free testosterone levels are greater than those observed in an orchidectomized male in a subject suffering from high-risk nmCRPC.

In one embodiment, the compounds as described herein and/or compositions comprising the same may be used in combination with LHRH agonist or antagonist for increasing the progression free survival or overall survival of a subject suffering from prostate cancer. In another embodiment, the prostate cancer is advanced prostate cancer. In another embodiment, the prostate cancer is castration resistant prostate cancer (CRPC). In another embodiment, the CRPC is metastatic CRPC (mCRPC). In another embodiment, the CRPC is non-metastatic CRPC (nmCRPC). In one embodiment, the nmCRPC is high-risk nmCRPC. In another embodiment, the subject is surgically castrated. In another embodiment, the subject is chemically castrated.

In one embodiment, the compounds as described herein and/or compositions comprising the same may be used in combination with anti-programmed death receptor 1 (anti-PD-1) drugs (e.g., AMP-224, nivolumab, pembrolizumab, pidilizumab, AMP-554, and the like) for increasing the progression free survival or overall survival of a subject suffering from prostate cancer. In another embodiment, the prostate cancer is advanced prostate cancer. In another embodiment, the prostate cancer is castration resistant prostate cancer (CRPC). In another embodiment, the CRPC is metastatic CRPC (mCRPC). In another embodiment, the CRPC is non-metastatic CRPC (nmCRPC). In one embodiment, the nmCRPC is high-risk nmCRPC. In another embodiment, the subject is surgically castrated. In another embodiment, the subject is chemically castrated.

In one embodiment, the compounds as described herein and/or compositions comprising the same may be used in combination with anti-PD-L1 drugs (e.g., BMS-936559, MEDI4736, MPDL3280A, MEDI4736, MSB0010718C, and the like) for increasing the progression free survival or overall survival of a subject suffering from prostate cancer. In another embodiment, the prostate cancer is advanced prostate cancer. In another embodiment, the prostate cancer is castration resistant prostate cancer (CRPC). In another embodiment, the CRPC is metastatic CRPC (mCRPC). In another embodiment, the CRPC is non-metastatic CRPC (nmCRPC). In one embodiment, the nmCRPC is high-risk nmCRPC. In another embodiment, the subject is surgically castrated. In another embodiment, the subject is chemically castrated.

In certain embodiments, treatment of prostate cancer, advanced prostate cancer, CRPC, mCRPC and/or nmCRPC may result in clinically meaningful improvement in prostate cancer related symptoms, function and/or survival. Clinically meaningful improvements include but are not limited to increasing radiographic progression free survival (rPFS) if cancer is metastatic, and increasing metastasis-free survival (MFS) if cancer is non-metastatic.

In one embodiment, the compounds as described herein and/or compositions comprising the same may be used for increasing the survival of men with castration resistant prostate cancer (CRPC). In another embodiment, the CRPC is metastatic CRPC (mCRPC). In another embodiment, the CRPC is non-metastatic CRPC (nmCRPC). In one embodiment, the nmCRPC is high-risk nmCRPC. In another embodiment, the subject further receives androgen deprivation therapy.

In one embodiment, levels of prostate specific antigen (PSA) considered normal are age dependent. In one embodiment, levels of prostate specific antigen (PSA) considered normal are dependent on the size of a male subject's prostate. In one embodiment, PSA levels in the range between 2.5-10 ng/mL are considered "borderline high". In another embodiment, PSA levels above 10 ng/mL are considered "high".

In one embodiment, the rate of change or "PSA velocity" is high. In one embodiment, a rate of change or "PSA velocity" greater than 0.75/year is considered high.

In one embodiment, this invention provides a method of lowering serum prostate specific antigen (PSA) levels in a male subject suffering from prostate cancer, advanced prostate cancer, metastatic prostate cancer or castration resistant prostate cancer (CRPC), comprising administering a therapeutically effective amount of a SARD compound or its isomer, pharmaceutically acceptable salt, pharmaceutical product, polymorph, hydrate or any combination thereof, said compound is represented by the structure of formula I-VIII, IXa-IXd, X, XIa-XId, XII, XIIIa-XIIId, XIV or XV or any one of compounds 11-27, 30-42, 11R, 70-75, 80, 90-93, 100-115, 130-137, or 200-205. In one embodiment, this invention is directed to treatment of a subject with high or increasing PSA levels comprising administering a SARD compound of this invention. In one embodiment, this invention is directed to treatment of a subject with high or increasing PSA levels despite ongoing ADT or a history of ADT, surgical castration or despite treatment with antiandrogens and/or LHRH agonist. In another embodiment, the treatment makes use of compounds of formula I-VIII, IXa-IXd, X, XIa-XId, XII, XIIIa-XIIId, XIV or XV or any one of compounds 11-27, 30-42, 11R, 70-75, 80, 90-93, 100-115, 130-137, or 200-205.

In one embodiment, this invention provides a method of treating, suppressing, reducing the incidence, reducing the severity, or inhibiting the progression of castration resistant prostate cancer (CRPC) and its symptoms, or increasing the survival of men with castration resistant prostate cancer comprising administering a therapeutically effective amount of a compound of formulas I-III, IXa, XIa, XIIIa or its isomer, pharmaceutically acceptable salt, pharmaceutical product, polymorph, hydrate or any combination thereof. In another embodiment, the compound is compound 11. In another embodiment, the compound is compound 11R. In another embodiment, the compound is compound 12. In another embodiment, the compound is compound 13. In another embodiment, the compound is compound 14. In another embodiment, the compound is compound 15. In another embodiment, the compound is compound 16. In another embodiment, the compound is compound 17. In another embodiment, the compound is compound 18. In another embodiment, the compound is compound 19. In another embodiment, the compound is compound 20. In another embodiment, the compound is compound 21. In another embodiment, the compound is compound 22. In another embodiment, the compound is compound 23. In another embodiment, the compound is compound 24. In another embodiment, the compound is compound 25. In another embodiment, the compound is compound 26. In another embodiment, the compound is compound 27. In another embodiment, the compound is compound 30. In another embodiment, the compound is compound 31. In another embodiment, the compound is compound 32. In another embodiment, the compound is compound 33. In another embodiment, the compound is compound 34. In another embodiment, the compound is compound 35. In another embodiment, the compound is compound 36. In another embodiment, the compound is compound 37. In another embodiment, the compound is compound 38. In another embodiment, the compound is compound 39. In another embodiment, the compound is compound 40. In another embodiment, the compound is compound 41. In another embodiment, the compound is compound 42. In another embodiment, the compound is compound 70. In another embodiment, the compound is compound 71. In another embodiment, the compound is compound 72. In another embodiment, the compound is compound 73. In another embodiment, the compound is compound 74. In another embodiment, the compound is compound 75. In another embodiment, the compound is compound 80. In another embodiment, the compound is compound 90. In another embodiment, the compound is compound 91. In another embodiment, the compound is compound 92. In another embodiment, the compound is compound 93.

In one embodiment, this invention provides a method of treating, suppressing, reducing the incidence, reducing the severity, or inhibiting the progression of castration resistant prostate cancer (CRPC) and its symptoms, or increasing the survival of men with castration resistant prostate cancer comprising administering a therapeutically effective amount of a compound of formulas II, IV-VIII, IXb-IXd, X, XIb-XId, XII, XIIIb-XIIId or its isomer, pharmaceutically acceptable salt, pharmaceutical product, polymorph, hydrate or any combination thereof. In another embodiment, the compound is compound 100. In another embodiment, the compound is compound 101. In another embodiment, the compound is compound 102. In another embodiment, the compound is compound 103. In another embodiment, the compound is compound 104. In another embodiment, the compound is compound 105. In another embodiment, the compound is compound 106. In another embodiment, the compound is compound 107. In another embodiment, the compound is compound 108. In another embodiment, the compound is compound 109. In another embodiment, the compound is compound 110. In another embodiment, the compound is compound 111. In another embodiment, the compound is compound 112. In another embodiment, the compound is compound 113. In another embodiment, the compound is compound 114. In another embodiment, the compound is compound 115. In another embodiment, the compound is compound 130. In another embodiment, the compound is compound 131. In another embodiment, the compound is compound 132. In another embodiment, the compound is compound 133. In another embodiment, the compound is compound 134. In another embodiment, the compound is compound 135. In another embodiment, the compound is compound 136. In another embodiment, the compound is compound 137.

In one embodiment, this invention provides a method of treating, suppressing, reducing the incidence, reducing the severity, or inhibiting the progression of castration resistant prostate cancer (CRPC) and its symptoms, or increasing the survival of men with castration resistant prostate cancer comprising administering a therapeutically effective amount of a compound of formulas XIV or XV or its isomer, pharmaceutically acceptable salt, pharmaceutical product, polymorph, hydrate or any combination thereof. In another embodiment, the compound is compound 200. In another embodiment, the compound is compound 201. In another embodiment, the compound is compound 202. In another embodiment, the compound is compound 203. In another embodiment, the compound is compound 204. In another embodiment, the compound is compound 205.

In one embodiment, this invention provides a method of secondary hormonal therapy that reduces serum PSA in a male subject suffering from castration resistant prostate cancer (CRPC) comprising administering a therapeutically effective amount of a compound of formulas I-VIII, IXa- IXd, X, XIa-XId, XII, XIIIa-XIIId, XIV, XV or its isomer, pharmaceutically acceptable salt, pharmaceutical product, polymorph, hydrate or any combination thereof. In another embodiment, the castration is surgical castration.

In another embodiment, with regards to the methods described above, the prostate cancer depends on AR-FL and/or AR-SV for proliferation. In another embodiment, the cancer is resistant to treatment with an androgen receptor antagonist. In another embodiment, the cancer is resistant to treatment with enzalutamide, flutamide, bicalutamide, abiraterone, ARN-509, AZD-3514, galeterone, ASC-J9, flutamide, hydroxyflutamide, nilutamide, cyproterone acetate, ketoconazole, spironolactone, or any combination thereof. In another embodiment, administration of the compounds of formulas I-VIII, IXa-IXd, X, XIa-XId, XII, XIIIa-XIIId, XIV or XV, reduces the levels of AR, AR-full length (AR-FL), AR-FL with antiandrogen resistance-conferring AR-LBD mutations, AR-splice variant (AR-SV), gene-amplified AR, or any combination thereof, in the subject. In another embodiment, the castration is surgical castration. In another embodiment, the castration is chemical castration. In another embodiment, the CRPC is metastatic CRPC (mCRPC). In another embodiment, the CRPC is non-metastatic CRPC (nmCRPC). In one embodiment, the nmCRPC is high-risk nmCRPC. In another embodiment, the method further increases radiographic progression free survival (rPFS) in a subject suffering from a metastatic cancer. In another embodiment, the method further increases metastasis-free survival (MFS) in a subject suffering from non-metastatic cancer. In one embodiment, the method may be used to provide a dual action, for example treating prostate cancer and preventing metastases. In another embodiment, the subject has failed androgen deprivation therapy (ADT). In another embodiment, the subject further receives androgen deprivation therapy (ADT). In another embodiment, the subject further receives LHRH agonist or antagonist. In another embodiment, the LHRH agonist is leuprolide acetate. In another embodiment, the subject had undergone orchidectomy. In another embodiment, the subject has high or increasing prostate specific antigen (PSA) levels. In another embodiment, the subject is a prostate cancer patient. In another embodiment, the subject is a prostate cancer patient on ADT. In another embodiment, the subject is a prostate cancer patient on ADT with castrate levels of total T. In another embodiment, the subject is an advanced prostate cancer patient. In another embodiment, the subject is an advanced prostate cancer patient on ADT. In another embodiment, the subject is an advanced prostate cancer patient on ADT with castrate levels of total T. In another embodiment, the subject is a CRPC patient. In another embodiment, the subject is a CRPC patient on ADT. In another embodiment, the subject is a CRPC patient on ADT with castrate levels of total T. In another embodiment, the subject is a metastatic castration resistant prostate cancer (mCRPC) patient. In another embodiment, the subject is a mCRPC patient maintained on ADT. In another embodiment, the subject is a mCRPC patient maintained on ADT with castrate levels of total T. In another embodiment, the subject is a non-metastatic castration resistant prostate cancer (nmCRPC) patient. In another embodiment, the subject is an nmCRPC patient maintained on ADT. In another embodiment, the subject is an nmCRPC patient maintained on ADT with castrate levels of total T. In one embodiment, the nmCRPC is high-risk nmCRPC. In another embodiment, the method further treats, suppresses, reduces the incidence, reduces the severity, or inhibits advanced prostate cancer. In another embodiment, the method further provides palliative treatment of advanced prostate cancer.

In one embodiment, this invention is directed to a method of reducing the levels of AR, AR-full length, AR-FL with antiandrogen resistance-conferring AR-LBD mutations, and/or AR-splice variants in a subject, comprising administering to said subject a therapeutically effective amount of a SARD compound according to this invention, or its isomer, pharmaceutically acceptable salt, pharmaceutical product, polymorph, hydrate or any combination thereof. In another embodiment, the reduction is achieved by degradation of said AR, AR-full length (AR-FL) and/or AR-splice variants (AR-SV). In another embodiment, the reduction is achieved by inhibition of said AR, AR-full length (AR-FL) and/or AR-splice variants (AR-SV). In another embodiment, the reduction is achieved by dual AR-SV/AR-FL degradation and AR-SV/AR-FL inhibitory functions.

In one embodiment, this invention is directed to a method of reducing the levels of AR-splice variants in a subject, comprising administering to said subject a therapeutically effective amount of a SARD compound according to this invention, or its isomer, pharmaceutically acceptable salt, pharmaceutical product, polymorph, hydrate or any combination thereof. In another embodiment, the method further reduces the levels of AR-full length (AR-FL) in the subject. In another embodiment, the reduction is achieved by degradation of said AR-splice variants (AR-SV). In another embodiment, the reduction is further achieved by degradation of said AR-FL. In another embodiment, the reduction is achieved by inhibition of said AR-splice variants (AR-SV). In another embodiment, the reduction is further achieved by inhibition of said AR-FL. In another embodiment, the reduction is achieved by dual AR-SV degradation and AR-SV inhibitory functions. In another embodiment, the reduction is achieved by dual AR-FL degradation and AR-FL inhibitory functions.

In one embodiment, "a subject suffering from castration resistant prostate cancer" refers to a subject which has been previously treated with androgen deprivation therapy (ADT), has responded to the ADT and currently has a serum PSA >2 ng/mL or >2 ng/mL and representing a 25% increase above the nadir achieved on the ADT. In another embodiment, the term refers to a subject which despite being maintained on androgen deprivation therapy is diagnosed to have serum PSA progression. In another embodiment, the subject has a castrate level of serum total testosterone (<50 ng/dL). In another embodiment, the subject has a castrate level of serum total testosterone (<20 ng/dL). In another embodiment, the subject has rising serum PSA on two successive assessments at least 2 weeks apart. In another embodiment, the subject had been effectively treated with ADT. In another embodiment, the subject has a history of serum PSA response after initiation of ADT. In another embodiment, the subject has been treated with ADT and had an initial serum PSA response, but now has a serum PSA >2 ng/mL and a 25% increase above the nadir observed on ADT. In one embodiment, the CRPC is metastatic CRPC (mCRPC). In another embodiment, the CRPC is non-metastatic CRPC (nmCRPC). In one embodiment, the nmCRPC is high-risk nmCRPC.

The term "serum PSA response" refers to, in one embodiment, at least 90% reduction in serum PSA value prior to the initiation of ADT, to <10 ng/mL or undetectable level of serum PSA (<0.2 ng/mL) at any time, or in another embodiment to at least 50% decline from baseline in serum PSA, or in another embodiment to at least 90% decline from baseline in serum PSA, or in another embodiment to at least 30% decline from baseline in serum PSA, or in another embodiment to at least 10% decline from baseline in serum PSA.

The term "serum PSA progression" refers to in one embodiment, a 25% or greater increase in serum PSA and an absolute increase of 2 ng/ml or more from the nadir; or in another embodiment, to serum PSA >2 ng/mL, or >2 ng/mL and a 25% increase above the nadir after the initiation of androgen deprivation therapy (ADT).

In another embodiment, the term "nadir" refers to the lowest PSA level while a patient is undergoing ADT.

Testosterone can be measured as "free" (that is, bioavailable and unbound) or as "total" (including the percentage which is protein bound and unavailable) serum levels. In one embodiment, total serum testosterone comprises free testosterone and bound testosterone.

The methods of this invention comprise administering a combination of forms of ADT and a compound of this invention. In one embodiment, forms of ADT include a LHRH agonist. In another embodiment, the LHRH agonist includes leuprolide acetate (Lupron®)(U.S. Pat. No. 5,480, 656; U.S. Pat. Nos. 5,575,987; 5,631,020; 5,643,607; 5,716, 640; 5,814,342; 6,036,976 which are all incorporated by reference herein) or goserelin acetate (Zoladex®) (U.S. Pat. Nos. 7,118,552; 7,220,247; 7,500,964 which are all incorporated by reference herein). In one embodiment, forms of ADT include an LHRH antagonist. In another embodiment, the LHRH antagonist includes degarelix. In another embodiment, the LHRH antagonist includes abarelix. In one embodiment, forms of ADT include reversible antiandrogens. In another embodiment, the antiandrogens include bicalutamide, flutamide, finasteride, dutasteride, enzalutamide, nilutamide, chlormadinone, abiraterone or any combination thereof. In one embodiment, forms of ADT include bilateral orchidectomy.

In one embodiment, this invention provides a method of treating, suppressing, reducing the incidence, reducing the severity, or inhibiting the progression of castration resistant prostate cancer (CRPC) and its symptoms, or increasing the survival of men with castration resistant prostate cancer comprising administering a therapeutically effective amount of a combination of one or more forms of ADT and a compound of formulas I-VIII, IXa-IXd, X, XIa-XId, XII, XIIIa-XIIId, XIV, XV or its isomer, pharmaceutically acceptable salt, pharmaceutical product, polymorph, hydrate or any combination thereof. In another embodiment, the subject has failed androgen deprivation therapy (ADT).

In one embodiment, this invention provides a method of lowering serum PSA levels in a male subject suffering from castration resistant prostate cancer (CRPC) comprising administering a therapeutically effective amount of a combination of one or more forms of ADT and a compound of formulas I-VIII, IXa-IXd, X, XIa-XId, XII, XIIIa-XIIId, XIV, XV or its isomer, pharmaceutically acceptable salt, pharmaceutical product, polymorph, hydrate or any combination thereof. In another embodiment, the subject has failed androgen deprivation therapy (ADT).

In one embodiment, the methods of this invention comprise administering a therapeutically effective amount of an antiandrogen and a compound of this invention. In one embodiment, the methods of this invention comprise administering a therapeutically effective amount of an LHRH agonist and a compound of this invention. In one embodiment, the methods of this invention comprise administering a therapeutically effective amount of an antiandrogen, LHRH agonist and a compound of this invention. In another embodiment, the compound is compound of formulas I-VIII, IXa-IXd, X, XIa-XId, XII, XIIIa-XIIId, XIV or XV. In another embodiment, the compound is any one of compounds 11-27, 30-42, 11R, 70-75, 80, 90-93, 100-115, 130-137, or 200-205.

In one embodiment, the methods of this invention comprise administering a therapeutically effective amount of an lyase inhibitor (e.g., abiraterone) and a compound of this invention. In another embodiment, the compound is a compound of formulas I-VIII, IXa-IXd, X, XIa-XId, XII, XIIIa-XIIId, XIV or XV. In another embodiment, the compound is any one of compounds 11-27, 30-42, 11R, 70-75, 80, 90-93, 100-115, 130-137, or 200-205.

In another embodiment, this invention provides a method for androgen deprivation therapy (ADT) in a subject, comprising administering a therapeutically effective amount of a compound of formulas I-VIII, IXa-IXd, X, XIa-XId, XII, XIIIa-XIIId, XIV, XV or its isomer, pharmaceutically acceptable salt, pharmaceutical product, polymorph, hydrate or any combination thereof. In another embodiment, said subject has prostate cancer. In another embodiment, the prostate cancer is castration resistant prostate cancer (CRPC). In another embodiment, the CRPC is metastatic CRPC (mCRPC). In one embodiment, the CRPC is non-metastatic castration resistant prostate cancer (nmCRPC). In one embodiment, the nmCRPC is high-risk nmCRPC. In another embodiment, the compound is any one of compounds 11-27, 30-42, 11R, 70-75, 80, 90-93, 100-115, 130-137, or 200-205. In another embodiment, the subject has failed androgen deprivation therapy (ADT). In another embodiment, the subject further receives androgen deprivation therapy (ADT).

In one embodiment, this invention provides a method of treating prostate cancer or delaying the progression of prostate cancer comprising administering a SARD compound of this invention. In one embodiment, this invention provides a method of preventing and/or treating the recurrence of prostate cancer comprising administering a SARD compound of this invention. In another embodiment, the prostate cancer is castration resistant prostate cancer (CRPC). In another embodiment, the CRPC is metastatic CRPC (mCRPC). In one embodiment, the CRPC is non-metastatic castration resistant prostate cancer (nmCRPC). In one embodiment, the nmCRPC is high-risk nmCRPC.

In one embodiment, this invention provides a method of increasing the survival of a subject having prostate cancer, advanced prostate cancer, castration resistant prostate cancer or metastatic castration resistant prostate cancer or non-metastatic castration resistant prostate cancer or high-risk non metastatic castration resistant prostate cancer, comprising administering a compound of this invention. In another embodiment, administering a compound of this invention in combination with LHRH analogs, reversible antiandrogens (such as bicalutamide, flutamide, or enzalutamide), anti-estrogens, estrogens (such as estradiol, ethinyl estradiol, or capesaris), anticancer drugs, 5-alpha reductase inhibitors, aromatase inhibitors, progestins, selective androgen receptor modulators (SARMs) or agents acting through other nuclear hormone receptors. In another embodiment, the subject has failed androgen deprivation therapy (ADT). In one embodiment, the compound is a compound of formulas I-VIII, IXa-IXd, X, XIa-XId, XII, XIIIa-XIIId, XIV or XV. In another embodiment, the compound is any one of compounds 11-27, 30-42, 11R, 70-75, 80, 90-93, 100-115, 130-137, or 200-205.

The term "advanced prostate cancer" refers to metastatic cancer having originated in the prostate, and having widely metastasized to beyond the prostate such as the surrounding tissues to include the seminal vesicles the pelvic lymph nodes or bone, or to other parts of the body. Prostate cancer pathologies are graded with a Gleason grading from 1 to 5 in order of increasing malignancy. In another embodiment, patients with significant risk of progressive disease and/or death from prostate cancer should be included in the definition and that any patient with cancer outside the prostate capsule with disease stages as low as IIB clearly has "advanced" disease. In another embodiment, "advanced prostate cancer" can refer to locally advanced prostate cancer.

Men with advanced prostate cancer often receive treatment to block the production of androgens, which are male sex hormones that may help prostate tumors grow. However, prostate cancers that initially respond to antiandrogen therapy eventually develop the ability to grow without androgens. Such cancers are often referred to as hormone refractory, androgen independent, or castration resistant.

In one embodiment, the advanced prostate cancer is castration resistant prostate cancer.

The term "castration resistant prostate cancer" (CRPC) refers to advanced prostate cancer that is worsening or progressing while the patient remains on ADT or other therapies to reduce testosterone, or prostate cancer which is considered hormone refractory, hormone naïve, androgen independent or chemical or surgical castration resistant. In another embodiment, CRPC is a result of AR activation by intracrine androgen synthesis. In another embodiment, CRPC is a result of expression of AR splice variants (AR-SV) that lack ligand binding domain (LBD). In another embodiment, CRPC is a result of expression of AR-LBD mutations with potential to resist antagonists. In another embodiment, castration resistant prostate cancer (CRPC) is an advanced prostate cancer which developed despite ongoing ADT and/or surgical castration. In one embodiment, castration resistant prostate cancer is defined as prostate cancer that continues to progress or worsen or adversely affect the health of the patient despite prior surgical castration, continued treatment with gonadotropin releasing hormone agonists (e.g., leuprolide) or antagonists (e.g., degarelix), antiandrogens (e.g., bicalutamide, flutamide, enzalutamide, ketoconazole, aminoglutethamide), chemotherapeutic agents (e.g., docetaxel, paclitaxel, cabazitaxel, adriamycin, mitoxantrone, estramustine, cyclophosphamide), kinase inhibitors (imatinib (Gleevec®) or gefitinib (Iressa®), cabozantinib (Cometriq™, also known as XL184)) or other prostate cancer therapies (e.g., vaccines (sipuleucel-T (Provenge®), GVAX, etc.), herbal (PC-SPES) and lyase inhibitor (abiraterone)) as evidenced by increasing or higher serum levels of prostate specific antigen (PSA), metastasis, bone metastasis, pain, lymph node involvement, increasing size or serum markers for tumor growth, worsening diagnostic markers of prognosis, or patient condition.

In one embodiment, castration resistant prostate cancer is defined as hormone naïve prostate cancer.

Many early prostate cancers require androgens for growth, but advanced prostate cancers are in some embodiments, androgen-independent, or hormone naïve. In one embodiment, in men with castration resistant prostate cancer, the tumor cells may have the ability to grow in the absence of androgens (hormones that promote the development and maintenance of male sex characteristics).

In one embodiment, the term "androgen deprivation therapy" (ADT) or "traditional androgen deprivation therapy" is directed to orchidectomy (surgical castration) wherein the surgeon removes the testicles. In another embodiment, the term "androgen deprivation therapy" or "traditional androgen deprivation therapy" is directed to administering luteinizing hormone-releasing hormone (LHRH) analogs: these drugs lower the amount of testosterone made by the testicles. Examples of LHRH analogs available in the United States include leuprolide (Lupron®, Viadur®, Eligard®), goserelin (Zoladex®), triptorelin (Trelstar®), and histrelin (Vantas®). In another embodiment, the term "androgen deprivation therapy" or "traditional androgen deprivation therapy" is directed to administering anti-androgens: Anti-androgens block the body's ability to use any androgens. Even after orchidectomy or during treatment with LHRH analogs, a small amount of androgens is still made by the adrenal glands. Examples of antiandrogens drugs include enzalutamide (Xtandi®), flutamide (Eulexin®), bicalutamide (Casodex®), and nilutamide (Nilandron®). In another embodiment, the term "androgen deprivation therapy" or "traditional androgen deprivation therapy" is directed to administering luteinizing hormone-releasing hormone (LHRH) antagonists such as abarelix (Plenaxis®) or degarelix (Firmagon®) (approved for use by the FDA in 2008 to treat advanced prostate cancer). In another embodiment, the term "androgen deprivation therapy" or "traditional androgen deprivation therapy" is directed to administering 5α-reductase inhibitors such as finasteride (Proscar®) and dutasteride (Avodart®): 5α-reductase inhibitors block the body's ability to convert testosterone to the more active androgen, 5α-dihydrotestosterone (DHT). In another embodiment, the term "androgen deprivation therapy" or "traditional androgen deprivation therapy" is directed to administering inhibitors of testosterone biosynthesis such as ketoconazole (Nizoral®). In another embodiment, the term "androgen deprivation therapy" or "traditional androgen deprivation therapy" is directed to administering estrogens such as diethylstilbestrol, ethinyl estradiol, capesaris, or 17β-estradiol. In another embodiment, the term "androgen deprivation therapy" or "traditional androgen deprivation therapy" is directed to administering 17α-hydroxylase/C17,20 lyase (CYP17A1) inhibitors such as abiraterone (Zytiga®).

In one embodiment, this invention provides a method of treating, suppressing, reducing the incidence, reducing the severity, increasing the survival, or inhibiting an antiandrogen-resistant prostate cancer. In another embodiment, the antiandrogen is bicalutamide, hydroxyflutamide, flutamide, or enzalutamide.

In one embodiment, this invention provides a method of treating, suppressing, reducing the incidence, reducing the severity, increasing the survival, or inhibiting an abiraterone-resistant prostate cancer.

In one embodiment, the terms "treating" or "treatment" includes preventative as well as disorder remitative treatment. The terms "reducing", "suppressing" and "inhibiting" have their commonly understood meaning of lessening or decreasing, in another embodiment, or delaying, in another embodiment, or reducing, in another embodiment, the incidence, severity or pathogenesis of a disease, disorder or condition. In embodiment, the term treatment refers to delayed progression of, prolonged remission of, reduced incidence of, or amelioration of symptoms associated with the disease, disorder or condition. In one embodiment, the terms "treating" "reducing", "suppressing" or "inhibiting" refer to a reduction in morbidity, mortality, or a combination thereof, in association with the indicated disease, disorder or condition. In one embodiment, the term "progression" refers to an increasing in scope or severity, advancing, growing or becoming worse. The term "recurrence" means, in another embodiment, the return of a disease after a remission. In one embodiment, the methods of treatment of the invention reduce the severity of the disease, or in another embodiment, symptoms associated with the disease, or in another embodiment, reduces the levels of biomarkers expressed during disease.

Muscle atrophy (MA) is characterized by wasting away or diminution of muscle and a decrease in muscle mass. For example, post-polio MA is a muscle wasting that occurs as part of the post-polio syndrome (PPS). The atrophy includes weakness, muscle fatigue, and pain.

Another type of MA is X-linked spinal-bulbar muscular atrophy (SBMA—also known as Kennedy's Disease). This disease arises from a defect in the androgen receptor gene on the X chromosome, affects only males, and its onset is in late adolescence to adulthood. Proximal limb and bulbar muscle weakness results in physical limitations including dependence on a wheelchair in some cases. The mutation results in an extended polyglutamine tract at the N-terminal domain of the androgen receptor (polyQ AR). Binding and activation of the polyQ AR by endogeneous androgens (testosterone and DHT) results in unfolding and nuclear translocation of the mutant androgen receptor. These steps are required for pathogenesis and results in partial loss of transactivation function (i.e., an androgen insensitivity) and a poorly understood neuromuscular degeneration. Currently there are no disease-modifying treatments but rather only symptom directed treatments. Efforts to target the polyQ AR as the proximal mediator of toxicity by harnessing cellular machinery to promote its degradation hold promise for therapeutic invention. Selective androgen receptor degraders such as those reported herein bind to and degrade a variety of androgen receptors (full length, splice variant, antiandrogen resistance mutants, etc.), indicating that they are promising leads for treatment of SBMA. This view is supported by the observation that peripheral polyQ AR anti-sense therapy rescues disease in mouse models of SBMA (*Cell Reports* 7, 774-784, May 8, 2014).

In one embodiment, this invention is directed to a method of treating, suppressing, reducing the incidence, reducing the severity, or inhibiting the progression of the Kennedy's disease comprising administering therapeutically effective amount of a compound of formulas I-VIII, IXa-IXd, X, XIa-XId, XII, XIIIa-XIIId, XIV, XV or its isomer, pharmaceutically acceptable salt, pharmaceutical product, polymorph, hydrate or any combination thereof. In another embodiment, the compound is any one of compounds 11-27, 30-42, 11R, 70-75, 80, 90-93, 100-115, 130-137, or 200-205.

As used herein, "androgen receptor associated conditions" or "androgen sensitive diseases or disorders" are conditions, diseases, or disorders that are modulated by or whose pathogenesis is dependent upon the activity of the androgen receptor. The androgen receptor is expressed in most tissues of the body however it is overexpressed in, inter alia, the prostate and skin. ADT has been the mainstay of prostate cancer treatment for many years, and a SARD may also be useful also in treating various prostate cancers, benign prostatic hypertrophy, prostamegaly, and other maladies of the prostate.

In one embodiment, this invention is directed to a method of treating, suppressing, reducing the incidence, reducing the severity, or inhibiting the progression of benign prostatic hypertrophy comprising administering a therapeutically effective amount of a compound of formulas I-VIII, IXa-IXd, X, XIa-XId, XII, XIIIa-XIIId, XIV, XV or its isomer, pharmaceutically acceptable salt, pharmaceutical product, polymorph, hydrate or any combination thereof. In another embodiment, the compound is any one of compounds 11-27, 30-42, 11R, 70-75, 80, 90-93, 100-115, 130-137, or 200-205.

In one embodiment, this invention is directed to a method of treating, suppressing, reducing the incidence, reducing the severity, or inhibiting the progression of prostamegaly comprising administering a therapeutically effective amount of a compound of formulas I-VIII, IXa-IXd, X, XIa-XId, XII, XIIIa-XIIId, XIV, XV or its isomer, pharmaceutically acceptable salt, pharmaceutical product, polymorph, hydrate or any combination thereof. In another embodiment, the compound is any one of compounds 11-27, 30-42, 11R, 70-75, 80, 90-93, 100-115, 130-137, or 200-205.

In one embodiment, this invention is directed to a method of treating, suppressing, reducing the incidence, reducing the severity, or inhibiting the progression of hyperproliferative prostatic disorders and diseases comprising administering a therapeutically effective amount of a compound of formulas I-VIII, IXa-IXd, X, XIa-XId, XII, XIIIa-XIIId, XIV, XV or its isomer, pharmaceutically acceptable salt, pharmaceutical product, polymorph, hydrate or any combination thereof. In another embodiment, the compound is any one of compounds 11-27, 30-42, 11R, 70-75, 80, 90-93, 100-115, 130-137, or 200-205.

The effect of the AR on the skin is apparent in the gender dimorphism and puberty related dermatological problems common to teens and early adults. The hyperandrogenism of puberty stimulates terminal hair growth, sebum production, and predisposes male teens to acne, acne vulgaris, seborrhea, excess sebum, hidradenitis suppurativa, hirsutism, hypertrichosis, hyperpilosity, androgenic alopecia, male pattern baldness, and other dermatological maladies. Although antiandrogens theoretically should prevent the hyperandrogenic dermatological diseases discussed, they are limited by toxicities, sexual side effects, and lack of efficacy when topically applied. The SARDs of this invention potently inhibit ligand-dependent and ligand-independent AR activation, and have short biological half-lives in the serum, suggesting that topically formulated SARDs of this invention could be applied to the areas affected by acne, seborrheic dermatitis, and/or hirsutism without risk of systemic side effects.

In one embodiment, this invention is directed to a method of treating, suppressing, reducing the incidence, reducing the severity, or inhibiting the progression of acne comprising administering a therapeutically effective amount of a compound of formulas I-VIII, IXa-IXd, X, XIa-XId, XII, XIIIa-XIIId, XIV, XV or its isomer, pharmaceutically acceptable salt, pharmaceutical product, polymorph, hydrate or any combination thereof. In another embodiment, the compound is any one of compounds 11-27, 30-42, 11R, 70-75, 80, 90-93, 100-115, 130-137, or 200-205.

In one embodiment, this invention is directed to a method of treating, suppressing, reducing the incidence, reducing the severity, or inhibiting the progression of acne vulgaris comprising administering a therapeutically effective amount of a compound of formulas I-VIII, IXa-IXd, X, XIa-XId, XII, XIIIa-XIIId, XIV, XV or its isomer, pharmaceutically acceptable salt, pharmaceutical product, polymorph, hydrate or any combination thereof. In another embodiment, the compound is any one of compounds 11-27, 30-42, 11R, 70-75, 80, 90-93, 100-115, 130-137, or 200-205.

In one embodiment, this invention is directed to a method of treating, suppressing, reducing the incidence, reducing the severity, or inhibiting the progression of seborrhea comprising administering a therapeutically effective amount of a compound of formulas I-VIII, IXa-IXd, X, XIa-XId, XII, XIIIa-XIIId, XIV, XV or its isomer, pharmaceutically acceptable salt, pharmaceutical product, polymorph, hydrate or any combination thereof. In another embodiment, the compound is any one of compounds 11-27, 30-42, 11R, 70-75, 80, 90-93, 100-115, 130-137, or 200-205.

In one embodiment, this invention is directed to a method of treating, suppressing, reducing the incidence, reducing the severity, or inhibiting the progression of seborrheic dermatitis comprising administering a therapeutically effective amount of a compound of formulas I-VIII, IXa-IXd, X, XIa-XId, XII, XIIIa-XIIId, XIV, XV or its isomer, pharmaceutically acceptable salt, pharmaceutical product, polymorph, hydrate or any combination thereof. In another embodiment, the compound is any one of compounds 11-27, 30-42, 11R, 70-75, 80, 90-93, 100-115, 130-137, or 200-205.

In one embodiment, this invention is directed to a method of treating, suppressing, reducing the incidence, reducing the severity, or inhibiting the progression of hidradenitis supporativa comprising administering a therapeutically effective amount of a compound of formulas I-VIII, IXa-IXd, X, XIa-XId, XII, XIIIa-XIIId, XIV, XV or its isomer, pharmaceutically acceptable salt, pharmaceutical product, polymorph, hydrate or any combination thereof. In another embodiment, the compound is any one of compounds 11-27, 30-42, 11R, 70-75, 80, 90-93, 100-115, 130-137, or 200-205.

In one embodiment, this invention is directed to a method of treating, suppressing, reducing the incidence, reducing the severity, or inhibiting the progression of hirsutism comprising administering a therapeutically effective amount of a compound of formulas I-VIII, IXa-IXd, X, XIa-XId, XII, XIIIa-XIIId, XIV, XV or its isomer, pharmaceutically acceptable salt, pharmaceutical product, polymorph, hydrate or any combination thereof. In another embodiment, the compound is any one of compounds 11-27, 30-42, 11R, 70-75, 80, 90-93, 100-115, 130-137, or 200-205.

In one embodiment, this invention is directed to a method of treating, suppressing, reducing the incidence, reducing the severity, or inhibiting the progression of hypertrichosis comprising administering a therapeutically effective amount of a compound of formulas I-VIII, IXa-IXd, X, XIa-XId, XII, XIIIa-XIIId, XIV, XV or its isomer, pharmaceutically acceptable salt, pharmaceutical product, polymorph, hydrate or any combination thereof. In another embodiment, the compound is any one of compounds 11-27, 30-42, 11R, 70-75, 80, 90-93, 100-115, 130-137, or 200-205.

In one embodiment, this invention is directed to a method of treating, suppressing, reducing the incidence, reducing the severity, or inhibiting the progression of hyperpilosity comprising administering a therapeutically effective amount of a compound of formulas I-VIII, IXa-IXd, X, XIa-XId, XII, XIIIa-XIIId, XIV, XV or its isomer, pharmaceutically acceptable salt, pharmaceutical product, polymorph, hydrate or any combination thereof. In another embodiment, the compound is any one of compounds 11-27, 30-42, 11R, 70-75, 80, 90-93, 100-115, 130-137, or 200-205.

In one embodiment, this invention is directed to a method of treating, suppressing, reducing the incidence, reducing the severity, or inhibiting the progression of alopecia comprising administering a therapeutically effective amount of a compound of formulas I-VIII, IXa-IXd, X, XIa-XId, XII, XIIIa-XIIId, XIV, XV or its isomer, pharmaceutically acceptable salt, pharmaceutical product, polymorph, hydrate or any combination thereof. In another embodiment, the compound is any one of compounds 11-27, 30-42, 11R, 70-75, 80, 90-93, 100-115, 130-137, or 200-205.

In some embodiments, the compounds as described herein and/or compositions may be used for applications in or treating hair loss, alopecia, androgenic alopecia, alopecia areata, alopecia secondary to chemotherapy, alopecia secondary to radiation therapy, alopecia induced by scarring or alopecia induced by stress. In one embodiment, "hair loss", or "alopecia", refers to baldness as in the very common type of male-pattern baldness. Baldness typically begins with patch hair loss on the scalp and sometimes progresses to complete baldness and even loss of body hair. Hair loss affects both males and females.

In one embodiment, this invention is directed to a method of treating, suppressing, reducing the incidence, reducing the severity, or inhibiting the progression of androgenic alopecia comprising administering a therapeutically effective amount of a compound of formulas I-VIII, IXa-IXd, X, XIa-XId, XII, XIIIa-XIIId, XIV, XV or its isomer, pharmaceutically acceptable salt, pharmaceutical product, polymorph, hydrate or any combination thereof. In another embodiment, the compound is any one of compounds 11-27, 30-42, 11R, 70-75, 80, 90-93, 100-115, 130-137, or 200-205.

SARDs of this invention may also be useful in the treatment of hormonal conditions in females such as precocious puberty, early puberty, dysmenorrhea, amenorrhea, multilocular uterus syndrome, endometriosis, hysteromyoma, abnormal uterine bleeding, early menarche, fibrocystic breast disease, fibroids of the uterus, ovarian cysts, polycystic ovary syndrome, pre-eclampsia, eclampsia of pregnancy, preterm labor, premenstrual syndrome, and vaginal dryness.

In one embodiment, this invention is directed to a method of treating, suppressing, reducing the incidence, reducing the severity, or inhibiting the progression of any hyperandrogenic diseases (for example polycystic ovary syndrome (PCOS)) comprising administering a therapeutically effective amount of a compound of formulas I-VIII, IXa-IXd, X, XIa-XId, XII, XIIIa-XIIId, XIV, XV or its isomer, pharmaceutically acceptable salt, pharmaceutical product, polymorph, hydrate or any combination thereof. In another embodiment, the compound is any one of compounds 11-27, 30-42, 11R, 70-75, 80, 90-93, 100-115, 130-137, or 200-205.

In one embodiment, this invention is directed to a method of treating, suppressing, reducing the incidence, reducing the severity, or inhibiting the progression of precocious puberty or early puberty comprising administering a therapeutically effective amount of a compound of formulas I-VIII, IXa-IXd, X, XIa-XId, XII, XIIIa-XIIId, XIV, XV or its isomer, pharmaceutically acceptable salt, pharmaceutical product, polymorph, hydrate or any combination thereof. In another embodiment, the compound is any one of compounds 11-27, 30-42, 11R, 70-75, 80, 90-93, 100-115, 130-137, or 200-205.

In one embodiment, this invention is directed to a method of treating, suppressing, reducing the incidence, reducing the severity, or inhibiting the progression of dysmenorrhea or amenorrhea comprising administering a therapeutically effective amount of a compound of formulas I-VIII, IXa-IXd, X, XIa-XId, XII, XIIIa-XIIId, XIV, XV or its isomer, pharmaceutically acceptable salt, pharmaceutical product, polymorph, hydrate or any combination thereof. In another embodiment, the compound is any one of compounds 11-27, 30-42, 11R, 70-75, 80, 90-93, 100-115, 130-137, or 200-205.

In one embodiment, this invention is directed to a method of treating, suppressing, reducing the incidence, reducing the severity, or inhibiting the progression of multilocular uterus syndrome, endometriosis, hysteromyoma, or abnormal uterine bleeding comprising administering a therapeutically effective amount of a compound of formulas I-VIII, IXa-IXd, X, XIa-XId, XII, XIIIa-XIIId, XIV, XV or its isomer, pharmaceutically acceptable salt, pharmaceutical product, polymorph, hydrate or any combination thereof. In another embodiment, the compound is any one of compounds 11-27, 30-42, 11R, 70-75, 80, 90-93, 100-115, 130-137, or 200-205.

In one embodiment, this invention is directed to a method of treating, suppressing, reducing the incidence, reducing the severity, or inhibiting the progression of fibrocystic breast disease, fibroids of the uterus, ovarian cysts, or polycystic ovary syndrome comprising administering a therapeutically effective amount of a compound of formulas I-VIII, IXa-IXd, X, XIa-XId, XII, XIIIa-XIIId, XIV, XV or its isomer, pharmaceutically acceptable salt, pharmaceutical product, polymorph, hydrate or any combination thereof. In another embodiment, the compound is any one of compounds 11-27, 30-42, 11R, 70-75, 80, 90-93, 100-115, 130-137, or 200-205.

In one embodiment, this invention is directed to a method of treating, suppressing, reducing the incidence, reducing the severity, or inhibiting the progression of pre-eclampsia, eclampsia of pregnancy, preterm labor, premenstrual syndrome, or vaginal dryness comprising administering a therapeutically effective amount of a compound of formulas I-VIII, IXa-IXd, X, XIa-XId, XII, XIIIa-XIIId, XIV, XV or its isomer, pharmaceutically acceptable salt, pharmaceutical product, polymorph, hydrate or any combination thereof. In another embodiment, the compound is any one of compounds 11-27, 30-42, 11R, 70-75, 80, 90-93, 100-115, 130-137, or 200-205.

SARDS of this invention may also find utility in treatment of sexual perversion, hypersexuality, paraphilias, androgen psychosis, virilization, androgen insensitivity syndromes (AIS) such as complete AIS (CAIS) and partial AIS (PAIS), and improving ovulation in an animal.

In one embodiment, this invention is directed to a method of treating, suppressing, reducing the incidence, reducing the severity, or inhibiting the progression of sexual perversion, hypersexuality, or paraphilias comprising administering a therapeutically effective amount of a compound of formulas I-VIII, IXa-IXd, X, XIa-XId, XII, XIIIa-XIIId, XIV, XV or its isomer, pharmaceutically acceptable salt, pharmaceutical product, polymorph, hydrate or any combination thereof. In another embodiment, the compound is any one of compounds 11-27, 30-42, 11R, 70-75, 80, 90-93, 100-115, 130-137, or 200-205.

In one embodiment, this invention is directed to a method of treating, suppressing, reducing the incidence, reducing the severity, or inhibiting the progression of androgen psychosis comprising administering a therapeutically effective amount of a compound of formulas I-VIII, IXa-IXd, X, XIa-XId, XII, XIIIa-XIIId, XIV, XV or its isomer, pharmaceutically acceptable salt, pharmaceutical product, polymorph, hydrate or any combination thereof. In another embodiment, the compound is any one of compounds 11-27, 30-42, 11R, 70-75, 80, 90-93, 100-115, 130-137, or 200-205.

In one embodiment, this invention is directed to a method of treating, suppressing, reducing the incidence, reducing the severity, or inhibiting the progression of virilization comprising administering a therapeutically effective amount of a compound of formulas I-VIII, IXa-IXd, X, XIa-XId, XII, XIIIa-XIIId, XIV, XV or its isomer, pharmaceutically acceptable salt, pharmaceutical product, polymorph, hydrate or any combination thereof. In another embodiment, the compound is any one of compounds 11-27, 30-42, 11R, 70-75, 80, 90-93, 100-115, 130-137, or 200-205.

In one embodiment, this invention is directed to a method of treating, suppressing, reducing the incidence, reducing the severity, or inhibiting the progression of androgen insensitivity syndromes comprising administering a therapeutically effective amount of a compound of formulas I-VIII, IXa-IXd, X, XIa-XId, XII, XIIIa-XIIId, XIV, XV or its isomer, pharmaceutically acceptable salt, pharmaceutical product, polymorph, hydrate or any combination thereof. In another embodiment, the compound is any one of compounds 11-27, 30-42, 11R, 70-75, 80, 90-93, 100-115, 130-137, or 200-205. In one embodiment, the androgen insensitivity syndrome is a complete androgen insensitivity syndrome. In another embodiment, the androgen insensitivity syndrome is a partial androgen insensitivity syndrome.

In one embodiment, this invention is directed to a method of increasing, modulating, or improving ovulation in an animal comprising administering a therapeutically effective amount of a compound of formulas I-VIII, IXa-IXd, X, XIa-XId, XII, XIIIa-XIIId, XIV, XV or its isomer, pharmaceutically acceptable salt, pharmaceutical product, polymorph, hydrate or any combination thereof. In another embodiment, the compound is any one of compounds 11-27, 30-42, 11R, 70-75, 80, 90-93, 100-115, 130-137, or 200-205.

SARDs of this invention may also be useful for the treating of hormone-dependent cancers such as prostate cancer, breast cancer, testicular cancer, ovarian cancer, and urogenital cancer, etc. Further, local or systemic SARD administration may be useful for treatment of precursors of hormone dependent cancers such as prostatic intraepithelial neoplasia (PIN) and atypical small acinar proliferation (ASAP).

In one embodiment, this invention is directed to a method of treating, suppressing, reducing the incidence, reducing the severity, or inhibiting the progression of AR related solid tumors. In another embodiment, the tumor is hepatocellular carcinoma. In another embodiment, the tumor is bladder cancer. Serum testosterone may be positively linked to the development of HCC. Based on epidemiologic, experimental observations, and notably the fact that men have a substantially higher risk of bladder cancer than women, androgens and/or the AR also play a role in bladder cancer initiation.

In one embodiment, this invention is directed to a method of treating, suppressing, reducing the incidence, reducing the severity, or inhibiting the progression of breast cancer comprising administering a therapeutically effective amount of a compound of formulas I-VIII, IXa-IXd, X, XIa-XId, XII, XIIIa-XIIId, XIV, XV or its isomer, pharmaceutically acceptable salt, pharmaceutical product, polymorph, hydrate or any combination thereof. In another embodiment, the compound is any one of compounds 11-27, 30-42, 11R, 70-75, 80, 90-93, 100-115, 130-137, or 200-205.

In one embodiment, this invention is directed to a method of treating, suppressing, reducing the incidence, reducing the severity, or inhibiting the progression of testicular cancer comprising administering a therapeutically effective amount of a compound of formulas I-VIII, IXa-IXd, X, XIa-XId, XII, XIIIa-XIIId, XIV, XV or its isomer, pharmaceutically acceptable salt, pharmaceutical product, polymorph, hydrate or any combination thereof. In another embodiment, the compound is any one of compounds 11-27, 30-42, 11R, 70-75, 80, 90-93, 100-115, 130-137, or 200-205.

In one embodiment, this invention is directed to a method of treating, suppressing, reducing the incidence, reducing the severity, or inhibiting the progression of uterine cancer comprising administering a therapeutically effective amount of a compound of formulas I-VIII, IXa-IXd, X, XIa-XId, XII, XIIIa-XIIId, XIV, XV or its isomer, pharmaceutically acceptable salt, pharmaceutical product, polymorph, hydrate or any combination thereof. In another embodiment, the compound is any one of compounds 11-27, 30-42, 11R, 70-75, 80, 90-93, 100-115, 130-137, or 200-205.

In one embodiment, this invention is directed to a method of treating, suppressing, reducing the incidence, reducing the severity, or inhibiting the progression of ovarian cancer comprising administering a therapeutically effective amount of a compound of formulas I-VIII, IXa-IXd, X, XIa-XId, XII, XIIIa-XIIId, XIV, XV or its isomer, pharmaceutically acceptable salt, pharmaceutical product, polymorph, hydrate or any combination thereof. In another embodiment, the compound is any one of compounds 11-27, 30-42, 11R, 70-75, 80, 90-93, 100-115, 130-137, or 200-205.

In one embodiment, this invention is directed to a method of treating, suppressing, reducing the incidence, reducing the severity, or inhibiting the progression of urogenital cancer comprising administering a therapeutically effective amount of a compound of formulas I-VIII, IXa-IXd, X, XIa-XId, XII, XIIIa-XIIId, XIV, XV or its isomer, pharmaceutically acceptable salt, pharmaceutical product, polymorph, hydrate or any combination thereof. In another embodiment, the compound is any one of compounds 11-27, 30-42, 11R, 70-75, 80, 90-93, 100-115, 130-137, or 200-205.

In one embodiment, this invention is directed to a method of treating, suppressing, reducing the incidence, reducing the severity, or inhibiting the progression of precursors of prostate cancer comprising local or systemic administration of a therapeutically effective amount of a compound of formulas I-VIII, IXa-IXd, X, XIa-XId, XII, XIIIa-XIIId, XIV, XV or its isomer, pharmaceutically acceptable salt, pharmaceutical product, polymorph, hydrate or any combination thereof. In another embodiment, the compound is any one of compounds 11-27, 30-42, 11R, 70-75, 80, 90-93, 100-115, 130-137, or 200-205. In one embodiment, the precursor of prostate cancers is prostatic intraepithelial neoplasia (PIN). In another embodiment, the precursor of prostate cancer is atypical small acinar proliferation (ASAP).

SARD of this invention may also be useful for the treating other cancers containing AR such as breast, brain, skin, ovarian, bladder, lymphoma, liver, kidney, pancreas, endometrium, lung (e.g., NSCLC) colon, perianal adenoma, osteosarcoma, CNS, melanoma, etc.

In one embodiment, this invention is directed to a method of treating, suppressing, reducing the incidence, reducing the severity, or inhibiting the progression of brain cancer comprising administering a therapeutically effective amount of a compound of formulas I-VIII, IXa-IXd, X, XIa-XId, XII, XIIIa-XIIId, XIV, XV or its isomer, pharmaceutically acceptable salt, pharmaceutical product, polymorph, hydrate or any combination thereof. In another embodiment, the compound is any one of compounds 11-27, 30-42, 11R, 70-75, 80, 90-93, 100-115, 130-137, or 200-205.

In one embodiment, this invention is directed to a method of treating, suppressing, reducing the incidence, reducing the severity, or inhibiting the progression of skin cancer comprising administering a therapeutically effective amount of a compound of formulas I-VIII, IXa-IXd, X, XIa-XId, XII, XIIIa-XIIId, XIV, XV or its isomer, pharmaceutically acceptable salt, pharmaceutical product, polymorph, hydrate or any combination thereof. In another embodiment, the compound is any one of compounds 11-27, 30-42, 11R, 70-75, 80, 90-93, 100-115, 130-137, or 200-205.

In one embodiment, this invention is directed to a method of treating, suppressing, reducing the incidence, reducing the severity, or inhibiting the progression of ovarian cancer comprising administering a therapeutically effective amount of a compound of formulas I-VIII, IXa-IXd, X, XIa-XId, XII, XIIIa-XIIId, XIV, XV or its isomer, pharmaceutically acceptable salt, pharmaceutical product, polymorph, hydrate or any combination thereof. In another embodiment, the compound is any one of compounds 11-27, 30-42, 11R, 70-75, 80, 90-93, 100-115, 130-137, or 200-205.

In one embodiment, this invention is directed to a method of treating, suppressing, reducing the incidence, reducing the severity, or inhibiting the progression of bladder cancer comprising administering a therapeutically effective amount of a compound of formulas I-VIII, IXa-IXd, X, XIa-XId, XII, XIIIa-XIIId, XIV, XV or its isomer, pharmaceutically acceptable salt, pharmaceutical product, polymorph, hydrate or any combination thereof. In another embodiment, the compound is any one of compounds 11-27, 30-42, 11R, 70-75, 80, 90-93, 100-115, 130-137, or 200-205.

In one embodiment, this invention is directed to a method of treating, suppressing, reducing the incidence, reducing the severity, or inhibiting the progression of lymphoma comprising administering a therapeutically effective amount of a compound of formulas I-VIII, IXa-IXd, X, XIa-XId, XII, XIIIa-XIIId, XIV, XV or its isomer, pharmaceutically acceptable salt, pharmaceutical product, polymorph, hydrate or any combination thereof. In another embodiment, the compound is any one of compounds 11-27, 30-42, 11R, 70-75, 80, 90-93, 100-115, 130-137, or 200-205.

In one embodiment, this invention is directed to a method of treating, suppressing, reducing the incidence, reducing the severity, or inhibiting the progression of liver cancer comprising administering a therapeutically effective amount of a compound of formulas I-VIII, IXa-IXd, X, XIa-XId, XII, XIIIa-XIIId, XIV, XV or its isomer, pharmaceutically acceptable salt, pharmaceutical product, polymorph, hydrate or any combination thereof. In another embodiment, the compound is any one of compounds 11-27, 30-42, 11R, 70-75, 80, 90-93, 100-115, 130-137, or 200-205.

In one embodiment, this invention is directed to a method of treating, suppressing, reducing the incidence, reducing the severity, or inhibiting the progression of renal cancer comprising administering a therapeutically effective amount of a compound of formulas I-VIII, IXa-IXd, X, XIa-XId, XII, XIIIa-XIIId, XIV, XV or its isomer, pharmaceutically acceptable salt, pharmaceutical product, polymorph, hydrate or any combination thereof. In another embodiment, the compound is any one of compounds 11-27, 30-42, 11R, 70-75, 80, 90-93, 100-115, 130-137, or 200-205.

In one embodiment, this invention is directed to a method of treating, suppressing, reducing the incidence, reducing the severity, or inhibiting the progression of osteosarcoma comprising administering a therapeutically effective amount of a compound of formulas I-VIII, IXa-IXd, X, XIa-XId, XII, XIIIa-XIIId, XIV, XV or its isomer, pharmaceutically acceptable salt, pharmaceutical product, polymorph, hydrate or any combination thereof. In another embodiment, the compound is any one of compounds 11-27, 30-42, 11R, 70-75, 80, 90-93, 100-115, 130-137, or 200-205.

In one embodiment, this invention is directed to a method of treating, suppressing, reducing the incidence, reducing the severity, or inhibiting the progression of pancreatic cancer comprising administering a therapeutically effective amount of a compound of formulas I-VIII, IXa-IXd, X, XIa-XId, XII, XIIIa-XIIId, XIV, XV or its isomer, pharmaceutically acceptable salt, pharmaceutical product, polymorph, hydrate or any combination thereof. In another embodiment, the compound is any one of compounds 11-27, 30-42, 11R, 70-75, 80, 90-93, 100-115, 130-137, or 200-205. In one embodiment, this invention is directed to a method of treating, suppressing, reducing the incidence, reducing the severity, or inhibiting the progression of endometrial cancer comprising administering a therapeutically effective amount of a compound of formulas I-VIII, IXa-IXd, X, XIa-XId, XII, XIIIa-XIIId, XIV, XV or its isomer, pharmaceutically acceptable salt, pharmaceutical product, polymorph, hydrate or any combination thereof. In another embodiment, the compound is any one of compounds 11-27, 30-42, 11R, 70-75, 80, 90-93, 100-115, 130-137, or 200-205.

In one embodiment, this invention is directed to a method of treating, suppressing, reducing the incidence, reducing the severity, or inhibiting the progression of lung cancer comprising administering a therapeutically effective amount of a compound of formulas I-VIII, IXa-IXd, X, XIa-XId, XII, XIIIa-XIIId, XIV, XV or its isomer, pharmaceutically acceptable salt, pharmaceutical product, polymorph, hydrate or any combination thereof. In another embodiment, the compound is any one of compounds 11-27, 30-42, 11R, 70-75, 80, 90-93, 100-115, 130-137, or 200-205.

In one embodiment, the lung cancer is non-small cell lung cancer (NSCLC).

In one embodiment, this invention is directed to a method of treating, suppressing, reducing the incidence, reducing the severity, or inhibiting the progression of a central nervous system cancer comprising administering a therapeutically effective amount of a compound of formulas I-VIII, IXa-IXd, X, XIa-XId, XII, XIIIa-XIIId, XIV, XV or its isomer, pharmaceutically acceptable salt, pharmaceutical product, polymorph, hydrate or any combination thereof. In another embodiment, the compound is any one of compounds 11-27, 30-42, 11R, 70-75, 80, 90-93, 100-115, 130-137, or 200-205.

In one embodiment, this invention is directed to a method of treating, suppressing, reducing the incidence, reducing the severity, or inhibiting the progression of colon cancer comprising administering a therapeutically effective amount of a compound of formulas I-VIII, IXa-IXd, X, XIa-XId, XII, XIIIa-XIIId, XIV, XV or its isomer, pharmaceutically acceptable salt, pharmaceutical product, polymorph, hydrate or any combination thereof. In another embodiment, the compound is any one of compounds 11-27, 30-42, 11R, 70-75, 80, 90-93, 100-115, 130-137, or 200-205.

In one embodiment, this invention is directed to a method of treating, suppressing, reducing the incidence, reducing the severity, or inhibiting the progression of melanoma comprising administering a therapeutically effective amount of a compound of formulas I-VIII, IXa-IXd, X, XIa-XId, XII, XIIIa-XIIId, XIV, XV or its isomer, pharmaceutically acceptable salt, pharmaceutical product, polymorph, hydrate or any combination thereof. In another embodiment, the compound is any one of compounds 11-27, 30-42, 11R, 70-75, 80, 90-93, 100-115, 130-137, or 200-205.

In one embodiment, this invention is directed to a method of treating, suppressing, reducing the incidence, reducing the severity, or inhibiting the progression of amyotrophic lateral sclerosis (ALS) in a subject, comprising administering a therapeutically effective amount of the compound of formulas I-VIII, IXa-IXd, X, XIa-XId, XII, XIIIa-XIIId, XIV, XV or its isomer, pharmaceutically acceptable salt, pharmaceutical product, polymorph, hydrate or any combination thereof. In another embodiment, the compound is any one of compounds 11-27, 30-42, 11R, 70-75, 80, 90-93, 100-115, 130-137, or 200-205.

In one embodiment, this invention is directed to a method of treating, suppressing, reducing the incidence, reducing the severity, or inhibiting the progression of uterine fibroids in a subject, comprising administering a therapeutically effective amount of the compound of formulas I-VIII, IXa-IXd, X, XIa-XId, XII, XIIIa-XIIId, XIV, XV or its isomer, pharmaceutically acceptable salt, pharmaceutical product, polymorph, hydrate or any combination thereof. In another embodiment, the compound is any one of compounds 11-27, 30-42, 11R, 70-75, 80, 90-93, 100-115, 130-137, or 200-205.

In one embodiment, this invention provides a method of treating a subject suffering from a wound, or reducing the incidence of, or mitigating the severity of, or enhancing or hastening healing of a wound in a subject, the method comprises administering to said subject a therapeutically effective amount of a compound of formulas I-VIII, IXa-IXd, X, XIa-XId, XII, XIIIa-XIIId, XIV, XV or its isomer, pharmaceutically acceptable salt, pharmaceutical product, polymorph, hydrate or any combination thereof. In another embodiment, the compound is any one of compounds 11-27, 30-42, 11R, 70-75, 80, 90-93, 100-115, 130-137, or 200-205.

In one embodiment, this invention provides a method of treating a subject suffering from a burn, or reducing the incidence of, or mitigating the severity of, or enhancing or hastening healing of a burn in a subject, the method comprises administering to said subject a therapeutically effective amount of a compound of formulas I-VIII, IXa-IXd, X, XIa-XId, XII, XIIIa-XIIId, XIV, XV or its isomer, pharmaceutically acceptable salt, pharmaceutical product, polymorph, hydrate or any combination thereof. In another embodiment, the compound is any one of compounds 11-27, 30-42, 11R, 70-75, 80, 90-93, 100-115, 130-137, or 200-205. Wounds and/or ulcers are normally found protruding from the skin or on a mucosal surface or as a result of an infarction in an organ. A wound may be a result of a soft tissue defect or a lesion or of an underlying condition. In one embodiment, the term "wound" denotes a bodily injury with disruption of the normal integrity of tissue structures. The term is also intended to encompass the terms "sore", "lesion", "necrosis" and "ulcer". In one embodiment, the term "sore" refers to any lesion of the skin or mucous membranes and the term "ulcer" refers to a local defect, or excavation, of the surface of an organ or tissue, which is produced by the sloughing of necrotic tissue. Lesion generally relates to any tissue defect. Necrosis is related to dead tissue resulting from infection, injury, inflammation or infarctions. All of these are encompassed by the term "wound", which denotes any wound at any particular stage in the healing process including the stage before any healing has initiated or even before a specific wound like a surgical incision is made (prophylactic treatment).

Examples of wounds which can be prevented and/or treated in accordance with the present invention are, e.g., aseptic wounds, contused wounds, incised wounds, lacerated wounds, non-penetrating wounds (i.e. wounds in which there is no disruption of the skin but there is injury to underlying structures), open wounds, penetrating wounds, perforating wounds, puncture wounds, septic wounds, subcutaneous wounds, etc. Examples of sores are bed sores, canker sores, chrome sores, cold sores, pressure sores etc.

Examples of ulcers are, e.g., peptic ulcer, duodenal ulcer, gastric ulcer, gouty ulcer, diabetic ulcer, hypertensive ischemic ulcer, stasis ulcer, ulcus cruris (venous ulcer), sublingual ulcer, submucous ulcer, symptomatic ulcer, trophic ulcer, tropical ulcer, veneral ulcer, e.g. caused by gonorrhoea (including urethritis, endocervicitis and proctitis). Conditions related to wounds or sores which may be successfully treated according to the invention are burns, anthrax, tetanus, gas gangrene, scalatina, erysipelas, sycosis barbae, folliculitis, impetigo contagiosa, or impetigo bullosa, etc. There is often a certain overlap between the use of the terms "wound" and "ulcer" and "wound" and "sore" and, furthermore, the terms are often used at random. Therefore as mentioned above, in the present context the term "wounds" encompasses the term "ulcer", "lesion", "sore" and "infarction", and the terms are indiscriminately used unless otherwise indicated.

The kinds of wounds to be treated according to the invention include also: i) general wounds such as, e.g., surgical, traumatic, infectious, ischemic, thermal, chemical and bullous wounds; ii) wounds specific for the oral cavity such as, e.g., post-extraction wounds, endodontic wounds especially in connection with treatment of cysts and abscesses, ulcers and lesions of bacterial, viral or autoimmunological origin, mechanical, chemical, thermal, infectious and lichenoid wounds; herpes ulcers, stomatitis aphthosa, acute necrotising ulcerative gingivitis and burning mouth syndrome are specific examples; and iii) wounds on the skin such as, e.g., neoplasm, burns (e.g. chemical, thermal), lesions (bacterial, viral, autoimmunological), bites and surgical incisions. Another way of classifying wounds is as: i) small tissue loss due to surgical incisions, minor abrasions and minor bites, or as ii) significant tissue loss. The latter group includes ischemic ulcers, pressure sores, fistulae, lacerations, severe bites, thermal burns and donor site wounds (in soft and hard tissues) and infarctions.

In other aspects of the invention, the wound to be prevented and/or treated is selected from the group consisting of aseptic wounds, infarctions, contused wounds, incised wounds, lacerated wounds, non-penetrating wounds, open wounds, penetrating wounds, perforating wounds, puncture wounds, septic wounds and subcutaneous wounds.

Other wounds which are of importance in connection with the present invention are wounds like ischemic ulcers, pressure sores, fistulae, severe bites, thermal burns and donor site wounds.

Ischemic ulcers and pressure sores are wounds, which normally only heal very slowly and especially in such cases an improved and more rapid healing is of course of great importance for the patient. Furthermore, the costs involved in the treatment of patients suffering from such wounds are markedly reduced when the healing is improved and takes place more rapidly.

Donor site wounds are wounds which e.g. occur in connection with removal of hard tissue from one part of the body to another part of the body e.g. in connection with transplantation. The wounds resulting from such operations are very painful and an improved healing is therefore most valuable.

The term "skin" is used in a very broad sense embracing the epidermal layer of the skin and in those cases where the skin surface is more or less injured also the dermal layer of the skin. Apart from the stratum corneum, the epidermal layer of the skin is the outer (epithelial) layer and the deeper connective tissue layer of the skin is called the dermis.

Since the skin is the most exposed part of the body, it is particularly susceptible to various kinds of injuries such as, e.g., ruptures, cuts, abrasions, burns and frostbites or injuries arising from various diseases. Furthermore, much skin is often destroyed in accidents. However, due to the important barrier and physiologic function of the skin, the integrity of the skin is important to the well-being of the individual, and any breach or rupture represents a threat that must be met by the body in order to protect its continued existence.

Apart from injuries on the skin, injuries may also be present in all kinds of tissues (i.e. soft and hard tissues). Injuries on soft tissues including mucosal membranes and/or skin are especially relevant in connection with the present invention.

Healing of a wound on the skin or on a mucosal membrane undergoes a series of stages that results either in repair or regeneration of the skin or mucosal membrane. In recent years, regeneration and repair have been distinguished as the two types of healing that may occur. Regeneration may be defined as a biological process whereby the architecture and function of lost tissue are completely renewed. Repair, on the other hand, is a biological process whereby continuity of disrupted tissue is restored by new tissues which do not replicate the structure and function of the lost ones.

The majority of wounds heal through repair, meaning that the new tissue formed is structurally and chemically unlike the original tissue (scar tissue). In the early stage of the tissue repair, one process which is almost always involved is the formation of a transient connective tissue in the area of tissue injury. This process starts by formation of a new extracellular collagen matrix by fibroblasts. This new extracellular collagen matrix is then the support for a connective tissue during the final healing process. The final healing is, in most tissues, a scar formation containing connective tissue. In tissues which have regenerative properties, such as, e.g., skin and bone, the final healing includes regeneration of the original tissue. This regenerated tissue has frequently also some scar characteristics, e.g. a thickening of a healed bone fracture.

Under normal circumstances, the body provides mechanisms for healing injured skin or mucosa in order to restore the integrity of the skin barrier or the mucosa. The repair process for even minor ruptures or wounds may take a period of time extending from hours and days to weeks. However, in ulceration, the healing can be very slow and the wound may persist for an extended period of time, i.e. months or even years.

Burns are associated with reduced testosterone levels, and hypogonadism is associated with delayed wound healing. In one embodiment, the methods of this invention, provide for treating a subject suffering from a wound or a burn via the administration of a SARD according to this invention. In one embodiment, the SARD promotes resolving of the burn or wound, or in another embodiment, participates in the healing process of a burn or a wound, or in another embodiment, treats a secondary complication of a burn or wound.

In one embodiment, the treatment of burns or wounds further incorporates the use of additional growth factors like epidermal growth factor (EGF), transforming growth factor-$\alpha$ (TGF-$\alpha$), platelet derived growth factor (PDGF), fibroblast growth factors (FGFs) including acidic fibroblast growth factor ($\alpha$-FGF) and basic fibroblast growth factor ($\beta$-FGF), transforming growth factor-$\beta$ (TGF-$\beta$) and insulin like growth factors (IGF-1 and IGF-2), or any combination thereof, which are promoters of wound healing.

Wound healing may be measured by many procedures known in the art, including wound tensile strength, hydroxyproline or collagen content, procollagen expression, and re-epithelialization. As an example, a SARD as described herein is administered orally or topically, at a dosage of about 0.1-1 mg per day. Therapeutic effectiveness is measured as effectiveness in enhancing wound healing. Enhanced wound healing may be measured by known techniques such as decrease in healing time, increase in collagen density, increase in hydroxyproline, reduction in complications, increase in tensile strength, and increased cellularity of scar tissue.

In one embodiment, the term "treating" and its included aspects, refers to the administration to a subject with the indicated disease, disorder or condition, or in some embodiments, to a subject predisposed to the indicated disease, disorder or condition. The term "predisposed to" is to be considered to refer to, inter alia, a genetic profile or familial relationship which is associated with a trend or statistical increase in incidence, severity, etc. of the indicated disease. In some embodiments, the term "predisposed to" is to be considered to refer to inter alia, a lifestyle which is associated with increased risk of the indicated disease. In some embodiments, the term "predisposed to" is to be considered to refer to inter alia, the presence of biomarkers which are associated with the indicated disease, for example, in cancer, the term "predisposed to" the cancer may comprise the presence of precancerous precursors for the indicated cancer.

In some embodiments, the term "reducing the pathogenesis" is to be understood to encompass reducing tissue damage, or organ damage associated with a particular disease, disorder or condition. In another embodiment, the term "reducing the pathogenesis" is to be understood to encompass reducing the incidence or severity of an associated disease, disorder or condition, with that in question. In another embodiment, the term "reducing the pathogenesis" is to be understood to encompass reducing the number of associated diseases, disorders or conditions with the indicated, or symptoms associated thereto.

Pharmaceutical Compositions

In some embodiments, this invention provides methods of use which comprise administering a composition comprising the described compounds. As used herein, "pharmaceutical composition" means a "therapeutically effective amount" of the active ingredient, i.e. the compound of this invention, together with a pharmaceutically acceptable carrier or diluent. A "therapeutically effective amount" as used herein refers to that amount which provides a therapeutic effect for a given condition and administration regimen.

As used herein, the term "administering" refers to bringing a subject in contact with a compound of the present invention. As used herein, administration can be accomplished in vitro, i.e. in a test tube, or in vivo, i.e. in cells or tissues of living organisms, for example humans. In one embodiment, the present invention encompasses administering the compounds of the present invention to a male subject. In one embodiment, the present invention encompasses administering the compounds of the present invention to a female subject.

This invention provides, in other embodiments, pharmaceutical products of the compounds described herein. The term "pharmaceutical product" refers, in other embodiments, to a composition suitable for pharmaceutical use (pharmaceutical composition), for example, as described herein.

The compounds of the invention can be administered alone or as an active ingredient of a formulation. Thus, the present invention also includes pharmaceutical compositions of compounds of formulas I-VIII, IXa-IXd, X, XIa-XId, XII, XIIIa-XIIId, XIV, XV or its isomer, pharmaceutically acceptable salt, pharmaceutical product, polymorph, hydrate or any combination thereof containing, for example, one or more pharmaceutically acceptable carriers.

Numerous standard references are available that describe procedures for preparing various formulations suitable for administering the compounds according to the invention. Examples of potential formulations and preparations are contained, for example, in the Handbook of Pharmaceutical Excipients, American Pharmaceutical Association (current edition); Pharmaceutical Dosage Forms: Tablets (Lieberman, Lachman and Schwartz, editors) current edition, published by Marcel Dekker, Inc., as well as Remington's Pharmaceutical Sciences (Arthur Osol, editor), 1553-1593 (current edition).

The mode of administration and dosage form are closely related to the therapeutic amounts of the compounds or compositions which are desirable and efficacious for the given treatment application.

The pharmaceutical compositions containing a compound of this invention can be administered to a subject by any method known to a person skilled in the art, such as orally, parenterally, intravascularly, paracancerally, transmucosally, transdermally, intramuscularly, intranasally, intravenously, intradermally, subcutaneously, sublingually, intraperitoneally, intraventricularly, intracranially, intravaginally, by inhalation, rectally, intratumorally, or by any means in which the composition can be delivered to tissue (e.g., needle or catheter). Alternatively, topical administration may be desired for application to the dermal, ocular or mucosal surfaces. Another method of administration is via aspiration or aerosol formulation. Further, in another embodiment, the pharmaceutical compositions may be administered topically to body surfaces, and are thus formulated in a form suitable for topical administration. Suitable topical formulations include gels, ointments, creams, lotions, drops and the like. For topical administration, the compounds of this invention or their physiologically tolerated derivatives such as salts, esters, N-oxides, and the like are prepared and applied as solutions, suspensions, or emulsions in a physiologically acceptable diluent with or without a pharmaceutical carrier.

Suitable dosage forms include but are not limited to oral, rectal, sub-lingual, mucosal, nasal, ophthalmic, subcutaneous, intramuscular, intravenous, transdermal, spinal, intrathecal, intra-articular, intra-arterial, sub-arachnoid, bronchial, lymphatic, and intra-uterile administration, and other dosage forms for systemic delivery of active ingredients. In some applications, formulations suitable for oral administration are preferred. In some applications, formulations suitable for topical administration are preferred.

Topical Administration:

In a typical embodiment, the compounds of formulas I-VIII, IXa-IXd, X, XIa-XId, XII, XIIIa-XIIId, XIV or XV are administered topically. Topical administration is especially appropriate for hirsutism, alopecia, acne and excess sebum. The dose will vary, but as a general guideline, the compound will be present in a dermatologically acceptable carrier in an amount of from about 0.01 to 50 w/w %, and more typically from about 0.1 to 10 w/w %. Typically, the dermatological preparation will be applied to the affected area from 1 to 4 times daily. "Dermatologically acceptable" refers to a carrier which may be applied to the skin or hair, and which will allows the drug to diffuse to the site of action. More specifically, it refers to a site where inhibition of androgen receptor or degradation of androgen receptor is desired.

In a further embodiment, the compounds of formulas I-VIII, IXa-IXd, X, XIa-XId, XII, XIIIa-XIIId, XIV or XV are used topically to relieve alopecia, especially androgenic alopecia. Androgens have a profound effect on both hair growth and hair loss. In most body sites, such as the beard and pubic skin, androgens stimulate hair growth by prolonging the growth phase of the hair cycle (anagen) and increasing follicle size. Hair growth on the scalp does not require androgens but, paradoxically, androgens are necessary for the balding on the scalp in genetically predisposed individuals (androgenic alopecia) where there is a progressive decline in the duration of anagen and in hair follicle size. Androgenic alopecia is also common in women where it usually presents as a diffuse hair loss rather than showing the patterning seen in men.

While the compounds of formulas I-VIII, IXa-IXd, X, XIa-XId, XII, XIIIa-XIIId, XIV or XV will most typically be used to alleviate androgenic alopecia, the invention is not limited to this specific condition. The compounds of formulas I-VIII, IXa-IXd, X, XIa-XId, XII, XIIIa-XIIId, XIV or XV may be used to alleviate any type of alopecia. Examples of non-androgenic alopecia include alopecia areata, alopecia due to radiotherapy or chemotherapy, scarring alopecia, stress related alopecia, etc. As used in this application "alopecia" refers to partial or complete hair loss on the scalp.

Thus, the compounds of formulas I-VIII, IXa-IXd, X, XIa-XId, XII, XIIIa-XIIId, XIV or XV can be applied topically to the scalp and hair to prevent, or alleviate balding. Further, the compound of formulas I-VIII, IXa-IXd, X, XIa-XId, XII, XIIIa-XIIId, XIV or XV can be applied topically in order to induce or promote the growth or regrowth of hair on the scalp.

In a further embodiment of the invention, a compound of formulas I-VIII, IXa-IXd, X, XIa-XId, XII, XIIIa-XIIId, XIV or XV is applied topically in order to prevent the growth of hair in areas where such hair growth in not desired. One such use will be to alleviate hirsutism. Hirsutism is excessive hair growth in areas that typically do not have hair (i.e., a female face). Such inappropriate hair growth occurs most commonly in women and is frequently seen at menopause. The topical administration of the compounds of formulas I-VIII, IXa-IXd, X, XIa-XId, XII, XIIIa-XIIId, XIV or XV will alleviate this condition leading to a reduction, or elimination of this inappropriate, or undesired, hair growth.

The compounds of formulas I-VIII, IXa-IXd, X, XIa-XId, XII, XIIIa-XIIId, XIV or XV may also be used topically to decrease sebum production. Sebum is composed of triglycerides, wax esters, fatty acids, sterol esters and squalene. Sebum is produced in the acinar cells of the sebaceous glands and accumulates as these cells age. At maturation, the acinar cells lyse, releasing sebum into the luminal duct so that it may be deposited on the surface of the skin.

In some individuals, an excessive quantity of sebum is secreted onto the skin. This can have a number of adverse consequences. It can exacerbate acne, since sebum is the primary food source for *Propionbacterium acnes*, the causative agent of acne. It can cause the skin to have a greasy appearance, typically considered cosmetically unappealing.

Formation of sebum is regulated by growth factors and a variety of hormones including androgens. The cellular and molecular mechanism by which androgens exert their influence on the sebaceous gland has not been fully elucidated. However, clinical experience documents the impact androgens have on sebum production. Sebum production is significantly increased during puberty, when androgen levels are their highest. Thus the compounds of formulas I-VIII, IXa-IXd, X, XIa-XId, XII, XIIIa-XIIId, XIV or XV inhibit the secretion of sebum and thus reduce the amount of sebum on the surface of the skin. The compounds of formulas I-VIII, IXa-IXd, X, XIa-XId, XII, XIIIa-XIIId, XIV or XV can be used to treat a variety of dermal diseases such as acne or seborrheic dermatitis.

In addition to treating diseases associated with excess sebum production, the compounds of formulas I-VIII, IXa-IXd, X, XIa-XId, XII, XIIIa-XIIId, XIV or XV can also be used to achieve a cosmetic effect. Some consumers believe that they are afflicted with overactive sebaceous glands. They feel that their skin is oily and thus unattractive. These individuals can utilize the compounds of formulas I-VIII, IXa-IXd, X, XIa-XId, XII, XIIIa-XIIId, XIV or XV to decrease the amount of sebum on their skin. Decreasing the secretion of sebum will alleviate oily skin in individuals afflicted with such conditions.

The compounds of formulas I-VIII, IXa-IXd, X, XIa-XId, XII, XIIIa-XIIId, XIV or XV of this invention will typically be administered topically. As used herein, topical refers to application of the compounds of formulas I-VIII, IXa-IXd, X, XIa-XId, XII, XIIIa-XIIId, XIV or XV (and optional carrier) directly to the skin and/or hair. The topical composition according to the present invention can be in the form of solutions, lotions, salves, creams, ointments, liposomes, sprays, gels, foams, roller sticks, and any other formulation routinely used in dermatology.

Thus, a further embodiment relates to cosmetic or pharmaceutical compositions, in particular dermatological compositions, which comprise at least one of the compounds corresponding to formulas I-VIII, IXa-IXd, X, XIa-XId, XII, XIIIa-XIIId, XIV or XV above. Such dermatological compositions will contain from 0.001% to 10% w/w % of the compounds in admixture with a dermatologically acceptable carrier, and more typically, from 0.1 to 5 w/w % of the compounds. Such compositions will typically be applied from 1 to 4 times daily. The reader's attention is directed to *Remington's Pharmaceutical Science*, Edition 17, Mark Publishing Co., Easton, Pa. for a discussion of how to prepare such formulations.

The compositions according to the invention can also consist of solid preparations constituting cleansing soaps or bars. These compositions are prepared according to the usual methods.

The compounds of formulas I-VIII, IXa-IXd, X, XIa-XId, XII, XIIIa-XIIId, XIV or XV can also be used for the hair in the form of aqueous, alcoholic or aqueous-alcoholic solutions, or in the form of creams, gels, emulsions or mousses, or alternatively in the form of aerosol compositions also comprising a propellant under pressure. The composition according to the invention can also be a hair care composition, and in particular a shampoo, a hair-setting lotion, a treating lotion, a styling cream or gel, a dye composition, a lotion or gel for preventing hair loss, etc. The amounts of the various constituents in the dermatological compositions according to the invention are those conventionally used in the fields considered.

The medicinal and cosmetics containing the compounds of formulas I-VIII, IXa-IXd, X, XIa-XId, XII, XIIIa-XIIId, XIV or XV will typically be packaged for retail distribution (i.e., an article of manufacture). Such articles will be labeled and packaged in a manner to instruct the patient how to use the product. Such instructions will include the condition to be treated, duration of treatment, dosing schedule, etc.

Antiandrogens, such as finasteride or flutamide, have been shown to decrease androgen activity or block androgen action in the skin to some extent but suffer from undesirable systemic effects. An alternative approach is to topically apply a selective androgen receptor degrader (SARD) compound to the affected areas. In one embodiment, such a SARD compound would exhibit potent but local inhibition of AR activity. In another embodiment, the SARD compound would exhibit potent but local degradation of AR activity. In another embodiment, the SARD compound would not penetrate to the systemic circulation of the subject. In another embodiment, the SARD compound would be rapidly metabolized upon entry into the blood, limiting systemic exposure.

To prepare such pharmaceutical dosage forms, the active ingredient may be mixed with a pharmaceutical carrier according to conventional pharmaceutical compounding techniques. The carrier may take a wide variety of forms depending on the form of preparation desired for administration.

As used herein "pharmaceutically acceptable carriers or diluents" are well known to those skilled in the art. The carrier or diluent may be a solid carrier or diluent for solid formulations, a liquid carrier or diluent for liquid formulations, or mixtures thereof.

Solid carriers/diluents include, but are not limited to, a gum, a starch (e.g. corn starch, pregeletanized starch), a sugar (e.g., lactose, mannitol, sucrose, dextrose), a cellulosic material (e.g. microcrystalline cellulose), an acrylate (e.g. polymethylacrylate), calcium carbonate, magnesium oxide, talc, or mixtures thereof.

Oral or Parenteral Administration:

In preparing the compositions in oral dosage form, any of the usual pharmaceutical media may be employed. Thus, for liquid oral preparations, such as, for example, suspensions, elixirs and solutions, suitable carriers and additives include water, glycols, oils, alcohols, flavoring agents, preservatives, coloring agents and the like. For solid oral preparations such as, for example, powders, capsules and tablets, suitable carriers and additives include starches, sugars, diluents, granulating agents, lubricants, binders, disintegrating agents and the like. Due to their ease in administration, tablets and capsules represent the most advantageous oral dosage unit form. If desired, tablets may be sugar coated or enteric coated by standard techniques.

For parenteral formulations, the carrier will usually comprise sterile water, though other ingredients, for example, ingredients that aid solubility or for preservation, may be included. Injectable solutions may also be prepared in which case appropriate stabilizing agents may be employed.

In some applications, it may be advantageous to utilize the active agent in a "vectorized" form, such as by encapsulation of the active agent in a liposome or other encapsulant medium, or by fixation of the active agent, e.g., by covalent bonding, chelation, or associative coordination, on a suitable biomolecule, such as those selected from proteins, lipoproteins, glycoproteins, and polysaccharides.

Treatment methods of the present invention using formulations suitable for oral administration may be presented as discrete units such as capsules, cachets, tablets, or lozenges, each containing a predetermined amount of the active ingredient as, for example, a powder or granules. Optionally, a suspension in an aqueous liquor or a non-aqueous liquid may be employed, such as a syrup, an elixir, an emulsion, or a draught.

A tablet may be made by compression or molding, or wet granulation, optionally with one or more accessory ingredients. Compressed tablets may be prepared by compressing in a suitable machine, with the active compound being in a free-flowing form such as a powder or granules which optionally is mixed with, for example, a binder, disintegrant, lubricant, inert diluent, surface active agent, or discharging agent. Molded tablets comprised of a mixture of the powdered active compound with a suitable carrier may be made by molding in a suitable machine.

A syrup may be made by adding the active compound to a concentrated aqueous solution of a sugar, for example sucrose, to which may also be added any accessory ingredient(s). Such accessory ingredient(s) may include flavorings, suitable preservative, agents to retard crystallization of the sugar, and agents to increase the solubility of any other ingredient, such as a polyhydroxy alcohol, for example glycerol or sorbitol.

Formulations suitable for parenteral administration may comprise a sterile aqueous preparation of the active compound, which preferably is isotonic with the blood of the recipient (e.g., physiological saline solution). Such formulations may include suspending agents and thickening agents and liposomes or other microparticulate systems which are designed to target the compound to blood components or one or more organs. The formulations may be presented in unit-dose or multi-dose form.

Parenteral administration may comprise any suitable form of systemic delivery. Administration may for example be intravenous, intra-arterial, intrathecal, intramuscular, subcutaneous, intramuscular, intra-abdominal (e.g., intraperitoneal), etc., and may be effected by infusion pumps (external or implantable) or any other suitable means appropriate to the desired administration modality.

Nasal and other mucosal spray formulations (e.g. inhalable forms) can comprise purified aqueous solutions of the active compounds with preservative agents and isotonic agents. Such formulations are preferably adjusted to a pH and isotonic state compatible with the nasal or other mucous membranes. Alternatively, they can be in the form of finely divided solid powders suspended in a gas carrier. Such formulations may be delivered by any suitable means or method, e.g., by nebulizer, atomizer, metered dose inhaler, or the like.

Formulations for rectal administration may be presented as a suppository with a suitable carrier such as cocoa butter, hydrogenated fats, or hydrogenated fatty carboxylic acids.

Transdermal formulations may be prepared by incorporating the active agent in a thixotropic or gelatinous carrier such as a cellulosic medium, e.g., methyl cellulose or hydroxyethyl cellulose, with the resulting formulation then being packed in a transdermal device adapted to be secured in dermal contact with the skin of a wearer.

In addition to the aforementioned ingredients, formulations of this invention may further include one or more accessory ingredient(s) selected from, for example, diluents, buffers, flavoring agents, binders, disintegrants, surface active agents, thickeners, lubricants, preservatives (including antioxidants), and the like.

The formulations of the present invention can have immediate release, sustained release, delayed-onset release or any other release profile known to one skilled in the art.

It is to be understood that this invention encompasses any embodiment of a compound as described herein, which in some embodiments is referred to as "a compound of this invention".

For administration to mammals, and particularly humans, it is expected that the physician will determine the actual dosage and duration of treatment, which will be most suitable for an individual and can vary with the age, weight and response of the particular individual.

In one embodiment, the methods of this invention may comprise administration of a compound of this invention at various dosages. In one embodiment, a compound of this invention is administered at a dosage of 1-3000 mg per day. In additional embodiments, a compound of this invention is administered at a dose of 1-10 mg per day, 3-26 mg per day, 3-60 mg per day, 3-16 mg per day, 3-30 mg per day, 10-26 mg per day, 15-60 mg, 50-100 mg per day, 50-200 mg per day, 100-250 mg per day, 125-300 mg per day, 20-50 mg per day, 5-50 mg per day, 200-500 mg per day, 125-500 mg per day, 500-1000 mg per day, 200-1000 mg per day, 1000-2000 mg per day, 1000-3000 mg per day, 125-3000 mg per day, 2000-3000 mg per day, 300-1500 mg per day or 100-1000 mg per day. In one embodiment, a compound of this invention is administered at a dosage of 25 mg per day. In one embodiment, a compound of this invention is administered at a dosage of 40 mg per day. In one embodiment, a compound of this invention is administered at a dosage of 50 mg per day. In one embodiment, a compound of this invention is administered at a dosage of 67.5 mg per day. In one embodiment, a compound of this invention is administered at a dosage of 75 mg per day. In one embodiment, a compound of this invention is administered at a dosage of 80 mg per day. In one embodiment, a compound of this invention is administered at a dosage of 100 mg per day. In one embodiment, a compound of this invention is administered at a dosage of 125 mg per day. In one embodiment, a compound of this invention is administered at a dosage of 250 mg per day. In one embodiment, a compound of this invention is administered at a dosage of 300 mg per day. In one embodiment, a compound of this invention is administered at a dosage of 500 mg per day. In one embodiment, a compound of this invention is administered at a dosage of 600 mg per day. In one embodiment, a compound of this invention is administered at a dosage of 1000 mg per day. In one embodiment, a compound of this invention is administered at a dosage of 1500 mg per day. In one embodiment, a compound of this invention is administered at a dosage of 2000 mg per day. In one embodiment, a compound of this invention is administered at a dosage of 2500 mg per day. In one embodiment, a compound of this invention is administered at a dosage of 3000 mg per day. In another embodiment, the compound is any one of compounds 11-27, 30-42, 11R, 70-75, 80, 90-93, 100-115, 130-137, or 200-205.

In one embodiment, the methods of this invention may comprise administration of a compound of this invention at various dosages. In one embodiment, a compound of this invention is administered at a dosage of 3 mg. In additional embodiments, a compound of this invention is administered at a dosage of 10 mg, 30 mg, 40 mg, 50 mg, 80 mg, 100 mg, 120 mg, 125 mg, 200 mg, 250 mg, 300 mg, 450 mg, 500 mg, 600 mg, 900 mg, 1000 mg, 1500 mg, 2000 mg, 2500 mg or 3000 mg. In another embodiment, the compound is any one of compounds 11-27, 30-42, 11R, 70-75, 80, 90-93, 100-115, 130-137, or 200-205.

In one embodiment, the methods of this invention may comprise administration of a compound of this invention at various dosages. In one embodiment, a compound of this invention is administered at a dosage of 0.1 mg/kg/day. In additional embodiments, a compound of this invention is administered at a dosage between 0.2 to 30 mg/kg/day, or 0.2 mg/kg/day, 0.3 mg/kg/day, 1 mg/kg/day, 3 mg/kg/day, 5 mg/kg/day, 10 mg/kg/day, 20 mg/kg/day, 30 mg/kg/day, 50 mg/kg/day or 100 mg/kg/day.

In one embodiment, the methods of this invention provide for the use of a pharmaceutical composition comprising a compound of formulas I-VIII, IXa-IXd, X, XIa-XId, XII, XIIIa-XIIId, XIV or XV or any one of compounds 11-27, 30-42, 11R, 70-75, 80, 90-93, 100-115, 130-137, or 200-205.

In certain embodiment, the pharmaceutical composition is a solid dosage form. In another embodiment, the pharmaceutical composition is a tablet. In another embodiment, the pharmaceutical composition is a capsule. In another embodiment, the pharmaceutical composition is a solution. In another embodiment, the pharmaceutical composition is a transdermal patch.

In one embodiment, use of a compound of this invention or a composition comprising the same, will have utility in inhibiting, suppressing, enhancing or stimulating a desired response in a subject, as will be understood by one skilled in the art. In another embodiment, the compositions may further comprise additional active ingredients, whose activity is useful for the particular application for which the compound of this invention is being administered.

For administration to mammals, and particularly humans, it is expected that the physician will determine the actual dosage and duration of treatment, which will be most suitable for an individual and can vary with the age, weight, genetics and/or response of the particular individual.

In some embodiments, any of the compositions of this invention will comprise a compound of this invention, in any form or embodiment as described herein. In some embodiments, any of the compositions of this invention will consist of a compound of this invention, in any form or embodiment as described herein. In some embodiments, of the compositions of this invention will consist essentially of a compound of this invention, in any form or embodiment as described herein. In some embodiments, the term "comprise" refers to the inclusion of the indicated active agent, such as the compound of this invention, as well as inclusion of other active agents, and pharmaceutically acceptable carriers, excipients, emollients, stabilizers, etc., as are known in the pharmaceutical industry. In some embodiments, the term "consisting essentially of" refers to a composition, whose only active ingredient is the indicated active ingredient, however, other compounds may be included which are for stabilizing, preserving, etc. the formulation, but are not involved directly in the therapeutic effect of the indicated active ingredient. In some embodiments, the term "consisting essentially of" may refer to components which facilitate the release of the active ingredient. In some embodiments, the term "consisting" refers to a composition, which contains the active ingredient and a pharmaceutically acceptable carrier or excipient.

It is to be understood that any use of any of the compounds as herein described may be used in the treatment of any disease, disorder or condition as described herein, and represents an embodiment of this invention. In one embodiment, the compounds are a free base, free acid, non charged or non-complexed compound.

The following examples are presented in order to more fully illustrate the preferred embodiments of the invention. They should in no way, however, be construed as limiting the broad scope of the invention.

EXAMPLES

Example 1

Synthesis of Indole/Pyrrolo-Pyridine SARD Compounds of this Invention

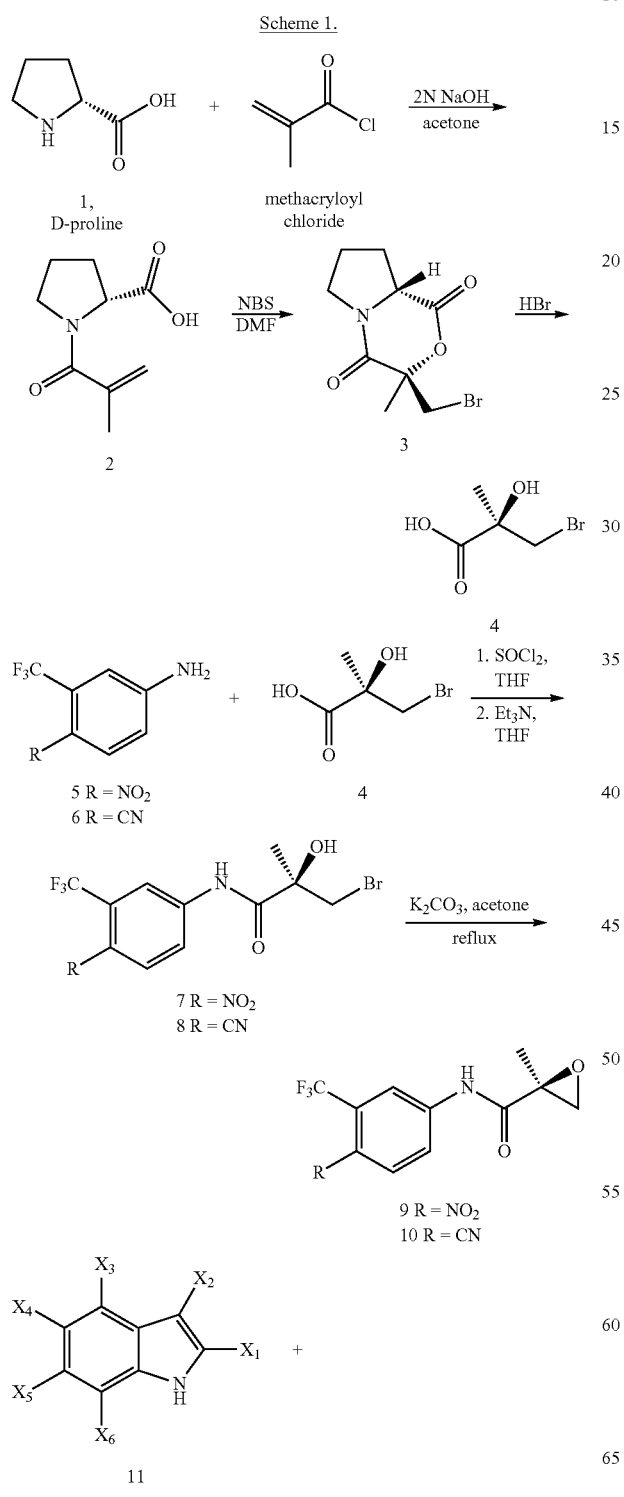

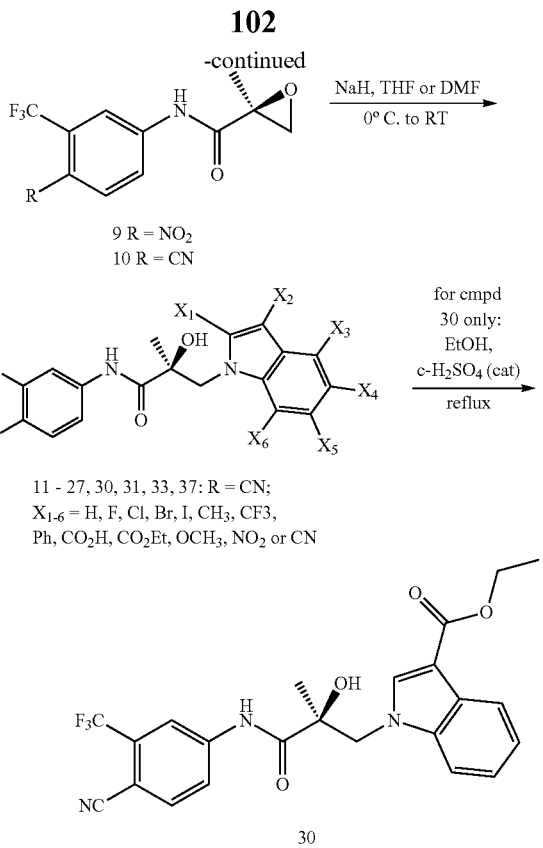

(2R)-1-Methacryloylpyrrolidin-2-carboxylic acid (2)

D-Proline (14.93 g, 0.13 mol) was dissolved in 71 mL of 2 N NaOH and cooled in an ice bath. The resulting alkaline solution was diluted with acetone (71 mL). An acetone solution (71 mL) of methacryloyl chloride (13.56 g, 0.13 mol) and 2 N NaOH solution (71 mL) were simultaneously added over 40 min to the aqueous solution of D-proline in an ice bath. The temperature of the mixture was kept at 10-11° C. during the addition of the methacryloyl chloride. After stirring (3 h, room temperature (RT)), the mixture was evaporated in vacuo at a temperature at 35-45° C. to remove acetone. The resulting solution was washed with ethyl ether and was acidified to pH 2 with concentrated HCl. The acidic mixture was saturated with NaCl and was extracted with EtOAc (100 mL×3). The combined extracts were dried over $Na_2SO_4$, filtered through Celite®, and evaporated in vacuo to give the crude product as a colorless oil. Recrystallization of the oil from ethyl ether and hexanes afforded 16.2 g (68%) of the desired compound as colorless crystals: mp 102.1-103.4° C. (Marhefka, C. A.; Moore, B. M., 2nd; Bishop, T. C.; Kirkovsky, L.; Mukherjee, A.; Dalton, J. T.; Miller, D. D. Homology modeling using multiple molecular dynamics simulations and docking studies of the human androgen receptor ligand binding domain bound to testosterone and nonsteroidal ligands. *J Med Chem* 2001, 44, 1729-40: mp 102.5-103.5° C.); the NMR spectrum of this compound demonstrated the existence of two rotamers of the title compound. $^1$H NMR (300 MHz, DMSO-$d_6$) δ 5.28 (s) and 5.15 (s) for the first rotamer, 5.15 (s) and 5.03 (s) for the second rotamer (totally 2H for both rotamers, vinyl $CH_2$), 4.48-4.44 for the first rotamer, 4.24-4.20 (m) for the second rotamer (totally 1H for both rotamers, CH at the chiral center), 3.57-3.38 (m, 2H, $CH_2$), 2.27-2.12 (1H, CH), 1.97-

1.72 (m, 6H, CH$_2$, CH, Me); $^{13}$C NMR (75 MHz, DMSO-d$_6$) δ for major rotamer 173.3, 169.1, 140.9, 116.4, 58.3, 48.7, 28.9, 24.7, 19.5: for minor rotamer 174.0, 170.0, 141.6, 115.2, 60.3, 45.9, 31.0, 22.3, 19.7; IR (KBr) 3437 (OH), 1737 (C=O), 1647 (CO, COOH), 1584, 1508, 1459, 1369, 1348, 1178 cm$^{-1}$; [α]$_D^{26}$ +80.8° (c=1, MeOH); Anal. Calcd. for C$_9$H$_{13}$NO$_3$: C, 59.00; H, 7.15; N, 7.65. Found: C, 59.13; H, 7.19; N, 7.61.

(3R,8aR)-3-Bromomethyl-3-methyl-tetrahydro-pyrrolo[2,1-c][1,4]oxazine-1,4-dione (3)

A solution of NBS (23.5 g, 0.132 mol) in 100 mL of DMF was added dropwise to a stirred solution of the (2R)-1-methacryloylpyrrolidin-2-carboxylic acid (2) (16.1 g, 88 mmol) in 70 mL of DMF under argon at RT, and the resulting mixture was stirred 3 days. The solvent was removed in vacuo, and a yellow solid was precipitated. The solid was suspended in water, stirred overnight at RT, filtered, and dried to give 18.6 g (81%) (smaller weight when dried ~34%) of the titled bromolactone (3) as a yellow solid: mp 158.1-160.3° C.; $^1$H NMR (300 MHz, DMSO-d$_6$) δ 4.69 (dd, J=9.6 Hz, J=6.7 Hz, 1H, CH at the chiral center), 4.02 (d, J=11.4 Hz, 1H, CHH$_a$), 3.86 (d, J=11.4 Hz, 1H, CHH$_b$), 3.53-3.24 (m, 4H, CH$_2$), 2.30-2.20 (m, 1H, CH), 2.04-1.72 (m, 3H, CH$_2$ and CH), 1.56 (s, 2H, Me); $^{13}$C NMR (75 MHz, DMSO-d$_6$) δ 167.3, 163.1, 83.9, 57.2, 45.4, 37.8, 29.0, 22.9, 21.6; IR (KBr) 3474, 1745 (C=O), 1687 (C=O), 1448, 1377, 1360, 1308, 1227, 1159, 1062 cm$^{-1}$; [α]$_D^{26}$ +124.5° (c=1.3, chloroform); Anal. Calcd. for C$_9$H$_{12}$BrNO$_3$: C, 41.24; H, 4.61; N, 5.34. Found: C, 41.46; H, 4.64; N, 5.32.

(2R)-3-Bromo-2-hydroxy-2-methylpropanoic acid (4)

A mixture of bromolactone (3) (18.5 g, 71 mmol) in 300 mL of 24% HBr was heated at reflux for 1 h. The resulting solution was diluted with brine (200 mL), and was extracted with ethyl acetate (100 mL×4). The combined extracts were washed with saturated NaHCO$_3$ (100 mL×4). The aqueous solution was acidified with concentrated HCl to pH=1, which, in turn, was extracted with ethyl acetate (100 mL×4). The combined organic solution was dried over Na$_2$SO$_4$, filtered through Celite®, and evaporated in vacuo to dryness. Recrystallization from toluene afforded 10.2 g (86%) of the desired compound as colorless crystals: mp 110.3-113.8° C.; $^1$H NMR (300 MHz, DMSO-d$_6$) δ 3.63 (d, J=10.1 Hz, 1H, CHH$_a$), 3.52 (d, J=10.1 Hz, 1H, CHH$_b$), 1.35 (s, 3H, Me); IR (KBr) 3434 (OH), 3300-2500 (COOH), 1730 (C=O), 1449, 1421, 1380, 1292, 1193, 1085 cm$^{-1}$; [α]$_D^{26}$ +10.5° (c=2.6, MeOH); Anal. Calcd. for C$_4$H$_7$BrO$_3$: C, 26.25; H, 3.86. Found: C, 26.28; H, 3.75.

(2R)-3-Bromo-N-[4-cyano-3-(trifluoromethyl)phenyl]-2-hydroxy-2-methylpropanamide (8)

Thionyl chloride (46.02 g, 0.39 mol) was added dropwise to a cooled solution (less than 4° C.) of (R)-3-bromo-2-hydroxy-2-methylpropanoic acid (4) (51.13 g, 0.28 mol) in 300 mL of THF under an argon atmosphere. The resulting mixture was stirred for 3 h under the same condition. To this was added Et$_3$N (39.14 g, 0.39 mol) and stirred for 20 min under the same condition. After 20 min, 5-amino-2-cyanobenzotrifluoride (40.0 g, 0.21 mol), 400 mL of THF were added and then the mixture was allowed to stir overnight at RT. The solvent was removed under reduced pressure to give a solid which was treated with 300 mL of H$_2$O, extracted with EtOAc (2×400 mL). The combined organic extracts were washed with saturated NaHCO$_3$ solution (2×300 mL) and brine (300 mL). The organic layer was dried over MgSO$_4$ and concentrated under reduced pressure to give a solid which was purified from column chromatography using CH$_2$Cl$_2$/EtOAc (80:20) to give a solid. This solid was recrystallized from CH$_2$Cl$_2$/hexane to give 55.8 g (73.9%) of (2R)-3-bromo-N-[4-cyano-3-(trifluoromethyl)phenyl]-2-hydroxy-2-methylpropanamide (8) as a light-yellow solid. M.p. 134.0-136.5° C.; $^1$H NMR (CDCl$_3$/TMS) δ 1.66 (s, 3H, CH$_3$), 3.11 (s, 1H, OH), 3.63 (d, J=10.8 Hz, 1H, CH$_2$), 4.05 (d, J=10.8 Hz, 1H, CH$_2$), 7.85 (d, J=8.4 Hz, 1H, ArH), 7.99 (dd, J=2.1, 8.4 Hz, 1H, ArH), 8.12 (d, J=2.1 Hz, 1H, ArH), 9.04 (bs, 1H, NH). Calculated Mass: 349.99, [M−H]$^-$ 349.0.

Structures of Compounds Synthesized with Different Substituents: (R)— or (S)—N-(4-cyano-3-(trifluoromethyl)-phenyl)-3-(Substituted-1H-indol-1-yl)-2-hydroxy-2-methylpropanamides (11-27, 11R, 30-32, and 80)

Compounds 11-27, 11R, 30-32, and 80 were prepared by the general procedures as shown in Scheme 1 or Scheme 2, or Example 2. 11R was synthesized by same procedures as the other compounds but using L-proline instead of D-proline as a starting material. And also, 19 was isolated from the synthetic product of 11 as a by-product.

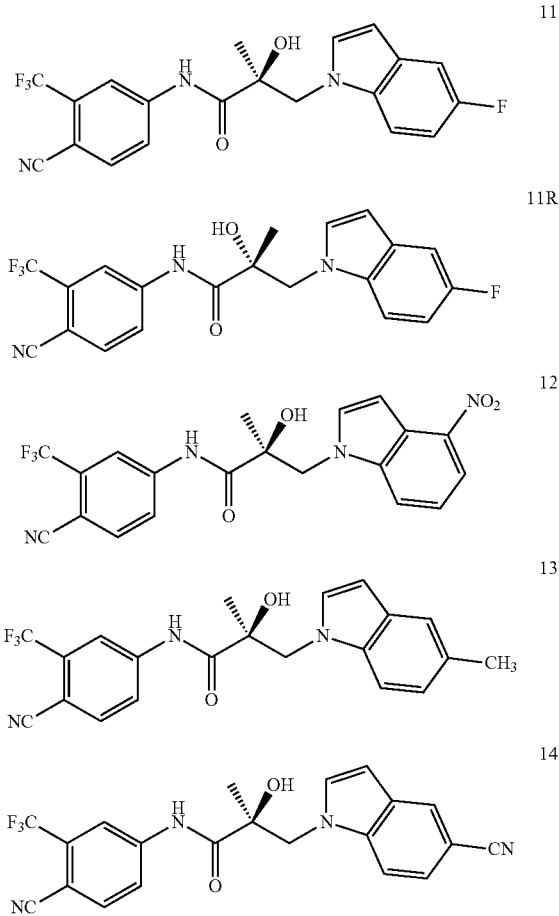

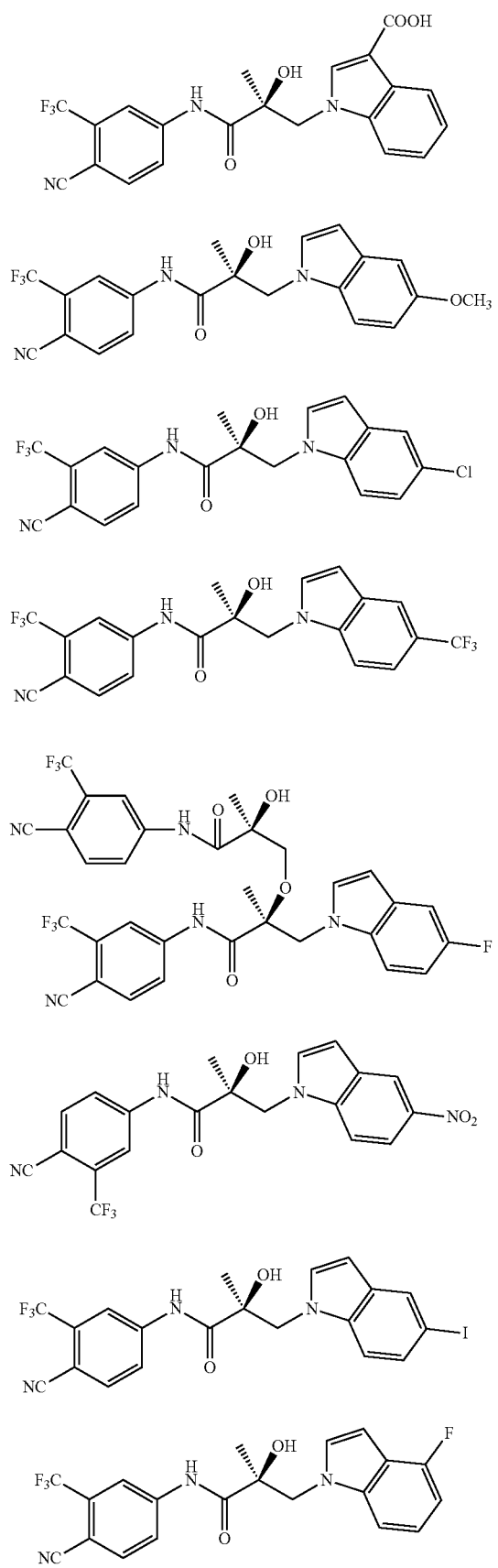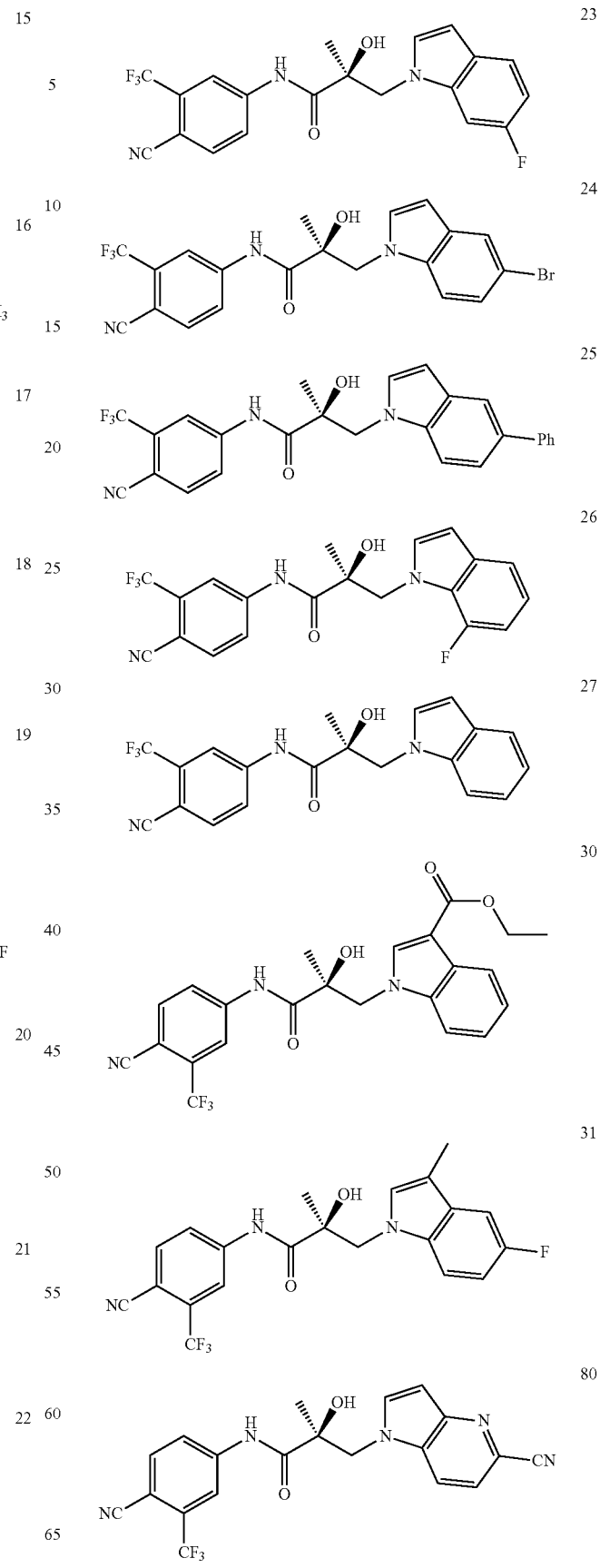

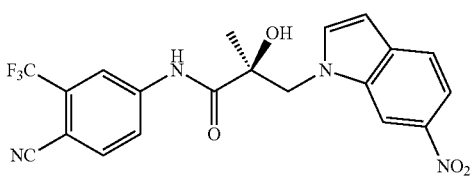

General Synthetic Procedure of Compounds 11-27, 11R, 30-32, and 80.

Step 1.

Preparation of (S)—N-(4-cyano-3-(trifluoromethyl)phenyl)-2-methyloxirane-2-carboxamide (10) in THF: A mixture of hydroxylbromide 8 (1.0 g, 2.84 mmol) and potassium carbonate (790 mg, 5.70 mmol) in 60 mL acetone was heated to reflux for 30 min. After complete conversion of starting bromide 8 to desired epoxide 10 as monitored by TLC, the solvent was evaporated under reduced pressure to give yellowish residue, which was poured into 20 mL of anhydrous EtOAc. The solution was filtered through Celite® pad to remove $K_2CO_3$ residue and condensed under reduced pressure to give a yellowish solid of epoxide 10, which was dissolved in 5 mL of anhydrous THF to prepare a solution of epoxide 10 in THF. The resulting solution was directly used as next reactant without analysis.

Step 2. NaH of 60% dispersion in mineral oil (228 mg, 5.7 mmol) was added in 30 mL of anhydrous THF solvent into a 100 mL dried two necked round bottom flask equipped with a dropping funnel and substituted indole/pyrrolo-pyridine (2.84 mmol) was added to the solution under argon atmosphere in ice-water bath, and the resulting solution was stirred for 30 min in an ice-water bath. Into the flask, the prepared solution of epoxide 10 (2.84 mmol in THF) was added through dropping funnel under argon atmosphere at the ice-water bath and stirred overnight at RT. After adding 1 mL of $H_2O$ (1N HCl in case for compound 15), the reaction mixture was condensed under reduced pressure, and then dispersed into 50 mL of EtOAc, washed with 50 mL (×2) water, brine, dried over anhydrous $MgSO_4$, and evaporated to dryness. The mixture was purified with flash column chromatography as an eluent EtOAc/hexane, and then the condensed compounds were then recrystallized in EtOAc/hexane to give any one of the target products 11-27, 11R, 30-32, and 80.

(S)—N-(4-Cyano-3-(trifluoromethyl)phenyl)-3-(5-fluoro-1H-indol-1-yl)-2-hydroxy-2-methylpropanamide (11)

Yield 68%; White solid. MS (ESI): 404.0 [M−H]⁻; 428.2 [M+Na]⁺; mp 147.5-148.9° C.; ¹H NMR (CDCl₃, 400 MHz) δ 8.77 (bs, 1H, NH), 7.90 (d, J=1.7 Hz, 1H), 7.78-7.76 (m, 2H), 7.38 (dd, J=9.0, 4.2 Hz, 1H), 7.23 (dd, J=9.3, 2.5 Hz, 1H), 7.19 (d, J=3.2 Hz, 1H), 6.98 (dt, J=9.0, 2.5 Hz, 1H), 6.50 (d, J=3.2 Hz, 1H), 4.62 (d, J=14.8 Hz, 1H), 4.38 (d, J=14.8 Hz, 1H), 2.49 (bs, 1H, OH), 1.61 (s, 3H).

(S)—N-(4-Cyano-3-(trifluoromethyl)phenyl)-2-hydroxy-2-methyl-3-(4-nitro-1H-indol-1-yl)propanamide (12)

Yield 41%; Yellowish solid; mp 152.9-154.8° C.; MS (ESI): 430.9 [M−H]⁻; ¹H NMR (CDCl₃, 400 MHz) δ 8.88 (bs, 1H), 8.04 (d, J=1.6 Hz, 1H), 7.89 (s, 1H), 7.79-7.75 (m, 3H), 7.31 (m, 1H), 7.26 (m, 2H), 4.69 (d, J=14.8 Hz, 1H), 4.42 (d, J=14.8 Hz, 1H), 2.43 (bs, 1H, OH), 1.63 (s, 3H).

(S)—N-(4-Cyano-3-(trifluoromethyl)phenyl)-2-hydroxy-2-methyl-3-(5-methyl-1H-indol-1-yl)propanamide (13)

Yield 59%; Yellowish solid: mp 148.6-150.2° C.; MS (ESI): 400.0 [M−H]⁻; 424.2 [M+Na]⁺; ¹H NMR (CDCl₃, 400 MHz) δ 8.72 (bs, 1H), 7.86 (d, J=2.0 Hz, 1H), 7.78 (m, 2H), 7.31 (d, J=8.8 Hz, 1H), 6.84 (dd, J=21.2, 3.2 Hz, 1H), 6.84 (dd, J=8.8, 2.4 Hz, 1H), 6.43 (d, J=2.4 Hz, 1H), 6.63 (d, J=14.8 Hz, 1H), 4.31 (d, J=14.8 Hz, 1H), 3.82 (s, 3H), 2.51 (s, 1H, OH), 1.60 (s, 3H).

(S)-3-(5-Cyano-1H-indol-1-yl)-N-(4-cyano-3-(trifluoromethyl)phenyl)-2-hydroxy-2-methylpropanamide (14)

Yield 54%; White solid: MS (ESI): 411.0 [M−H]⁻; ¹H NMR (CDCl₃, 400 MHz) δ 8.85 (bs, 1H), 7.91 (d, J=1.6 Hz, 1H), 7.85 (s, 1H), 7.80-7.73 (m, 2H), 7.53 (d, J=8.6 Hz, 1H), 7.34 (d, J=8.6 Hz, 1H), 7.26 (m, 1H), 6.59 (d, J=3.2 Hz, 1H), 4.68 (d, J=14.8 Hz, 1H), 4.40 (d, J=14.8 Hz, 1H), 2.94 (bs, 1H, OH), 1.64 (s, 3H).

(S)-1-(3-((4-Cyano-3-(trifluoromethyl)phenyl)amino)-2-hydroxy-2-methyl-3-oxopropyl)-1H-indole-3-carboxylic acid (15)

Yield 31%; Light yellowish solid: MS (ESI): 429.9 [M−H]⁻; ¹H NMR (CDCl₃, 400 MHz) δ 9.10 (bs, 1H), 8.11 (m, 1H), 8.01 (s, 1H), 7.91 (m, 2H), 7.84 (d, J=1.6 Hz, 1H), 7.74-7.67 (m, 2H), 7.51-7.49 (m, 1H), 7.22-7.20 (m, 1H), 4.62 (d, J=14.8 Hz, 1H), 4.43 (d, J=14.8 Hz, 1H), 2.94 (s, 1H, OH), 1.61 (s, 3H).

(S)—N-(4-Cyano-3-(trifluoromethyl)phenyl)-2-hydroxy-3-(5-methoxy-1H-indol-1-yl)-2-methylpropanamide (16)

Yield 53%; Brown solid: MS (ESI): 416.0 [M−H]⁻; 418.2 [M+H]⁺; 440.2 [M+Na]⁺; ¹H NMR (CDCl₃, 400 MHz) δ 8.74 (bs, 1H), 7.87 (d, J=2.2 Hz, 1H), 7.81-7.75 (m, 2H), 7.30 (d, J=3.2 Hz, 1H), 7.09 (d, J=3.2 Hz, 1H), 7.03 (d, J=2.2 Hz, 1H), 6.43 (d, J=2.8 Hz, 1H), 4.63 (d, J=14.8 Hz, 1H), 4.30 (d, J=14.8 Hz, 1H), 3.82 (s, 3H), 2.60 (bs, 1H, OH), 1.62 (s, 3H).

(S)-3-(5-Chloro-1H-indol-1-yl)-N-(4-cyano-3-(trifluoromethyl)phenyl)-2-hydroxy-2-methylpropanamide (17)

Yield 62%; White solid: MS (ESI): 420.0 [M−H]⁻; ¹H NMR (CDCl₃, 400 MHz) δ 8.85 (bs, 1H), 7.88 (d, J=1.6 Hz, 1H), 7.78 (m, 2H), 7.62 (s, 1H), 7.32 (d, J=3.2 Hz, 1H), 7.12 (m, 2H), 6.65 (d, J=3.2 Hz, 1H), 4.65 (d, J=14.8 Hz, 1H), 4.31 (d, J=14.8 Hz, 1H), 2.52 (bs, 1H, OH), 1.61 (s, 3H).

(S)—N-(4-Cyano-3-(trifluoromethyl)phenyl)-2-hydroxy-2-methyl-3-(5-(trifluoromethyl)-1H-indol-1-yl)propanamide (18)

Yield 57%; White solid: MS (ESI): 453.9 [M−H]⁻; ¹H NMR (CDCl₃, 400 MHz) δ 8.80 (bs, 1H), 7.83 (d, J=1.6 Hz, 1H), 7.75 (m, 2H), 7.51 (d, J=3.2 Hz, 1H), 7.41 (m, 1H), 7.21 (m, 1H), 6.62 (d, J=3.2 Hz, 1H), 4.68 (d, J=14.8 Hz, 1H), 4.38 (d, J=14.8 Hz, 1H), 2.49 (s, 1H, OH), 1.61 (s, 3H).

(S)—N-(4-Cyano-3-(trifluoromethyl)phenyl)-2-((S)-3-((4-cyano-3-(trifluoromethyl)phenyl)amino)-2-hydroxy-2-methyl-3-oxopropoxy)-3-(5-fluoro-1H-indol-1-yl)-2-methylpropanamide (19)

White solid: MS (ESI): 673.9 [M−H]⁻; 698.2 [M+Na]⁺; ¹H NMR (CDCl₃, 400 MHz) δ 9.14 (bs, 1H), 8.62 (bs, 1H), 8.16 (d, J=1.8 Hz, 1H), 8.06 (dd, J=8.8, 1.8 Hz, 1H), 7.94 (d, J=1.8 Hz, 1H), 7.84 (d, J=8.8 Hz, 1H), 7.75 (d, J=8.8 Hz, 1H), 7.55 (dd, J=8.4, 2.0 Hz, 1H), 7.45 (s, 1H), 7.35 (m, 1H), 7.24 (m, 1H), 6.98 (d, J=3.2 Hz, 1H), 6.24 (d, J=3.2 Hz, 1H), 4.54 (d, J=14.8 Hz, 1H), 4.36 (d, J=14.8 Hz, 1H), 3.96 (d, J=8.8 Hz, 1H), 3.55 (d, J=8.8 Hz, 1H), 2.76 (s, 1H, OH), 1.69 (s, 3H), 1.38 (s, 3H).

(S)—N-(4-Cyano-3-(trifluoromethyl)phenyl)-2-hydroxy-2-methyl-3-(5-nitro-1H-indol-1-yl)propanamide (20)

Yield 47%; Yellowish solid: MS (ESI): 431.0 [M−H]⁻; ¹H NMR (Acetone-d₆, 400 MHz) δ 9.68 (bs, 1H, NH), 8.35 (d, J=2.0 Hz, 1H), 8.16 (s, 1H), 8.01 (m, 1H), 7.88-7.81 (m, 2H), 7.58 (d, J=8.8 Hz, 1H), 7.38 (d, J=3.4 Hz, 1H), 6.58 (d, J=3.4 Hz, 1H), 5.49 (s, 1H, OH), 4.66 (d, J=14.8 Hz, 1H), 4.38 (d, J=14.8 Hz, 1H), 1.50 (s, 3H).

(S)—N-(4-Cyano-3-(trifluoromethyl)phenyl)-2-hydroxy-3-(5-iodo-1H-indol-1-yl)-2-methylpropanamide (21)

Yield 48%; MS (ESI) 511.9 [M−H]⁻; ¹H NMR (CDCl₃, 400 MHz) δ 8.71 (bs, 1H, NH), 7.91 (d, J=1.6 Hz, 1H), 7.74 (m, 2H), 7.43 (dd, J=8.8, 1.6 Hz, 1H), 7.21 (d, J=8.8 Hz, 1H), 7.08 (d, J=3.2 Hz, 1H), 6.44 (d, J=3.2 Hz, 1H), 4.62 (d, J=15.0 Hz, 1H), 4.32 (d, J=15.0 Hz, 1H), 2.44 (bs, 1H, OH), 1.61 (s, 3H).

(S)—N-(4-Cyano-3-(trifluoromethyl)phenyl)-3-(4-fluoro-1H-indol-1-yl)-2-hydroxy-2-methylpropanamide (22)

Yield 48%; MS (ESI) 511.9 [M−H]⁻; ¹H NMR (CDCl₃, 400 MHz) δ 8.71 (bs, 1H, NH), 7.91 (d, J=1.6 Hz, 1H), 7.74 (m, 2H), 7.43 (dd, J=8.8, 1.6 Hz, 1H), 7.21 (d, J=8.8 Hz, 1H), 7.08 (d, J=3.2 Hz, 1H), 6.44 (d, J=3.2 Hz, 1H), 4.62 (d, J=15.0 Hz, 1H), 4.32 (d, J=15.0 Hz, 1H), 2.44 (bs, 1H, OH), 1.61 (s, 3H).

(S)—N-(4-Cyano-3-(trifluoromethyl)phenyl)-3-(6-fluoro-1H-indol-1-yl)-2-hydroxy-2-methylpropanamide (23)

Yield 48%; White solid; MS (ESI) 404.0 [M−H]⁻; ¹H NMR (CDCl₃, 400 MHz) δ 8.79 (bs, 1H, NH), 7.89 (d, J=1.6 Hz, 1H), 7.83 (d, J=8.4 Hz, 1H), 7.77 (d, J=8.0 Hz, 1H), 7.51 (dd, J=8.4, 5.2 Hz, 1H), 7.14 (dd, J=10.0, 2.0 Hz, 1H), 7.11 (d, J=3.2 Hz, 1H), 6.87 (dt, J=8.8, 2.0 Hz, 1H), 6.51 (d, J=3.2 Hz, 1H), 4.62 (d, J=14.8 Hz, 1H), 4.32 (d, J=14.8 Hz, 1H), 2.56 (bs, 1H, OH), 1.65 (s, 3H).

(S)-3-(5-Bromo-1H-indol-1-yl)-N-(4-cyano-3-(trifluoromethyl)phenyl)-2-hydroxy-2-methylpropanamide (24)

Yield; 71%; MS (ESI) 465.1 [M−H]⁻; ¹H NMR (CDCl₃, 400 MHz) d 8.73 (bs, 1H, NH), 7.88 (s, 1H), 7.74 (d, J=1.8 Hz, 1H), 7.69 (d, J=1.8 Hz, 1H), 7.30 (d, J=8.8 Hz, 1H), 7.24 (m, 1H), 7.24 (dd, J=8.8, 2.0 Hz, 1H), 7.13 (d, J=3.2 Hz, 1H), 6.45 (d, J=3.2 Hz, 1H), 4.39 (d, J=14.8 Hz, 1H), 2.60 (bs, 1H, OH), 1.65 (s, 3H).

(S)—N-(4-Cyano-3-(trifluoromethyl)phenyl)-2-hydroxy-3-(1H-indol-1-yl)-2-methylpropanamide (27)

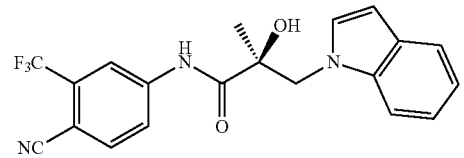

Yield 55%; Light brown solid; MS (ESI) 358.9 [M−H]⁻; ¹H NMR (CDCl₃, 400 MHz) δ 8.67 (bs, 1H, NH), 7.96 (dd, J=8.4, 2.0 Hz, 1H), 7.80 (s, 1H), 7.71-7.65 (m, 2H), 7.51 (d, J=8.0 Hz, 1H), 7.35 (d, J=8.0 Hz, 1H), 7.12 (t, J=8.0 Hz, 1H), 7.02 (m, 1H), 6.45 (d, J=3.2 Hz, 1H), 4.58 (d, J=14.8 Hz, 1H), 4.30 (d, J=14.8 Hz, 1H), 2.50 (bs, 1H, OH), 1.54 (s, 3H).

Preparation of 30 from 15:

(S)-Ethyl 1-(3-((4-cyano-3-(trifluoromethyl)phenyl)amino)-2-hydroxy-2-methyl-3-oxopropyl)-1H-indole-3-carboxylate (30)

To a solution of carboxylic acid 15 (200 mg, 0.46 mmol) in absolute ethanol of 10 mL was added dropwise a catalytic amount of c-H₂SO₄ under argon atmosphere. The solution was heated to reflux for 30 min and cooled down to room temperature. The solution was concentrated under reduced pressure and dispersed in EtOAc and then washed with water. The resulting solution was dried over anhydrous Na₂SO₄ and purified with flash column chromatography as an eluent EtOAc/hexane (1/2, v/v) to give the title compound.

Yield; 92%; MS (ESI) r/z 458.1 [M−H]⁻; 482.4 [M+Na]⁺; ¹H NMR (400 MHz, CDCl₃) δ 8.86 (bs, 1H, NH), 8.00 (m, 2H), 7.81 (s, 1H), 7.65 (s, 2H), 7.46 (d, J=8.0 Hz, 1H), 7.24-7.18 (m, 2H), 4.65 (d, J=14.4 Hz, 1H), 4.39 (d, J=14.4 Hz, 1H), 4.36 (bs, 1H, OH), 4.23-4.11 (m, 2H), 1.66 (s, 3H), 1.35 (t, J=7.2 Hz, 3H).

(S)—N-(4-Cyano-3-(trifluoromethyl)phenyl)-3-(5-fluoro-3-methyl-1H-indol-1-yl)-2-hydroxy-2-methylpropanamide (31)

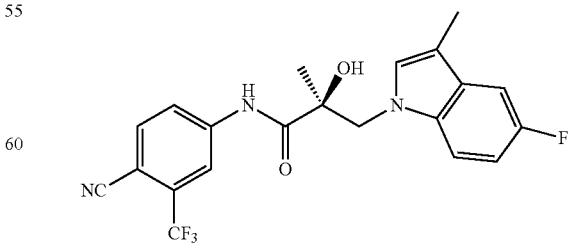

Yield; 64%; MS (ESI) m/z 418.1 [M H]⁻; ¹H NMR (400 MHz, CDCl₃) δ 8.85 (bs, 1H, NH), 7.86 (m, 1H), 7.81-7.74

(m, 2H), 7.29 (dd, J=9.0, 4.0 Hz, 1H), 7.14 (dd, J=9.0, 2.4 Hz, 1H), 6.92 (m, 2H), 4.60 (d, J=15.2 Hz, 1H), 4.27 (d, J=15.2 Hz, 1H), 2.22 (s, 3H), 1.57 (s, 3H).

(S)-3-(5-Cyano-1H-pyrrolo[3,2-b]pyridin-1-yl)-N-(4-cyano-3-(trifluoromethyl)phenyl)-2-hydroxy-2-methylpropanamide (80)

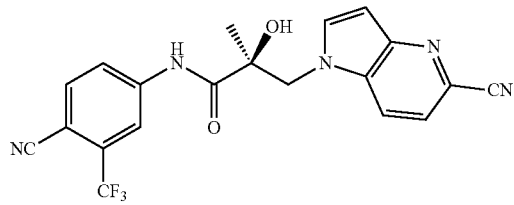

Yield; 67%; MS (ESI) r/z 412.1 [M−H]$^-$; 436.1 [M+Na]$^+$; $^1$H NMR (400 MHz, acetone-d$_6$) δ 9.84 (bs, 1H, NH), 8.31 (s, 1H), 8.14 (m, 2H), 8.01 (m, 1H), 7.81 (d, J=2.8 Hz, 1H), 7.60 (d, J=8.4 Hz, 1H), 6.67 (d, J=2.8 Hz, 1H), 5.64 (bs, 1H), 4.84 (d, J=14.8 Hz, 1H), 4.52 (d, J=14.8 Hz, 1H), 1.66 (s, 3H).

(S)—N-(4-Cyano-3-(trifluoromethyl)phenyl)-2-hydroxy-2-methyl-3-(6-nitro-1H-indol-1-yl)propanamide (32)

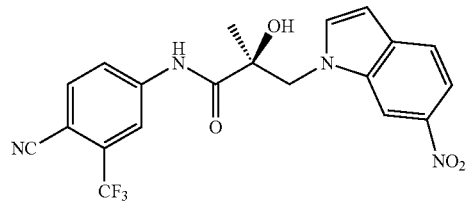 [SMILES: C[C@](O)(Cn1ccc2ccc([N+](=O)[O-])cc21)C(=O)Nc1ccc(C#N)c(C(F)(F)F)c1]

Yield; 31%; MS (ESI) m/z 431.1 [M−H]$^-$; $^1$H NMR (400 MHz, CDCl$_3$) δ 8.87 (bs, 1H, NH), 8.53 (m, 1H), 8.01 (dd, J=8.8, 2.0 Hz, 1H), 7.92 (d, J=2.0 Hz, 1H), 7.86 (dd, J=8.4, 2.0 Hz, 1H), 7.78 (d, J=8.4 Hz, 1H), 7.64 (d, J=8.8 Hz, 1H), 7.43 (d, J=3.0 Hz, 1H), 6.61 (d, J=3.0 Hz, 1H), 4.76 (d, J=14.8 Hz, 1H), 4.48 (d, J=14.8 Hz, 1H), 3.14 (s, 1H, OH), 1.74 (s, 3H).

(R)—N-(4-Cyano-3-(trifluoromethyl)phenyl)-3-(5-fluoro-1H-indol-1-yl)-2-hydroxy-2-methylpropanamide (11R)

11R was synthesized by the same procedures as the other compounds but using L-proline instead of D-proline as a starting material.

Scheme 2:

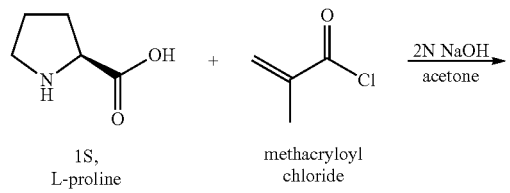

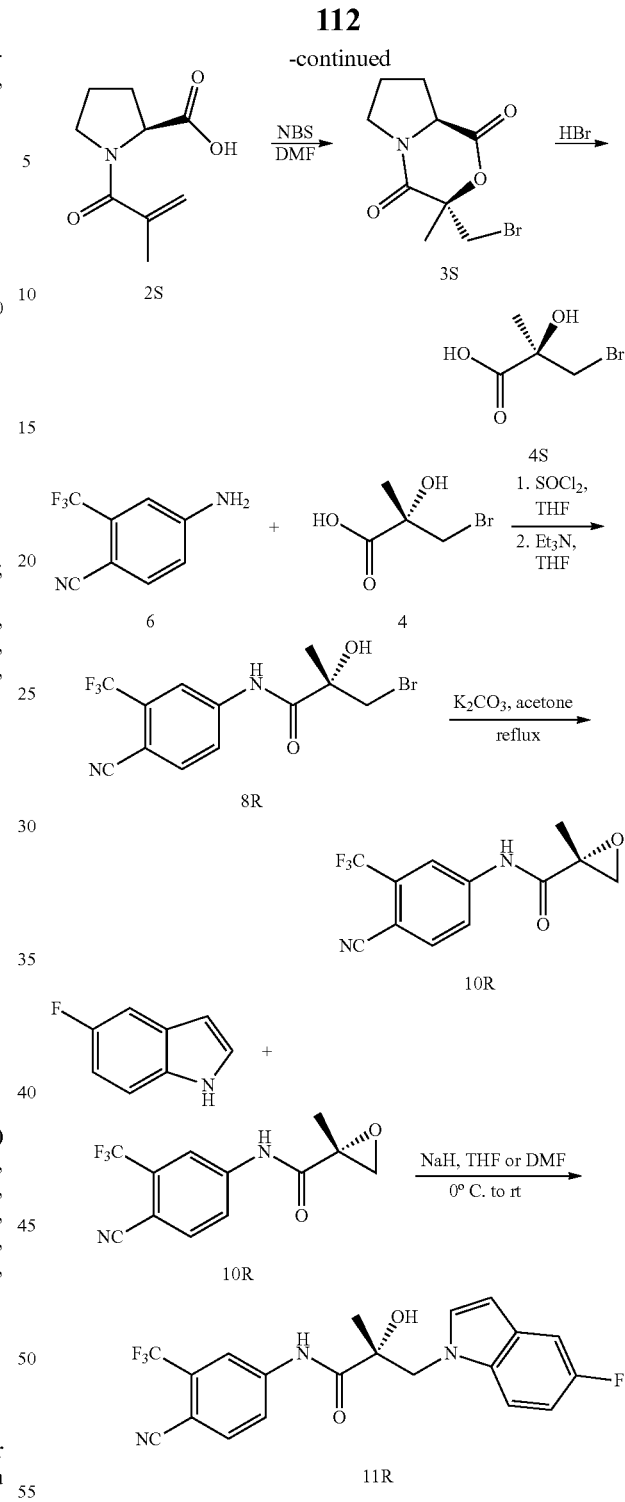

NaH of 60% dispersion in mineral oil (228 mg, 5.7 mmol) was added in 20 mL of anhydrous THF solvent into a 100 mL dried two necked round bottom flask equipped with a dropping funnel. 5-Fluoroindole (390 mg, 2.84 mmol) was added to the solution under argon atmosphere in ice-water bath, and the resulting solution was stirred for 30 min in an ice-water bath. Into the flask, epoxide 10R (2.84 mmol in THF) was added through a dropping funnel under argon atmosphere in an ice-water bath and stirred overnight at RT. After adding 1 mL of H$_2$O, the reaction mixture was condensed under reduced pressure, and then dispersed into 50 mL of EtOAc, washed with 50 mL (×2) water, brine, dried over anhydrous MgSO$_4$, and evaporated to dryness. The mixture was purified with flash column chromatography as an eluent EtOAc/hexane, and then the condensed compounds were then recrystallized in EtOAc/hexane to give a target product 11R.

Yield 69%; White solid. MS (ESI): 404.1 [M−H]$^-$; 428.1 [M+Na]$^+$; $^1$H NMR (CDCl$_3$, 400 MHz) δ 8.69 (bs, 1H, NH), 7.80 (d, J=1.2 Hz, 1H), 7.71-7.66 (m, 2H), 7.29-7.26 (m, 2H), 7.14 (dd, J=9.2, 2.4 Hz, 1H), 7.09 (d, J=3.2 Hz, 1H), 6.86 (dt, J=9.0, 2.5 Hz, 1H), 6.39 (d, J=3.2 Hz, 1H), 4.56 (d, J=14.8 Hz, 1H), 4.26 (d, J=14.8 Hz, 1H), 2.51 (bs, 1H, OH), 1.54 (s, 3H).

Example 2

Synthesis of Benzimidazole and Indazole SARD Compounds of this Invention

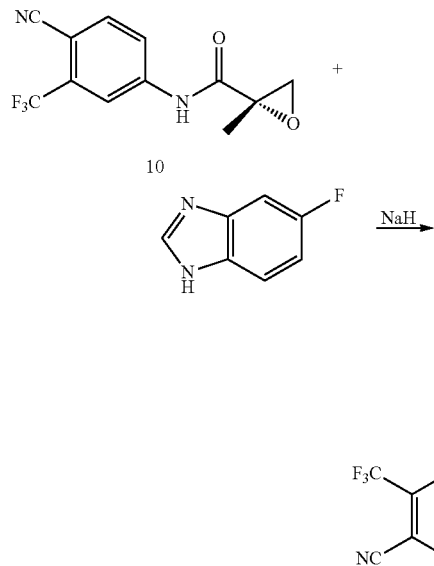

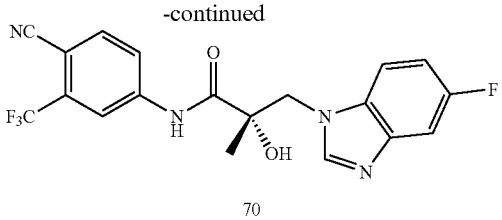

(S)—N-(4-Cyano-3-trifluoromethyl-phenyl)-3-(5-fluoro-benzoimidazol-1-yl)-2-hydroxy-2-methyl-propionamide (C$_{19}$H$_{14}$F$_4$N$_4$O$_2$) (70)

To a solution of 5-fluoro-1H-benzoimidazole (0.50 g, 0.00367 mol) in anhydrous THF (10 mL), which was cooled in an ice water bath under an argon atmosphere, was added sodium hydride (60% dispersion in oil, 0.44 g, 0.011 mol). After addition, the resulting mixture was stirred for 2 h. (S)—N-(4-cyano-3-(trifluoromethyl)phenyl)-2-methyloxirane-2-carboxamide (1.29 g, 0.00367 mol) was added to above solution, and the resulting reaction mixture was allowed to stir overnight at room temperature under argon. The reaction was quenched by water, extracted with ethyl acetate. The organic layer was dried with MgSO$_4$, filtered, and concentrated under vacuum. The product was purified by a silicon gel column using methylene chloride and methanol (19:1) as eluent to afford 0.17 g of the desired compound as white solid.

$^1$H NMR (400 MHz, DMSO-d$_6$) δ 10.37 (s, 1H, NH), 8.31 (d, J=17.2 Hz, 1H, ArH), 8.16-8.05 (m, 3H, ArH), 7.62-7.56 (m, 1H, ArH), 7.44 (dd, J=9.60 Hz, J=2.4 Hz, 1H, ArH), 7.04 (dd, J=9.60 Hz, J=2.4 Hz, 1H, ArH), 6.49 (s, 1H, OH), 4.65 (d, J=5.6 Hz, 1H, CH), 4.62 (d, J=5.6 Hz, 1H, CH), 1.47 (s, 3H, CH$_3$). Mass (ESI, Negative): 404.8[M−H]$^-$; (ESI, Positive): 429.0[M+Na]$^+$.

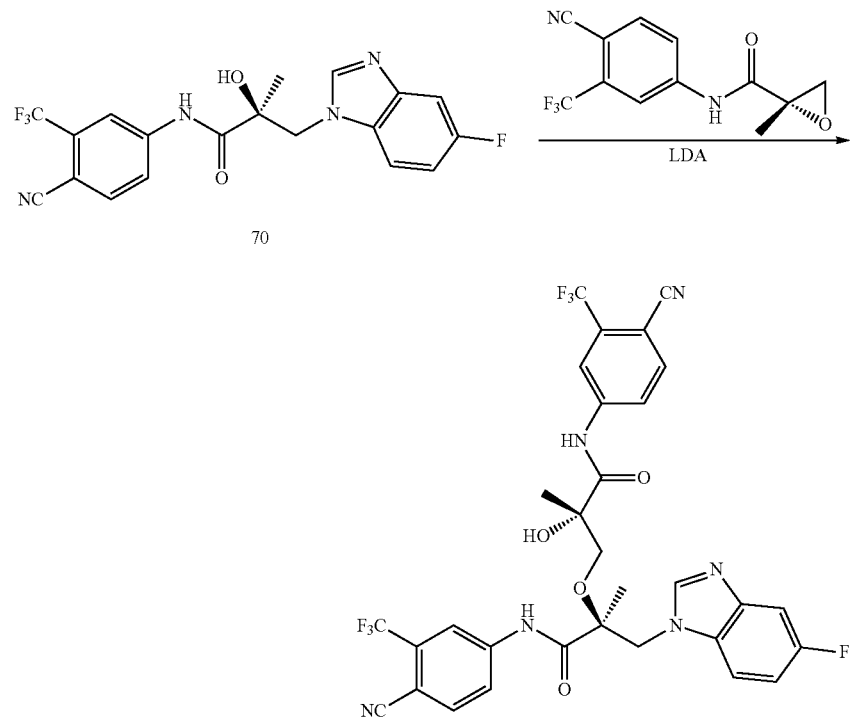

(S)—N-(4-Cyano-3-(trifluoromethyl)phenyl)-2-((S)-3-((4-cyano-3-(trifluoromethyl)phenyl)amino)-2-hydroxy-2-methyl-3-oxopropoxy)-3-(5-fluoro-1H-benzo[d]imidazol-1-yl)-2-methylpropanamide ($C_{31}H_{23}F_7N_6O_4$) (72)

This byproduct was purified by a silicon gel column using methylene chloride and methanol (19:1) as eluent to afford 50 mg of the titled compound as yellowish solid.

$^1$H NMR (400 MHz, DMSO-$d_6$) δ 10.75 (s, 1H, NH), 9.64 (s, 1H, NH), 8.31 (d, J=17.2 Hz, 1H, ArH), 8.33-8.30 (m, 1H, ArH), 8.11-7.86 (m, 6H, ArH), 7.54-7.52 (m, 1H, ArH), 7.35-7.33 (m, 1H, ArH), 6.77-6.73 (m, 1H, ArH), 6.31 (s, 1H, OH), 4.66-4.63 (m, 1H, CH), 4.50-4.44 (m, 1H, CH), 3.83-3.82 (m, 1H, CH), 3.66-3.64 (m, 1H, CH), 1.54 (s, 3H, CH$_3$), 1.34 (s, 3H, CH$_3$). Mass (ESI, Negative): 675.0[M−H]$^−$; (ESI, Positive): 699.3[M+Na]$^+$.

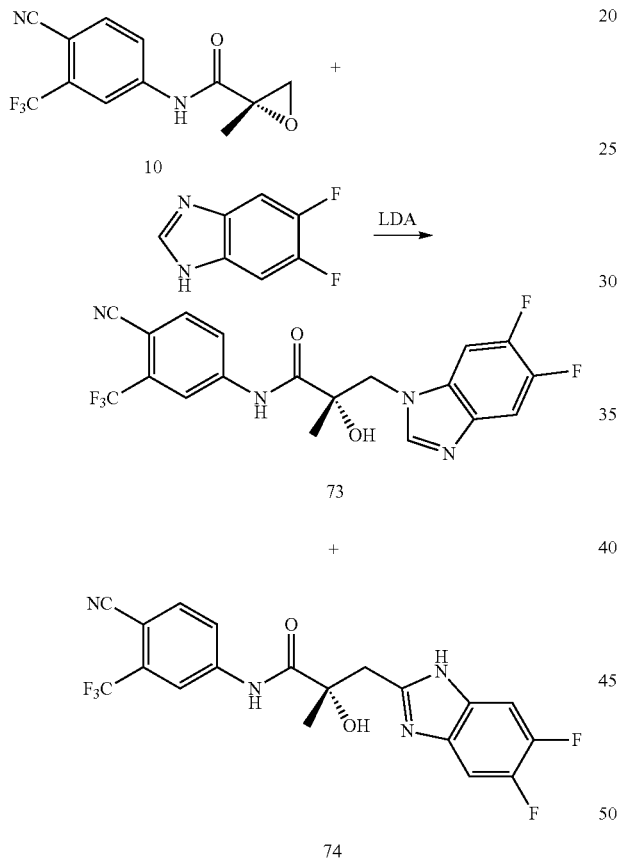

To a solution of 5,6-difluoro-1H-benzoimidazole (0.23 g, 0.00148 mol) in anhydrous THF (10 mL), which was cooled in an dry-ice acetone bath under an argon atmosphere, was added LDA (2.0 M in THF, 1.11 mL, 0.0022 mol). After addition, the resulting mixture was stirred for 2 h. (S)—N-(4-Cyano-3-(trifluoromethyl)phenyl)-2-methyloxirane-2-carboxamide (0.40 g, 0.00148 mol) was added to above solution, and the resulting reaction mixture was allowed to stir overnight at room temperature under argon. The reaction was quenched by water, extracted with ethyl acetate. The organic layer was dried with MgSO$_4$, filtered, and concentrated under vacuum. The product was purified by a silicon gel column using methylene chloride and methanol (19:1) as eluent to afford the desired compound as white solid.

(S)—N-(4-Cyano-3-trifluoromethyl-phenyl)-3-(5,6-difluoro-benzoimidazol-1-yl)-2-hydroxy-2-methyl-propionamide ($C_{19}H_{13}F_5N_4O_2$) (73)

$^1$H NMR (400 MHz, DMSO-$d_6$) δ 10.36 (s, 1H, NH), 8.25 (d, J=2.0 Hz, 1H, ArH), 8.21 (s, 1H, ArH), 8.14 (dd, J=8.8 Hz, J=2.0 Hz, 1H, ArH), 8.06 (d, J=8.8 Hz, 1H, ArH), 7.43-7.40 (m, 1H, ArH), 7.26-7.19 (m, 1H, ArH), 6.51 (s, 1H, OH), 4.65 (d, J=14.8 Hz, 1H, CH), 4.41 (d, J=14.8 Hz, 1H, CH), 1.42 (s, 3H, CH$_3$). Mass (ESI, Negative): 422.7 [M−H]$^−$; (ESI, Positive): 447.0 [M+Na]$^+$.

(S)—N-(4-Cyano-3-(trifluoromethyl)phenyl)-3-(5,6-difluoro-1H-benzo[d]imidazol-2-yl)-2-hydroxy-2-methylpropanamide ($C_{19}H_{13}F_5N_4O_2$) (74)

$^1$H NMR (400 MHz, DMSO-$d_6$) δ 10.44 (s, 1H, NH), 8.36 (d, J=2.0 Hz, 1H, ArH), 8.17 (dd, J=8.4 Hz, J=2.0 Hz, 1H, ArH), 8.11 (s, 1H, ArH), 8.07 (d, J=8.4 Hz, 1H, ArH), 7.44-7.41 (m, 1H, ArH), 7.21-7.14 (m, 1H, ArH), 6.54 (s, 1H, OH), 4.62 (d, J=14.4 Hz, 1H, CH), 4.52 (d, J=14.4 Hz, 1H, CH), 1.41 (s, 3H, CH$_3$). Mass (ESI, Negative): 422.7 [M−H]$^−$; (ESI, Positive): 447.0[M+Na]$^+$.

(S)—N-(4-Cyano-3-(trifluoromethyl)phenyl)-3-(7-fluoro-1H-benzo[d]imidazol-1-yl)-2-hydroxy-2-methylpropanamide ($C_{19}H_{14}F_4N_4O_2$) (75)

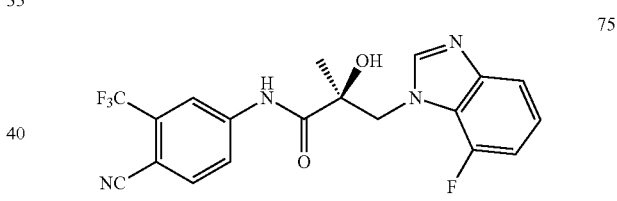

To a solution of 7-fluoro-benzimidazole (0.30 g, 0.0022 mol) in anhydrous THF (10 mL), which was cooled in an ice water bath under an argon atmosphere, was added sodium hydride (60% dispersion in oil, 0.132 g, 0.00331 mol). After addition, the resulting mixture was stirred for two hours. (R)-3-Bromo-N-(4-cyano-3-trifluoromethyl-phenyl)-2-hydroxy-2-methylpropanamide (0.77 g, 0.0022 mol) was added to above solution, and the resulting reaction mixture was allowed to stir overnight at room temperature under argon. The reaction was quenched by water, extracted with ethyl acetate. The organic layer was dried with MgSO$_4$, filtered, and concentrated under vacuum. The product was purified by a silica gel column using methylene chloride and methanol (19:1) as eluent to afford 0.18 g of the titled compound as yellowish solid.

$^1$H NMR (400 MHz, DMSO-$d_6$) δ 10.49 (s, 1H, NH), 8.39 (d, J=2.0 Hz, 1H, ArH), 8.21 (dd, J=8.8 Hz, J=2.0 Hz, 1H, ArH), 8.11 (s, 1H, ArH), 8.08 (d, J=8.8 Hz, 1H, ArH), 7.46 (d, J=8.0 Hz, 1H, ArH), 7.16-7.10 (m, 1H, ArH), 7.05-7.00 (m, 1H, ArH), 6.52 (s, 1H, OH), 4.64-4.56 (m, 2H, CH), 1.35 (s, 3H, CH$_3$). Mass (ESI, Negative): 404.8[M−H]$^−$.

Synthesis of Indazole SARDs:

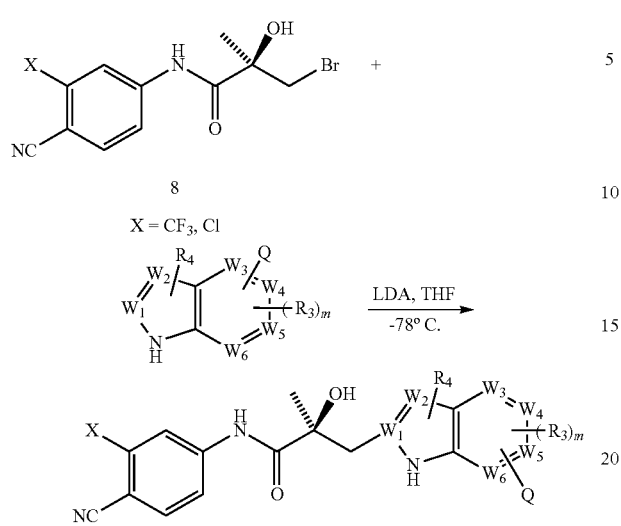

X = CF₃, Cl

To a solution of substituted-1H-indazole (0.00148 mol; e.g., 5-fluoro-1H-indazole for 90) in anhydrous THF (10 mL), which was cooled in an dry-ice acetone bath under an argon atmosphere, was added LDA (2.0 M in THF, 1.11 mL, 0.0022 mol). After addition, the resulting mixture was stirred for 2 h. (S)—N-(4-Cyano-3-(trifluoromethyl)phenyl)-2-methyloxirane-2-carboxamide (0.40 g, 0.00148 mol) was added to above solution, and the resulting reaction mixture was allowed to stir overnight at room temperature under argon. The reaction was quenched by water, extracted with ethyl acetate. The organic layer was dried with MgSO₄, filtered, and concentrated under vacuum. The product was purified by a silicon gel column using methylene chloride and methanol (19:1) as eluent to afford the desired compound as white solid.

Example 3

Synthesis of Quinoline, Isoquinoline, and Indoline SARD Compounds of this Invention Quinoline Compounds

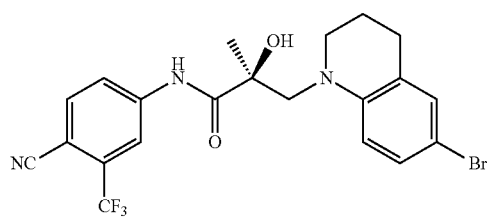
134

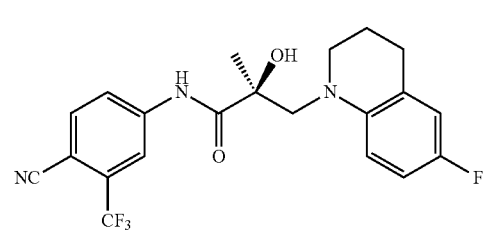
132

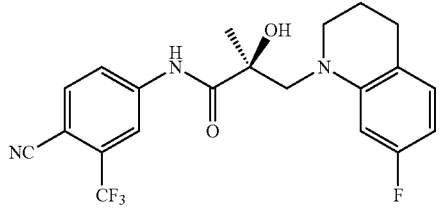
136

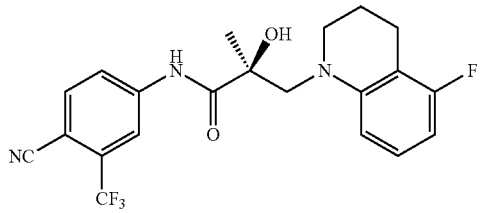
137

Isoquinoline Compounds

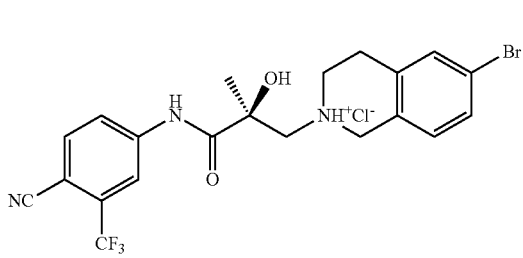
130

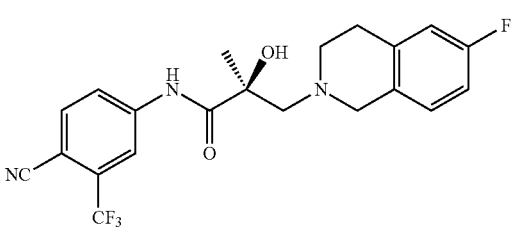
131

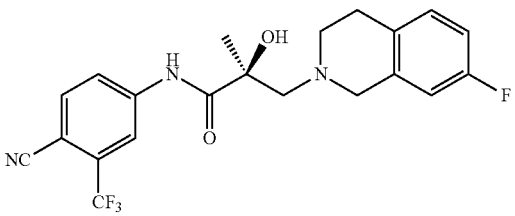
132

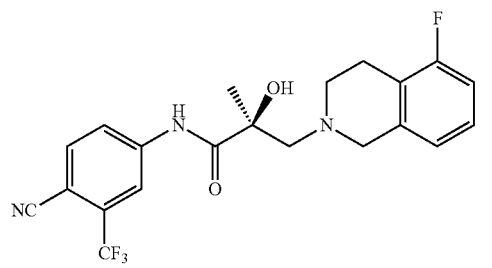
133

Indoline Compounds
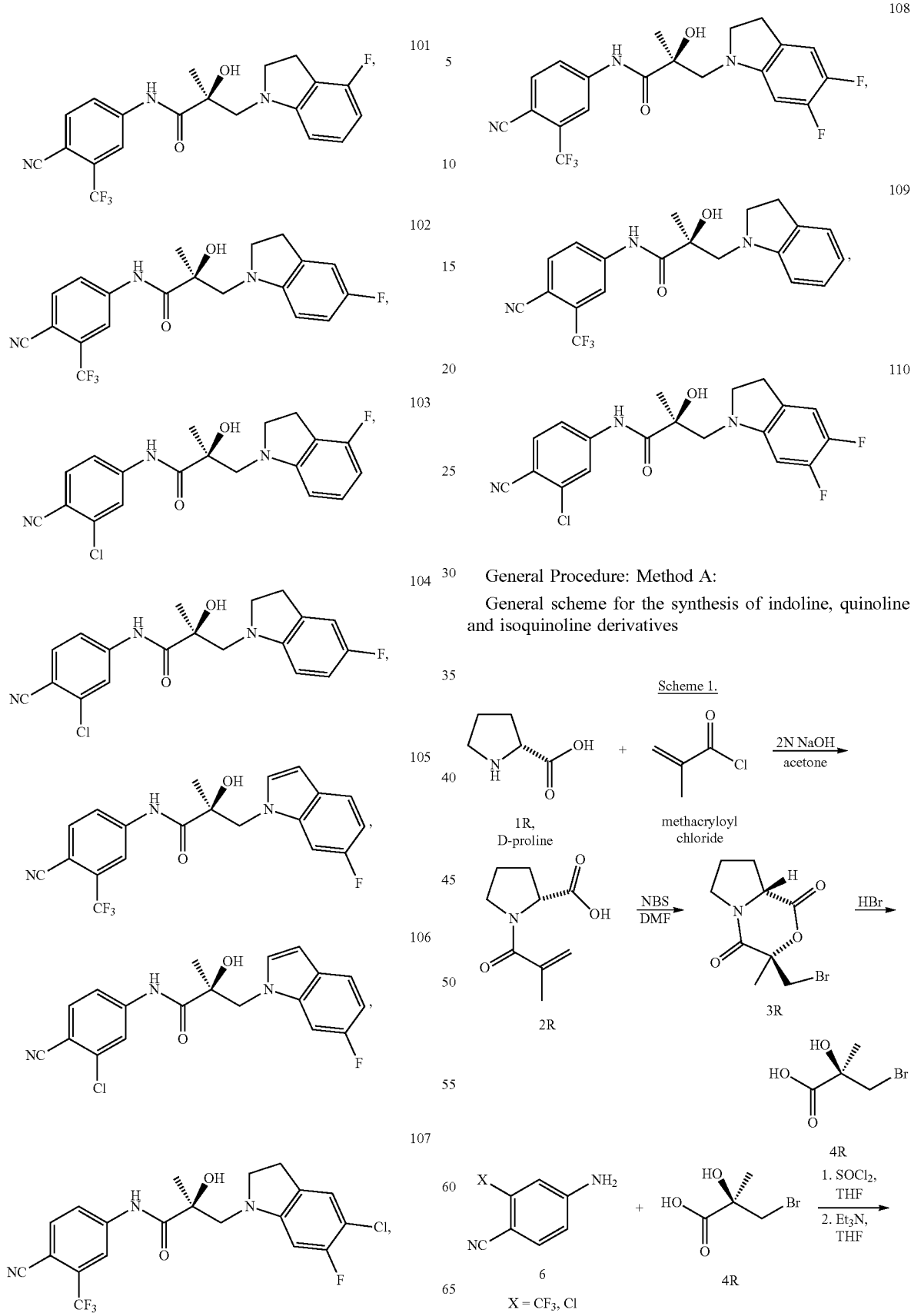
General Procedure: Method A:
General scheme for the synthesis of indoline, quinoline and isoquinoline derivatives

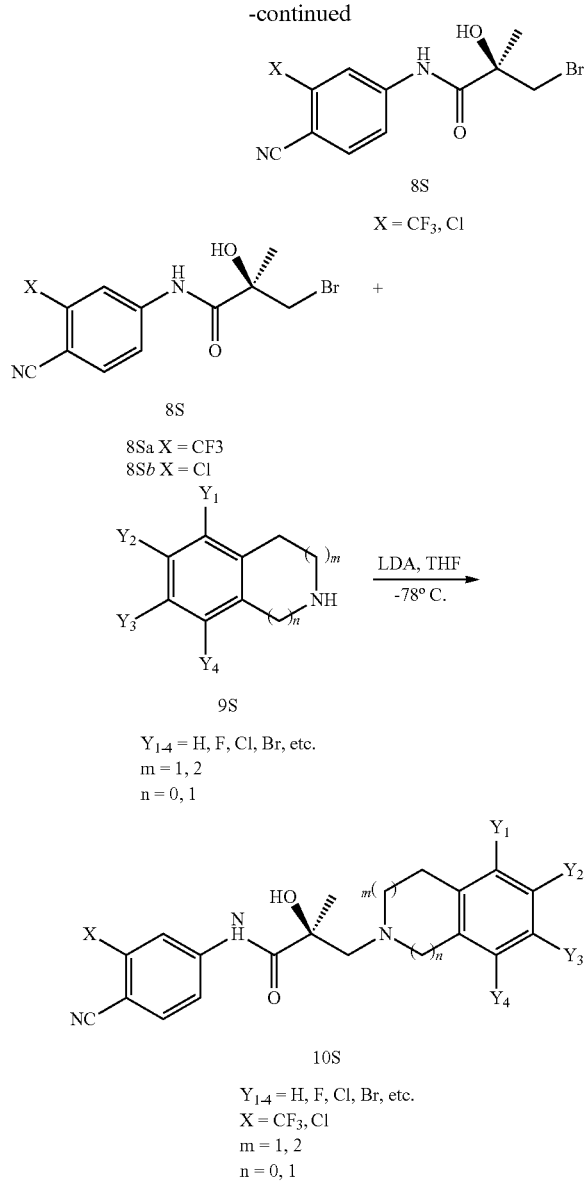

8S

X = CF₃, Cl

8Sa X = CF₃
8Sb X = Cl

9S

Y₁₋₄ = H, F, Cl, Br, etc.
m = 1, 2
n = 0, 1

10S

Y₁₋₄ = H, F, Cl, Br, etc.
X = CF₃, Cl
m = 1, 2
n = 0, 1

(2R)-1-Methacryloylpyrrolidin-2-carboxylic acid (2R)

D-Proline (1R) (14.93 g, 0.13 mol) was dissolved in 71 mL of 2 N NaOH and cooled in an ice bath; the resulting alkaline solution was diluted with acetone (71 mL). An acetone solution (71 mL) of methacryloyl chloride (13.56 g, 0.13 mol) and 2 N NaOH solution (71 mL) were simultaneously added over 40 min to the aqueous solution of D-proline in an ice bath. The temperature of the mixture was kept at 10-11° C. during the addition of the methacryloyl chloride. After stirring (3 h, room temperature (RT)), the mixture was evaporated in vacuo at a temperature at 35-45° C. to remove acetone. The resulting solution was washed with ethyl ether and was acidified to pH 2 with concentrated HCl. The acidic mixture was saturated with NaCl and was extracted with EtOAc (100 mL×3). The combined extracts were dried over Na₂SO₄, filtered through Celite®, and evaporated in vacuo to give the crude product as a colorless oil. Recrystallization of the oil from ethyl ether and hexanes afforded 16.2 g (68%) of the desired compound as colorless crystals: mp 102.1-103.4° C. (Marhefka, C. A.; Moore, B. M., 2nd; Bishop, T. C.; Kirkovsky, L.; Mukherjee, A.; Dalton, J. T.; Miller, D. D. Homology modeling using multiple molecular dynamics simulations and docking studies of the human androgen receptor ligand binding domain bound to testosterone and nonsteroidal ligands. *J Med Chem* 2001, 44, 1729-40) mp 102.5-103.5° C.; the NMR spectrum of this compound demonstrated the existence of two rotamers of the title compound.

¹H NMR (300 MHz, DMSO-d₆) δ 5.28 (s) and 5.15 (s) for the first rotamer, 5.15 (s) and 5.03 (s) for the second rotamer (totally 2H for both rotamers, vinyl CH₂), 4.48-4.44 for the first rotamer, 4.24-4.20 (m) for the second rotamer (totally 1H for both rotamers, CH at the chiral center), 3.57-3.38 (m, 2H, CH₂), 2.27-2.12 (1H, CH), 1.97-1.72 (m, 6H, CH₂, CH, Me); ¹³C NMR (75 MHz, DMSO-d₆) δ for major rotamer 173.3, 169.1, 140.9, 116.4, 58.3, 48.7, 28.9, 24.7, 19.5: for minor rotamer 174.0, 170.0, 141.6, 115.2, 60.3, 45.9, 31.0, 22.3, 19.7; IR (KBr) 3437 (OH), 1737 (C=O), 1647 (CO, COOH), 1584, 1508, 1459, 1369, 1348, 1178 cm⁻¹; [α]$_D^{26}$ +80.8° (c=1, MeOH); Anal. Calcd. for C₉H₁₃NO₃: C, 59.00; H, 7.15; N, 7.65. Found: C, 59.13; H, 7.19; N, 7.61.

(3R,8aR)-3-Bromomethyl-3-methyl-tetrahydro-pyrrolo[2,1-c][1,4]oxazine-1,4-dione (3R)

A solution of NBS (23.5 g, 0.132 mol) in 100 mL of DMF was added dropwise to a stirred solution of the (2R)-1-methacryloylpyrrolidin-2-carboxylic acid (2R) (16.1 g, 88 mmol) in 70 mL of DMF under argon at RT, and the resulting mixture was stirred 3 days. The solvent was removed in vacuo, and a yellow solid was precipitated. The solid was suspended in water, stirred overnight at RT, filtered, and dried to give 18.6 g (81%) (smaller weight when dried 34%) of the titled bromolactone (3R) as a yellow solid: mp 158.1-160.3° C.;

¹H NMR (300 MHz, DMSO-d₆) δ 4.69 (dd, J=9.6 Hz, J=6.7 Hz, 1H, CH at the chiral center), 4.02 (d, J=11.4 Hz, 1H, CHH$_a$), 3.86 (d, J=11.4 Hz, 1H, CHH$_b$), 3.53-3.24 (m, 4H, CH₂), 2.30-2.20 (m, 1H, CH), 2.04-1.72 (m, 3H, CH₂ and CH), 1.56 (s, 2H, Me); ¹³C NMR (75 MHz, DMSO-d₆) δ 167.3, 163.1, 83.9, 57.2, 45.4, 37.8, 29.0, 22.9, 21.6; IR (KBr) 3474, 1745 (C=O), 1687 (C=O), 1448, 1377, 1360, 1308, 1227, 1159, 1062 cm⁻¹; [α]$_D^{26}$ +124.5° (c=1.3, chloroform); Anal. Calcd. for C₉H₁₂BrNO₃: C, 41.24; H, 4.61; N, 5.34. Found: C, 41.46; H, 4.64; N, 5.32.

(2R)-3-Bromo-2-hydroxy-2-methylpropanoic acid (4R)

A mixture of bromolactone (3R) (18.5 g, 71 mmol) in 300 mL of 24% HBr was heated at reflux for 1 h. The resulting solution was diluted with brine (200 mL), and was extracted with ethyl acetate (100 mL×4). The combined extracts were washed with saturated NaHCO₃ (100 mL×4). The aqueous solution was acidified with concentrated HCl to pH=1, which, in turn, was extracted with ethyl acetate (100 mL×4). The combined organic solution was dried over Na₂SO₄, filtered through Celite, and evaporated in vacuo to dryness. Recrystallization from toluene afforded 10.2 g (86%) of the desired compound as colorless crystals: mp 110.3-113.8° C.;

¹H NMR (300 MHz, DMSO-d₆) δ 3.63 (d, J=10.1 Hz, 1H, CHH$_a$), 3.52 (d, J=10.1 Hz, 1H, CHH$_b$), 1.35 (s, 3H, Me);

IR (KBr) 3434 (OH), 3300-2500 (COOH), 1730 (C=O), 1449, 1421, 1380, 1292, 1193, 1085 cm$^{-1}$;
$[\alpha]_D^{26}$ +10.5° (c=2.6, MeOH);
Anal. Calcd. for $C_4H_7BrO_3$: C, 26.25; H, 3.86. Found: C, 26.28; H, 3.75.

(2R)-3-Bromo-N-[4-cyano-3-(trifluoromethyl)phenyl]-2-hydroxy-2-methylpropanamide (8S, X=CF$_3$)

Thionyl chloride (46.02 g, 0.39 mol) was added dropwise to a cooled solution (less than 4° C.) of (R)-3-bromo-2-hydroxy-2-methylpropanoic acid (4R) (51.13 g, 0.28 mol) in 300 mL of THF under an argon atmosphere. The resulting mixture was stirred for 3 h under the same condition. To this was added Et$_3$N (39.14 g, 0.39 mol) and stirred for 20 min under the same condition. After 20 min, 5-amino-2-cyanobenzotrifluoride (40.0 g, 0.21 mol), 400 mL of THF were added and then the mixture was allowed to stir overnight at RT. The solvent was removed under reduced pressure to give a solid which was treated with 300 mL of H$_2$O, extracted with EtOAc (2×400 mL). The combined organic extracts were washed with saturated NaHCO$_3$ solution (2×300 mL) and brine (300 mL). The organic layer was dried over MgSO$_4$ and concentrated under reduced pressure to give a solid which was purified from column chromatography using CH$_2$Cl$_2$/EtOAc (80:20) to give a solid. This solid was recrystallized from CH$_2$Cl$_2$/hexane to give 55.8 g (73.9%) of (2R)-3-bromo-N-[4-cyano-3-(trifluoromethyl)phenyl]-2-hydroxy-2-methylpropanamide (8S, X=CF$_3$) as a light-yellow solid. M.p. 134.0-136.5° C.
$^1$H NMR (CDCl$_3$/TMS) δ 1.66 (s, 3H, CH$_3$), 3.11 (s, 1H, OH), 3.63 (d, J=10.8 Hz, 1H, CH$_2$), 4.05 (d, J=10.8 Hz, 1H, CH$_2$), 7.85 (d, J=8.4 Hz, 1H, ArH), 7.99 (dd, J=2.1, 8.4 Hz, 1H, ArH), 8.12 (d, J=2.1 Hz, 1H, ArH), 9.04 (bs, 1H, NH). Calculated Mass: 349.99, [M–H]-349.0.

General Procedure for Preparation of Indoline, Quinoline and Isoquinoline Derivatives (Last Step):
Preparation of LDA Solution in THF.
To a stirred solution of freshly distilled diisopropylamine (0.14 mL, 1.2 mmol) in anhydrous 5 mL of THF was added a solution of n-butyllithium (0.53 mL, 1.32 mmol, 2.5 M solution in hexane) at −78° C. under argon atmosphere. The prepared solution of LDA or 2.0 M LDA was slowly warmed to 0° C. and stirred for 10 min and cooled again to −78° C.

To the LDA solution was added dropwise a solution of 9S (1.0 mmol) in 5 mL of THF for 20 min. The reaction mixture was stirred at the same temperature for 30 min and quenched by addition of sat. NH$_4$Cl. The solution was concentrated under reduced pressure and dispersed into excess EtOAc and dried over Na$_2$SO$_4$. The solution was concentrated and the resulting solid was recrystallized from EtOAc/hexane or DCM/hexane to give desired compound 10S. The mother liquor was concentrated and purified by flash column chromatography (EtOAc/hexane) to give additional 10S.

Alternative Procedure for Preparation of Indoline Compounds (Last Step):

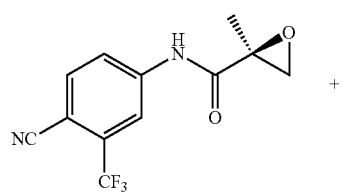

(S)-N-(4-cyano-3-(trifluoromethyl)phenyl)-2-methyloxirane-2-carboxamide

+

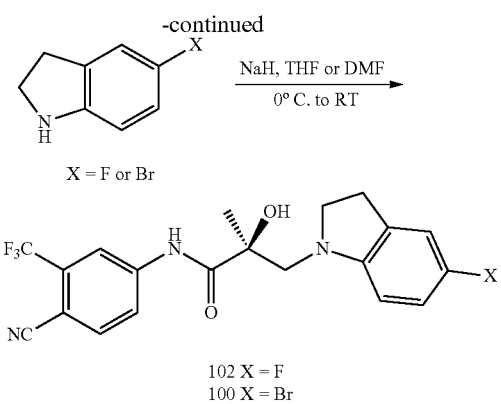

X = F or Br

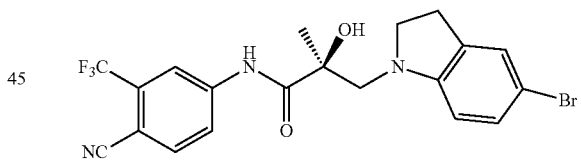

102 X = F
100 X = Br

NaH of 60% dispersion in mineral oil (61 mg, 1.5 mmol) was added in 5 mL of anhydrous THF solvent into a 50 mL dried two necked round bottom flask equipped with a dropping funnel. 5-Fluoroindoline or 5-bromoindoline (1.48 mmol) was added to the solution under argon atmosphere in an ice-water bath, and the resulting solution was stirred for 30 min in an ice-water bath. Into the flask, the prepared solution of the oxirane: (S)—N-(4-cyano-3-(trifluoromethyl)phenyl)-2-methyloxirane-2-carboxamide, (1.48 mmol in THF) was added through dropping funnel under argon atmosphere in an ice-water bath and stirred overnight at RT. After adding 1 mL of H$_2$O, the reaction mixture was condensed under reduced pressure, and then dispersed into 20 mL of EtOAc, washed with 20 mL (×2) water, brine, dried over anhydrous Na$_2$SO$_4$, and evaporated to dryness. The mixture was purified with flash chromatography (EtOAc/hexane 40% solvent, SIO$_2$) and afforded the desired products 100 or 102.

(S)-3-(5-Bromoindolin-1-yl)-N-(4-cyano-3-(trifluoromethyl)phenyl)-2-hydroxy-2-methylpropanamide (100)

Yield 45%; Light brown solid; MS (ESI) 466.3 [M–H]$^-$; $^1$H NMR (CDCl$_3$, 400 MHz) δ 9.17 (bs, 1H, NH), 8.09 (d, J=2.0 Hz, 1H), 7.96 (dd, J=8.4, 2.0 Hz, 1H), 7.80 (d, J=8.4 Hz, 1H), 7.19-7.16 (m, 2H), 6.49 (d, J=8.4 Hz, 1H), 3.66 (d, J=14.4 Hz, 1H), 3.48 (bs, 1H, OH), 3.47-3.41 (m, 1H), 3.34 (q, J=9.2 Hz, 1H), 3.25 (d, J=14.4 Hz, 1H), 3.00-2.91 (m, 2H), 1.56 (s, 3H).

(S)-3-(6-Bromo-3,4-dihydroquinolin-1(2H)-yl)-N-(4-cyano-3-(trifluoromethyl) phenyl)-2-hydroxy-2-methylpropanamide (134)

Yield; 62%; MS (ESI) m/z 481.6 [M–H]$^-$; $^1$H NMR (400 MHz, CDCl$_3$) δ 9.19 (bs, 1H, NH), 8.00 (s, 1H), 7.97-7.92 (m, 1H), 7.78 (d, J=8.4 Hz, 1H), 7.12 (dd, J=8.8, 2.4 Hz, 1H), 7.08 (d, J=2.4 Hz, 1H), 6.67 (d, J=8.8 Hz, 1H), 3.86 (d, J=15.2 Hz, 1H), 3.45 (d, J=15.2 Hz, 1H), 3.21 (t, J=5.4 Hz, 2H), 2.74 (m, 2H), 1.87 (m, 2H), 1.60 (s, 3H).

(S)—N-(4-Cyano-3-(trifluoromethyl)phenyl)-3-(4-fluoroindolin-1-yl)-2-hydroxy-2-methylpropanamide (101)

Yield; 68%; MS (ESI) m/z 406.0 [M−H]⁻; ¹H NMR (400 MHz, CDCl₃) δ 9.21 (bs, 1H, NH), 8.10 (d, J=2.4 Hz, 1H), 7.96 (dd, J=8.8, 2.4 Hz, 1H), 7.89 (d, J=8.8 Hz, 1H), 7.07-7.02 (m, 1H), 6.47 (t, J=8.4 Hz, 1H), 6.39 (d, J=8.0 Hz, 1H), 3.69 (d, J=14.4 Hz, 1H), 3.53 (bs, 1H, OH), 3.50 (m, 1H), 3.40 (q, J=8.0 Hz, 1H), 3.29 (d, J=14.4 Hz, 1H), 3.09 (m, 1H), 2.99 (m, 1H), 1.57 (s, 3H).

(S)—N-(4-Cyano-3-(trifluoromethyl)phenyl)-3-(5-fluoroindolin-1-yl)-2-hydroxy-2-methylpropanamide (102)

Yield; 75%; MS (ESI) m/z 406.0 [M−H]⁻; ¹H NMR (400 MHz, CDCl₃) δ 9.24 (bs, 1H, NH), 8.10 (d, J=2.2 Hz, 1H), 7.95 (dd, J=8.8, 2.2 Hz, 1H), 7.79 (d, J=8.8 Hz, 1H), 6.83 (dd, J=8.4, 2.4 Hz, 1H), 6.77 (m. 1H), 6.52 (dd, J=8.4, 4.0 Hz, 1H), 3.75 (bs, 1H, OH), 3.64 (d, J=14.0 Hz, 1H), 3.44 (m, 1H), 3.30 (q, J=9.2 Hz, 1H), 3.22 (d, J=14.0 Hz, 1H), 2.94 (m, 2H), 1.56 (s, 3H).

(S)—N-(4-Cyano-3-(trifluoromethyl)phenyl)-3-(6-fluoro-3,4-dihydroquinolin-1(2H)-yl)-2-hydroxy-2-methylpropanamide (135)

Yield; 42%; MS (ESI) m/z 420.0 [M−H]⁻; ¹H NMR (400 MHz, CDCl₃) δ 9.25 (bs, 1H, NH), 8.09 (d, J=2.0 Hz, 1H), 7.95 (dd, J=8.4, 2.0 Hz, 1H), 7.80 (d, J=8.4 Hz, 1H), 6.78-6.69 (m, 1H), 6.77 (m. 3H), 3.88 (d, J=15.2 Hz, 1H), 3.82 (bs, 1H, OH), 3.36 (d, J=15.2 Hz, 1H), 3.16 (m, 2H), 3.16-2.70 (m, 2H), 1.94-1.83 (m, 2H), 1.56 (s, 3H).

(S)—N-(4-Cyano-3-(trifluoromethyl)phenyl)-3-(6-fluoro-3,4-dihydroisoquinolin-2(1H)-yl)-2-hydroxy-2-methylpropanamide (131)

Yield; 43%; MS (ESI) m/z 419.9 [M−H]⁻; ¹H NMR (400 MHz, CDCl₃) δ 9.51 (bs, 1H, NH), 8.10 (d, J=1.8 Hz, 1H), 7.95 (dd, J=8.6, 1.8 Hz, 1H), 7.79 (d, J=8.6 Hz, 1H), 6.88 (m, 1H), 6.81 (m. 2H), 3.69 (s, 2H), 3.42 (d, J=13.2 Hz, 1H), 2.91 (m, 4H), 2.60 (d, J=13.2 Hz, 1H), 2.17 (s, 1H, OH), 1.46 (s, 3H).

(S)—N-(4-Cyano-3-(trifluoromethyl)phenyl)-3-(6-fluoroindolin-1-yl)-2-hydroxy-2-methylpropanamide (105)

Yield; 70%; MS (ESI) m/z 405.9 [M−H]⁻; ¹H NMR (400 MHz, CDCl₃) δ 9.21 (bs, 1H, NH), 8.10 (s, 1H), 7.97 (d, J=8.4 Hz, 1H), 7.79 (d, J=8.4 Hz, 1H), 6.98 (t, J=6.8 Hz, 1H), 6.41 (t, J=7.6 Hz, 1H), 3.35 (m, 1H), 3.66 (d, J=14.0 Hz, 1H), 3.52 (bs, 1H, OH), 3.47 (m, 1H), 3.41 (q, J=9.2 Hz, 1H), 3.24 (d, J=14.0 Hz, 1H), 3.00-2.87 (m, 2H), 1.57 (s, 3H).

(S)—N-(4-Cyano-3-(trifluoromethyl)phenyl)-3-(7-fluoro-3,4-dihydroisoquinolin-2(1H)-yl)-2-hydroxy-2-methylpropanamide (132)

Yield; 69%; MS (ESI) m/z 420.0 [M−H]⁻; ¹H NMR (400 MHz, CDCl₃) δ 9.09 (bs, 1H, NH), 7.93 (d, J=8.4 Hz, 1H), 7.80 (d, J=8.4 Hz, 1H), 7.05 (t, J=8.0 Hz, 1H), 6.86 (m, 1H), 6.63 (d, J=8.0 Hz, 1H), 3.71 (s, 2H), 3.42 (d, J=13.2 Hz, 1H), 2.91-2.82 (m, 5H), 2.60 (d, J=13.2 Hz, 1H), 1.46 (s, 3H).

Example 4

Synthesis of SARD Compounds of this Invention

Method A.
General Scheme for Preparation of Indoline, Quinolone and Isoquinoline Derivatives

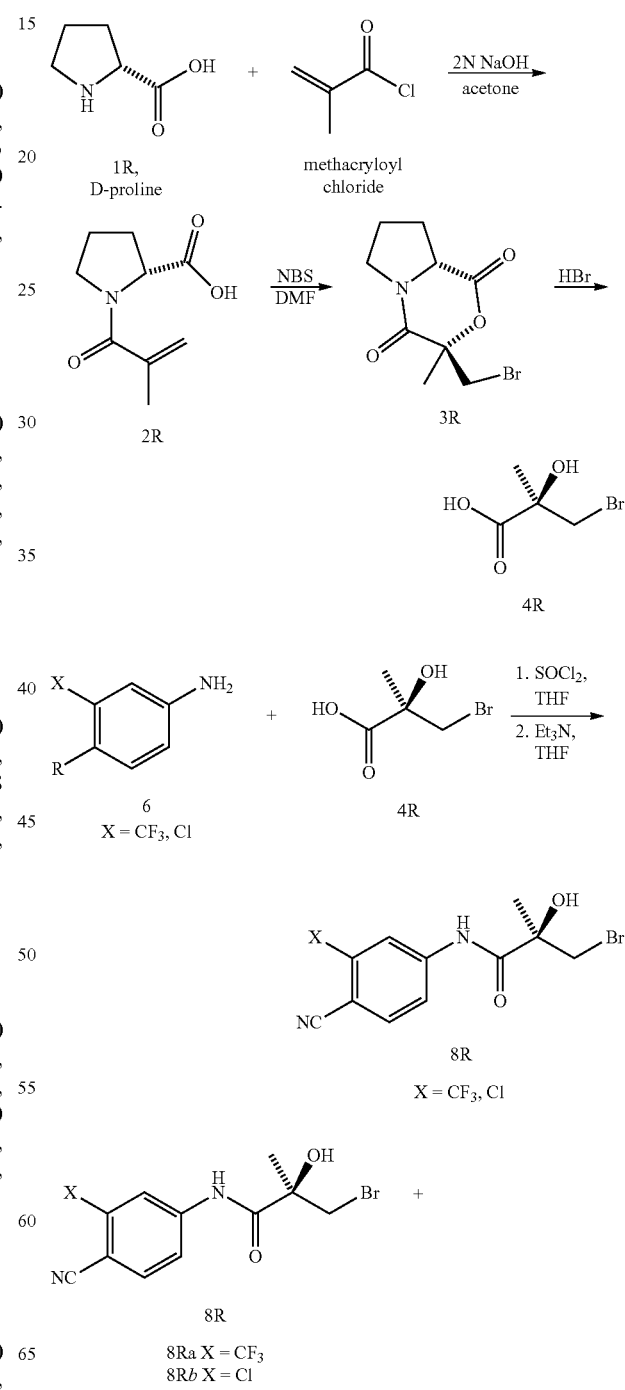

127

-continued

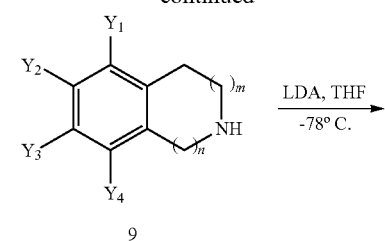

9

Y$_{1-4}$ = H, F, Cl, Br, etc.
m = 0, 1, 2
n = 0, 1

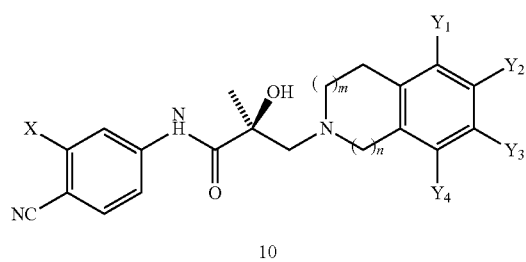

10

Y$_{1-4}$ = H, F, Cl, Br, etc.
X = CF$_3$, Cl
m = 0, 1, 2
n = 0, 1

Preparation of LDA solution in THF: To a stirred solution of freshly distilled diisopropylamine (0.14 mL, 1.2 mmol) in anhydrous 5 mL of THF was added a solution of n-butyllithium (0.53 mL, 1.32 mmol, 2.5 M solution in hexane) at −78° C. under argon atmosphere. The prepared solution of LDA or commercial 2.0 M LDA was slowly warmed to 0° C. and stirred for 10 min and cooled again to −78° C. To the LDA solution was added dropwise a solution of 9 (1.0 mmol) in 5 mL of THF for 20 min. 8R in THF was added dropwise through dropping funnel under argon atmosphere at −78° C. The reaction mixture was stirred at the same temperature for 30 min and quenched by addition of sat. NH$_4$Cl. The solution was concentrated under reduced pressure and dispersed into excess EtOAc and dried over Na$_2$SO$_4$. The solution was concentrated and the resulting solid was recrystallized from EtOAc/hexane or DCM/hexane to give designed compound 10. The mother liquor was concentrated and purified by flash column chromatography (EtOAc/hexane) to give the 10 additionally.

Method B.

Preparation of Indoles and Carbazoles

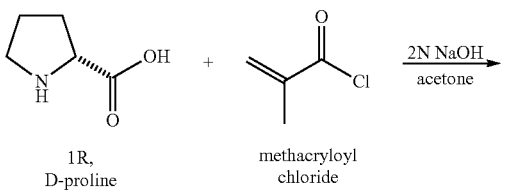

1R,
D-proline methacryloyl
chloride

128

-continued

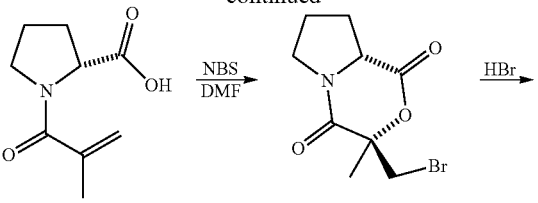

2R

3R

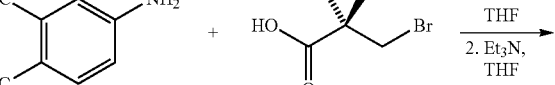

4R

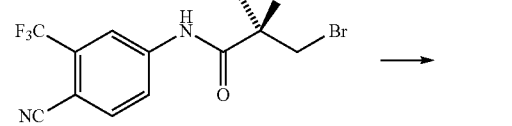

6         4R

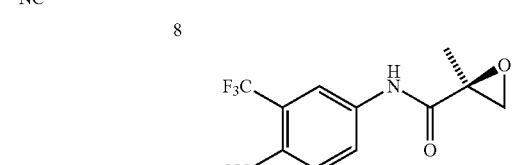

8

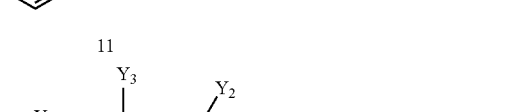

11

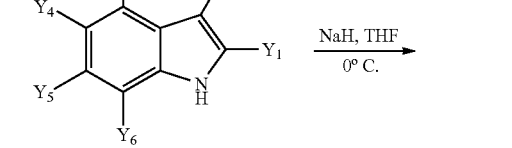

11

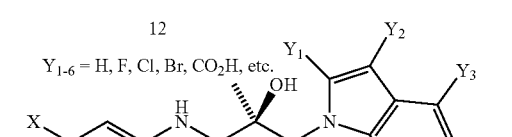

12

Y$_{1-6}$ = H, F, Cl, Br, CO$_2$H, etc.

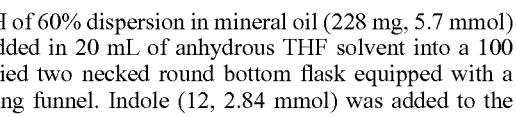

13

Y$_{1-6}$ = H, F, Cl, Br, CH$_3$, CO$_2$H, Ph, etc.
X = CF$_3$, Cl

NaH of 60% dispersion in mineral oil (228 mg, 5.7 mmol) was added in 20 mL of anhydrous THF solvent into a 100 mL dried two necked round bottom flask equipped with a dropping funnel. Indole (12, 2.84 mmol) was added to the solution under argon atmosphere in ice-water bath, and the resulting solution was stirred for 30 min at the ice-water bath. Into the flask, epoxide 11 (2.84 mmol in THF) was added through dropping funnel under argon atmosphere at the ice-water bath and stirred overnight at room temperature. After adding 1 mL of $H_2O$, the reaction mixture was condensed under reduced pressure, and then dispersed into 50 mL of EtOAc, washed with 50 mL (×2) water, brine, dried over anhydrous $MgSO_4$, and evaporated to dryness. The mixture was purified with flash column chromatography with an eluent of EtOAc/hexane, and then the condensed compounds were then recrystallized in EtOAc/hexane to give a target product 13.

(S)—N-(3-Chloro-4-cyanophenyl)-2-methyloxirane-2-carboxamide (epoxide intermediate)

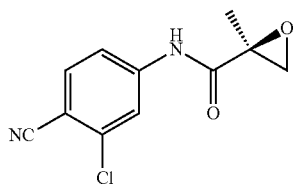 [SMILES: C[C@@]1(C(=O)Nc2ccc(C#N)c(Cl)c2)CO1]

Yield 98%;
Light Brown solid;
MS (ESI) m/z 235.4 [M−H]$^-$;
$^1$H NMR (CDCl$_3$, 400 MHz) □ 400 MHz) H] idH), 7.90 (d, J=2.0 Hz, 1H), 7.61 (d, J=8.4 Hz, 1H), 7.50 (dd, J=8.4, 2.0 Hz, 1H), 2.99 (s, 2H), 1.67 (s, 3H).

Indole Derivatives (S)—N-(4-Cyano-3-(trifluoromethyl)phenyl)-3-(5-fluoro-6-phenyl-1H-indol-1-yl)-2-hydroxy-2-methyl-propanamide (33)

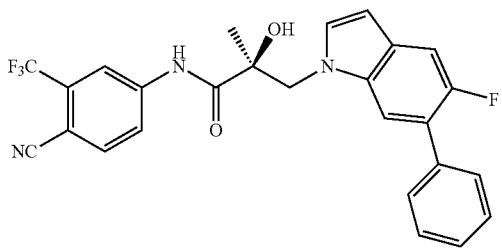 [SMILES: C[C@](O)(Cn1ccc2cc(F)c(-c3ccccc3)cc21)C(=O)Nc1ccc(C#N)c(C(F)(F)F)c1]

To a solution of 5-fluoro-6-phenyl-1H-indole (0.37 g, 0.00175 mol) in anhydrous THF (10 mL), which was cooled in an ice water bath under an argon atmosphere, was added sodium hydride (60% dispersion in oil, 0.11 g, 0.00263 mol). After addition, the resulting mixture was stirred for three hours. (S)—N-(4-Cyano-3-(trifluoromethyl)phenyl)-2-methyloxirane-2-carboxamide (0.47 g, 0.002175 mol) was added to above solution, and the resulting reaction mixture was allowed to stir overnight at room temperature under argon. The reaction was quenched by water, extracted with ethyl acetate. The organic layer was washed with brine, dried with $MgSO_4$, filtered, and concentrated under vacuum. The product was purified by a silica gel column using ethyl acetate and hexanes (1:2) as eluent to afford 0.83 g (98%) of the titled compound as off-white foam.

$^1$H NMR (400 MHz, DMSO-d$_6$) δ 10.29 (s, 1H, NH), 8.28 (s, 1H, ArH), 8.08 (d, J=8.8 Hz, 1H, ArH), 7.96 (d, J=8.8 Hz, 1H, ArH), 7.58 (d, J=6.8 Hz, 1H, ArH), 7.49-7.31 (m, 7H, ArH), 6.42 (d, J=3.2 Hz, 1H, ArH), 6.35 (s, 1H, OH), 4.61 (d, J=14.4 Hz, 1H, CH), 4.35 (d, J=14.4 Hz, 1H, CH), 1.46 (s, 3H, CH$_3$).
Mass (ESI, Negative): 479.9[M−H]$^-$; (ESI, Positive): 504.1[M+Na]$^+$.

(S)—N-(3-Chloro-4-cyanophenyl)-3-(5-fluoro-6-phenyl-1H-indol-1-yl)-2-hydroxy-2-methylpropanamide (34)

5-Fluoro-6-phenyl-1H-indole (C$_{14}$H$_{10}$FN)

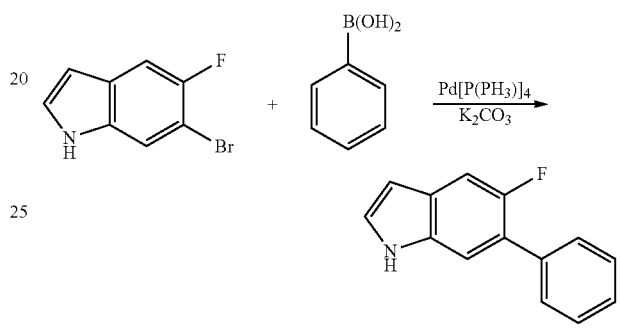

To a suspension of tetrakis(triphenylphosphine)palladium (0) [Pd(PPh$_3$)$_4$, 0.54 g, 0.467 mmol] in 20 mL of ethylene glycol dimethyl ether (DME) was added 6-bromo-5-fluoroindole (1.00 g, 4.67 mmol), and the mixture was stirred for 15 minutes under argon at room temperature. A solution of phenylboronic acid (0.57 g, 4.67 mmol) in 2-3 mL of ethanol was added and the mixture was stirred for 10 minutes under the same conditions. A solution of potassium carbonate (0.97 g, 7.01 mmol) in 2 mL of water was added to above mixture and the resulting reaction mixture was heated at reflux for 3-4 hours under the argon atmosphere. After the end of the reaction was established by TLC, the reaction was diluted by brine, extracted with ethyl acetate. The organic layer was washed with brine, dried with MgSO$_4$, filtered, and concentrated under vacuum. The product was purified by a silica gel column using ethyl acetate and hexanes (1:3) as eluent to afford 0.90 g (92% yield) of the titled compound as light brown solid.+

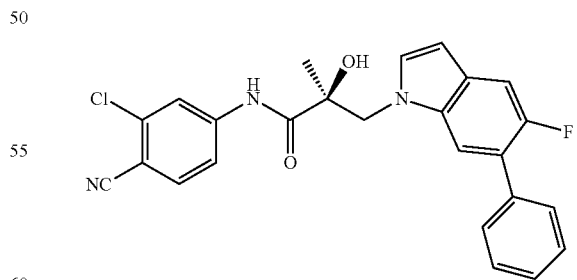

To a solution of 5-fluoro-6-phenyl-1H-indole (0.20 g, 0.000947 mol) in anhydrous THF (10 mL), which was cooled in an ice water bath under an argon atmosphere, was added sodium hydride (60% dispersion in oil, 0.076 g, 0.00189 mol). After addition, the resulting mixture was stirred for three hours. (R)-3-Bromo-N-(4-cyano-3-chlorophenyl)-2-hydroxy-2-methylpropanamide (0.30 g, 0.000947 mol) was added to the above solution, and the resulting reaction mixture was allowed to stir overnight at room temperature under argon. The reaction was quenched by water, extracted with ethyl acetate. The organic layer was washed with brine, dried with MgSO$_4$, filtered, and concentrated under vacuum. The product was purified by a silica gel column using ethyl acetate and hexanes (1:2) as eluent to afford 0.26 g of the titled compound as yellowish solid.

$^1$H NMR (400 MHz, DMSO-d$_6$) δ 10.11 (s, 1H, NH), 8.04 (d, J=1.6 Hz, 1H, ArH), 7.80 (d, J=8.8 Hz, 1H, ArH), 7.74 (dd, J=8.2 Hz, J=2.0 Hz, 1H, ArH), 7.62 (d, J=6.4 Hz, 1H, ArH), 7.51-7.44 (m, 4H, ArH), 7.39-7.32 (m, 3H, ArH), 6.42 (d, J=3.2 Hz, 1H, ArH), 6.33 (s, 1H, OH), 4.60 (d, J=15.2 Hz, 1H, CH), 4.35 (d, J=15.2 Hz, 1H, CH), 1.45 (s, 3H, CH$_3$).

Mass (ESI, Negative): 445.8[M−H]$^-$; (ESI, Positive): 470.0[M+Na]$^+$.

(S)—N-(3-Chloro-4-cyanophenyl)-3-(6-fluoro-1H-indol-1-yl)-2-hydroxy-2-methylpropanamide (35)

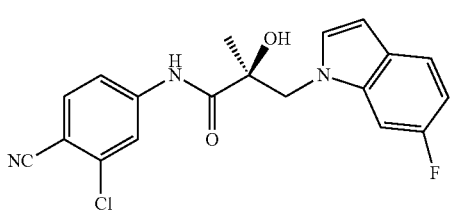 [SMILES: C[C@](O)(Cn1ccc2ccc(F)cc21)C(=O)Nc1ccc(C#N)c(Cl)c1]

Method B
Yield 67%;
White solid;
MS (ESI) m/z 376.9 [M−H]$^-$;
$^1$H NMR (CDCl$_3$, 400 MHz) δ 8.67 (bs, 1H, NH), 7.79 (d, J=2.0 Hz, 1H), 7.56 (d, J=8.4 Hz, 1H), 7.49 (dd, J=8.4, 5.4 Hz, 1H), 7.38 (dd, J=8.4, 2.0 Hz, 1H), 7.13 (dd, J=10.0, 2.0 Hz, 1H), 7.09 (d, J=3.2 Hz, 1H), 6.86 (m, 2H), 6.48 (d, J=3.2 Hz, 1H), 4.58 (d, J=14.8 Hz, 1H), 4.28 (d, J=14.8 Hz, 1H), 2.61 (bs, 1H, OH), 1.60 (s, 3H);
$^{19}$F NMR (CDCl$_3$) δ −120.03.

(S)—N-(3-Chloro-4-cyanophenyl)-3-(4-fluoro-1H-indol-1-yl)-2-hydroxy-2-methylpropanamide (36)

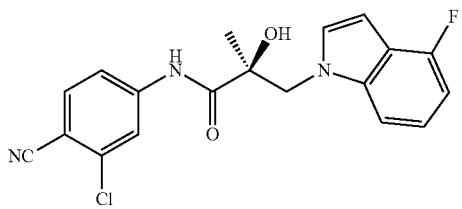 [SMILES: C[C@](O)(Cn1ccc2c(F)cccc21)C(=O)Nc1ccc(C#N)c(Cl)c1]

Method B
Under argon atmosphere into a 100 mL, dried, two-necked round bottom flask equipped with a dropping funnel in ice-water bath, NaH of 60% dispersion in mineral oil (228 mg, 5.70 mmol) was added in 20 mL of anhydrous THF solvent into the flask and 4-fluoroindole (390 mg, 2.84 mmol) solution in 10 mL of anhydrous THF was added to the solution under the argon atmosphere in the ice-water bath, and then the resulting solution was stirred at the ice-water bath. After 30 min, into the flask, a solution of (S)—N-(3-chloro-4-cyanophenyl)-2-methyloxirane-2-carboxamide (2.84 mmol in THF) was added through dropping funnel under argon atmosphere at the ice-water bath and stirred overnight at room temperature. After adding 1 mL of H$_2$O, the reaction mixture was condensed under reduced pressure, and then dispersed into 50 mL of EtOAc, washed with 50 mL (×2) water, brine, dried over anhydrous MgSO$_4$, and evaporated to dryness. The mixture was purified with flash column chromatography as an eluent EtOAc/hexane, and then the condensed compounds were then recrystallized in EtOAc/hexane to give a target product, 36.

Yield 73%;
White solid;
MS (ESI) m/z 369.9 [M−H]$^-$; HRMS (ESI) m/z calcd for C$_{19}$H$_{16}$ClFN$_3$O$_2$: 372.0915. Found: 372.0915 [M+H]$^+$.

$^1$H NMR (CDCl$_3$, 400 MHz) δ 8.64 (bs, 1H, NH), 7.81 (s, 1H), 7.57 (d, J=8.4 Hz, 1H), 7.35 (d, J=7.2 Hz, 1H), 7.21 (d, J=8.4 Hz, 1H), 7.14-7.10 (m, 2H), 6.77 (t, J=8.4 Hz, 1H), 6.63 (d, J=2.8 Hz, 1H), 6.60 (s, 1H), 4.64 (d, J=14.8 Hz, 1H), 4.35 (d, J=14.8 Hz, 1H), 2.48 (bs, 1H, OH), 1.60 (s, 3H);

$^{13}$C NMR (acetone-d$_6$, 100 MHz) δ 174.8, 158.1, 155.7, 144.3, 141.5 (d, J=11.0 Hz), 137.2, 135.5, 130.7, 122.4 (d, J=7.0 Hz), 121.0, 119.3, 118.0 (d, J=22.0 Hz), 116.6, 107.9 (t, J=5.0 Hz), 104.4 (d, J=19.0 Hz), 97.7, 77.6, 55.0, 24.2.

$^{19}$F NMR (CDCl$_3$, decoupled) δ −121.78.

(S)—N-(3-Chloro-4-cyanophenyl)-3-(5-fluoro-1H-indol-1-yl)-2-hydroxy-2-methylpropanamide (37)

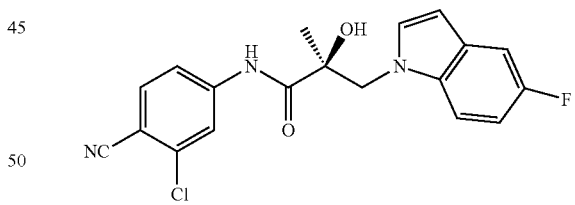

Method B
Yield 79%;
White solid;
MS (ESI) m/z 371.0 [M−H]$^-$; HRMS (ESI) m/z calcd for C$_{19}$H$_{16}$ClFN$_3$O$_2$: 372.0915. Found: 372.0922 [M+H]$^+$.

$^1$H NMR (CDCl$_3$, 400 MHz) δ 8.62 (bs, 1H, NH), 7.80 (d, J=2.0 Hz, 1H), 7.56 (d, J=8.4 Hz, 1H), 7.38-7.34 (m, 2H), 7.23 (dd, J=9.2, 2.4 Hz, 1H), 7.15 (d, J=3.2 Hz, 1H), 7.22 (dt, J=9.2, 2.8 Hz, 1H), 6.47 (d, J=3.2 Hz, 1H), 4.63 (d, J=14.8 Hz, 1H), 4.32 (d, J=14.8 Hz, 1H), 2.49 (bs, 1H, OH), 1.60 (s, 3H);

$^{19}$F NMR (CDCl$_3$) δ −124.52.

(S)—N-(3-Chloro-4-cyanophenyl)-3-(3-fluoro-1H-indol-1-yl)-2-hydroxy-2-methylpropanamide (38)

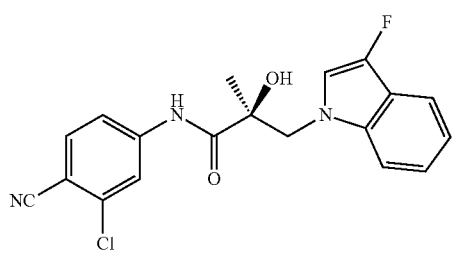 [SMILES: C[C@](O)(Cn1cc(F)c2ccccc21)C(=O)Nc1ccc(C#N)c(Cl)c1]

Method B

Yield 68%;

Mp 168.9-170.1° C.;

Light Brown solid;

MS (ESI) m/z 369.8 [M−H]⁻; LCMS (ESI) m/z calcd for $C_{19}H_{16}ClFN_3O_2$: 372.0915. Found: 372.0910 [M+H]⁺.

$^1$H NMR (CDCl$_3$, 400 MHz) δ 8.66 (bs, 1H, NH), 7.81 (d, J=2.0 Hz, 1H), 7.60-7.56 (m, 2H), 7.37 (dd, J=8.4, 2.0 Hz, 2H), 7.23 (m, 1H), 7.12 (t, J=7.4 Hz, 1H), 6.93 (d, J=2.8 Hz, 1H), 4.56 (d, J=15.2 Hz, 1H), 4.27 (d, J=15.2 Hz, 1H), 2.44 (s, 1H, OH), 1.59 (s, 3H).

$^{19}$F NMR (CDCl$_3$) δ −173.91

(S)—N-(3-Chloro-4-cyanophenyl)-3-(7-fluoro-1H-indol-1-yl)-2-hydroxy-2-methylpropanamide (39)

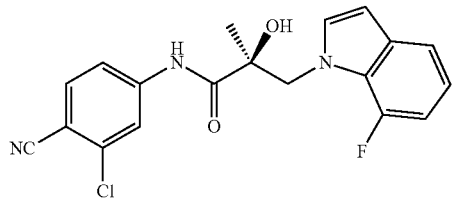 [SMILES: C[C@](O)(Cn1ccc2cccc(F)c21)C(=O)Nc1ccc(C#N)c(Cl)c1]

Method B

Yield 73%;

White solid;

MS (ESI) m/z 370.0 [M−H]⁻;

$^1$H NMR (CDCl$_3$, 400 MHz) δ 8.60 (bs, 1H, NH), 8.82 (d, J=2.0 Hz, 1H), 7.55 (d, J=8.4 Hz, 1H), 7.37-7.34 (m, 2H), 7.02 (d, J=3.2 Hz, 1H), 7.00 (m, 1H), 7.01-6.98 (m, 1H), 6.91 (m, 1H), 6.46 (t, J=2.8 Hz, 1H), 4.68 (d, J=15.0 Hz, 1H), 4.62 (d, J=15.0 Hz, 1H), 2.73 (d, J=4.4 Hz, 1H, OH), 1.61 (s, 3H);

$^{19}$F NMR (CDCl$_3$) δ −133.54.

(S)—N-(3-Chloro-4-cyanophenyl)-3-(5-fluoro-3-phenyl-1H-indol-1-yl)-2-hydroxy-2-methylpropanamide (40)

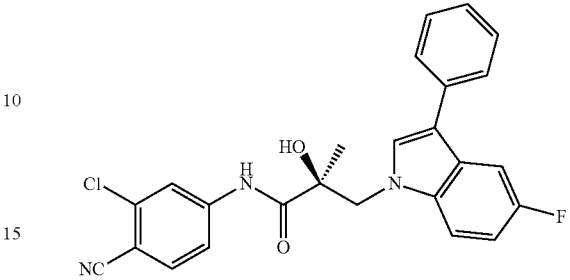

To a solution of 5-fluoro-3-phenyl-1H-indole (0.50 g, 0.002267 mol) in anhydrous THF (10 mL), which was cooled in an ice water bath under an argon atmosphere, was added sodium hydride (60% dispersion in oil, 0.24 g, 0.005918 mol). After addition, the resulting mixture was stirred for three hours. (R)-3-Bromo-N-(4-cyano-3-chlorophenyl)-2-hydroxy-2-methylpropanamide (0.75 g, 0.002267 mol) was added to above solution, and the resulting reaction mixture was allowed to stir overnight at room temperature under argon. The reaction was quenched by water, extracted with ethyl acetate. The organic layer was washed with brine, dried with MgSO$_4$, filtered, and concentrated under vacuum. The product was purified by a silica gel column using ethyl acetate and hexanes (1:2 to 1:1) as eluent to afford 0.43 g of the titled compound as yellowish solid.

$^1$H NMR (400 MHz, DMSO-d$_6$) δ 10.17 (s, 1H, NH), 8.06 (d, J=2.0 Hz, 1H, ArH), 7.86-7.79 (m, 2H, ArH), 7.64 (s, 1H, ArH), 7.62-7.58 (m, 1H, ArH), 7.55-7.52 (m, 2H, ArH), 7.50 (dd, J=10.4 Hz, J=2.4 Hz, 1H, ArH), 7.43-7.40 (m, 2H, ArH), 7.26-7.22 (m, 1H, ArH), 7.03-6.98 (m, 1H, ArH), 6.37 (s, 1H, OH), 4.60 (d, J=14.8 Hz, 1H, CH), 4.38 (d, J=14.8 Hz, 1H, CH), 1.46 (s, 3H, CH$_3$).

Mass (ESI, Negative): 446.8[M−H]⁻; (ESI, Positive): 448.1248[M+H]⁺.

(S)—N-(4-Cyano-3-(trifluoromethyl)phenyl)-2-hydroxy-2-methyl-3-(4-phenyl-1H-indol-1-yl)propanamide (41)

Phenyl-1H-indole (C$_{14}$H$_{11}$N)

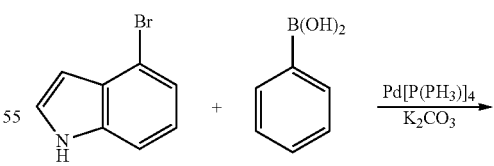

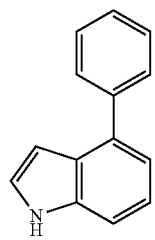

To a suspension of tetrakis(triphenylphosphine)palladium (0) [Pd(PPh₃)₄, 1.179 g, 1.0212 mmol] in 40 mL of ethylene glycol dimethyl ether (DME) was added 4-bromo-indole (2.00 g, 10.202 mmol), and the mixture was stirred for 15 minutes under argon at room temperature. A solution of phenylboronic acid (1.24 g, 10.202 mmol) in 4.5 mL of ethanol was added and the mixture was stirred for 10 minutes under the same conditions. A solution of potassium carbonate (2.16 g, 15.306 mmol) in 3.5 mL of water was added to above mixture and the resulting reaction mixture was heated at reflux for 3-4 hours under the argon atmosphere. After the end of the reaction was established by TLC, the reaction was diluted by brine, extracted with ethyl acetate. The organic layer was washed with brine, dried with MgSO₄, filtered, and concentrated under vacuum. The product was purified by a silica gel column using ethyl acetate and hexanes (1:3 to 2:1) as eluent to afford 1.67 g (84.8% yield) of the titled compound as yellowish oil.

41

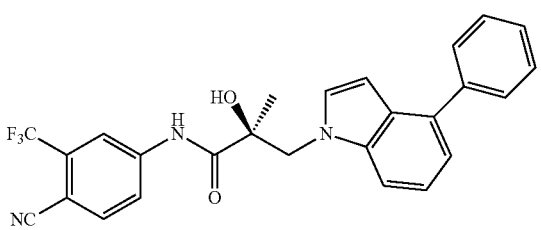

To a solution of 4-phenyl-1H-indole (0.42 g, 0.002173 mol) in anhydrous THF (10 mL), which was cooled in an ice water bath under an argon atmosphere, was added sodium hydride (60% dispersion in oil, 0.22 g, 0.005434 mol). After addition, the resulting mixture was stirred for three hours. (S)—N-(4-Cyano-3-(trifluoromethyl)phenyl)-2-methyloxirane-2-carboxamide (0.76 g, 0.002173 mol) was added to above solution, and the resulting reaction mixture was allowed to stir overnight at room temperature under argon. The reaction was quenched by water, extracted with ethyl acetate. The organic layer was washed with brine, dried with MgSO₄, filtered, and concentrated under vacuum. The product was purified by a silica gel column using ethyl acetate and hexanes (1:2) as eluent to afford 0.69 g (69%) of the titled compound as off-white solid.

¹H NMR (400 MHz, DMSO-d₆) δ 10.37 (s, 1H, NH), 8.37 (d, J=2.0 Hz, 1H, ArH), 8.18 (dd, J=8.4 Hz, J=2.0 Hz, 1H, ArH), 8.05 (d, J=8.4 Hz, 1H, ArH), 7.60-7.54 (m, 3H, ArH), 7.49-7.45 (m, 2H, ArH), 7.38-7.34 (m, 2H, ArH), 7.18-7.14 (m, 1H, ArH), 7.04 (d, J=7.2 Hz, 1H, ArH), 6.51 (d, J=3.2 Hz, 1H, ArH), 6.35 (s, 1H, OH), 4.58 (d, J=14.4 Hz, 1H, CH), 4.38 (d, J=14.4 Hz, 1H, CH), 1.45 (s, 3H, CH₃).

Mass (ESI, Positive): 464.1536[M+H]⁺; 486.1351 [M+Na]⁺.

(S)—N-(4-Cyano-3-(trifluoromethyl)phenyl)-3-(4-fluoro-5-phenyl-1H-indol-1-yl)-2-hydroxy-2-methyl-propanamide (42)

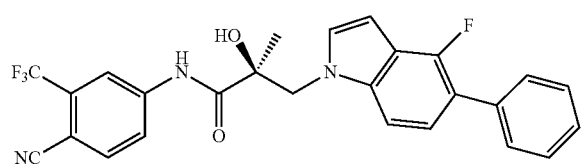 [SMILES: C[C@](O)(Cn1ccc2c(F)c(-c3ccccc3)ccc21)C(=O)Nc1ccc(C#N)c(C(F)(F)F)c1]

To a solution of 4-fluoro-5-phenyl-1H-indole (0.33 g, 0.00156 mol) in anhydrous THF (10 mL), which was cooled in an ice water bath under an argon atmosphere, was added sodium hydride (60% dispersion in oil, 0.16 g, 0.00391 mol). After addition, the resulting mixture was stirred for three hours. (S)—N-(4-Cyano-3-(trifluoromethyl)phenyl)-2-methyloxirane-2-carboxamide (0.55 g, 0.00156 mol) was added to above solution, and the resulting reaction mixture was allowed to stir overnight at room temperature under argon. The reaction was quenched by water, extracted with ethyl acetate. The organic layer was washed with brine, dried with MgSO₄, filtered, and concentrated under vacuum. The product was purified by a silica gel column using ethyl acetate and hexanes (1:2) as eluent to afford 0.47 g (63%) of the titled compound as off-white solid.

¹H NMR (400 MHz, DMSO-d₆) δ 10.33 (s, 1H, NH), 8.35 (d, J=2.0 Hz, 1H, ArH), 8.17 (dd, J=8.4 Hz, J=2.0 Hz, 1H, ArH), 8.05 (d, J=8.4 Hz, 1H, ArH), 7.51-7.40 (m, 5H, ArH), 7.36-7.32 (m, 2H, ArH and indole-H), 7.17-7.13 (m, 1H, ArH), 6.53 (d, J=3.2 Hz, 1H, ArH), 6.38 (s, 1H, OH), 4.60 (d, J=14.8 Hz, 1H, CH), 4.38 (d, J=14.8 Hz, 1H, CH), 1.45 (s, 3H, CH₃).

Mass (ESI, Negative): [M−H]⁻; (ESI, Positive): 482.1490 [M+H]⁺; 504.1310[M+Na]⁺.

Carbazole

Methods A and B: Preparation of Carbazoles

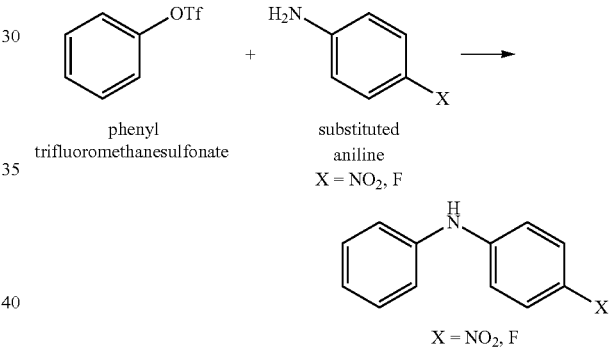

Method A (Non Microwave):

A mixture of phenyl trifluoromethanesulfonate (500 mg, 2.21 mmol), palladium acetate (II) (50 mg, 0.22 mmol), (±) 2,2'-bis(diphenylphosphino)-1,1'-binaphthyl (317 mg, 0.66 mmol) and cesium carbonate (1.09 g, 3.31 mmol) in 50 mL of toluene were inertized with argon. Then, substituted aniline (2.43 mmol) was added and the mixture was heated at 110° C. overnight. The reaction mixture was allowed to cool to room temperature and filtered through a pad of Celite®. The filtrate was diluted with CH₂Cl₂ and water. The phases were separated and the aqueous phase was reextracted 2 times with CH₂Cl₂. The combined organic phases were dried over Na₂SO₄ and the solvent was evaporated.

Method B (Microwave):

A mixture of phenyl trifluoromethanesulfonate (200 mg, 0.88 mmol), palladium acetate (II) (20 mg, 0.09 mmol), (±) 2,2'-bis(diphenylphosphino)-1,1'-binaphthyl (64 mg, 0.13 mmol) and cesium carbonate (430 mg, 1.32 mmol), and substituted aniline (0.97 mmol) in 5 mL of toluene were loaded into a vessel with a cap. Reaction vessels were placed in a reactor block in the microwave. A programmable microwave irradiation cycle of 30 min at 300 W at 110° C. and 25 min of fan-cooling was executed (irradiation time, 30 min). The mixture was transferred to a round bottom flask to be concentrated under reduced pressure and poured into EtOAc, which was washed with water and dried over anhydrous MgSO₄, concentrated. The crude product obtained was purified by chromatography on silica gel using EtOAc/hexane (6/1, v/v) as an eluent to produce the target product (~89%) as deep brown oil.

4-Fluoro-N-phenyl aniline

¹H NMR (400 MHz, CDCl₃) δ 7.27-7.24 (m, 2H), 7.07-7.02 (m, 2H), 7.01-6.95 (m, 4H), 6.89 (t, J=7.2 Hz, 1H), 5.57 (bs, 1H, NH).

3-Nitro-9H-carbazole

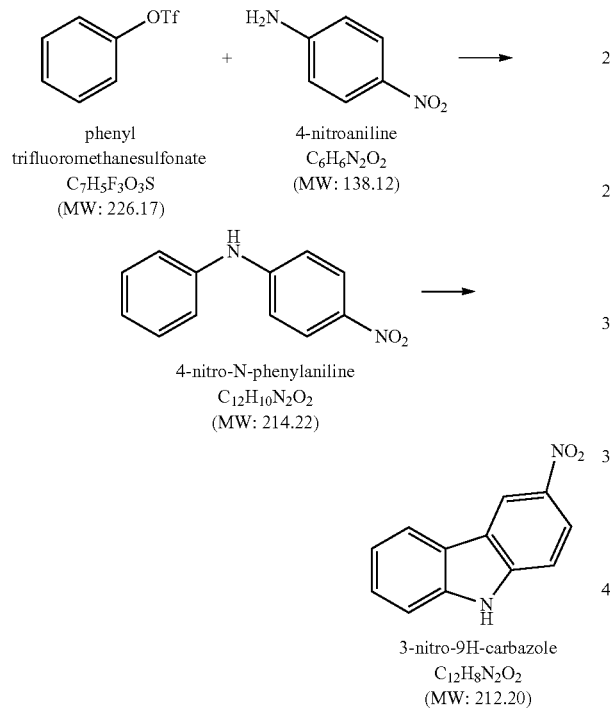

A mixture of phenyl trifluoromethanesulfonate (500 mg, 2.21 mmol), palladium acetate (II) (50 mg, 0.22 mmol), (±) 2,2'-bis(diphenylphosphino)-1,1'-binaphthyl (317 mg, 0.66 mmol) and cesium carbonate (1.09 g, 3.31 mmol) in 50 mL of toluene were inertized with argon. Then, 4-nitroaniline (331 mg, 2.43 mmol) was added and the mixture was heated at 110° C. overnight. The reaction mixture was allowed to cool to room temperature and filtered through a pad of Celite®. The filtrate was diluted with CH₂Cl₂ and water. The phases were separated and the aqueous phase was re-extracted 2 times with CH₂Cl₂. The combined organic phases were dried over Na₂SO₄ and the resulting solution was dried over anhydrous Na₂SO₄ and purified with flash column chromatography as an eluent EtOAc/hexane (1/6, v/v) to give 4-nitro-N-phenylaniline. The aniline (450 mg, 2 mmol), Pd(OAc)₂ (23 mg, 0.1 mmol), K₂CO₃ (30 mg, 0.2 mmol), and pivalic acid (408 mg, 4 mmol) was placed into a glass test tube. The uncapped test tube was placed in an oil bath and the mixture was stirred under air at the indicated temperature. The solution was then cooled to room temperature, diluted with EtOAc, washed with a saturated Na₂CO₃, dried over Na₂SO₄, concentrated, and purified by flash column chromatography as an eluent of EtOAc/hexane to give 3-nitro-9H-carbazole.

(S)-3-(9H-Carbazol-9-yl)-N-(4-cyano-3-(trifluoromethyl)phenyl)-2-hydroxy-2-methylpropanamide (200)

Method B:

Yield 88%; MS (ESI) m/z 436.1 [M−H]⁻;

¹H NMR (CDCl₃, 400 MHz) δ 8.82 (bs, 1H, NH), 8.09-8.06 (m, 3H), 7.84 (d, J=1.6 Hz, 1H), 7.77-7.71 (m, 2H), 7.54 (d, J=8.4 Hz, 2H), 7.45-7.39 (m, 3H), 7.24-7.23 (m, 2H), 4.80 (d, J=15.2 Hz, 1H), 4.63 (d, J=15.2 Hz, 1H) 2.57 (s, 1H, OH), 1.69 (s, 3H).

(S)—N-(4-Cyano-3-(trifluoromethyl)phenyl)-2-hydroxy-2-methyl-3-(3-nitro-9H-carbazol-9-yl)propanamide (201)

Method B:

MS (ESI) m/z 481.1 [M−H]⁻

¹H NMR (CDCl₃, 400 MHz) δ 9.01 (s, 1H), 8.92 (bs, 1H, NH), 8.39 (m, 1H), 8.08 (m, 1H), 7.92 (d, J=1.6 Hz, 1H), 7.78 (d, J=8.4 Hz, 1H), 7.62 (dd, J=8.4, 1.6 Hz, 1H), 7.45 (m, 1H), 7.48-7.22 (m, 3H), 4.91 (d, J=15.0 Hz, 1H), 4.85 (d, J=15.0 Hz, 1H) 2.62 (s, 1H, OH), 1.70 (s, 3H).

(S)—N-(4-Cyano-3-(trifluoromethyl)phenyl)-3-(3-fluoro-9H-carbazol-9-yl)-2-hydroxy-2-methylpropanamide (202)

To a solution of 4-fluoro-carbazole (0.20 g, 0.00108 mol) in anhydrous THF (10 mL), which was cooled in an ice water bath under an argon atmosphere, was added sodium hydride (60% dispersion in oil, 0.09 g, 0.00216 mol). After addition, the resulting mixture was stirred for two hours. (R)-3-Bromo-N-(4-cyano-3-trifluoromethyl-phenyl)-2-hydroxy-2-methylpropanamide (0.38 g, 0.00108 mol) was added to the above solution, and the resulting reaction mixture was allowed to stir overnight at room temperature under argon. The reaction was quenched by water, extracted with ethyl acetate. The organic layer was dried with MgSO₄, filtered, and concentrated under vacuum. The product was purified by a silica gel column using methylene chloride as eluent to afford 0.36 g (73.5%) of the titled compound as white solid.

¹H NMR (400 MHz, DMSO-d₆) δ 10.36 (s, 1H, NH), 8.25 (d, J=1.6 Hz, 1H, ArH), 8.12-8.09 (m, 2H, ArH), 8.04 (d, J=8.8 Hz, 1H, ArH), 7.95 (dd, J=9.2 Hz, J=2.1 Hz, 1H, ArH), 7.66 (t, J=4.8 Hz, 1H, ArH), 7.64 (s, 1H, ArH), 7.37 (dt, J=9.2 Hz, J=1.2 Hz, 1H, ArH), 7.20 (td, J=9.2 Hz, J=2.0 Hz, 1H, ArH), 7.13 (t, J=8.0 Hz, 1H, ArH), 6.34 (s, 1H, OH), 4.70 (d, J=14.8 Hz, 1H, CH), 4.55 (d, J=14.8 Hz, 1H, CH), 1.52 (s, 3H, CH3).

Mass (ESI, Negative): 453.9 [M−H]−; (ESI, Positive): 478.1 [M+Na]+.

(S)—N-(3-Chloro-4-cyanophenyl)-3-(3-fluoro-9H-carbazol-9-yl)-2-hydroxy-2-methylpropanamide (203)

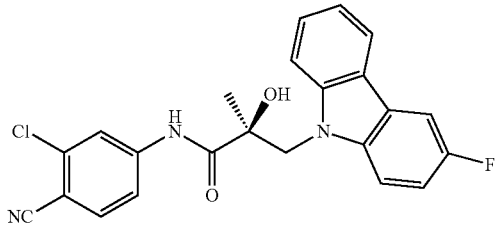 [SMILES: C[C@](O)(Cn1c2ccccc2c2cc(F)ccc21)C(=O)Nc1ccc(C#N)c(Cl)c1]

To a solution of 3-fluoro-carbazole (0.10 g, 0.00054 mol) in anhydrous THF (5 mL), which was cooled in an ice water bath under an argon atmosphere, was added sodium hydride (60% dispersion in oil, 0.033 g, 0.00081 mol). After addition, the resulting mixture was stirred for two hours. (R)-3-Bromo-N-(4-cyano-3-chloro-phenyl)-2-hydroxy-2-methyl-propanamide (0.17 g, 0.00054 mol) was added to above solution, and the resulting reaction mixture was allowed to stir overnight at room temperature under argon. The reaction was quenched by water, extracted with ethyl acetate. The organic layer was dried with MgSO$_4$, filtered, and concentrated under vacuum. The product was purified by a silica gel column using hexanes and ethyl acetate (2:1) as eluent to afford 0.22 g (98%) of the titled compound as white solid/needles.

$^1$H NMR (400 MHz, DMSO-d$_6$) δ 10.20 (s, 1H, NH), 8.12 (d, J=7.6 Hz, 1H, ArH), 8.05 (d, J=2.0 Hz, 1H, ArH), 7.96 (dd, J=9.2 Hz, J=2.0 Hz, 1H, ArH), 7.86 (d, J=8.8 Hz, 1H, ArH), 7.80 (dd, J=8.4 Hz, J=2.0 Hz, 1H, ArH), 7.69-7.66 (m, 2H, ArH), 7.41 (t, J=8.0 Hz, 1H, ArH), 7.24 (dt, J=9.6 Hz, J=2.4 Hz, 1H, ArH), 7.16 (t, J=7.2 Hz, 1H, ArH), 6.34 (s, 1H, OH), 4.70 (d, J=15.2 Hz, 1H, CH), 4.54 (d, J=15.2 Hz, 1H, CH), 1.52 (s, 3H, CH$_3$).

Mass (ESI, Negative): 420.1[M−H]$^-$; (ESI, Positive): 444.1[M+Na]$^+$.

(S)—N-(4-Cyano-3-(trifluoromethyl)phenyl)-3-(3,6-difluoro-9H-carbazol-9-yl)-2-hydroxy-2-methylpropanamide (204)

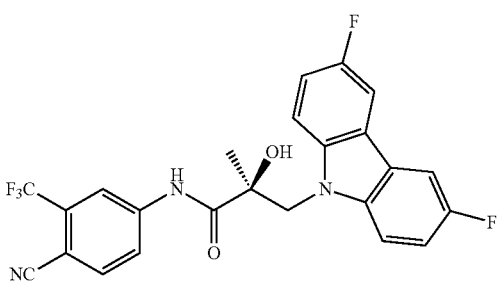 [SMILES: C[C@](O)(Cn1c2ccc(F)cc2c2cc(F)ccc21)C(=O)Nc1ccc(C#N)c(C(F)(F)F)c1]

To a solution of 3,6-difluorocarbazole (0.20 g, 0.00098 mol) in anhydrous THF (10 mL), which was cooled in an ice water bath under an argon atmosphere, was added sodium hydride (60% dispersion in oil, 0.06 g, 0.001476 mol). After addition, the resulting mixture was stirred for three hours. (S)—N-(4-Cyano-3-(trifluoromethyl)phenyl)-2-methyloxirane-2-carboxamide (0.266 g, 0.00098 mol) was added to above solution, and the resulting reaction mixture was allowed to stir overnight at room temperature under argon. The reaction was quenched by water, extracted with ethyl acetate. The organic layer was washed with brine, dried with MgSO$_4$, filtered, and concentrated under vacuum. The product was purified by a silica gel column using ethyl acetate and hexanes (1:2) as eluent to afford 0.40 g of the titled compound as white solid.

$^1$H NMR (400 MHz, DMSO-d$_6$) δ 10.33 (s, 1H, NH), 8.22 (d, J=1.6 Hz, 1H, ArH), 8.11 (dd, J=8.8 Hz, J=2.0 Hz, 1H, ArH), 8.05 (d, J=8.8 Hz, 1H, ArH), 7.98 (d, J=2.4 Hz, 1H, ArH), 7.96 (d, J=2.4 Hz, 1H, ArH), 7.68-7.65 (m, 2H, ArH), 7.27-7.22 (m, 2H, ArH), 6.36 (s, 1H, OH), 4.72 (d, J=15.2 Hz, 1H, CH), 4.54 (d, J=15.2 Hz, 1H, CH), 1.53 (s, 3H, CH$_3$).

Mass (ESI, Negative): 471.9[M−H]$^-$; (ESI, Positive): 496.1[M+Na]$^+$.

(S)-3-(9H-Carbazol-9-yl)-N-(3-chloro-4-cyanophenyl)-2-hydroxy-2-methylpropanamide (205)

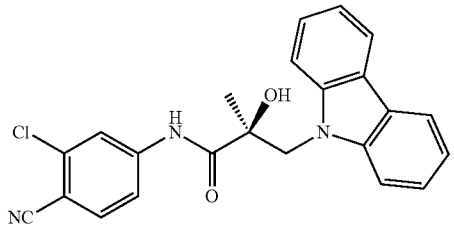

Method B
Yield 77%;
MS (ESI) m/z 402.3 [M−H]$^-$;
$^1$H NMR (400 MHz, CDCl$_3$) δ 8.75 (bs, 1H, NH), 8.08 (d, J=7.6 Hz, 2H), 7.78 (d, J=1.6 Hz, 1H), 7.56-7.54 (m, 3H), 7.44 (t, J=7.6 Hz, 2H), 7.37 (dd, J=8.8, 1.8 Hz, 1H), 7.27-7.25 (m, 2H), 4.78 (d, J=15.6 Hz, 1H), 4.63 (d, J=15.6 Hz, 1H), 2.65 (bs, 1H, OH), 1.66 (s, 3H).

Isoquinoline

(S)—N-(4-Cyano-3-(trifluoromethyl)phenyl)-3-(7-fluoro-3,4-dihydroisoquinolin-2(1H)-yl)-2-hydroxy-2-methylpropanamide (132)

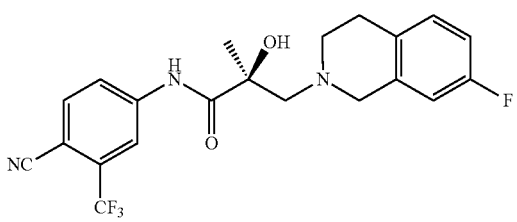

Method A
Yield 69%;
MS (ESI) m/z 420.0 [M−H]$^-$;
$^1$H NMR (400 MHz, CDCl$_3$) δ 9.09 (bs, 1H, NH), 7.93 (d, J=8.4 Hz, 1H), 7.80 (d, J=8.4 Hz, 1H), 7.05 (t, J=8.0 Hz, 1H), 6.86 (m, 1H), 6.63 (d, J=8.0 Hz, 1H), 3.71 (s, 2H), 3.42 (d, J=13.2 Hz, 1H), 2.91-2.82 (m, 5H), 2.60 (d, J=13.2 Hz, 1H), 1.46 (s, 3H).

Indoline Derivatives (S)—N-(3-Chloro-4-cyanophenyl)-3-(4-fluoroindolin-1-yl)-2-hydroxy-2-methylpropanamide (103)

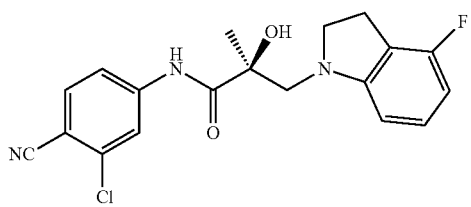 [SMILES: C[C@](O)(CN1CCc2c(F)cccc21)C(=O)Nc1ccc(C#N)c(Cl)c1]

Preparation of LDA solution in THF.

To a stirred solution of freshly distilled diisopropylamine (0.14 mL, 1.2 mmol) in anhydrous 5 mL of THF was added a solution of n-butyllithium (0.53 mL, 1.32 mmol, 2.5 M solution in hexane) at −78° C. under argon atmosphere.

Under the argon atmosphere into a 100 mL dried two necked round bottom flask equipped with a dropping funnel, the prepared solution of LDA or commercial 2.0 M LDA solution (1.2 mmol, Aldrich) in THF was placed in the flask, and then 4-fluoroindoline (1.0 mmol) in 10 mL of anhydrous THF was dropwise added to the LDA solution at the −78° C. under argon atmosphere. The solution was stirred for 10 min and warmed to 0° C. and cooled down again to −78° C. To the solution, a solution of (R)-3-bromo-N-(3-chloro-4-cyanophenyl)-2-hydroxy-2-methylpropanamide (1.0 mmol in THF) was added through dropping funnel under argon atmosphere at −78° C. and allowed to warm gradually to room temperature and stirred overnight. And then quenched by an addition of 0.5 mL of sat. NH$_4$Cl. The solution was reduced in volume under reduced pressure and dispersed into excess EtOAc, and then dried over anhydrous MgSO$_4$. The solution was concentrated on and purified by flash column chromatography (EtOAc/hexane) or recrystallized from EtOAc/hexane (or DCM/hexane) to give the designed compound, 573.

Yield 71%;

White solid;

MS (ESI) m/z 372.0 [M−H]$^-$;

HRMS (ESI) m/z calcd for C$_{19}$H$_{18}$ClFN$_3$O$_2$: 374.1072. Found: 374.1072 [M+H]$^+$.

$[\alpha]_D^{20}$ −173° (c 1.0, CH$_3$OH);

$^1$H NMR (acetone-d$_6$, 400 MHz) δ 9.84 (bs, 1H, NH), 8.26 (d, J=2.0 Hz, 1H), 7.90 (dd, J=8.4, 2.0 Hz, 1H), 7.80 (d, J=8.4 Hz, 1H), 6.99 (m, 1H), 6.43 (d, J=8.0 Hz, 1H), 6.31 (t, J=8.4 Hz, 1H), 5.21 (bs, 1H, OH), 3.66 (m, 1H), 3.63 (d, J=14.4 Hz, 1H), 3.53 (q, J=8.0 Hz, 1H), 3.26 (d, J=14.4 Hz, 1H), 2.89 (m, 2H), 1.53 (s, 3H).

$^{13}$C NMR (acetone-d$_6$, 100 MHz) δ 175.9, 160.6 (d, J=239.7 Hz), 160.6 (d, J=9.3 Hz), 144.6, 137.3, 135.6, 129.9 (d, J=8.7 Hz), 120.8, 119.2, 116.7, 114.8 (d, J=21.7 Hz), 107.8, 105.1 (d, J=21.0 Hz), 104.1 (d, J=8.0 Hz), 77.8, 60.4, 56.7, 25.4, 24.3.

$^{19}$F NMR (CDCl$_3$, decoupled) δ 118.95.

(S)—N-(3-Chloro-4-cyanophenyl)-3-(5-fluoroindolin-1-yl)-2-hydroxy-2-methylpropanamide (104)

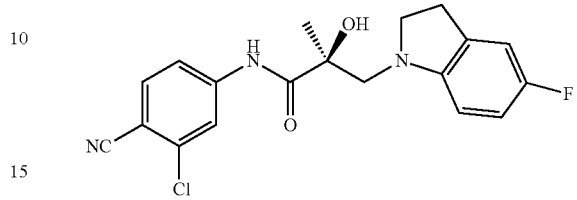

Method A

Yield; 68%;

$^1$H NMR (400 MHz, CDCl$_3$) δ 9.09 (bs, 1H, NH), 7.98 (d, J=2.0 Hz, 1H), 7.61 (d, J=8.4 Hz, 1H), 7.52 (dd, J=8.4, 2.0 Hz, 1H), 6.83 (m, 1H), 6.77 (m, 1H), 6.51 (m, 1H), 3.62 (d, J=14.4 Hz, 1H), 3.56 (bs, 1H, OH), 3.42 (m, 1H), 3.30 (q, J=9.2 Hz, 1H), 3.21 (d, J=14.4 Hz, 1H), 3.01 (t, J=8.4 Hz, 2H), 1.54 (s, 3H).

MS (ESI) m/z 372.0 [M−H]$^-$;

$[\alpha]_D^{20}$ −202° (c 1.0, CH$_3$OH)

$^{19}$F NMR (CDCl$_3$, decoupled) δ 125.35.

(S)—N-(3-Chloro-4-cyanophenyl)-3-(6-fluoroindolin-1-yl)-2-hydroxy-2-methylpropanamide (106)

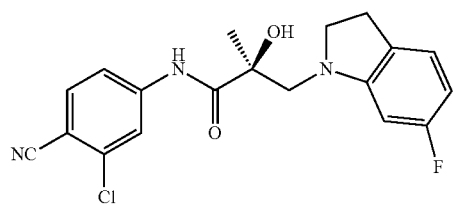 [SMILES: C[C@](O)(CN1CCc2ccc(F)cc21)C(=O)Nc1ccc(C#N)c(Cl)c1]

Method A

Yield 76%;

MS (ESI) m/z 372.1 [M−H]$^-$;

$^1$H NMR (400 MHz, CDCl$_3$) δ 9.08 (bs, 1H, NH), 7.97 (d, J=1.6 Hz, 1H), 7.60 (d, J=8.4 Hz, 1H), 7.53 (dd, J=8.4, 1.6 Hz, 1H), 6.77 (t, J=6.4 Hz, 1H), 6.39 (m, 1H), 6.33 (d, J=10.0 Hz, 1H), 3.64 (d, J=14.2 Hz, 1H), 3.49 (bs, 1H, OH), 3.47 (m, 1H), 3.38 (q, J=9.2 Hz, 1H), 3.23 (d, J=14.2 Hz, 1H), 2.95 (m, 2H), 1.56 (s, 3H).

(S)-3-(5-Chloro-6-fluoroindolin-1-yl)-N-(4-cyano-3-(trifluoromethyl)phenyl)-2-hydroxy-2-methylpropanamide (107)

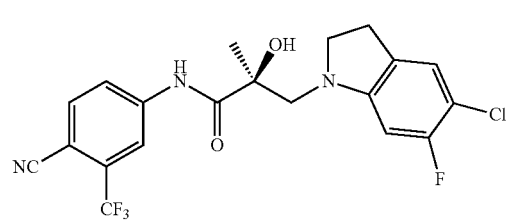 [SMILES: C[C@](O)(CN1CCc2cc(Cl)c(F)cc21)C(=O)Nc1ccc(C#N)c(C(F)(F)F)c1]

Method A

Yield; 47%

MS (ESI) m/z 440.3 [M−H]⁻;

¹H NMR (400 MHz, CDCl₃) δ 9.15 (bs, 1H, NH), 8.08 (s, 1H), 7.97 (d, J=8.4 Hz, 1H), 7.80 (d, J=8.4 Hz, 1H), 7.03 (d, J=7.2 Hz, 1H), 6.42 (d, J=10.0 Hz, 1H), 3.66 (d, J=14.4 Hz, 1H), 3.52-3.42 (m, 2H), 3.38 (s, 1H, OH), 3.21 (d, J=14.4 Hz, 1H), 2.96-2.80 (m, 2H), 1.52 (s, 3H).

(S)—N-(4-Cyano-3-(trifluoromethyl)phenyl)-3-(5,6-difluoroindolin-1-yl)-2-hydroxy-2-methylpropanamide (108)

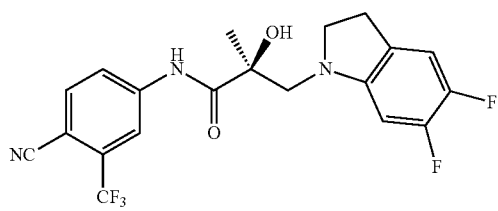 [SMILES: C[C@](O)(CN1CCc2cc(F)c(F)cc21)C(=O)Nc1ccc(C#N)c(C(F)(F)F)c1]

Method A

Yield; 59%

MS (ESI) m/z 423.9 [M−H]⁻

¹H NMR (400 MHz, CDCl₃) δ 9.18 (bs, 1H, NH), 8.09 (d, J=2.0 Hz, 1H), 7.97 (dd, J=8.4, 2.0 Hz, 1H), 7.80 (d, J=8.4 Hz, 1H), 6.89 (t, J=8.8 Hz, 1H), 6.43 (m, 1H), 3.64 (d, J=14.4 Hz, 1H), 3.46 (s, 1H, OH), 3.40-3.35 (m, 2H), 3.17 (d, J=14.4 Hz, 1H), 2.99-2.91 (m, 2H), 1.57 (s, 3H).

(S)—N-(4-Cyano-3-(trifluoromethyl)phenyl)-2-hydroxy-3-(indolin-1-yl)-2-methylpropanamide (109)

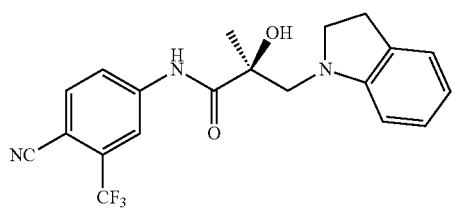 [SMILES: C[C@](O)(CN1CCc2ccccc21)C(=O)Nc1ccc(C#N)c(C(F)(F)F)c1]

Method A

Yield; 69%;

MS (ESI) m/z 387.8 [M−H]⁻;

¹H NMR (400 MHz, CDCl₃) δ 9.24 (bs, 1H, NH), 8.09 (d, J=2.0 Hz, 1H), 7.94 (dd, J=8.8, 2.0 Hz, 1H), 7.79 (d, J=2.0 Hz, 1H), 7.13-7.10 (m, 2H), 6.78 (dt, J=8.0, 0.8 Hz, 1H), 6.62 (d, J=8.0, 1H), 3.77 (bs, 1H, OH), 3.66 (d, J=14.4 Hz, 1H), 3.54 (t, J=8.4 Hz, 1H), 3.46-3.40 (m, 1H), 3.30 (d, J=14.4 Hz, 1H), 3.04-2.92 (m, 2H), 1.57 (s, 3H).

(S)—N-(3-Chloro-4-cyanophenyl)-3-(5,6-difluoroindolin-1-yl)-2-hydroxy-2-methylpropanamide (110)

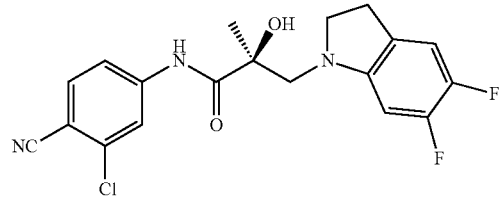 [SMILES: C[C@](O)(CN1CCc2cc(F)c(F)cc21)C(=O)Nc1ccc(C#N)c(Cl)c1]

Method A

Yield 64%;

MS (ESI) m/z 390.0 [M−H]⁻;

¹H NMR (400 MHz, CDCl₃) δ 9.05 (bs, 1H, NH), 7.98 (s, 1H), 7.62 (d, J=8.2 Hz, 1H), 7.53 (d, J=8.2 Hz, 1H), 6.88 (t, J=8.8 Hz, 1H), 6.43 (m, 1H), 3.64 (d, J=14.4 Hz, 1H), 3.46 (s, 1H, OH), 3.44 (m, 1H), 3.42-3.34 (m, 1H), 3.16 (d, J=14.4 Hz, 1H), 3.95-3.88 (m, 2H), 1.55 (s, 3H).

(S)-3-(5-Bromoindolin-1-yl)-N-(3-chloro-4-cyanophenyl)-2-hydroxy-2-methylpropanamide (114)

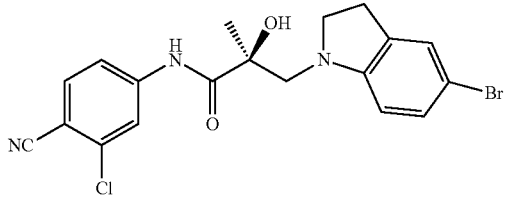 [SMILES: C[C@](O)(CN1CCc2cc(Br)ccc21)C(=O)Nc1ccc(C#N)c(Cl)c1]

Method A

Yield 54%;

MS (ESI) m/z 433.6 [M−H]⁻;

¹H NMR (400 MHz, CDCl₃) δ 9.04 (bs, 1H, NH), 7.98 (d, J=2.0 Hz, 1H), 7.60 (d, J=6.0 Hz, 1H), 7.52 (dd, J=6.0, 2.0 Hz, 1H), 7.19-7.17 (m, 2H), 6.49 (d, J=8.4 Hz, 1H), 3.65 (d, J=14.4 Hz, 1H), 3.47 (bs, 1H, OH), 3.36-3.41 (m, 1H), 3.32 (q, J=9.2 Hz, 1H), 3.23 (d, J=14.4 Hz, 1H), 2.99-2.91 (m, 2H), 1.56 (s, 3H).

(S)—N-(3-Chloro-4-cyanophenyl)-3-(5-fluoro-6-phenylindolin-1-yl)-2-hydroxy-2-methylpropanamide (115)

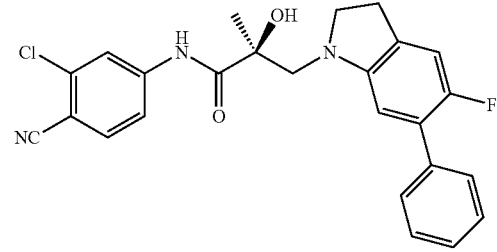 [SMILES: C[C@](O)(CN1CCc2cc(F)c(-c3ccccc3)cc21)C(=O)Nc1ccc(C#N)c(Cl)c1]

To a solution of (S)—N-(3-chloro-4-cyanophenyl)-3-(5-fluoro-6-phenyl-1H-indol-1-yl)-2-hydroxy-2-methylpropanamide (34, 0.185 g, 0.000413 mol) in 5 mL of glacial acetic acid, which was cooled in an ice-water bath, was added drop-wise sodium cyanoborohydride (1.0 M in THF, 0.62 mL, 0.00124 mol) under as argon atmosphere. After addition, the resulting reaction mixture was allowed to stir for overnight at room temperature under argon. The reaction was quenched by aqueous $NH_4Cl$ solution, extracted with ethyl acetate. The organic layer was washed with brine twice, dried with $MgSO_4$, filtered, and concentrated under vacuum. The product was purified by a silica gel column using ethyl acetate and hexanes (1:2) as eluent to afford 0.17 g of the titled compound as yellowish foam.

$^1$H NMR (400 MHz, DMSO-$d_6$) δ 10.29 (s, 1H, NH), 8.21 (d, J=2.0 Hz, 1H, ArH), 7.92-7.84 (m, 2H, ArH), 7.45-7.34 (m, 5H, ArH), 6.95 (d, J=10.4 Hz, 1H, ArH), 6.55 (d, J=6.4 Hz, 1H, ArH), 6.02 (s, 1H, OH), 3.61 (q, J=8.8 Hz, 1H, CH), 4.50 (d, J=14.4 Hz, 1H, CH), 3.40 (d, J=14.4 Hz, 1H, CH), 4.19 (d, J=14.4 Hz, 1H, CH), 2.91 (t, J=8.4 Hz, 2H, $CH_2$), 1.42 (s, 3H, $CH_3$).

Mass (ESI, Negative): [M–H]$^-$; (ESI, Positive): 450.1394 [M+H]$^+$.

Indazole Derivatives (S)—N-(4-Cyano-3-(trifluoromethyl)phenyl)-3-(5-fluoro-1H-indazol-1-yl)-2-hydroxy-2-methylpropanamide (90, 91)

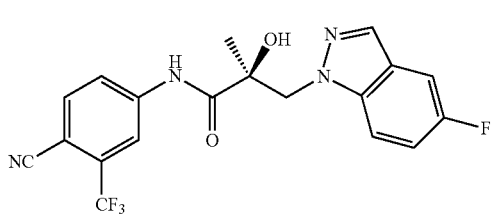

90

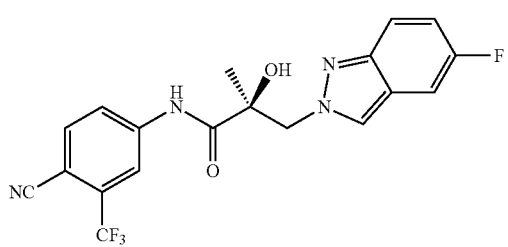

91

Method B
Yield; 67%
MS (ESI) 405.1 [M–H]$^-$ $^1$H NMR (400 MHz, CDCl$_3$) δ 9.16 (bs, 1H, NH), 8.05-7.88 (m, 2H), 7.81-7.72 (m, 2H), 7.62-7.13 (m, 4H), 6.72 (bs, OH, 0.56H), 6.15 (s, OH, 0.44H), 4.94 (d, J=13.6 Hz, 0.56H), 4.95 (d, J=14.2 Hz, 0.46H), 4.52 (d, J=13.6 Hz, 0.56H), 4.43 (d, J=14.2 Hz, 0.46H), 1.53 (s, 3H).

(S)—N-(3-Chloro-4-cyanophenyl)-3-(5-fluoro-1H-indazol-1-yl)-2-hydroxy-2-methylpropanamide (92, 93)

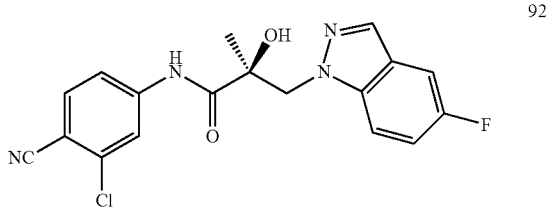

92

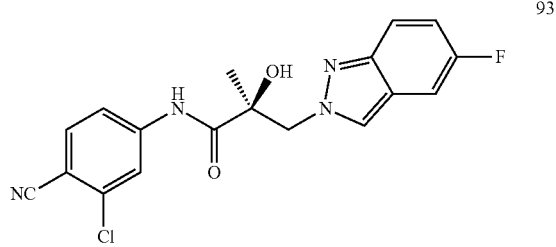

93

Method B
Yield; 74%
MS (ESI) 370.8 [M–H]$^-$ $^1$H NMR (400 MHz, CDCl$_3$) δ 8.97 (bs, 1H, NH), 7.99 (s, 0.56H), 7.95 (s, 0.46H), 7.83 (d, J=2.4 Hz, 0.46H), 7.83 (d, J=2.0 Hz, 0.54H), 7.64-7.45 (m, 2H), 7.39-7.31 (m, 1H), 7.24-7.22 (m, 1H), 7.16-7.11 (m, 1H), 6.63 (s, OH, 0.46H), 6.04 (s, OH, 0.54H), 4.92 (d, J=13.6 Hz, 0.46H), 4.92 (d, J=14.0 Hz, 0.54H), 4.50 (d, J=13.6 Hz, 0.46H), 4.40 (d, J=14.0 Hz, 0.54H), 1.58 (s, 3H).

Example 5

Androgen Receptor Binding, Transactivation, and Metabolism of Indole Based SARDs Ligand Binding Assay Objective:
To determine SARD binding affinity to the AR-LBD.
Method:
hAR-LBD (633-919) was cloned into pGex4t.1. Large scale GST-tagged AR-LBD was prepared and purified using a GST column. Recombinant AR-LBD was combined with [$^3$H]mibolerone (PerkinElmer, Waltham, Mass.) in buffer A (10 mM Tris, pH 7.4, 1.5 mM disodium EDTA, 0.25 M sucrose, 10 mM sodium molybdate, 1 mM PMSF) to determine the equilibrium dissociation constant (Kd) of [$^3$H]mibolerone. Protein was incubated with increasing concentrations of [$^3$H]mibolerone with and without a high concentration of unlabeled mibolerone at 4° C. for 18 h in order to determine total and non-specific binding. Non-specific binding was then subtracted from total binding to determine specific binding and non-linear regression for ligand binding curve with one site saturation to determine the Kd of mibolerone.

Increasing concentrations of SARDs or DHT (range: $10^{-12}$ to $10^{-2}$ M) were incubated with [$^3$H]mibolerone and AR LBD using the conditions described above. Following incubation, the ligand bound AR-LBD complex was isolated using biogelHT hydroxyapatite, washed and counted in a scintillation counter after adding scintillation cocktail. Values are expressed as Ki.

Transactivation Assay for Wt and Mutant AR

Objective:

To determine the effect of SARDs on androgen-induced transactivation of AR wildtype (wt) or AR carrying known AR-LBD mutants (i.e., W741L or T877A).

Figure 1B:
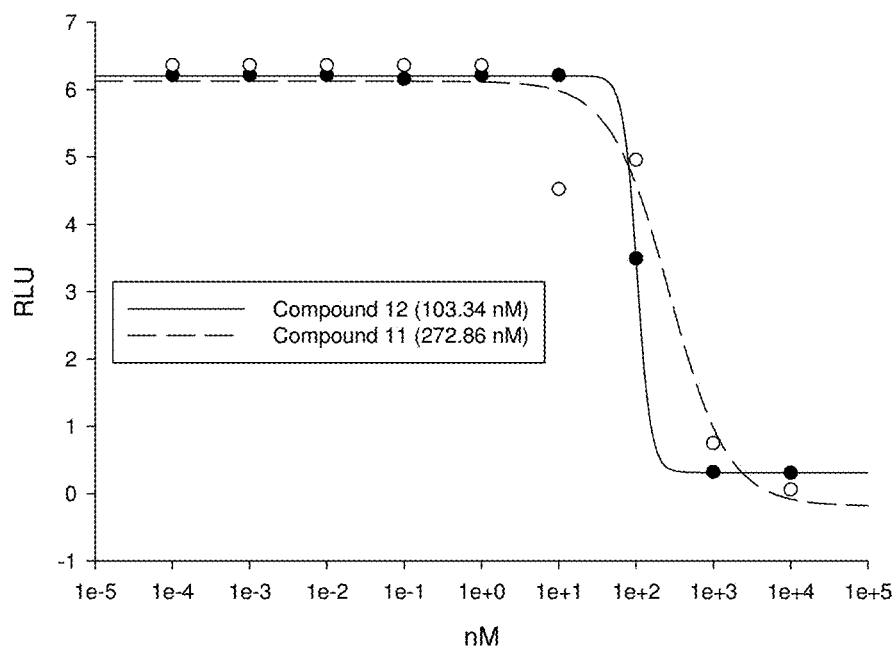
Figure 1B:
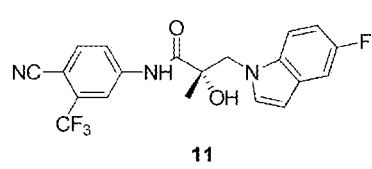
Figure 1B:
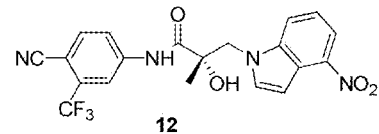
Figure 1C:
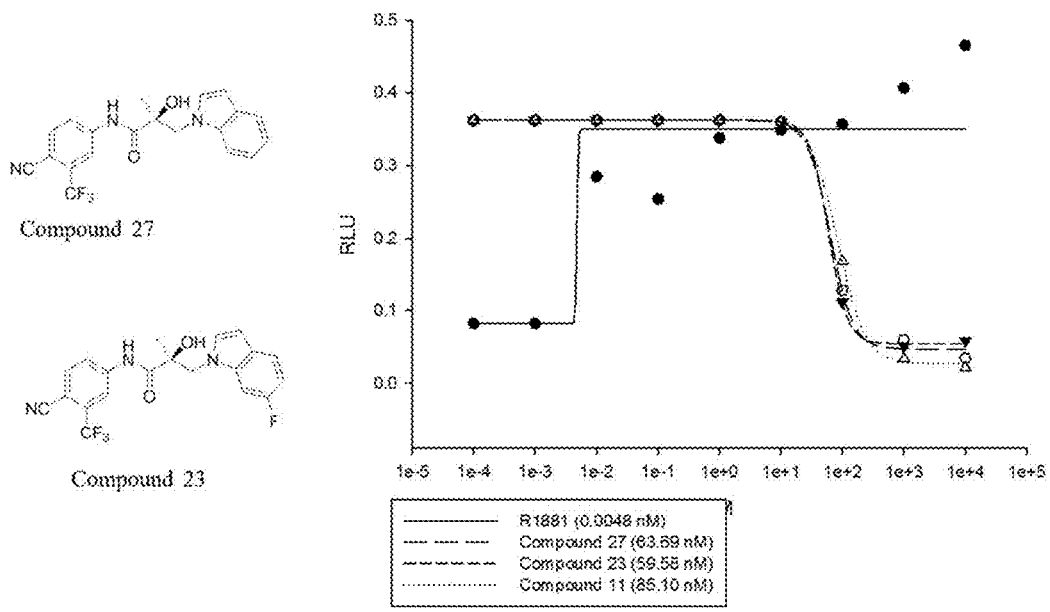

Method:

HEK-293 cells were plated at 125,000 cells/well of a 24 well plate in DME+5% csFBS without phenol red. Cells were transfected with 0.25 ug GRE-LUC, 10 ng CMV-renilla LUC, and 50 ng CMV-hAR(wt) or CMV-hAR (W741L) or CMV-hAR(T877A) using lipofectamine transfection reagent in optiMEM medium. Medium was changed 24 h after transfection to DME+5% csFBS without phenol red and treated with a dose response of various drugs (Table 1: 11-18, 20-27, 30, 31, 33, 70-74) (1 pM to 10 uM). SARDs and antagonists were treated in combination with 0.1 nM R1881. Luciferase assay was performed 24 h after treatment on a Biotek synergy 4 plate reader. Firefly luciferase values were normalized to renilla luciferase values. For FIG. 1A-FIG. 1C, the following variation of the method was used:

HEK cells were plated in 24 well plates at 60,000 cells per well in DMEM+5% csFBS without phenol red. After overnight incubation, changed medium to OptiMEM (0.25 ml). All the wells were transfected with 0.25 ug GRE-LUC, 5 ng CMV-renilla LUC, and 25 ng CMV-hAR. Twenty four hours after transfection, medium was replaced with 1 ml of DME+ 5% csFBS without phenol red. Twenty-four hrs after transfection, the cells were treated with 20, 18, and 14 (FIG. 1A), 12 and 11 (FIG. 1B), 11, 27, and 23 (FIG. 1C), 34-42 (FIG. 29A, FIG. 29B, FIG. 29D, FIG. 29E, FIG. 29F, FIG. 29G, FIG. 29H, FIG. 29I, FIG. 29K, FIG. 29O) and were harvested 48 hrs after transfection and firefly and renilla luciferase assay performed.

Transactivation.

HEK-293 cells were plated at 120,000 cells per well of a 24 well plate in DME+5% csFBS. The cells were transfected using Lipofectamine (Invitrogen, Carlsbad, Calif.) with 0.25 µg GRE-LUC, 0.01 µg CMV-LUC (renilla luciferase) and 25 ng of the AR. The cells were treated 24 hrs after transfection as indicated in the figures and the luciferase assay performed 48 hrs after transfection. Data are represented as $IC_{50}$ obtained from four parameter logistics curve.

AR Degradation Using Compounds of this Invention

Objective:

To determine the efficacy and potency of AR degradation by SARD compounds in AD1 cells, LNCaP (T877A AR) or 22RV-1 (full length AR and truncated splice variant AR (AR-V7)) cell lines.

Method:

See Example 6 below.

Determination of Metabolic Stability (In Vitro $CL_{int}$) of Test Compounds:

Phase I Metabolism

The assay was done in a final volume of 0.5 ml in duplicates (n=2). Test compound (1 µM) was pre-incubated for 10 minutes at 37° C. in 100 mM Tris-HCl, pH 7.5 containing 0.5 mg/ml liver microsomal protein. After pre-incubation, reaction was started by addition of 1 mM NADPH (pre-incubated at 37° C.). Incubations were carried out in triplicate and at various time-points (0, 5, 10, 15, 30 and 60 minutes) 100 µl aliquots were removed and quenched with 100 µl of acetonitrile containing internal standard. Samples were vortex mixed and centrifuged at 4000 rpm for 10 minutes. The supernatants were transferred to 96 well plates and submitted for LC-MS/MS analysis. As control, sample incubations done in absence of NADPH were included. From % PCR (% Parent Compound Remaining), rate of compound disappearance is determined (slope) and in vitro $CL_{int}$ (µl/min/mg protein) was calculated.

Metabolic Stability in Phase I & Phase II Pathways

In this assay, test compound was incubated with liver microsomes and disappearance of drug was determined using discovery grade LC-MS/MS. To stimulate Phase II metabolic pathway (glucuronidation), UDPGA and alamethicin was included in the assay.

LC-MS/MS Analysis:

The analysis of the compounds under investigation was performed using LC-MS/MS system consisting of Agilent 1100 HPLC with an MDS/Sciex 4000 Q-Trap™ mass spectrometer. The separation was achieved using a $C_{18}$ analytical column (Alltima™, 2.1×100 mm, 3 m) protected by a $C_{18}$ guard cartridge system (SecurityGuard™ ULTRA Cartridges UHPLC for 4.6 mm ID columns, Phenomenex). Mobile phase was consisting of channel A (95% acetonitrile+5% water+0.1% formic acid) and channel C (95% water+5% acetonitrile+0.1% formic acid) and was delivered at a flow rate of 0.4 mL/min. The volume ratio of acetonitrile and water was optimized for each of the analytes. Multiple reaction monitoring (MRM) scans were made with curtain gas, collision gas, nebulizer gas, and auxiliary gas optimized for each compound, and source temperature at 550° C. Molecular ions were formed using an ion spray voltage (IS) of −4200 V (negative mode). Declustering potential (DP), entrance potential (EP), collision energy (CE), product ion mass, and cell exit potential (CXP) were optimized for each compound.

TABLE 1

AR Binding, Inhibition of AR Transactivation, AR Degradation and in vitro Metabolic Stability of SARDs:

| | | Transcriptional Activation (+0.1 nM R1881; R1881 $EC_{50}$ = 0.11 nM) | | | SARD activity | $T_{1/2}$ (min) |
|---|---|---|---|---|---|---|
| Compound | Binding $K_i$ (nM) | Wt. $IC_{50}$ (nM) | W741L $IC_{50}$ (nM) | T877A $IC_{50}$ (nM) | (Figure Numbers) | $CL_{int}$ (µl/min/mg) |
| DHT | 1 | — | — | — | | |
| Bicalutamide | 545.5 | 248.2 | — | 557 | | |
| Enzalutamide | 205.2 | 216.3 | 939 | 331.94 | | |
| ARN-509 | — | 297.0 | 1939.41 | 390.50 | | |

TABLE 1-continued

AR Binding, Inhibition of AR Transactivation, AR Degradation and in vitro Metabolic Stability of SARDs:

| Compound | Binding $K_i$ (nM) | Transcriptional Activation (+0.1 nM R1881; R1881 $EC_{50}$ = 0.11 nM) | | | SARD activity (Figure Numbers) | $T_{1/2}$ (min) $CL_{int}$ (µl/min/mg) |
| | | Wt. $IC_{50}$ (nM) | W741L $IC_{50}$ (nM) | T877A $IC_{50}$ (nM) | | |
| --- | --- | --- | --- | --- | --- | --- |
| ASC-J9 | — | 1008.0 | 3487.68 | 2288.16 | | |
| 11 | 57.8 | 50.9 | 13.68 | 48.47 | 2A, 3, 5, 6C | 12.35 min 56.14 mL/min/kg |
| 11R | — | 351.21 | — | — | | |
| 12 | 314.22 | 103.34 | | | 11, 14 | 37.27 18.6 |
| 13 | 625.01 | — | | | 3 | |
| 14 | 223.74 | 71.81 (partial) | | | | 15.97 43.4 |
| 15 | >10,000 | — | | | | 29.79 23.28 |
| 16 | 489.88 | 2285.14 | | | | |
| 17 | 80.43 | | | | | |
| 18 | 416.03 | 335.98 | | | | 21.07 32.9 |
| 20 | 432.69 | 88.03 | | | 2A, 3, 4, 11, 12 | 19.27 35.97 |
| 21 | 293.84 | 984.52 | | | | 20.37 34.02 |
| 22 | 419.35 | 126.73 | | | | 36.32 19.08 |
| 23 | 212.49 | 85.10 | | | 11 | 22.39 30.96 |
| 24 | 315.84 | 917.68 | | | 12 | 17.02 40.73 |
| 27 | 2079.94 | 63.69 | | | 11 | 13.66 50.75 |
| 30 | 995.23 | 971.78 (UT-155 38 nM in the same exp) | | | 12 | 25.78 26.89 |
| 31 | 547.27 | 157.41 | | | 13, 15 | 21.77 31.84 |
| 33 | >10,000 | 684.64 | | | | |
| 70 | 530.72 | 299.78 | | | 16 | |
| 72 | — | 1016 | | | | |
| 32 | 46.58 | 57.76 | | | | 13.48 51.43 |
| 73 | 724.07 | 998.56 | | | 16 | |
| 74 | 1399.69 | 720.61 | | | | |

The short half-lives ($t_{1/2}$) and high metabolic clearance ($CL_{int}$) values in vitro of many of the compounds of this invention suggest rapid plasma clearance which could be favorable for topical treatment of androgenic dermatologic disorders as it would limit the risk of systemic side effects, even if the skin is penetrated.

TABLE 2

Binding Affinity of SARD Compounds of this Invention

| Compound | $K_i$ (nM) | Relative binding affinity (RBA) |
| --- | --- | --- |
| DHT | 8.88 6.62 | 1.00 |
| 12 | 817.3 | 0.011 |
| 11 | 57.8 | 0.152 |
| 11R | 333.07 | 0.027 |
| 14 | 179.77 | 0.049 |
| 15 | 663.05 | 0.010 |

FIG. 1A-FIG. 1C and FIG. 29A-FIG. 29O and Tables 1-3 show that many of the SARDs of this invention had higher AR binding affinity (see tables) and more potent AR antagonism in vitro (see Tables 1, 2, & 3 and figures referenced above and in the tables) than all the other AR antagonists tested (bicalutamide, enzalutamide, ARN-509, and ASC-J9). Further compound 11 retained highly potent antagonist activity in the two resistance mutants tested (Table 1) unlike the known antiandrogens tested.

TABLE 3

AR Binding, Inhibition of AR Transactivation, AR Degradation and Metabolic Stability of SARDs

| Compd ID | Structure | Log P (−0.4 to +5.6) | Binding/Wt. Ki (nM) (DHT = 1 nM) | IC$_{50}$ (nM) | SARD Activity Full Length % inhibition at 1, 10 uM | S.V. (22RV1) % inhibition at 10 uM | DMPK (MLM) T$_{1/2}$ Clint |
|---|---|---|---|---|---|---|---|
| Enobosarm | 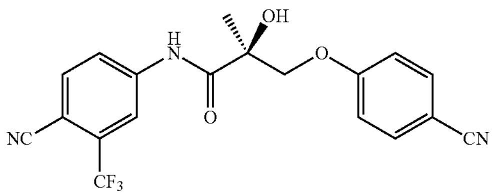 [SMILES: C[C@](O)(COc1ccc(C#N)cc1)C(=O)Nc1ccc(C#N)c(C(F)(F)F)c1] | 3.44 | 20.21 | ~20 | | | |
| R-Bicalutamide | 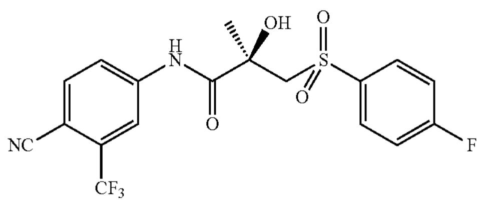 [SMILES: C[C@](O)(CS(=O)(=O)c1ccc(F)cc1)C(=O)Nc1ccc(C#N)c(C(F)(F)F)c1] | 2.57 | 508.84 | 248.2 | | | |
| Enzalutamide | 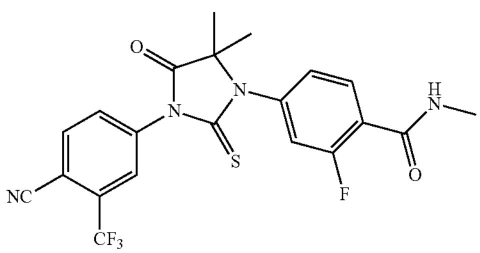 [SMILES: CNC(=O)c1ccc(N2C(=S)N(c3ccc(C#N)c(C(F)(F)F)c3)C(=O)C2(C)C)cc1F] | 4.56 | 3641.29 | 216.3 | | | |
| ARN-509 | 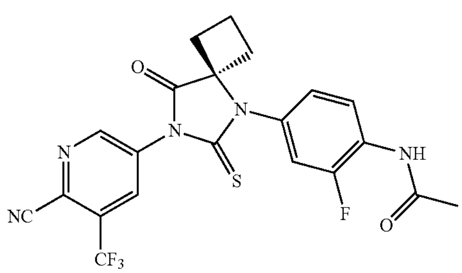 | 3.47 | 1452.29 | | 0 | 0 | |
| | | 2.57 | 87.67 | — | | | |
| | | 1.86 | 407.08 | | | | |

TABLE 3-continued

AR Binding, Inhibition of AR Transactivation, AR Degradation and Metabolic Stability of SARDs

| Compd ID | Structure | Log P (−0.4 to +5.6) | Binding/Wt. Ki (nM) (DHT = 1 nM) | IC$_{50}$ (nM) | SARD Activity Full Length % inhibition at 1, 10 uM | S.V. (22RV1) % inhibition at 10 uM | DMPK (MLM) T$_{1/2}$ Clint |
|---|---|---|---|---|---|---|---|
| 27 | 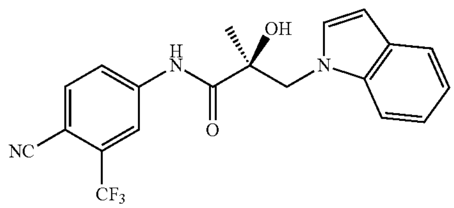 [SMILES: C[C@](O)(Cn1ccc2ccccc21)C(=O)Nc1ccc(C#N)c(C(F)(F)F)c1] | 3.31 | 2079.94 | 63.69 | 13, 89 | | 13.66 50.75 |
| 22 | 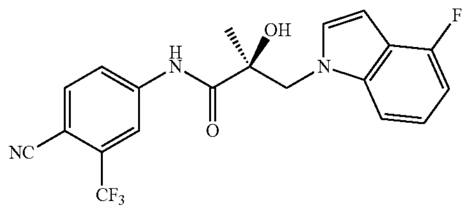 [SMILES: C[C@](O)(Cn1ccc2c(F)cccc21)C(=O)Nc1ccc(C#N)c(C(F)(F)F)c1] | 3.47 | 419.35 | 126.73 | 54, 81 | | 36.32 19.08 |
| 11 | 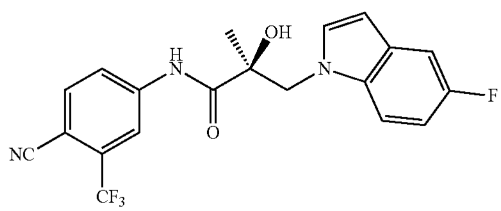 [SMILES: C[C@](O)(Cn1ccc2cc(F)ccc21)C(=O)Nc1ccc(C#N)c(C(F)(F)F)c1] | 3.47 | 267.39 | 85.10 | 65-83 | 60-100 | 12.35 56.14 |
| 11R | | 3.47 | >10000 | 589.84 | 83 | | |
| 23 | 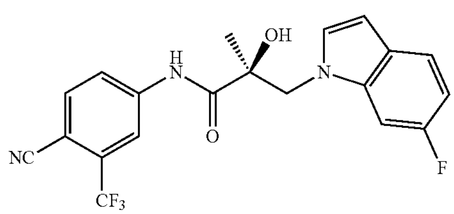 [SMILES: C[C@](O)(Cn1ccc2ccc(F)cc21)C(=O)Nc1ccc(C#N)c(C(F)(F)F)c1] | 3.47 | 212.49 | 85.10 | 0, 100 | | 22.39 30.96 |
| 12 | 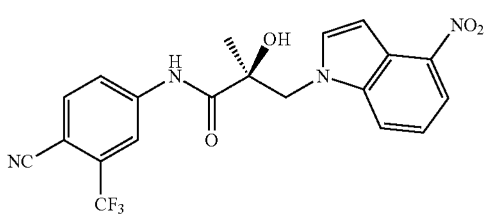 [SMILES: C[C@](O)(Cn1ccc2c([N+](=O)[O-])cccc21)C(=O)Nc1ccc(C#N)c(C(F)(F)F)c1] | 3.34 | 314.22 | 103.34 | 43, 100 | | 37.27 18.6 |

TABLE 3-continued

AR Binding, Inhibition of AR Transactivation, AR Degradation and Metabolic Stability of SARDs

| Compd ID | Structure | Log P (−0.4 to +5.6) | Binding/Wt. Ki (nM) (DHT = 1 nM) | IC$_{50}$ (nM) | SARD Activity Full Length % inhibition at 1, 10 uM | S.V. (22RV1) % inhibition at 10 uM | DMPK (MLM) T$_{1/2}$ Clint |
|---|---|---|---|---|---|---|---|
| 20 | (structure: NC, CF$_3$-phenyl-NH-C(O)-C(CH$_3$)(OH)-CH$_2$-N-indole-5-NO$_2$) | 3.34 | 432.69 | 88.03 | 45, 100 | 78 | 19.27 35.97 |
| 32 | (structure: NC, CF$_3$-phenyl-NH-C(O)-C(CH$_3$)(OH)-CH$_2$-N-indole-6-NO$_2$) | 3.34 | 46.58 | 57.76 | 0, 100 | | 13.48 51.43 |
| 24 | (structure: NC, CF$_3$-phenyl-NH-C(O)-C(CH$_3$)(OH)-CH$_2$-N-indole-5-Br) | 4.14 | 315.84 | 917.68 | | 0 | 17.02 40.73 |
| 21 | (structure: NC, CF$_3$-phenyl-NH-C(O)-C(CH$_3$)(OH)-CH$_2$-N-indole-5-I) | 4.67 | 293.84 | 984.52 | | 13 | 20.37 34.02 |
| 18 | (structure: NC, CF$_3$-phenyl-NH-C(O)-C(CH$_3$)(OH)-CH$_2$-N-indole-5-CF$_3$) | 4.23 | 416.03 | 335.98 | 74, 79 | 47 | 21.07 32.9 |
| 16 | (structure: NC, CF$_3$-phenyl-NH-C(O)-C(CH$_3$)(OH)-CH$_2$-N-indole-5-OCH$_3$) | 3.18 | 489.88 | 2285.14 | | | |

TABLE 3-continued

AR Binding, Inhibition of AR Transactivation, AR Degradation and Metabolic Stability of SARDs

| Compd ID | Structure | Log P (−0.4 to +5.6) | Binding/Wt. Ki (nM) (DHT = 1 nM) | IC$_{50}$ (nM) | SARD Activity Full Length % inhibition at 1, 10 uM | S.V. (22RV1) % inhibition at 10 uM | DMPK (MLM) T$_{1/2}$ Clint |
|---|---|---|---|---|---|---|---|
| 13 | | 3.80 | 625.01 | — | 52, 86 | | |
| 17 | | 3.87 | 80.43 | 545.48 | 0, 0 | | |
| 14 | | 3.34 | 223.74 | 71.81 (partial) 1018.73 (Agonist | | | 15.97 43.4 |
| 80 | | 2.85 | >10,000 | 684.64 | | | |
| 15 | | 2.87 | >10,000 | — | | | 29.79 23.28 |

TABLE 3-continued

AR Binding, Inhibition of AR Transactivation, AR Degradation and Metabolic Stability of SARDs

| Compd ID | Structure | Log P (−0.4 to +5.6) | Binding/Wt. Ki (nM) (DHT = 1 nM) | IC$_{50}$ (nM) | SARD Activity Full Length % inhibition at 1, 10 uM | S.V. (22RV1) % inhibition at 10 uM | DMPK (MLM) T$_{1/2}$ Clint |
|---|---|---|---|---|---|---|---|
| 19 | 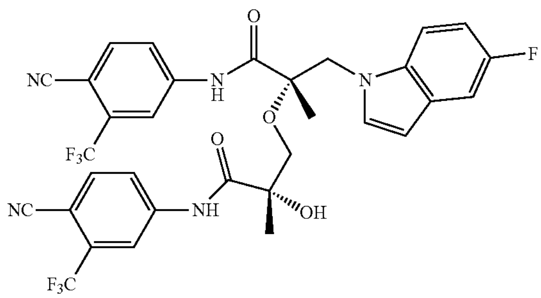 [SMILES: C[C@](O)(CO[C@@](C)(Cn1ccc2cc(F)ccc21)C(=O)Nc1ccc(C#N)c(C(F)(F)F)c1)C(=O)Nc1ccc(C#N)c(C(F)(F)F)c1] | 5.33 | | — | | | |
| | | 6.09 | | — | | | |
| 30 | 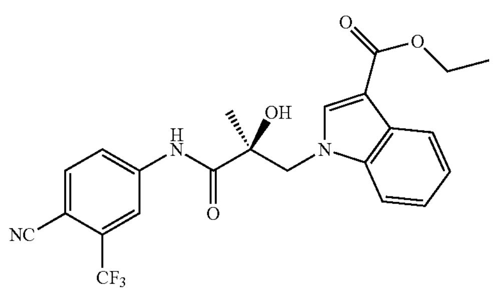 [SMILES: CCOC(=O)c1cn(C[C@](C)(O)C(=O)Nc2ccc(C#N)c(C(F)(F)F)c2)c2ccccc12] | 3.47 | 995.23 | 971.78 (UT-155 38 nM in the same exp) | | | 25.78 26.89 |
| 31 | 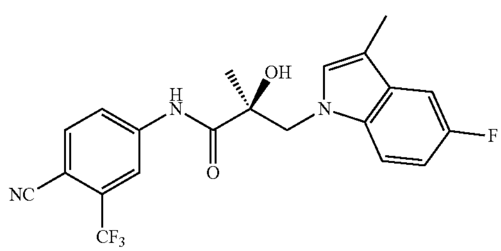 [SMILES: Cc1cn(C[C@](C)(O)C(=O)Nc2ccc(C#N)c(C(F)(F)F)c2)c2ccc(F)cc12] | 3.95 | 547.27 | 157.41 | | | 21.77 31.84 |
| 70, 71 (mixture) | 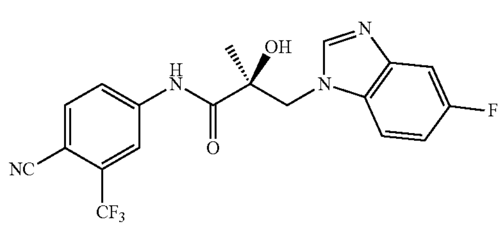 [SMILES: C[C@](O)(Cn1cnc2cc(F)ccc21)C(=O)Nc1ccc(C#N)c(C(F)(F)F)c1] | 2.70 | 530.72 | 299.78 | 50 | | 48.58 14.27 |

TABLE 3-continued

AR Binding, Inhibition of AR Transactivation, AR Degradation and Metabolic Stability of SARDs

| Compd ID | Structure | Log P (−0.4 to +5.6) | Binding/Wt. Ki (nM) (DHT = 1 nM) | IC$_{50}$ (nM) | SARD Activity Full Length % inhibition at 1, 10 uM | S.V. (22RV1) % inhibition at 10 uM | DMPK (MLM) T$_{1/2}$ Clint |
|---|---|---|---|---|---|---|---|
| 72 | | 4.56 | — | 1016 | | | |
| 73 | | 2.86 | 724.07 | 998.56 | 7, 68 | | |
| 74 | | 3.50 | 1399.69 | 720.61 | | | |
| 75 | | 2.70 | >1000 | 973.15 | 14 | | |
| 90, 91 (mixture) | | 3.08, 3.45 | 806.67 | 851.94 | 0 | 8 | |

TABLE 3-continued

AR Binding, Inhibition of AR Transactivation, AR Degradation and Metabolic Stability of SARDs

| Compd ID | Structure | Log P (−0.4 to +5.6) | Binding/Wt. Ki (nM) (DHT = 1 nM) | IC₅₀ (nM) | SARD Activity Full Length % inhibition at 1, 10 uM | S.V. (22RV1) % inhibition at 10 uM | DMPK (MLM) T₁/₂ Clint |
|---|---|---|---|---|---|---|---|
| | (structure with indazole-F) | | | | | | |
| 33 | (structure) | 5.14 | 124.66 | 214.66 | 54 | 22 | 15.43 44.94 |
| 34 | (structure) | 4.78 | 132.94 See FIG. 29O | 202.67 See FIG. 29O | 55 | 41 | 9.131 75.91 |
| 35 | (structure) | 3.10 | 155.74 See FIG. 29K | 98.47 | 65, 80 | 0 | |
| 36 | (structure) | 3.10 | 315.32 See FIG. 29I | 141.99 See FIG. 29I | 71 | 41 | 11.77 58.8 |
| 37 | (structure) | 3.10 | 252.58 See FIG. 29H | 94.33 See FIG. 29H | 81 | 30 | |

TABLE 3-continued

AR Binding, Inhibition of AR Transactivation, AR Degradation and Metabolic Stability of SARDs

| Compd ID | Structure | Log P (−0.4 to +5.6) | Binding/Wt. Ki (nM) (DHT = 1 nM) | IC$_{50}$ (nM) | SARD Activity Full Length % inhibition at 1, 10 uM | S.V. (22RV1) % inhibition at 10 uM | DMPK (MLM) T$_{1/2}$ Clint |
|---|---|---|---|---|---|---|---|
| 38 | 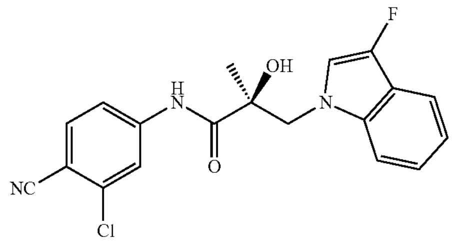 [SMILES: C[C@](O)(Cn1cc(F)c2ccccc21)C(=O)Nc1ccc(C#N)c(Cl)c1] | 3.10 | 331.79 See FIG. 29G | 44.50 See FIG. 29G | 68 (100 nM) | 62 | 9.291 74.6 |
| 39 | 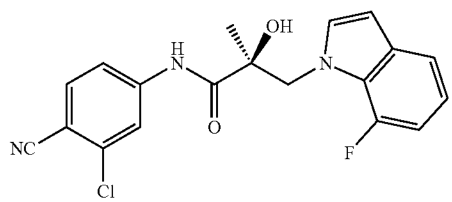 [SMILES: C[C@](O)(Cn1ccc2cccc(F)c21)C(=O)Nc1ccc(C#N)c(Cl)c1] | 3.10 | 719.81 See FIG. 29F | 233.8 See FIG. 29F | 40 | 45 | |
| 92, 93 (mixture) | 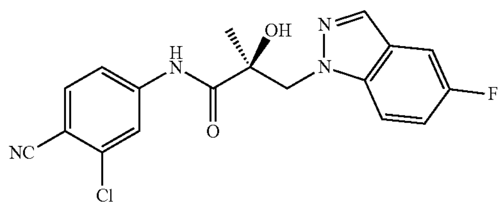 [SMILES: C[C@](O)(Cn1ncc2cc(F)ccc21)C(=O)Nc1ccc(C#N)c(Cl)c1] | 2.72, 3.08 | No binding See FIG. 29E | 946.84 See FIG. 29E | 40 | 80 | |
| 40 | 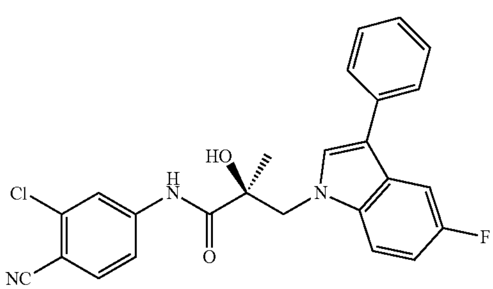 [SMILES: C[C@](O)(Cn1cc(-c2ccccc2)c2cc(F)ccc21)C(=O)Nc1ccc(C#N)c(Cl)c1] | 4.78 | 134.88 See FIG. 29D | 1032.14 See FIG. 29D | 0 | 0 | |
| 41 | 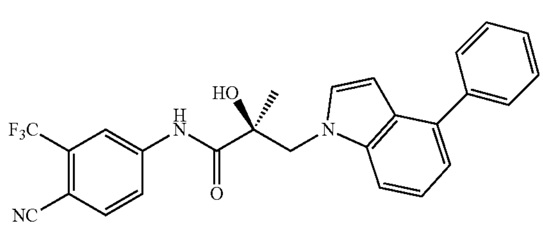 [SMILES: C[C@](O)(Cn1ccc2c(-c3ccccc3)cccc21)C(=O)Nc1ccc(C#N)c(C(F)(F)F)c1] | 4.98 | 84.32 See FIG. 29B | >10000 See FIG. 269 | 0 | 0 | |

TABLE 3-continued

AR Binding, Inhibition of AR Transactivation, AR Degradation and Metabolic Stability of SARDs

| Compd ID | Structure | Log P (−0.4 to +5.6) | Binding/Wt. Ki (nM) (DHT = 1 nM) | IC$_{50}$ (nM) | SARD Activity Full Length % inhibition at 1, 10 uM | S.V. (22RV1) % inhibition at 10 uM | DMPK (MLM) T$_{1/2}$ ClInt |
|---|---|---|---|---|---|---|---|
| 42 | [structure] | 5.14 | 86.18 See FIG. 29A | 1015.12 See FIG. 29A | 0 | 0 | |

TABLE 4

Liver Microsome Data of Indole Based SARDs

| Compd ID | MLM T1/2 | MLM ClInt | HLM T1/2 | HLM ClInt | RLM T1/2 | RLM ClInt | DLM T1/2 | DLM ClInt |
|---|---|---|---|---|---|---|---|---|
| 27 | 13.66 | 50.75 | | | | | | |
| 22 (4-F) | 36.32 | 19.08 | | | | | | |
| 11 (5-F) | 14.35 | 48.30 | 14.62 | 47.40 | | | | |
| 23 (6-F) | 22.39 | 30.96 | | | | | | |
| 12 (4-NO$_2$) | 37.27 | 18.60 | | | | | | |
| 20 (5-NO$_2$) | 19.27 | 35.97 | 17.97 | 38.57 | | | | |
| 32 (6-NO$_2$) | 13.48 | 51.43 | | | | | | |
| 24 (5-Br) | 17.02 | 40.73 | | | | | | |
| 21 (5-I) | 29.39 | 20.37 | | | | | | |
| 18 (5-CF$_3$) | 37.71 | 18.38 | | | | | | |
| 14 (5-CN) | 15.97 | 43.40 | | | | | | |
| 15 (3-CO$_2$H) | 29.78 | 23.28 | | | | | | |
| 30 | 25.78 | 26.89 | 13.77 | 0.05034 | | | | |
| 70, 71 | 48.58 | 14.27 | 16.36 | 42.37 | | | | |
| 33 | 15.43 | 44.94 | 7.31 | 94.82 | | | | |
| 34 | | | 9.131 | 75.91 | 15.50 | 58.87 | | |
| 38 | 9.291 | 74.6 | 6.611 | 104.9 | | | | |
| 36 | 11.77 | 58.8 | 12.66 | 54.7 | | | | |

Example 6

Androgen Receptor Binding and Transactivation, AR Degradation, and In Vitro Metabolism of Indoline, Quinolone and Isoquinoline Based SARDs Ligand Binding Assay
Objective:
To determine SARDs binding affinity to the AR-LBD.
Method:
hAR-LBD (633-919) was cloned into pGex4t.1. Large scale GST-tagged AR-LBD was prepared and purified using a GST column. Recombinant ARLBD was combined with [$^3$H]mibolerone (PerkinElmer, Waltham, Mass.) in buffer A (10 mM Tris, pH 7.4, 1.5 mM disodium EDTA, 0.25 M sucrose, 10 mM sodium molybdate, 1 mM PMSF) to determine the equilibrium dissociation constant (Kd) of [$^3$H] mibolerone. Protein was incubated with increasing concentrations of [$^3$H]mibolerone with and without a high concentration of unlabeled mibolerone at 4° C. for 18 h in order to determine total and non-specific binding. Non-specific binding was then subtracted from total binding to determine specific binding and non-linear regression for ligand binding curve with one site saturation to determine the Kd of mibolerone.

Increasing concentrations of SARDs or DHT (range: 10$^{-12}$ to 10$^{-2}$ M) were incubated with [$^3$H]mibolerone and AR LBD using the conditions described above. Following incubation, the ligand bound AR-LBD complex was isolated using BiogelHT® hydroxyapatite, washed and counted in a scintillation counter after adding scintillation cocktail. Values are expressed as Ki.

Transactivation Assay-Wt and Mutant AR

Objective:
To determine the effect of SARDs on androgen-induced transactivation of AR wildtype (wt) or AR carrying known AR-LBD mutants (i.e., W741L or T877A).
Method:
HEK-293 cells were plated at 125,000 cells/well of a 24 well plate in DME+5% csFBS without phenol red. Cells were transfected with 0.25 ug GRE-LUC, 10 ng CMV-renilla LUC, and 50 ng CMV-hAR(wt) or CMV-hAR (W741L) or CMV-hAR(T877A) using lipofectamine transfection reagent in optiMEM medium. Medium was changed 24 h after transfection to DME+5% csFBS without phenol red and treated with a dose response of various drugs (1 pM to 10 uM). SARDs and antagonists were treated in combination with 0.1 nM R1881. Luciferase assay was performed 24 h after treatment on a Biotek synergy 4 plate reader. Firefly luciferase values were normalized to renilla luciferase values. (Table 3)

Plasmid Constructs and Transient Transfection.
Human AR cloned into CMV vector backbone was used for the transactivation study. HEK-293 cells were plated at 120,000 cells per well of a 24 well plate in DME+5% csFBS. The cells were transfected using Lipofectamine (Invitrogen, Carlsbad, Calif.) with 0.25 μg GRE-LUC, 0.01 μg CMV-LUC (renilla luciferase) and 25 ng of the AR. The cells were treated 24 hrs after transfection as indicated in the figures and the luciferase assay performed 48 hrs after transfection. Data are represented as $IC_{50}$ obtained from four parameter logistics curve.

Ligand Binding Assay.
hAR-LBD (633-919) was cloned into pGex4t.1. Large scale GST-tagged AR-LBD was prepared and purified using a GST column. Recombinant ARLBD was combined with [$^3$H]mibolerone (PerkinElmer, Waltham, Mass.) in buffer A (10 mM Tris, pH 7.4, 1.5 mM disodium EDTA, 0.25 M sucrose, 10 mM sodium molybdate, 1 mM PMSF) to determine the equilibrium dissociation constant ($K_d$) of [$^3$H] mibolerone. Protein was incubated with increasing concentrations of [$^3$H]mibolerone with and without a high concentration of unlabeled mibolerone at 4° C. for 18 h in order to determine total and non-specific binding. Non-specific binding was then subtracted from total binding to determine specific binding and non-linear regression for ligand binding curve with one site saturation to determine the $K_d$ of mibolerone.

Increasing concentrations of SARDs or DHT (range: $10^{-12}$ to $10^{-4}$ M) were incubated with [$^3$H]mibolerone and AR LBD using the conditions described above. Following incubation, the ligand bound AR-LBD complex was isolated using biogelHT hydroxyapatite, washed and counted in a scintillation counter after adding scintillation cocktail. Values are expressed as $K_i$.

LNCaP Gene Expression Assay.
Method:
LNCaP cells were plated at 15,000 cells/well of a 96 well plate in RPMI+1% csFBS without phenol red. Forty-eight hours after plating, cells were treated with a dose response of SARDs. Twenty four hours after treatment, RNA was isolated using cells-to-ct reagent, cDNA synthesized, and expression of various genes was measured by realtime rtPCR (ABI 7900) using taqman primers and probes. Gene expression results were normalized to GAPDH.

LNCaP Growth Assay.
Method:
LNCaP cells were plated at 10,000 cells/well of a 96 well plate in RPMI+1% csFBS without phenol red. Cells were treated with a dose response of SARDs. Three days after treatment, cells were treated again. Six days after treatment, cells were fixed and cell viability was measured by SRB assay.

LNCaP or AD1 Degradation.
Method:
LNCaP or AD1 cells expressing full length AR were plated at 750,000-1,000,000 cells/well of a 6 well plate in growth medium (RPMI+10% FBS). Twenty four hours after plating, medium was changed to RPMI+1% csFBS without phenol red and maintained in this medium for 2 days. Medium was again changed to RPMI+1% csFBS without phenol red and cells were treated with SARDs (1 nM to 10 uM) in combination with 0.1 nM R1881. After 24 h of treatment, cells were washed with cold PBS and harvested. Protein was extracted using salt-containing lysis buffer with three free-thaw cycles. Protein concentration was estimated and five microgram of total protein was loaded on a SDS-PAGE, fractionated, and transferred to a PVDF membrane. The membrane was probed with AR N-20 antibody from SantaCruz and actin antibody from Sigma.

22RV1 and D567es Degradation.
Method:
22RV1 and D567es cells expressing AR splice variants were plated at 750,000-1,000,000 cells/well of a 6 well plate in growth medium (RPMI+10% FBS). Twenty four hours after plating, medium was changed and treated. After 24-30 h of treatment, cells were washed with cold PBS and harvested. Protein was extracted using salt-containing lysis buffer with three free-thaw cycles. Protein concentration was estimated and five microgram of total protein was loaded on a SDS-PAGE, fractionated, and transferred to a PVDF membrane. The membrane was probed with AR N-20 antibody from SantaCruz and actin antibody from Sigma.

22RV1 Growth and Gene Expression.
Methods:
Cell growth was evaluated as described before by SRB assay. Cells were plated in 96 well plate in full serum and treated for 6 days with medium change after day 3. Gene expression studies were performed in 22RV1 cells plated in 96 well plate at 10,000 cells/well in RPMI+10% FBS. Twenty four hours after plating, cells were treated for 3 days and gene expression studies were performed as described before.

Determination of Metabolic Stability (In Vitro $CL_{int}$) of Test Compounds:
Phase I Metabolism
The assay was done in a final volume of 0.5 ml in duplicates (n=2). Test compound (1 μM) was pre-incubated for 10 minutes at 37° C. in 100 mM Tris-HCl, pH 7.5 containing 0.5 mg/ml liver microsomal protein. After pre-incubation, reaction was started by addition of 1 mM NADPH (pre-incubated at 37° C.). Incubations were carried out in triplicate and at various time-points (0, 5, 10, 15, 30 and 60 minutes) 100 μl aliquots were removed and quenched with 100 μl of acetonitrile containing internal standard. Samples were vortex mixed and centrifuged at 4000 rpm for 10 minutes. The supernatants were transferred to 96 well plates and submitted for LC-MS/MS analysis. As control, sample incubations done in absence of NADPH were included. From % PCR (% Parent Compound Remaining), rate of compound disappearance is determined (slope) and in vitro $CL_{int}$ (µl/min/mg protein) was calculated.

Metabolic Stability in Phase I & Phase II Pathways

In this assay, test compound was incubated with liver microsomes and disappearance of drug was determined using discovery grade LC-MS/MS. To stimulate Phase II metabolic pathway (glucuronidation), UDPGA and alamethicin was included in the assay.

LC-MS/MS Analysis:

The analysis of the compounds under investigation was performed using LC-MS/MS system consisting of Agilent 1100 HPLC with an MDS/Sciex 4000 Q-Trap™ mass spectrometer. The separation was achieved using a $C_{18}$ analytical column (Alltima™, 2.1×100 mm, 3 µm) protected by a $C_{18}$ guard cartridge system (SecurityGuard™ ULTRA Cartridges UHPLC for 4.6 mm ID columns, Phenomenex). Mobile phase was consisting of channel A (95% acetonitrile+5% water+0.1% formic acid) and channel C (95% water+5% acetonitrile+0.1% formic acid) and was delivered at a flow rate of 0.4 mL/min. The volume ratio of acetonitrile and water was optimized for each of the analytes. Multiple reaction monitoring (MRM) scans were made with curtain gas, collision gas, nebulizer gas, and auxiliary gas optimized for each compound, and source temperature at 550° C. Molecular ions were formed using an ion spray voltage (IS) of −4200 V (negative mode). Declustering potential (DP), entrance potential (EP), collision energy (CE), product ion mass, and cell exit potential (CXP) were optimized for each compound.

TABLE 5

AR Binding, Inhibition of AR Transactivation, AR Degradation and in vitro Metabolic Stability of SARDs

| Comp ID | Structure | Binding/Wt. Ki (nM) | Binding/Wt. IC$_{50}$ (nM) | SARD activity (estimated median effect (nM) | DMPK (MLM) T$_{1/2}$ (min) CL$_{int}$ (µl/min/mg) |
|---|---|---|---|---|---|
| Enobosarm | 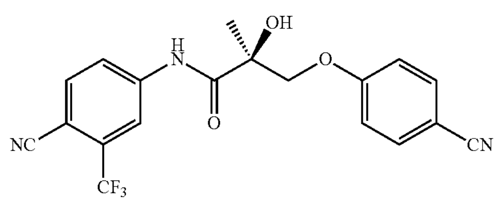 [SMILES: C[C@](O)(COc1ccc(C#N)cc1)C(=O)Nc1ccc(C#N)c(C(F)(F)F)c1] | 8.385 | ~20 | | |
| R-Bicalutamide | 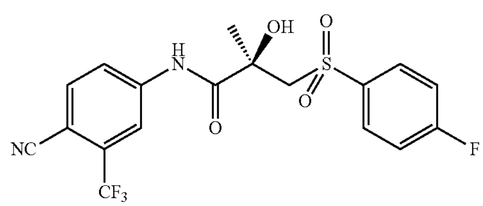 [SMILES: C[C@](O)(CS(=O)(=O)c1ccc(F)cc1)C(=O)Nc1ccc(C#N)c(C(F)(F)F)c1] | 211.12 | 248.2 | — | |
| Enzalutamide | 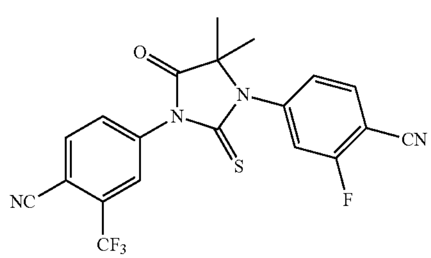 [SMILES: CC1(C)C(=O)N(c2ccc(C#N)c(C(F)(F)F)c2)C(=S)N1c1ccc(C#N)c(F)c1] | 678.9 | 216.3 | — | |
| ARN-509 | 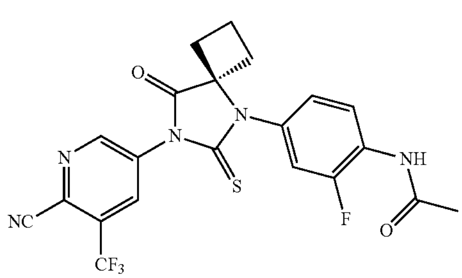 | >1000 | | + | |

TABLE 5-continued

AR Binding, Inhibition of AR Transactivation, AR Degradation and in vitro Metabolic Stability of SARDs

| Comp ID | Structure | Binding/Wt. | | SARD activity (estimated median effect (nM) | DMPK (MLM) T$_{1/2}$ (min) CL$_{int}$ (µl/min/mg) |
|---|---|---|---|---|---|
| | | Ki (nM) | IC$_{50}$ (nM) | | |
| 100 | 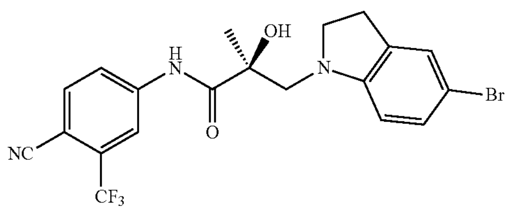 [SMILES: C[C@](O)(CN1CCc2cc(Br)ccc21)C(=O)Nc1ccc(C#N)c(C(F)(F)F)c1] | 23.17 34.16 | 530.95 | 10-100 (FIG. 18 & FIG. 19) | 66.87 min 10.38 µl/min/mg |
| 101 | 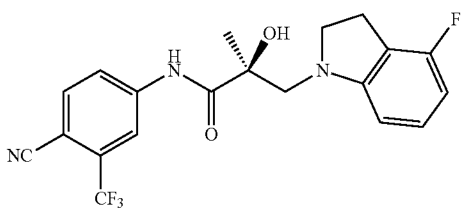 [SMILES: C[C@](O)(CN1CCc2c(F)cccc21)C(=O)Nc1ccc(C#N)c(C(F)(F)F)c1] | 83.1 | 58.96 | 100-500 (FIG. 25) | 25.06 min 27.67 µl/min/mg |
| 102 | 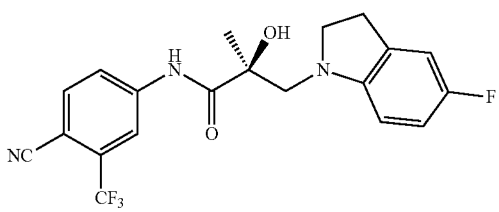 | 126.8 | 26.28 | 100-500 (FIG. 19 & FIG. 21) | 55.14 min 12.57 µl/min/mg |
| 103 | 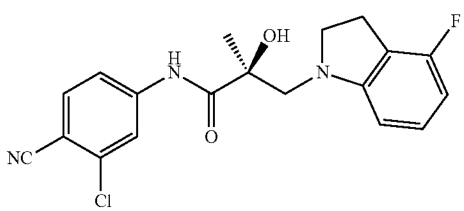 [SMILES: C[C@](O)(CN1CCc2c(F)cccc21)C(=O)Nc1ccc(C#N)c(Cl)c1] | 382.44 | 126.13 | 10000 (FIG. 22) | |
| 104 | 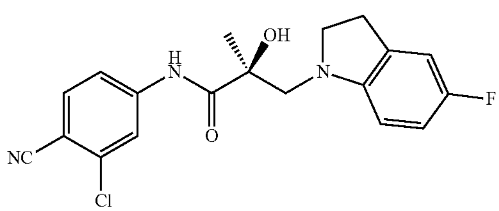 [SMILES: C[C@](O)(CN1CCc2cc(F)ccc21)C(=O)Nc1ccc(C#N)c(Cl)c1] | 326.14 | 130.37 | 10-100 (FIG. 22) | 29.16 min 23.77 µl/min/mg |
| 105 | 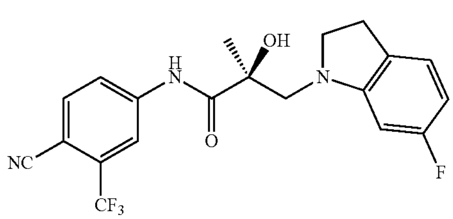 [SMILES: C[C@](O)(CN1CCc2ccc(F)cc21)C(=O)Nc1ccc(C#N)c(C(F)(F)F)c1] | 273.04 | 38.74 | (FIG. 25) | |

TABLE 5-continued

AR Binding, Inhibition of AR Transactivation, AR Degradation and in vitro Metabolic Stability of SARDs

| Comp ID | Structure | Binding/Wt. | | SARD activity (estimated median effect (nM) | DMPK (MLM) $T_{1/2}$ (min) $CL_{int}$ (µl/min/mg) |
|---|---|---|---|---|---|
| | | $K_i$ (nM) | $IC_{50}$ (nM) | | |
| 106 | 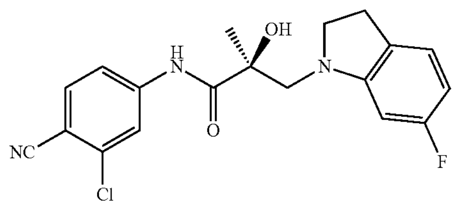 [SMILES: C[C@](O)(CN1CCc2ccc(F)cc21)C(=O)Nc1ccc(C#N)c(Cl)c1] | 489.95 | 36.45 | (FIG. 25) | |
| 130 | 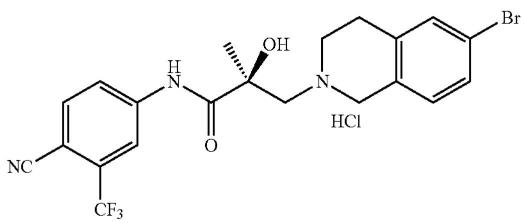 [SMILES: C[C@](O)(CN1CCc2cc(Br)ccc2C1)C(=O)Nc1ccc(C#N)c(C(F)(F)F)c1 ; Cl] | 1530.58 | 420.07 | 1000-5000 (FIGS. 19, FIG. 20, FIG. 23 & FIG. 24) | 161.7 min 4.286 µl/min/mg |
| 134 | 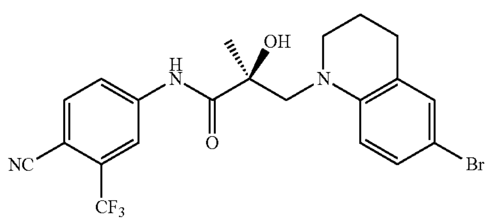 [SMILES: C[C@](O)(CN1CCCc2cc(Br)ccc21)C(=O)Nc1ccc(C#N)c(C(F)(F)F)c1] | 201.98 | 573.98 | 5000-10000 (FIG. 7A and FIG. 7B) | 38.25 min 18.12 µl/min/mg |
| 135 | 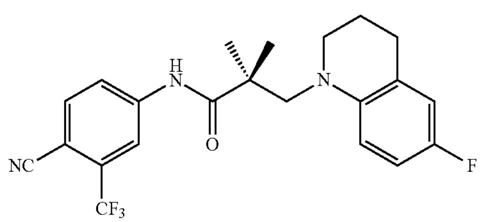 | 3112.73 | 867.48 | 10-100 nM (FIG. 21) | 15.25 min 45.45 µl/min/mg |
| 131 | 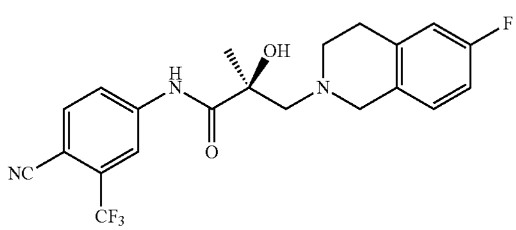 [SMILES: C[C@](O)(CN1CCc2cc(F)ccc2C1)C(=O)Nc1ccc(C#N)c(C(F)(F)F)c1] | 398.63 | 1002.73 | — | 25.42 min 27.27 µl/min/mg |
| 107 | 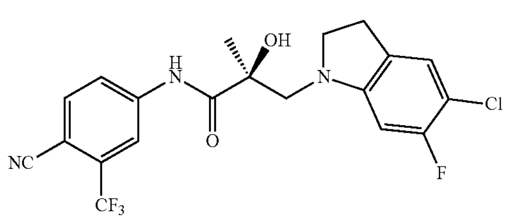 [SMILES: C[C@](O)(CN1CCc2cc(Cl)c(F)cc21)C(=O)Nc1ccc(C#N)c(C(F)(F)F)c1] | 67.65 | 74.65 | (FIG. 25) | |

TABLE 5-continued

AR Binding, Inhibition of AR Transactivation, AR Degradation and in vitro Metabolic Stability of SARDs

| Comp ID | Structure | Binding/Wt. Ki (nM) | IC$_{50}$ (nM) | SARD activity (estimated median effect (nM) | DMPK (MLM) T$_{1/2}$ (min) CL$_{int}$ (μl/min/mg) |
|---|---|---|---|---|---|
| 108 | 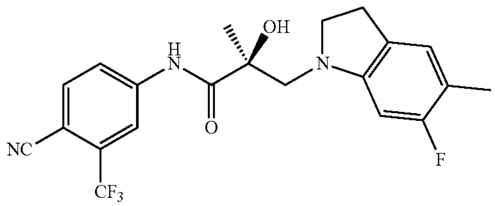 [SMILES: Cc1cc2c(cc1F)N(C[C@](C)(O)C(=O)Nc1ccc(C#N)c(C(F)(F)F)c1)CC2] | 114.84 | 100.55 | (FIG. 25) | |

The short half-lives ($t_{1/2}$) and high metabolic clearance (CL$_{int}$) values in vitro of some of the compounds of this invention suggest rapid plasma clearance for those compounds which could be favorable for topical treatment of androgenic dermatologic disorders as it would limit the risk of systemic side effects, even if the skin is penetrated. Other compounds demonstrate relatively long half-lives and low metabolic clearances values in vitro suggesting that these compounds may be able to achieve systemic exposures necessary to have systemic antiandrogen effects such as would be necessary to treat prostate cancer.

TABLE 6

AR Binding, Inhibition of AR Transactivation, AR Degradation and Metabolic Stability of SARDs

| Compd ID | Structure | Log P (−0.4 to +5.6) | Binding/Wt. Ki (nM) (DHT = 1 nM) | IC$_{50}$ (nM) | SARD Activity Full Length % inhibition at 1, 10 uM | S.V. (22RV1) % inhibition at 10 uM | DMPK (MLM) T$_{1/2}$ Clint |
|---|---|---|---|---|---|---|---|
| Enobosarm | 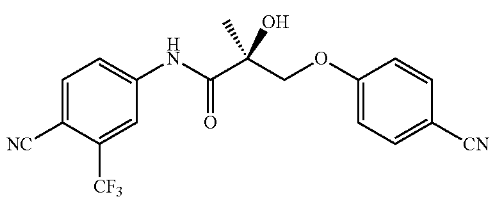 [SMILES: C[C@](O)(COc1ccc(C#N)cc1)C(=O)Nc1ccc(C#N)c(C(F)(F)F)c1] | 3.44 | 20.21 | ~20 | | | |
| R-Bicalutamide | 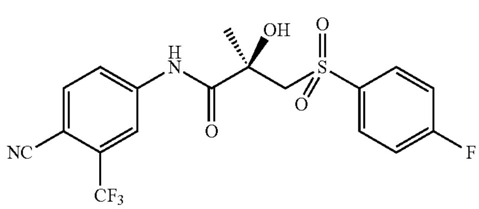 [SMILES: C[C@](O)(CS(=O)(=O)c1ccc(F)cc1)C(=O)Nc1ccc(C#N)c(C(F)(F)F)c1] | 2.57 | 508.84 | 248.2 | | | |
| Enzalutamide | 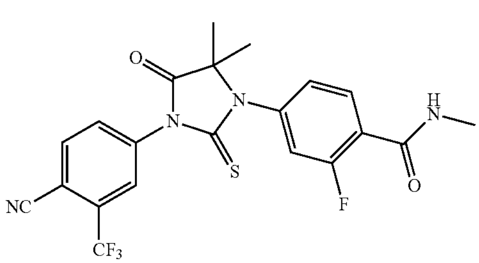 [SMILES: CNC(=O)c1ccc(N2C(=S)N(c3ccc(C#N)c(C(F)(F)F)c3)C(=O)C2(C)C)cc1F] | 4.56 | 3641.29 | 216.3 | | | |

TABLE 6-continued

AR Binding, Inhibition of AR Transactivation, AR Degradation and Metabolic Stability of SARDs

| Compd ID | Structure | Log P (−0.4 to +5.6) | Ki (nM) (DHT = 1 nM) | IC$_{50}$ (nM) | SARD Activity Full Length % inhibition at 1, 10 uM | S.V. (22RV1) % inhibition at 10 uM | DMPK (MLM) T$_{1/2}$ Clint |
|---|---|---|---|---|---|---|---|
| ARN-509 | 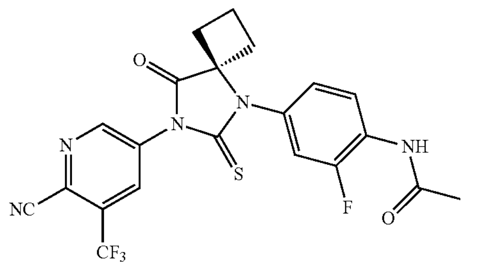 | 3.47 | 1452.29 | | 0 | 0 | |
| DJ-I-223 | 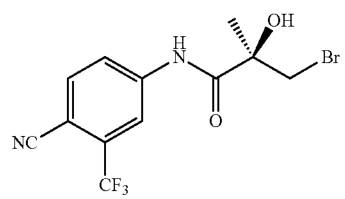 [SMILES: C[C@](O)(CBr)C(=O)Nc1ccc(C#N)c(C(F)(F)F)c1] | 2.57 | 87.67 | — | | | |
| DJ-VI-5E | 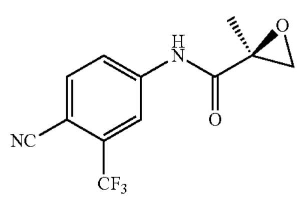 [SMILES: C[C@@]1(C(=O)Nc2ccc(C#N)c(C(F)(F)F)c2)CO1] | 1.86 | 407.08 | | | | |
| 100 | 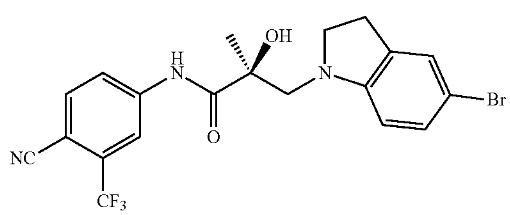 | 4.62 | 197.67 | 530.95 | 60 | 41 | 66.87 10.38 |
| 101 | 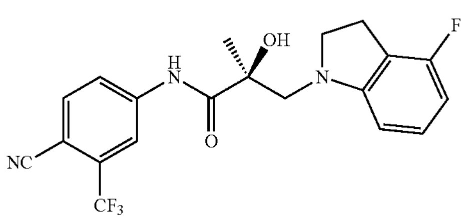 [SMILES: C[C@](O)(CN1CCc2c(F)cccc21)C(=O)Nc1ccc(C#N)c(C(F)(F)F)c1] | 3.95 | 169.86 | 58.96 | 61 | 5 | 25.06 27.67 |
| 102 | 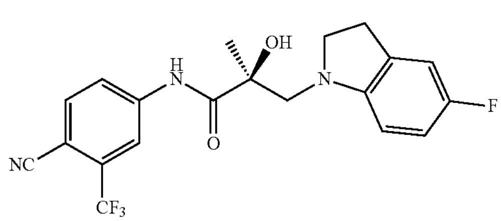 [SMILES: C[C@](O)(CN1CCc2cc(F)ccc21)C(=O)Nc1ccc(C#N)c(C(F)(F)F)c1] | 3.95 | 807.22 | 137.04 | 95 | 63 | 55.14 12.57 |

TABLE 6-continued

AR Binding, Inhibition of AR Transactivation, AR Degradation and Metabolic Stability of SARDs

| Compd ID | Structure | Log P (−0.4 to +5.6) | Binding/Wt. Ki (nM) (DHT = 1 nM) | IC$_{50}$ (nM) | SARD Activity Full Length % inhibition at 1, 10 uM | S.V. (22RV1) % inhibition at 10 uM | DMPK (MLM) T$_{1/2}$ Clint |
|---|---|---|---|---|---|---|---|
| 103 | 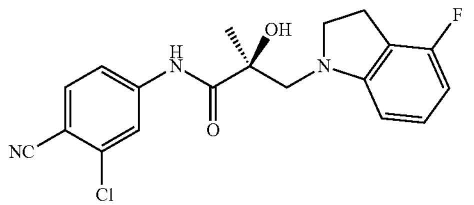 [SMILES: C[C@](O)(CN1CCc2c(F)cccc21)C(=O)Nc1ccc(C#N)c(Cl)c1] | 3.59 | 382.44 | 126.13 | 58 | 71 | 15 46.22 |
| 104 | 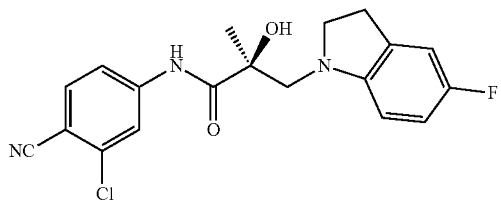 | 3.59 | 326.14 | 130.37 | 47, 69 | 15 | 29.16 23.77 |
| 105 | 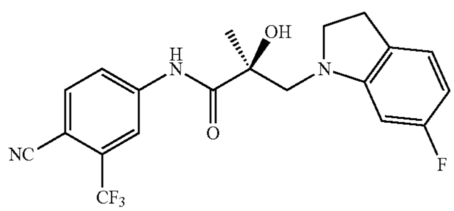 | 3.95 | 273.04 | 38.74 | 60 | 30 | |
| 105 106 | | 3.59 | 489.95 | 36.45 | 99 | 12 | |
| 107 | 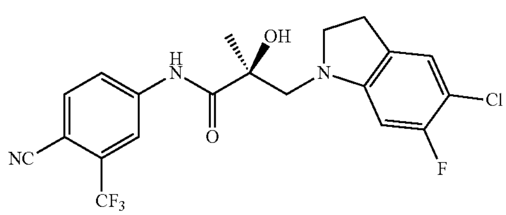 [SMILES: C[C@](O)(CN1CCc2cc(Cl)c(F)cc21)C(=O)Nc1ccc(C#N)c(C(F)(F)F)c1] | 4.51 | 67.65 | Agonist | 30-48 | 0 | |
| 108 | 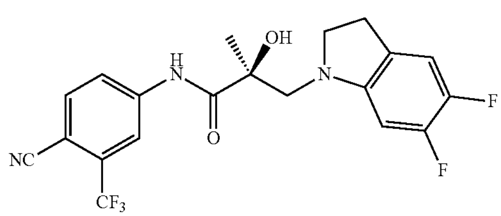 [SMILES: C[C@](O)(CN1CCc2cc(F)c(F)cc21)C(=O)Nc1ccc(C#N)c(C(F)(F)F)c1] | 4.11 | 114.84 | 100.55 | 54 | 36 | |

TABLE 6-continued

AR Binding, Inhibition of AR Transactivation, AR Degradation and Metabolic Stability of SARDs

| Compd ID | Structure | Log P (−0.4 to +5.6) | Binding/Wt. Ki (nM) (DHT = 1 nM) | IC$_{50}$ (nM) | SARD Activity Full Length % inhibition at 1, 10 uM | S.V. (22RV1) % inhibition at 10 uM | DMPK (MLM) T$_{1/2}$ Clint |
|---|---|---|---|---|---|---|---|
| 109 | | 3.80 | >1000 | 142.13 | 84 | 45 | |
| 110 | | 3.75 | 251.94 | 31.71 | 79 | 40 | |
| 114 | | 4.25 | 204.36 See FIG. 26L | 834.68 See FIG. 26L | 37, 84 | 0 | 17.35 39.36 |
| 115 | | 5.27 | 71.48 See FIG. 26I | 244.43 See FIG. 26I | 93 (100 nM) | 90 | 21.37 32.44 |
| 130 | | 4.28 | 1530.58 | 420.07 | 70, 78 | 65 | 161.7 4.286 |
| 131 | | 3.61 | 398.63 | 1002.73 | | 24 | 25.42 27.27 |

TABLE 6-continued

AR Binding, Inhibition of AR Transactivation, AR Degradation and Metabolic Stability of SARDs

| Compd ID | Structure | Log P (−0.4 to +5.6) | Ki (nM) (DHT = 1 nM) | IC$_{50}$ (nM) | SARD Activity Full Length % inhibition at 1, 10 uM | S.V. (22RV1) % inhibition at 10 uM | DMPK (MLM) T$_{1/2}$ ClInt |
|---|---|---|---|---|---|---|---|
| 132 | (structure) | 3.61 | 353.19 See FIG. 26C | 978.91 See FIG. 26C | 0 | 60 | |
| 134 | (structure) | 5.04 | 201.98 | 573.98 | | | 38.25 18.12 |
| 135 | (structure) | 4.37 | 3112.73 | 867.48 | | 21 | 15.25 45.45 |

TABLE 7

Liver Microsome Data of Indoline Based SARDs

| Compd ID | MLM T1/2 | MLM ClInt | HLM T1/2 | HLM ClInt | RLM T1/2 | RLM ClInt | DLM T1/2 | DLM ClInt |
|---|---|---|---|---|---|---|---|---|
| 102 (5F-indoline) | 55.14 | 0.01257 | | | | | | |
| 100 (5Br-indoline) | 66.87 | 10.38 | 64.84 | 0.01069 | | | | |
| 102 | 28.13 | 24.64 | 17.71 | 39.13 | | | | |
| 101 | 25.06 | 27.67 | | | | | | |
| 135 | 15.21 | 45.57 | 7.54 | 91.94 | | | | |
| 131 | 25.42 | 27.27 | 6.553 | 105.8 | | | | |
| 104 | 29.16 | 23.77 | 24.7 | 28.06 | 3.33 | 208 | 49.44 | 14 |
| 103 | 15 | 46.22 | 20.07 | 34.54 | 2.09 | 330 | 42.8 | 16.19 |
| 114 | | | 17.35 | 39.96 | 6.084 | 113.9 | | |
| 115 | 21.37 | 32.44 | 11.77 | 58.87 | | | | |

Example-7

AR Degradation Using Compounds of this Invention (Indoles)

LNCaP Gene Expression Assay
Objective:
To determine the effect of SARDs on AR-target gene expression in LNCaP cells.
Method:
LNCaP cells were plated at 15,000 cells/well of a 96 well plate in RPMI+1% csFBS without phenol red. Forty-eight hours after plating, cells were treated with a dose response of SARDs. Sixteen-twenty four hours after treatment, RNA was isolated using cells-to-ct reagent, cDNA synthesized, and expression of various genes was measured by realtime rtPCR (ABI 7900) using taqman primers and probes. Gene expression results were normalized to GAPDH.

LNCaP Growth Assay
Objective:
To determine the effect of SARDs on LNCaP cell growth.
Method:
LNCaP cells were plated at 10,000 cells/well of a 96 well plate in RPMI+1% csFBS without phenol red. Cells were treated with a dose response of SARDs. Three days after treatment, cells were treated again. Six days after treatment, cells were fixed and cell viability was measured by SRB assay.

LNCaP Degradation Assay
Objective:
To determine the effect of SARDs on AR expression in LNCaP cells.
Method:
LNCaP cells were plated at 750,000-1,000,000 cells/well of a 6 well plate in growth medium (RPMI+10% FBS). Twenty four hours after plating, medium was changed to RPMI+1% csFBS without phenol red and maintained in this medium for 2 days. Medium was again changed to RPMI+1% csFBS without phenol red and cells were treated with SARDs (1 nM to 10 uM) in combination with 0.1 nM R1881. After 16-20 h of treatment, cells were washed with cold PBS and harvested. Protein was extracted using salt-containing lysis buffer with three free-thaw cycles. Protein concentration was estimated and five microgram of total protein was loaded on a SDS-PAGE, fractionated, and transferred to a PVDF membrane. The membrane was probed with AR N-20 antibody from SantaCruz and actin antibody from Sigma.

22RV-1 Degradation Assay
Objective:
To determine the effect of SARDs on AR full length and splice variant expression in 22RV-1 cells.
Method:
22RV-1 cells were plated at 750,000-1,000,000 cells/well of a 6 well plate in growth medium (RPMI+10% FBS). Twenty four hours after plating, medium was changed and treated. After 16-20 h of treatment, cells were washed with cold PBS and harvested. Protein was extracted using salt-containing lysis buffer with three free-thaw cycles. Protein concentration was estimated and five microgram of total protein was loaded on a SDS-PAGE, fractionated, and transferred to a PVDF membrane. The membrane was probed with AR N-20 antibody from SantaCruz and actin antibody from Sigma.

Figure 2A:
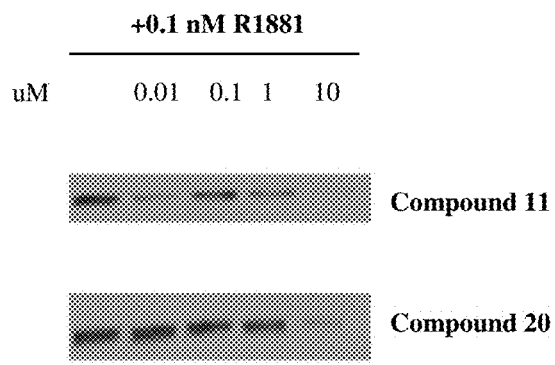
FIG. 2A demonstrates degradation in LNCaP cells using SARD compounds of this invention (11 and 20): LNCaP cells were plated in 6 well plates at 1 million cells/well. The cells were maintained in serum free conditions for 3 days. The cells were treated as indicated in the figure, harvested, protein extracted, and Western blotted for AR.

FIG. 2A presents degradation in LNCaP cells using 11 and 20. LNCaP cells were plated in 6 well plates at 1 million cells/well. The cells were maintained in serum free condition for 3 days. The cells were treated as indicated in the figure, harvested, protein extracted, and Western blotted for AR. 11 demonstrated selective degradation of AR (i.e., SARD activity) in nM range, i.e., at concentrations comparable to its antagonist $IC_{50}$ value. LNCaP cells are known to express the AR mutant T877A, demonstrating the ability to degrade resistance conferring mutant androgen receptors.

Figure 2B:
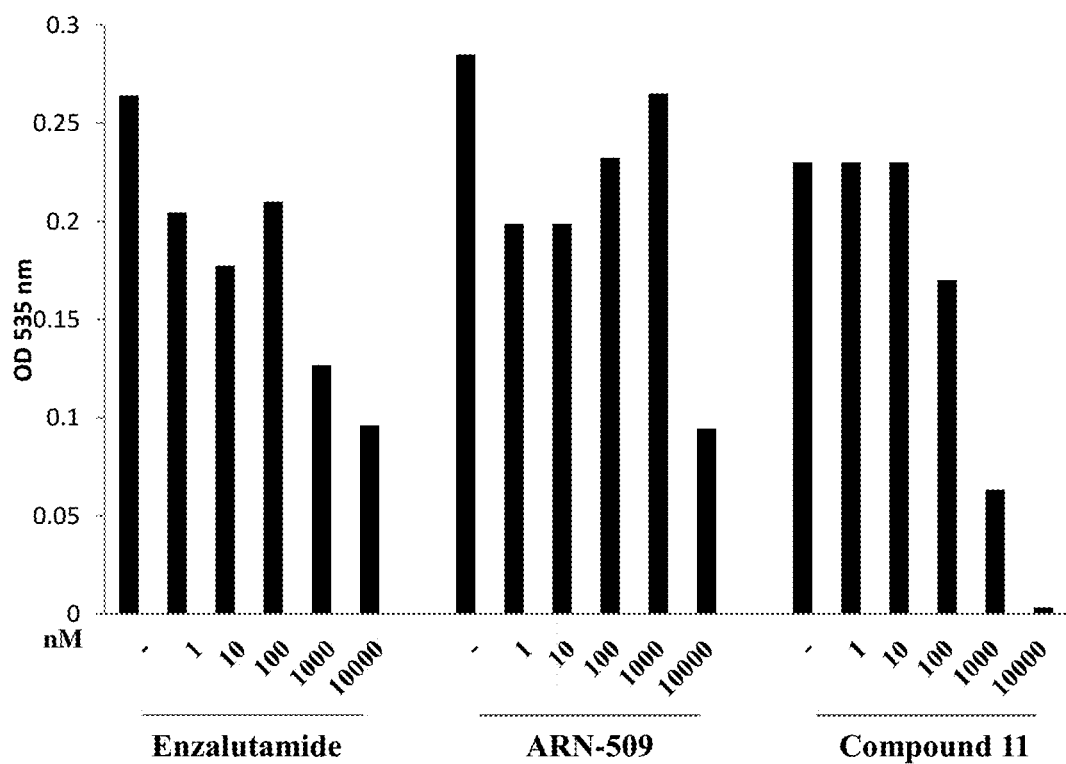
FIG. 2B presents the effect of AR antagonists and SARD 11 on LNCaP cell growth: LNCaP cells were plated in 96 well plates at 10,000 cells/well in RPMI+1% csFBS without phenol red. Cells were treated as indicated in the figure in combination with 0.1 nM R1881 for 6 days with medium change on day 3. At the end of 6 days, the cells were fixed and stained with sulphorhodamine blue stain.

FIG. 2B presents the effect of AR antagonists and SARDs on LNCaP cell growth: LNCaP cells were plated in 96 well plates at 10,000 cells/well in RPMI+1% csFBS without phenol red. Cells were treated as indicated in the figure in combination with 0.1 nM R1881 for 6 days with medium change on day 3. At the end of 6 days, the cells were fixed and stained with sulphorhodamine blue stain. 11 demonstrated more potent anti-proliferative activity in LNCaP cells at 1 and 10 µM when compared to enzalutamide and ARN-509.

Figure 3:
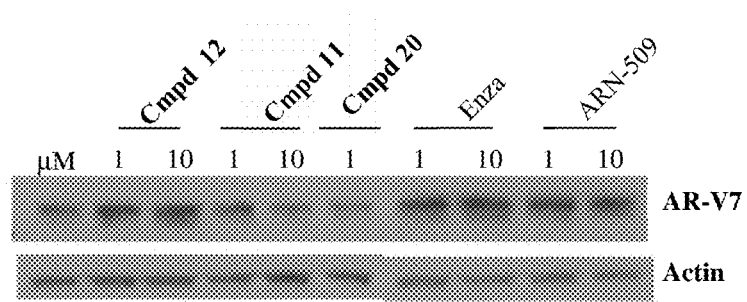
FIG. 3 presents AR-V7 degradation (PC3-AR-V7 cells) using SARD compounds of this invention (11, 12 and 20). PC-3 prostate cancer cells were serum stably transfected with a lentivirus construct for AR-V7. Once the stable cells were selected, the cells were plated in 6 well plates at 1 million cells/well. The cells were treated as indicated in the figure (μM) and Western blot performed for AR and actin. The results show that the SARDs have the potential to degrade truncated versions of AR such AR-V7, while enzalutamide or ARN-509 have no effect of the AR-V7 expression, suggesting that SARDs of this invention, unlike enzalutamide and ARN-509, can treat AR-V7 dependent CRPC.
Figure 4:
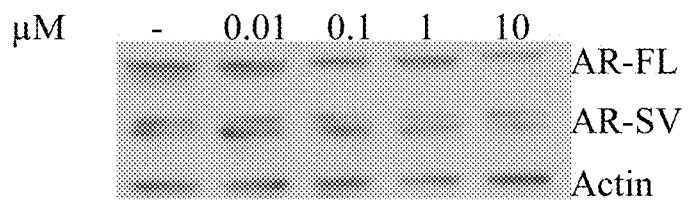
FIG. 4 demonstrates via Western blot that 20 degraded AR-FL and AR-SV in 22RV-1 cells, further supporting their use in the treatment of AR-SV-driven CRPC.

FIG. 3 presents AR-V7 degradation (PC3-AR-V7 cells) using 11, 12 and 20 at 1 µM and 10 µM. PC-3 prostate cancer cells were serum stably transfected with a lentivirus construct for AR-V7. Once the stable cells were selected, the cells were plated in 6 well plates at 1 million cells/well. The cells were treated as indicated in the figure and Western blot performed for AR and actin. The results show that the SARDs have the potential to degrade the truncated version of AR, while enzalutamide or ARN-509 had no effect of the AR-V7 expression.

SARD Compounds of this Invention Degrade AR-SV in 22RV-1 Cells

Figure 5:
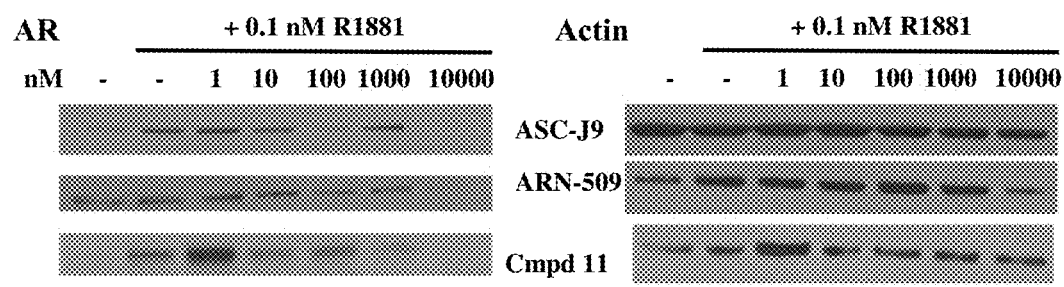
FIG. 5 presents SARD degradation of AR in LNCaP cells using 11.
Figure 6A:
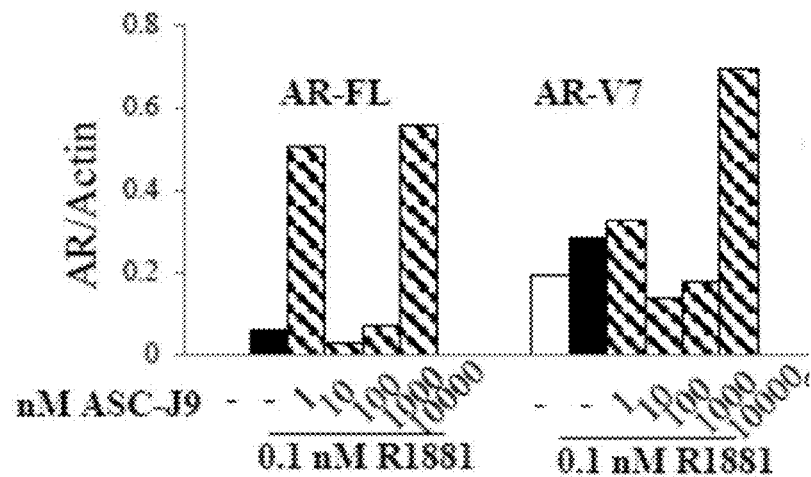
FIG. 6A-FIG. 6C presents SARD degradation of AR-FL and AR-V7 in 22RV-1 cells using (FIG. 6A) ASC-J9, (FIG. 6B) ARN-509 and (FIG. 6C) 11.
Figure 6B:
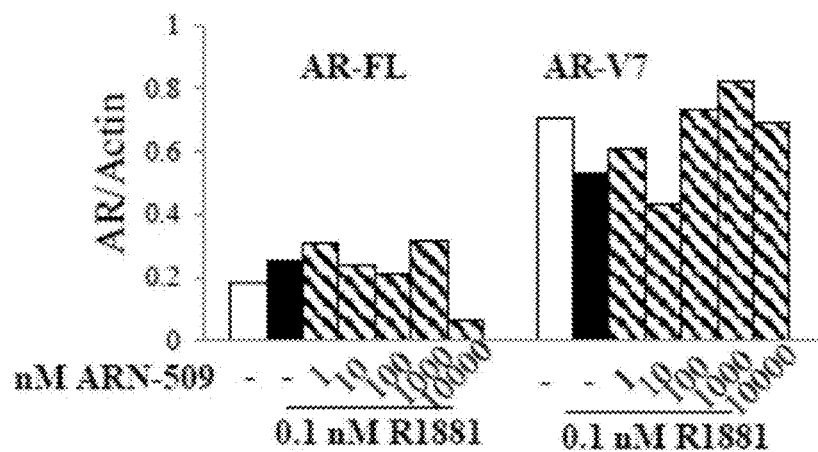
Figure 6C:
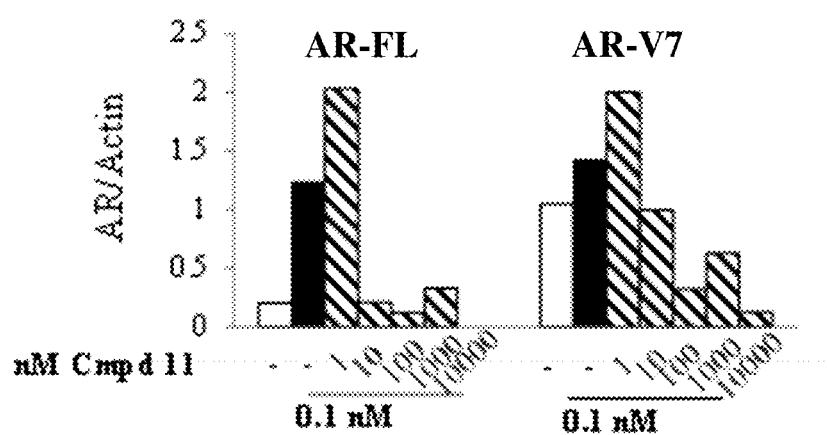

FIG. 4—22RV-1 Western blot: 22RV-1 cells were plated in 6 well plate at 1-1.5 million cells/well in growth medium (RPMI+10% FBS). Next day, medium was changed and treated with vehicle or a dose response of 20. After overnight treatment (12-16 hrs), cells were washed in ice cold PBS and harvested by scrapping in 1 mL PBS. Cells were pelleted, protein extracted, quantified using BCA assay, and equal quantity of protein was fractionated on a SDS-PAGE. The proteins were transferred to nylon membrane and Western blotted with AR antibody (N20 from SCBT) and actin antibody. 20 was capable of degrading full length androgen receptor (AR-FL) and truncated AR (AR-SV) in 22RV-1 cells, suggesting that SARDs may be able to overcome AR-V7 dependent prostate cancers (e.g., CRPC). 11 degraded AR-FL but not actin in LNCaP cells (FIG. 5) and AR-FL and AR-SV in 22RV-1 cells (FIG. 6A-FIG. 6C). FIG. 6A-FIG. 6C shows that 11 degraded AR-FL and AR-V7 at nM concentrations (FIG. 6C) whereas ARN-509 did not degrade either (FIG. 6B). Although ASC-J9 did exhibit some degradation in the nM range, µM concentrations failed to degrade AR (FIG. 6A). 11 also inhibited AR-dependent gene expression in LNCaP cells, transactivation of AR in 22RV-1 cells and cellular growth in both the cell types (Table 8 and Table 9). Cumulatively, these observations suggest that SARDs of this invention may be useful in prostate cancers that are dependent on mutant ARs, AR-FL and/or AR-SV.

Figure 11:
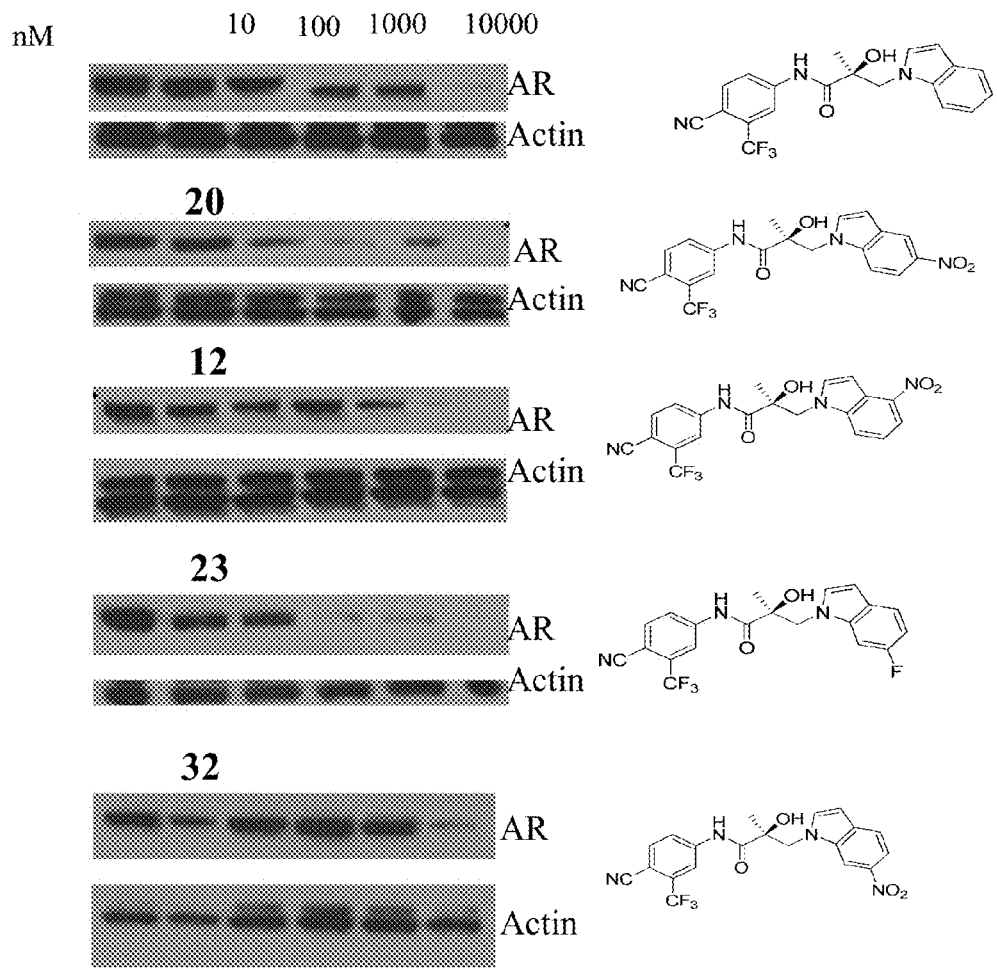
FIG. 11 presents degradation in LNCaP cells using 27, 20, 12, 23 and 32. LNCaP cells were plated in 6 well plates at 1 million cells/well. The cells were maintained in serum free conditions for 3 days. The cells were treated as indicated in the figure, harvested, protein extracted, and Western blotted for AR. SARDs demonstrated selective degradation of AR (i.e., SARD activity) in the nM range, i.e., at concentrations comparable to their antagonist $IC_{50}$ values. LNCaP cells are known to express the AR mutant T877A, demonstrating the ability to degrade resistance conferring mutant androgen receptors.

FIG. 11 presents degradation in LNCaP cells using 27, 20, 12, 23 and 32. LNCaP cells were plated in 6 well plates at 1 million cells/well. The cells were maintained in serum free conditions for 3 days. The cells were treated as indicated in the figure, harvested, protein extracted, and Western blotted for AR. All SARDs demonstrated selective degradation of AR (i.e., SARD activity) at concentrations comparable to their antagonist $IC_{50}$ values. LNCaP cells are known to express the AR mutant T877A, demonstrating the ability to degrade antiandrogen resistance conferring mutant androgen receptors (i.e., advanced prostate cancers and CRPC).

Figure 12:
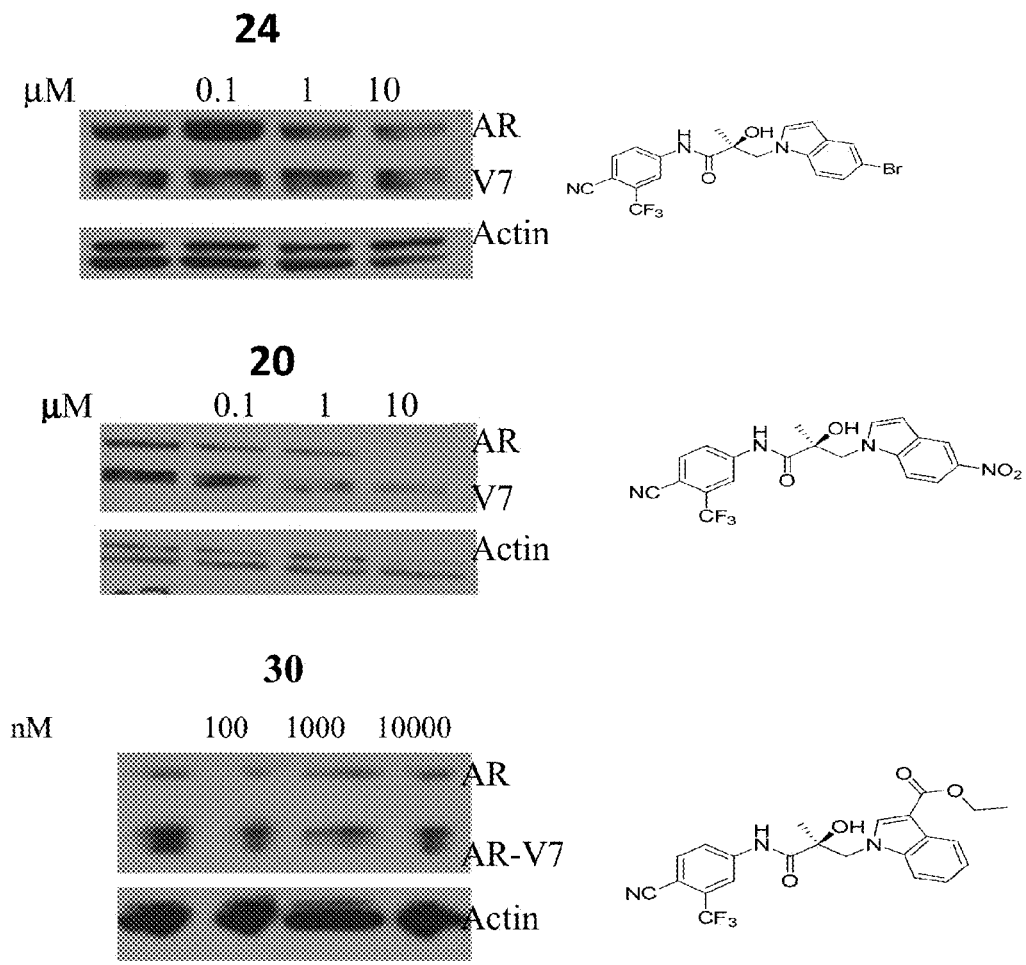
FIG. 12 presents 22RV-1 Western blots: 22RV-1 cells were plated in 6 well plates at 1-1.5 million cells/well in growth medium (RPMI+10% FBS). Next day, medium was changed and treated with vehicle or a dose response of compounds 20, 24 and 30. After overnight treatment (12-16 hrs), cells were washed in ice cold PBS and harvested by scrapping in 1 mL PBS. Cells were pelleted, protein extracted, quantified using BCA assay, and equal quantity of protein was fractionated on a SDS-PAGE. The proteins were transferred to nylon membrane and Western blotted with AR antibody (N20 from SCBT) and actin antibody. Compounds 20, 24 and 30 were capable of degrading full length androgen receptor (AR-FL) and truncated AR (AR-SV) in 22RV-1 cells, suggesting that SARDs may be able to overcome wildtype or AR-V7 dependent prostate cancers.

FIG. 12: 22RV-1 Western blot: 22RV-1 cells were plated in 6 well plates at 1-1.5 million cells/well in growth medium (RPMI+10% FBS). Next day, medium was changed and treated with vehicle or a dose response of 20, 24 and 30. After overnight treatment (12-16 hrs), cells were washed in ice cold PBS and harvested by scrapping in 1 mL PBS. Cells were pelleted, protein extracted, quantified using BCA assay, and equal quantity was fractionated on a SDS-PAGE. The proteins were transferred to nylon membrane and Western blotted with AR antibody (N20 from SCBT) and actin antibody. 20, 24 and 30 were capable of degrading full length androgen receptor (AR-FL) and truncated AR (AR-V7) in 22RV-1 cells, suggesting that SARDs may be able to overcome AR-V7 dependent prostate cancers (i.e., CRPC).

Figure 13:
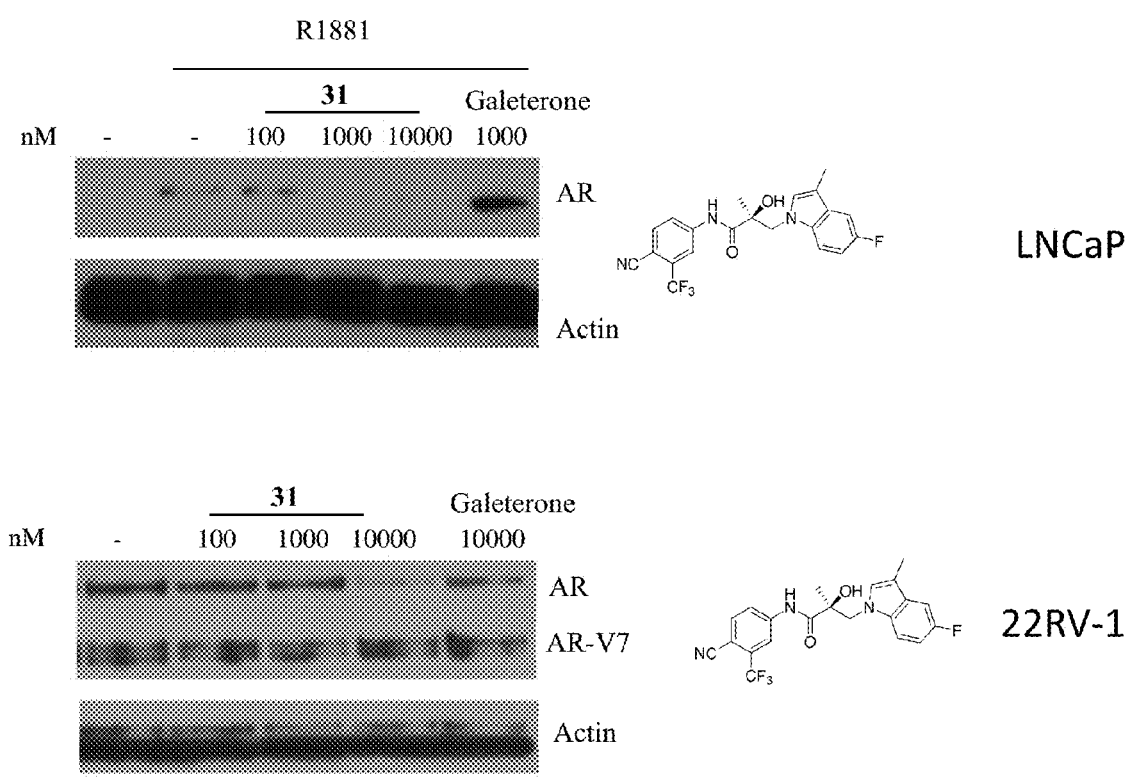
FIG. 13 presents degradation in LNCaP cells (top) and 22RV-1 cells (bottom) using 31 vs. galeterone. Using the methods described in the legends for FIG. 11 (LNCaP) and FIG. 12 (22RV-1), 31 was compared to galeterone (a clinical lead SARD). While 31 demonstrated SARD activity in both LNCaP (mutant AR harboring T877A mutation) and 22RV-1 (growth dependent on AR-SV lacking a LBD) cells, galeterone demonstrated little to no AR degradation in these models.

FIG. 13 presents degradation in LNCaP cells and 22RV-1 cells using 31 vs. galeterone. The experiments were performed by the methods cited above. A dose response of SARD 31 demonstrated the ability to degrade full length AR in LNCaP and 22RV-1 cell lines, whereas galeterone was not able to substantially degrade AR in either cell line.

Figure 14:
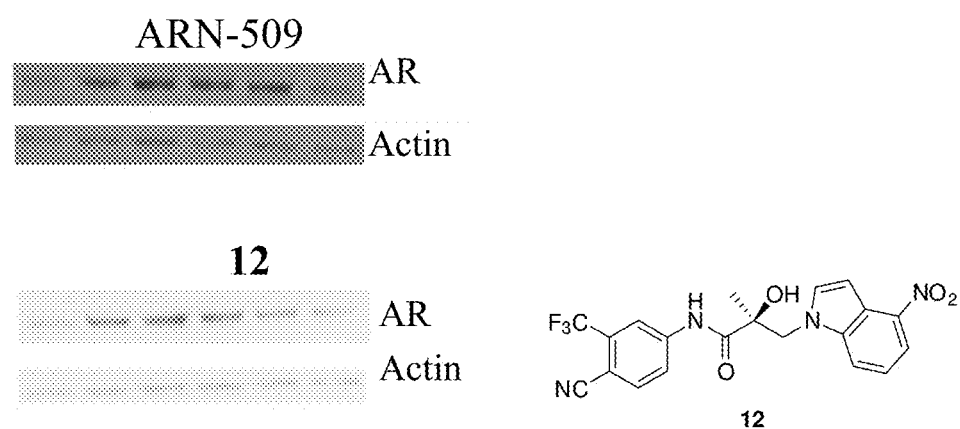
FIG. 14 presents degradation in LNCaP cells using a dose-response of 12 or ARN-509. Using the methods described in the legend for FIG. 11 (LNCaP), SARD activity for 12 was compared to known SARD ARN-509. 12 demonstrated activity in the nM range (100-1000 nM) whereas ARN-509 only had activity at 10,000 nM.

FIG. 14 presents degradation in LNCaP cells using 12 vs. ARN-509. 12 and ARN-509 both demonstrated the ability to degrade AR in LNCaP cells, however 12 demonstrated activity at 1 µM whereas ARN-509 only demonstrated activity at 10 µM.

Figure 15:
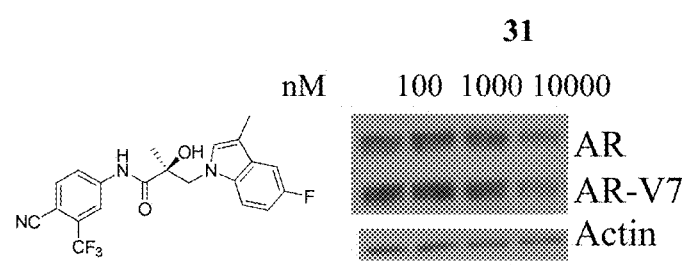
FIG. 15 presents degradation in 22RV-1 cells using 31. Using the methods described in the legend for FIG. 12 (22RV-1), SARD activity for 31 was demonstrated as degradation of full length (AR) and truncated splice variant (AR-V7) androgen receptor.

FIG. 15 presents degradation in 22RV-1 cells using 31. 31 demonstrated the ability to degrade AR-FL and AR-SV in 22RV-1 cells at 10 µM affecting actin levels (i.e., selective AR degradation).

Figure 16:
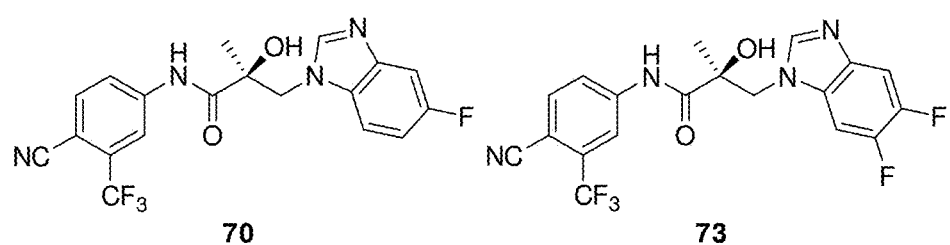
FIG. 16 presents degradation in LNCaP cells using 70 and 73. Using the methods described in the legend for FIG. 11 (LNCaP), SARD activity for 70 and 73 was demonstrated at concentrations as low as 100 nM. This demonstrates that benzimidazoles of this invention also demonstrate potent SARD activity.
Figure 16:
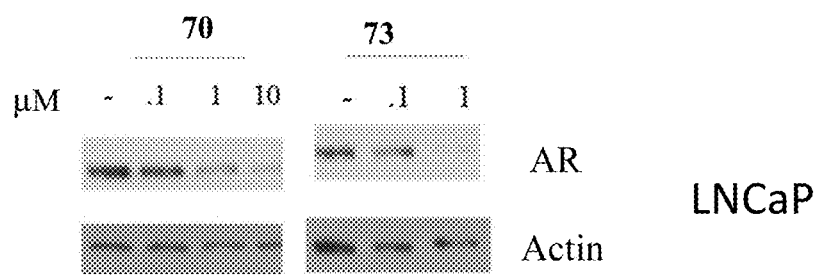

FIG. 16 presents degradation in LNCaP cells using 70 and 73. Using the methods described in the legend for FIG. 11 (LNCaP), SARD activity for 70 and 73 was demonstrated at concentrations as low as 100 nM. This demonstrates that benzimidazoles of this invention also demonstrate potent SARD activity.

These SARD activity demonstrations suggest the compounds of this invention are able to degrade a variety of AR variants, and hence should provide the ability to inhibit the AR-axis activity whether it is androgen-dependent or androgen-independent. Degradation of the AR removes the possibility of promiscuous activation of mutant ARs, activation by intracellular processes such as signal transduction and kinase activation, etc.; and suggests that the SARDs should also degrade the polyQ polymorphisms in hyperandrogenic dermatologic disorders (shortened polyQ) or Kennedy's disease (extended polyQ), providing a rationale for treating either type of disease by destroying the AR in the affected tissues (skin and neuromuscular system, respectively).

TABLE 8

Inhibition of Growth and Gene Expression of LNCaP PCa Cells

| Compound | Gene Expression IC$_{50}$ (nM) | | Growth IC$_{50}$ (nM) |
| --- | --- | --- | --- |
| | PSA | TMPRSS2 | |
| Bicalutamide | 783.7 | 831.4 | |
| Enzalutamide | 384.4 | 72.3 | 872 |
| Compound 11 | 5.0 | 13.1 | 271 |
| ARN-509 | 169.7 | 517.1 | 994 |
| ASC-J9 | >10,000 | >10,000 | 1064 |

TABLE 9

Effects of SARDs on AR-transactivation and growth of 22RV-1

| Compound | Transactivation IC$_{50}$ (nM) | Growth IC$_{50}$ (nM) |
| --- | --- | --- |
| Bicalutamide | 3133.52 | >10,000 |
| Enzalutamide | 101.87 | >10,000 |
| Compound 11 | 420.62 | 1041 |
| ARN-509 | 64.54 | >10,000 |
| ASC-J9 | 1026.91 | >10,000 |

Example 8

AR Degradation Using Indoline, Quinoline, or Isoquinoline SARD Compounds of this Invention Plasmid Constructs and Transient Transfection.

Human AR cloned into CMV vector backbone was used for the transactivation study. HEK-293 cells were plated at 120,000 cells per well of a 24 well plate in DME+5% csFBS. The cells were transfected using Lipofectamine (Invitrogen, Carlsbad, Calif.) with 0.25 µg GRE-LUC, 0.01 µg CMV-LUC (renilla luciferase) and 25 ng of the AR. The cells were treated 24 hrs after transfection as indicated in the figures and the luciferase assay performed 48 hrs after transfection. Data are represented as IC$_{50}$ obtained from four parameter logistics curve.

Ligand Binding Assay.

hAR-LBD (633-919) was cloned into pGex4t.1. Large scale GST-tagged AR-LBD was prepared and purified using a GST column. Recombinant ARLBD was combined with [$^3$H]mibolerone (PerkinElmer, Waltham, Mass.) in buffer A (10 mM Tris, pH 7.4, 1.5 mM disodium EDTA, 0.25 M sucrose, 10 mM sodium molybdate, 1 mM PMSF) to determine the equilibrium dissociation constant ($K_d$) of [$^3$H]mibolerone. Protein was incubated with increasing concentrations of [$^3$H]mibolerone with and without a high concentration of unlabeled mibolerone at 4° C. for 18 h in order to determine total and non-specific binding. Non-specific binding was then subtracted from total binding to determine specific binding and non-linear regression for ligand binding curve with one site saturation to determine the $K_d$ of mibolerone.

Increasing concentrations of SARDs or DHT (range: $10^{-12}$ to $10^{-4}$ M) were incubated with [$^3$H]mibolerone and AR LBD using the conditions described above. Following incubation, the ligand bound AR-LBD complex was isolated using biogelHT hydroxyapatite, washed and counted in a scintillation counter after adding scintillation cocktail. Values are expressed as $K_i$.

LNCaP Gene Expression Assay.

Method:

LNCaP cells were plated at 15,000 cells/well of a 96 well plate in RPMI+1% csFBS without phenol red. Forty-eight hours after plating, cells were treated with a dose response of SARDs. Twenty four hours after treatment, RNA was isolated using cells-to-ct reagent, cDNA synthesized, and expression of various genes was measured by realtime rtPCR (ABI 7900) using taqman primers and probes. Gene expression results were normalized to GAPDH.

LNCaP Growth Assay.

Method:

LNCaP cells were plated at 10,000 cells/well of a 96 well plate in RPMI+1% csFBS without phenol red. Cells were treated with a dose response of SARDs. Three days after treatment, cells were treated again. Six days after treatment, cells were fixed and cell viability was measured by SRB assay.

LNCaP or AD1 Degradation.

Method:

LNCaP or AD1 cells expressing full length AR were plated at 750,000-1,000,000 cells/well of a 6 well plate in growth medium (RPMI+10% FBS). Twenty four hours after plating, medium was changed to RPMI+1% csFBS without phenol red and maintained in this medium for 2 days. Medium was again changed to RPMI+1% csFBS without phenol red and cells were treated with SARDs (1 nM to 10 uM) in combination with 0.1 nM R1881. After 24 h of treatment, cells were washed with cold PBS and harvested. Protein was extracted using salt-containing lysis buffer with three free-thaw cycles. Protein concentration was estimated and five microgram of total protein was loaded on a SDS-PAGE, fractionated, and transferred to a PVDF membrane. The membrane was probed with AR N-20 antibody from SantaCruz and actin antibody from Sigma.

22RV1 and D567es Degradation.

Method:

22RV1 and D567es cells expressing AR splice variants were plated at 750,000-1,000,000 cells/well of a 6 well plate in growth medium (RPMI+10% FBS). Twenty four hours after plating, medium was changed and treated. After 24-30 h of treatment, cells were washed with cold PBS and harvested. Protein was extracted using salt-containing lysis buffer with three free-thaw cycles. Protein concentration was estimated and five microgram of total protein was loaded on a SDS-PAGE, fractionated, and transferred to a PVDF membrane. The membrane was probed with AR N-20 antibody from SantaCruz and actin antibody from Sigma.

22RV1 growth and gene expression.

Methods:

Cell growth was evaluated as described before by SRB assay. Cells were plated in 96 well plate in full serum and treated for 6 days with medium change after day 3. Gene expression studies were performed in 22RV1 cells plated in 96 well plate at 10,000 cells/well in RPMI+10% FBS. Twenty four hours after plating, cells were treated for 3 days and gene expression studies were performed as described before.

Figure 18:
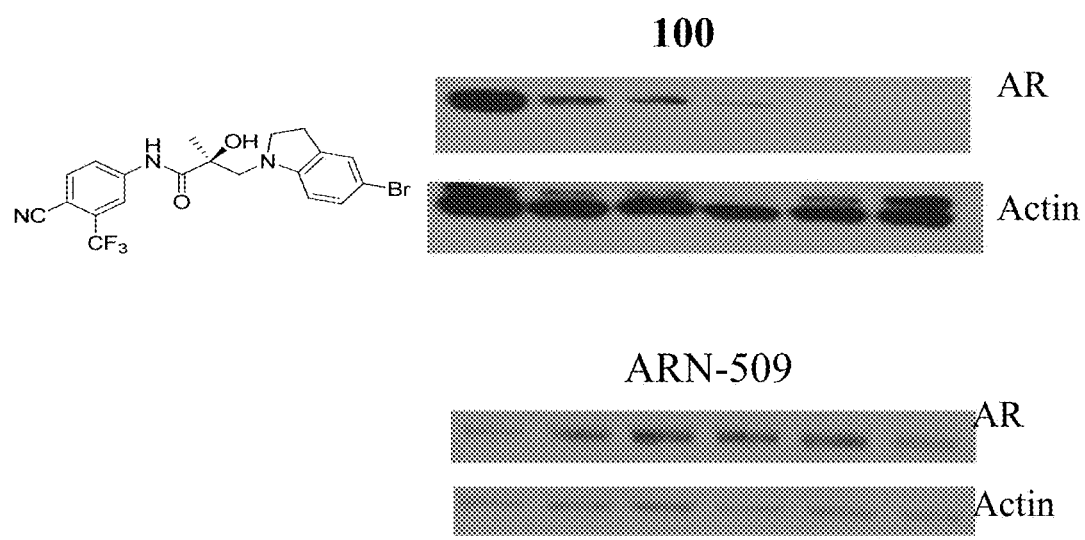
FIG. 18 demonstrates degradation in LNCaP cells using a SARD compound of this invention (100). LNCaP cells were plated in 6 well plates at 1 million cells/well. The cells were maintained in serum free conditions for 3 days. The cells were treated as indicated in the figure, harvested, protein extracted, and Western blotted for AR.

Results:

FIG. 18 presents degradation in LNCaP cells using 100 compared to ARN-509. LNCaP cells were plated in 6 well plates at 1 million cells/well. The cells were maintained in serum free conditions for 3 days. The cells were treated as indicated in the figure, harvestedprotein extracted, and Western blotted for AR. 100 demonstrated selective degradation of AR (i.e., SARD activity) in the nM range, i.e., at concentrations comparable to its antagonist $IC_{50}$ value whereas ARN-509 only demonstrated SARD activity at the highest concentration tested. LNCaP cells are known to express the AR mutant T877A, demonstrating the ability of compounds of this invention to degrade antiandrogen resistance conferring mutant androgen receptors.

Figure 19:
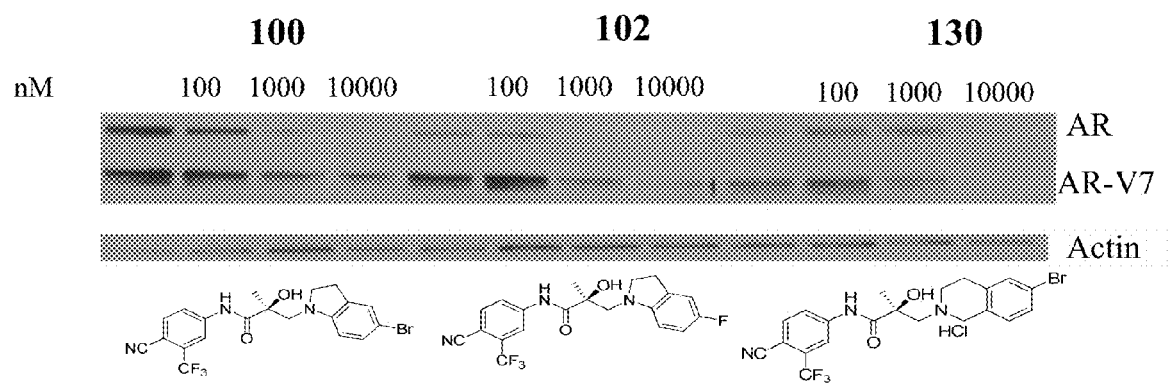
FIG. 19 demonstrates via Western blot as described above for FIG. 12, that 100, 102, and 130 degraded AR-FL and AR-SV in 22RV-1 cells. 100, 102, and 130 were capable of degrading full length androgen receptor (AR-FL) and truncated AR (AR-SV) in 22RV-1 cells, suggesting that indoline and isoquinoline SARDs of this invention may be able to overcome AR-V7 dependent prostate cancers.

FIG. 19 demonstrates via Western blot that 100, 102, and 130 degraded AR-FL and AR-SV in 22RV-1 cells. 22RV-1 cells were plated in 6 well plate at 1-1.5 million cells/well in growth medium (RPMI+10% FBS). Next day, medium was changed and treated with vehicle or a dose response of 100, 102, and 130. After overnight treatment (12-16 hrs), cells were washed in ice cold PBS and harvested by scrapping in 1 mL PBS. Cells were pelleted, protein extracted, quantified using BCA assay, and equal quantity of protein was fractionated on a SDS-PAGE. The proteins were transferred to nylon membrane and Western blotted with AR antibody (N20 from SCBT) and actin antibody. 87, 43, and 35 were capable of degrading full length androgen receptor (AR-FL) and truncated AR (AR-SV) in 22RV-1 cells, suggesting that SARDs may be able to overcome AR-V7 dependent prostate cancers.

Figure 20:
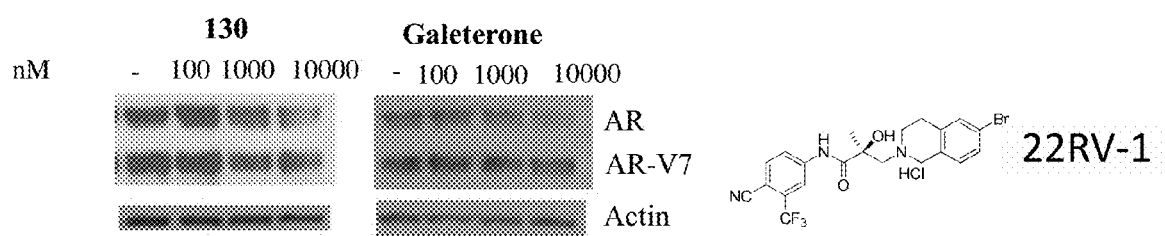
FIG. 20 presents degradation in 22RV-1 cells as described above for FIG. 12, using 130 vs. galeterone. 130 was compared to galeterone (a clinical lead SARD). 114 demonstrated SARD activity in 22RV-1 (growth dependent on AR-SV, an AR variant lacking a LBD) cells which was comparable to galeterone.

FIG. 20 presents degradation in 22RV-1 cells using 130 vs. galeterone. Using the methods described in the legend for FIG. 18 (22RV-1), 130 was compared to galeterone (a clinical lead SARD). 130 demonstrated SARD activity in 22RV-1 (growth dependent on AR-SV, an AR variant lacking a LBD) cells which was comparable to galeterone.

Figure 21:
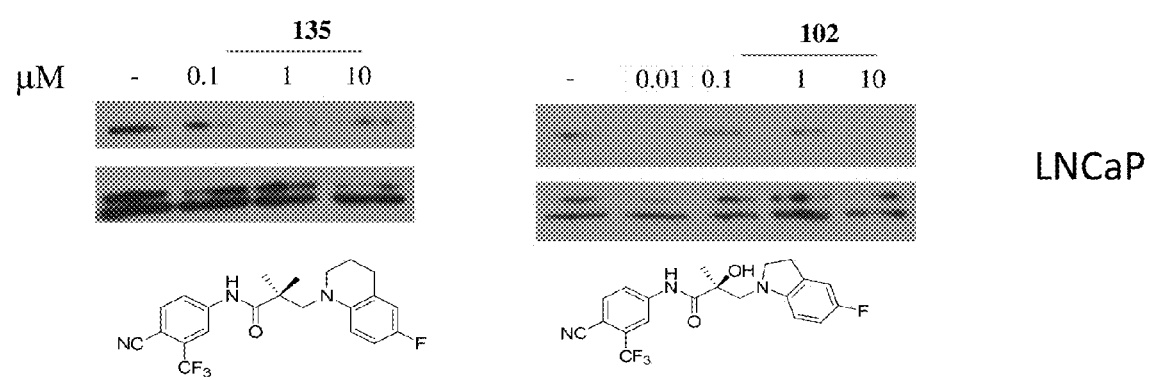
FIG. 21 presents degradation in LNCaP cells using 135 and 102. Using the methods described in the legend for FIG. 11, SARD activities for 135 and 102 were demonstrated. These compounds partially to fully degraded mutant AR (T877A), suggesting that quinoline and indoline SARDs of this invention such as these may be useful in advanced prostate cancer and/or CRPC.

FIG. 21 presents degradation in LNCaP cells using 135 and 102. Using the methods described in the legend for FIG. 1A-FIG. 1C, SARD activities for 135 and 102 was demonstrated. These compounds partially and fully degraded mutant AR (T877A), suggesting that SARDs such as these may be useful in advanced prostate cancer and/or CRPC.

Figure 22:
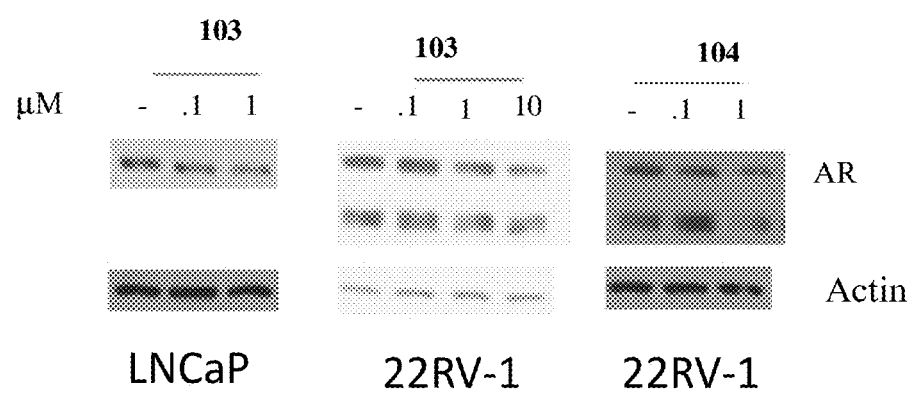
FIG. 22 presents degradation in LNCaP cells and 22RV-1 cells using 103 and 104. Using the methods described in the legends for FIG. 11 (LNCaP) and FIG. 12 (22RV-1), 103 and 104 demonstrated SARD activity in both LNCaP (mutant AR harboring T877A mutation) and 22RV-1 (growth dependent on AR-SV lacking a LBD) cells.
Figure 22:
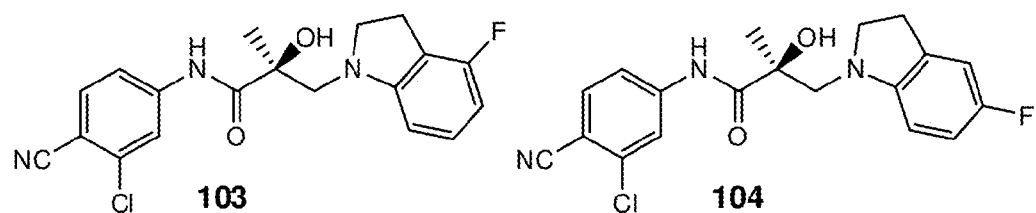

FIG. 22 presents degradation in LNCaP cells and 22RV-1 cells using 103 and 104. Using the methods described in the legends for FIG. 1A-FIG. 1C (LNCaP) and FIG. 2A-FIG. 2B (22RV-1), 103 and 104 demonstrated SARD activity in both LNCaP (mutant AR harboring T877A mutation) and 22RV-1 (growth dependent on AR-SV lacking a LBD) cell.

Figure 23:
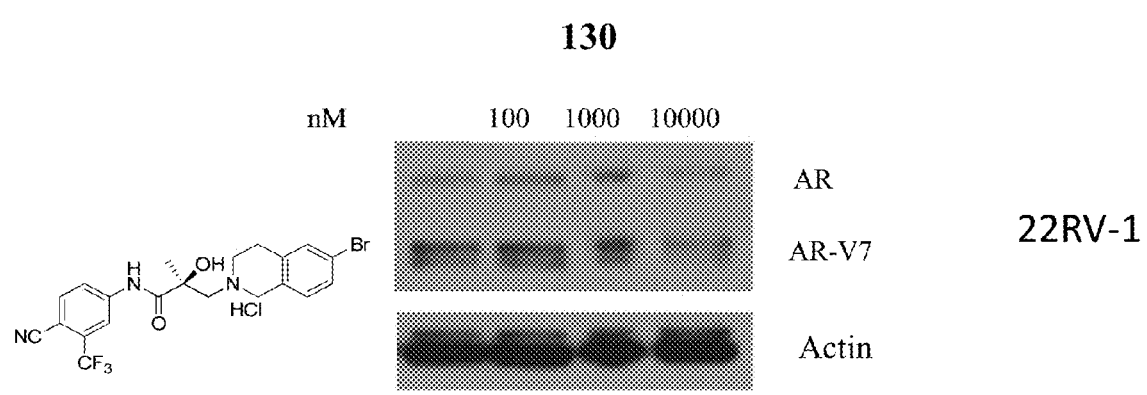
FIG. 23 presents degradation in 22RV-1 cells using 130. Using the methods described in the legend for FIG. 12, compound 130 demonstrated SARD activity at least at the 10 µM concentration.

FIG. 23 presents degradation in 22RV-1 cells using 130. Using the methods described in the legend for FIG. 19, compound 130 demonstrated SARD activity at least at the 10 µM concentration.

Figure 24:
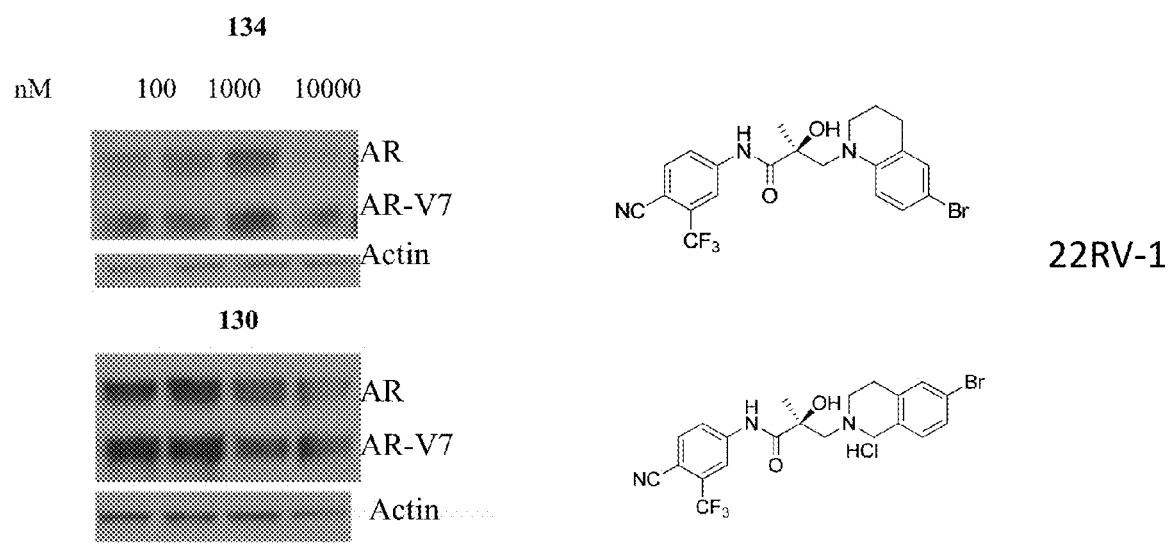
FIG. 24 presents degradation in 22RV-1 cells using 134 and 130. Using the methods described in the legend for FIG. 12, compounds 134 and 130 each demonstrated SARD activity at least at the 10 µM concentration.

FIG. 24 presents degradation in 22RV-1 cells using 134 and 130. Using the methods described in the legend for FIG. 19, compounds 134 and 130 each demonstrated SARD activity at least at the 10 µM concentration.

Figure 25:
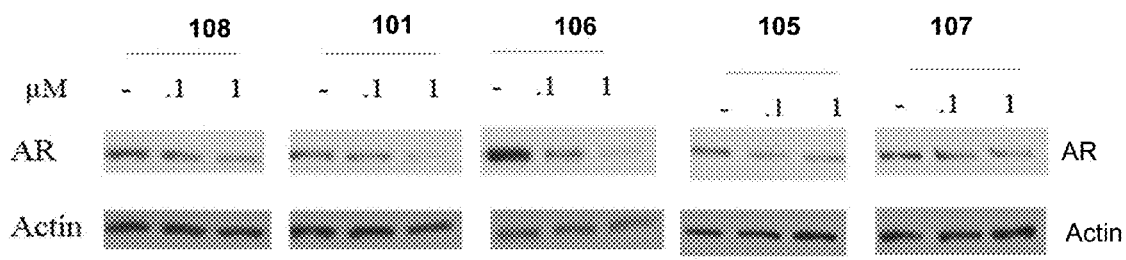
FIG. 25 presents degradation in LNCaP cells using 101, 105, 106, 107 and 108. Using the methods for FIG. 11 above, 101, 105, 106, 107 and 108 each demonstrated the ability to degrade the AR in the nM range.
Figure 25:
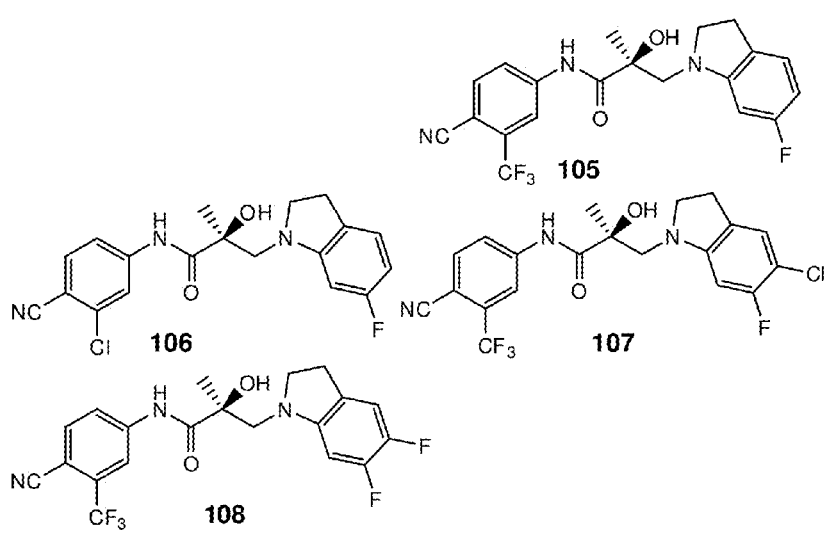

FIG. 25 presents degradation in LNCaPcells using −101, 105, 106, 107 and 108 LNCaP cells plated in 6 well plates at 500,000 cells/well were maintained in RPMI+1% csFBS without phenol red for 2 days. Cells were treated as indicated above in combination with 0.1 nM R1881 for 24 hrs. Cells were harvested 24 hrs after treatment, protein extracted, Western blotted with AR antibody (Santacruz AR N-20) and actin antibody. 101, 105, 106, 107 and 108 each demonstrated the ability to degrade the AR in the nM range.

These SARD activity demonstrations suggest the compounds of this invention are able to degrade a variety of AR variants, and hence should provide the ability to inhibit the AR-axis activity whether it is androgen-dependent or androgen-independent. Degradation of the AR removes the possibility of promiscuous activation of mutant ARs, activation by intracellular processes such as signal transduction and kinase activation, etc.; and suggests that the SARDs should also degrade the polyQ polymorphisms in hyperandrogenic dermatologic disorders (shortened polyQ) or Kennedy's disease (extended polyQ), providing a rationale for treating either type of diseases by destroying the AR in the affected tissues (skin and neuromuscular system, respectively). Further, a spectrum of in vitro metabolic stabilities were observed suggesting the possibility of either topical administration (short half-life such that systemic exposure are limited) or systemic (e.g., oral; requires relatively long half-lives) administration.

Example 9

SARDs (Indoles) Inhibit Ligand Independent AR Transcription

Figure 7A:
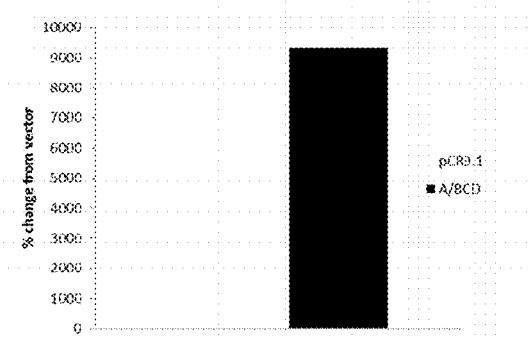
FIG. 7A-FIG. 7D present that 11 inhibits transactivation of AR-NTD-DBD-hinge (A/BCD) AR construct which lacks the LBD.
Figure 7B:
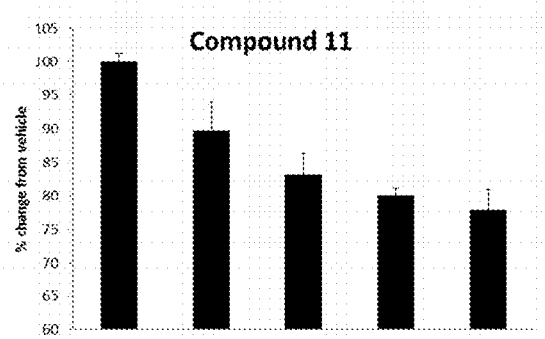
Figure 7C:
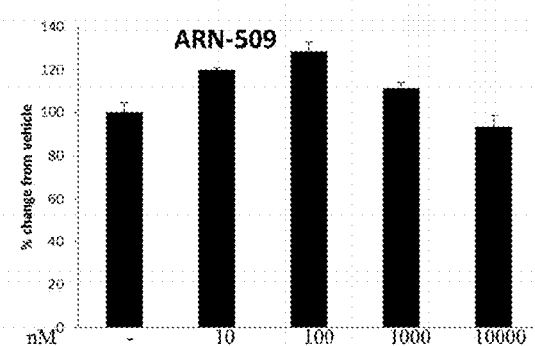
Figure 7D:
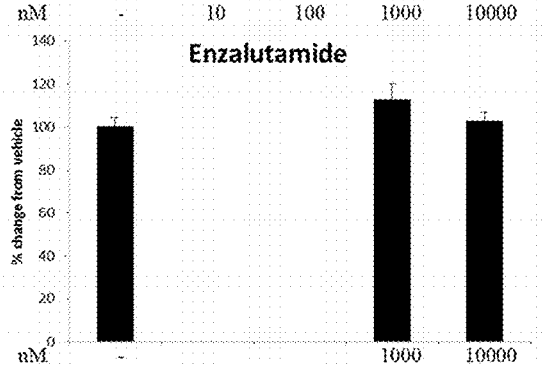

Compound 11 inhibited transactivation in the AR-NTD-DBD-hinge (A/BCD) AR construct which lacks the ligand binding domain (FIG. 7A-FIG. 7D). (FIG. 7A.) AR A/BCD increased GRE-LUC reporter activity. AR A/BCD construct that lacks the ligand binding domain or empty vector was transfected into HEK-293 cells along with GRE-LUC and CMV-renilla LUC. Forty eight hours after transfection cells were harvested and luciferase assay performed. (FIG. 7B.-FIG. 7D.) AR A/BCD activity was inhibited by 11. AR A/BCD construct that lacks the ligand binding domain (LBD) was transfected along with GRE-LUC and CMV-LUC. Cells were treated 24 hrs after transfection as indicated in the figure and luciferase assay performed 48 hrs after transfection. 11 (a SARD) inhibited the activity of construct lacking LBD confirming the binding to an alternate site in addition to the LBD. Non-SARD antagonists ARN-509 and enzalutamide did not inhibit the activity of this AR construct lacking the LBD, suggesting that SARDs can inhibit ligand independent AR activity via an alternative binding and degradation domain (BDD) located outside of the LBD.

Example 10

Comparison of SARDs and Clinical Candidates in Binding and Transactivation

Plasmid Constructs and Transient Transfection.

Human AR cloned into CMV vector backbone was used for the transactivation study. HEK-293 cells were plated at 120,000 cells per well of a 24 well plate in DME+5% csFBS. The cells were transfected using Lipofectamine (Invitrogen, Carlsbad, Calif.) with 0.25 mg GRE-LUC, 0.02 mg CMV-LUC (renilla luciferase) and 25 ng of the AR. The cells were treated 24 h after transfection as indicated in the figures and the luciferase assay performed 48 h after transfection. Data are represented as $IC_{50}$ obtained from a four parameter logistics curve.

Figure 8A:
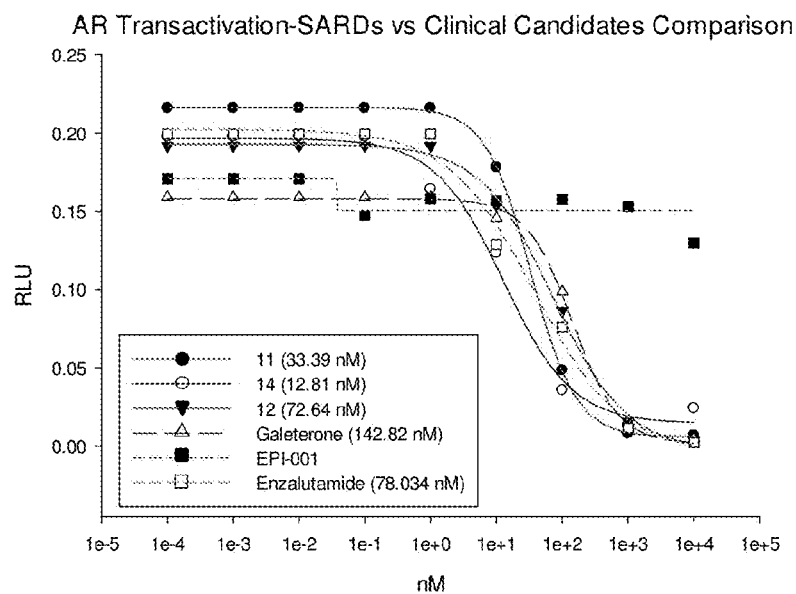
FIG. 8A-FIG. 8B presents data comparing compounds 11, 12, and 14 with galeterone, EPI-001, and enzalutamide in AR transactivation studies.
Figure 8B:
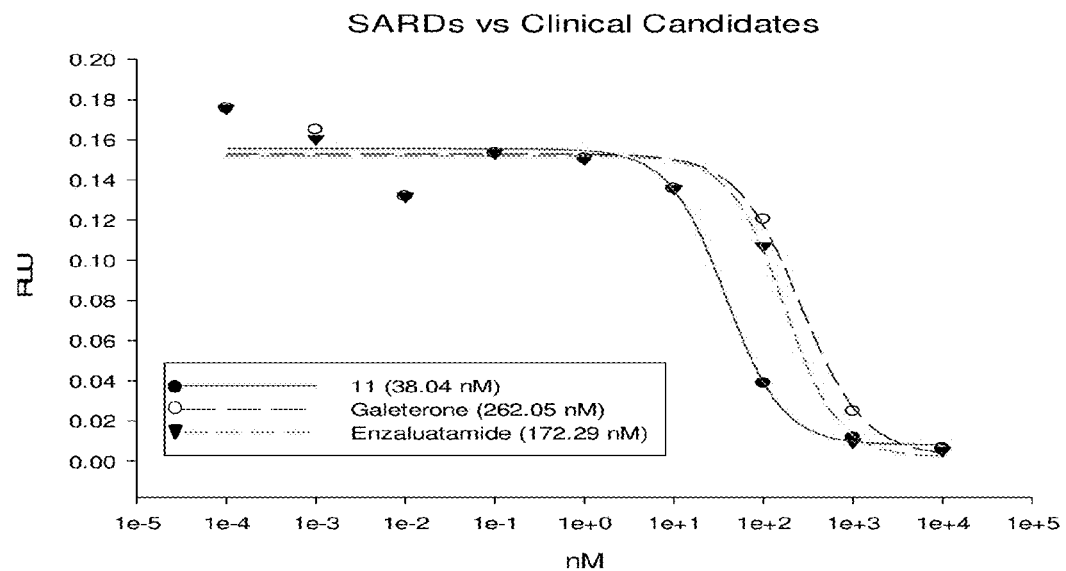

FIG. 8A presents the data comparing 11, 12, and 14 with galeterone, EPI-001, and enzalutamide, in the transactivation study. FIG. 8B shows the data comparing 11 with galeterone and enzalutamide in the transactivation study. The results show that the SARD compounds of the present invention were several more potent than galeterone and enzalutamide in inhibition of DHT activated AR transactivation in vitro.

Ligand Binding Assay.

hAR-LBD (633-919) was cloned into pGex4t.1. Large scale GST-tagged AR-LBD was prepared and purified using a GST column. Recombinant AR-LBD was combined with [$^3$H]mibolerone (PerkinElmer, Waltham, Mass.) in buffer A (10 mM Tris, pH 7.4, 1.5 mM disodium EDTA, 0.25 M sucrose, 10 mM sodium molybdate, 1 mM PMSF) to determine the equilibrium dissociation constant ($K_D$) of [$^3$H] mibolerone. Protein was incubated with increasing concentrations of [$^3$H]mibolerone with and without a high concentration of unlabeled mibolerone at 4° C. for 18 h in order to determine total and non-specific binding. Non-specific binding was then subtracted from total binding to determine specific binding and non-linear regression for ligand binding curve with one site saturation to determine the $K_D$ of mibolerone.

Increasing concentrations of SARDs or DHT (range: $10^{-12}$ to $10^{-4}$ M) were incubated with [$^3$H]mibolerone and AR-LBD using the conditions described above. Following incubation, the ligand bound AR-LBD complex was isolated using BiogelHT hydroxyapatite, washed and counted in a scintillation counter after adding scintillation cocktail. Values are expressed as $K_i$. Table 10 shows that the SARD compounds of the present invention are at least approximately 8-10 fold more tightly bound than galeterone and enzalutamide in AR binding assay studies.

TABLE 10

| Binding Assay Results | |
|---|---|
| Compound | Binding (Ki) nM |
| 11 | 62.7 |
| 14 | 47.9 |
| 12 | 72.9 |
| Galeterone | 922.8 |
| Enzalutamide | 678.9 |
| EPI-001 | Does Not Bind |

Example 11

Compound 11 Inhibits Tumor Growth of an Aggressive Prostate Cancer Expressing AR Splice Variant Xenograft Experiment.

NOD SCID gamma (NSG) mice (n=8-10) were housed as five animals per cage and were allowed free access to tap water and commercial rat chow (Harlan Teklad 22/5 rodent diet—8640). Cell line xenografts were performed as previously published (Narayanan et al., 2010; Yepuru et al., 2013). LNCaP tumors were grown in intact mice, while 22RV-1 tumors were grown in castrated mice. Once tumor size reached 100 mm$^3$, the animals were randomized and treated with vehicle control (polyethylene glycol: DMSO 9:1 ratio) or 11 (50 mg/kg/day s.c.). Tumor volume was calculated using the formula length*width*width*0.5236. At the end of the experiment, animals were sacrificed, tumors were collected, weighed, and stored for further analysis. Blood was collected, serum separated, and serum PSA was measured using ELISA.

All experiments were performed thrice and each in vitro experiment was performed in triplicate. Statistical analysis was performed using JMP-Pro software (SAS; Cary, N.C.). Experiments containing only two groups were analyzed by simple t-test, while experiments containing more than two groups were analyzed by One Way ANOVA, followed by appropriate post-hoc test.

Figure 9A:
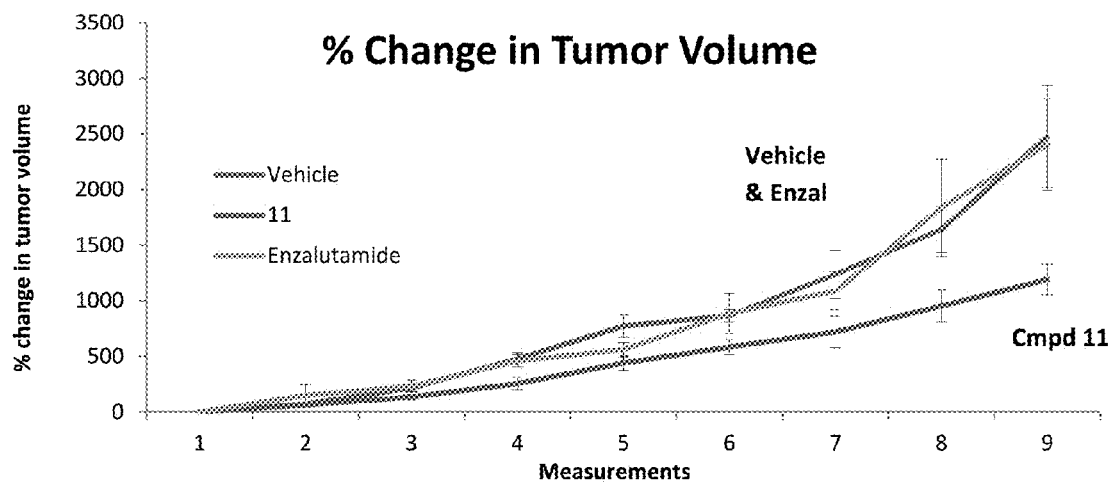
FIG. 9A-FIG. 9D demonstrates that 11 inhibited tumor growth of an aggressive prostate cancer (22RV-1) that expresses an AR splice variant (growth driven by AR-V7).
Figure 9B:
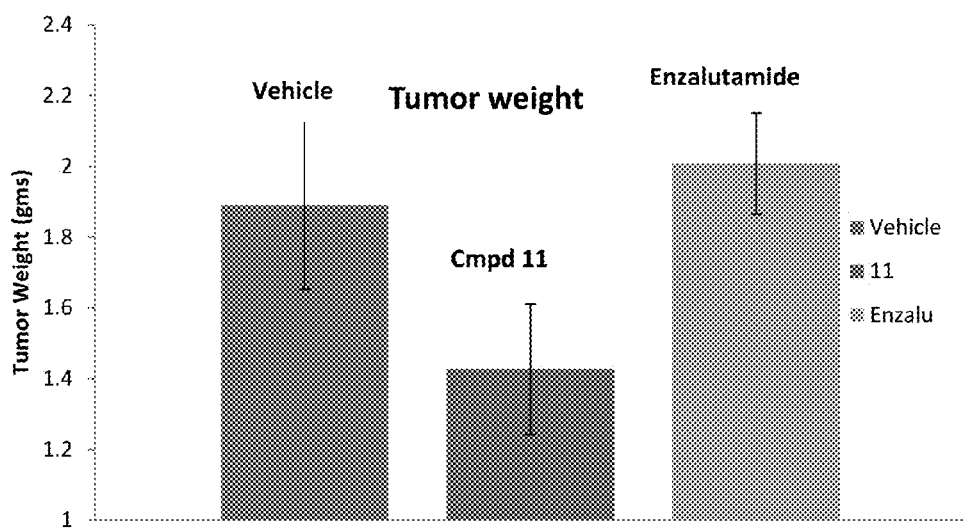
Figure 9C:
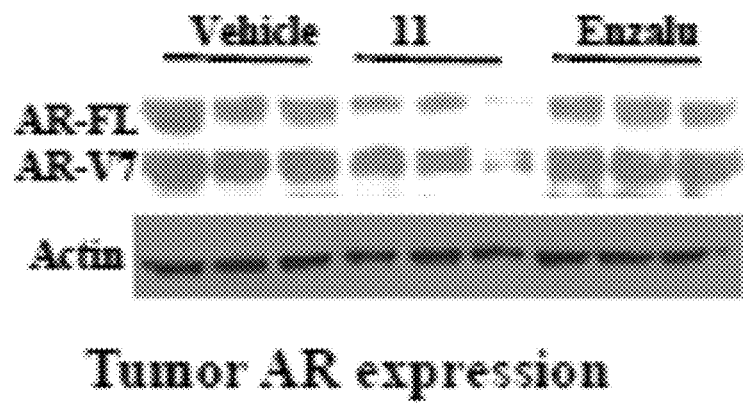
Figure 9D:
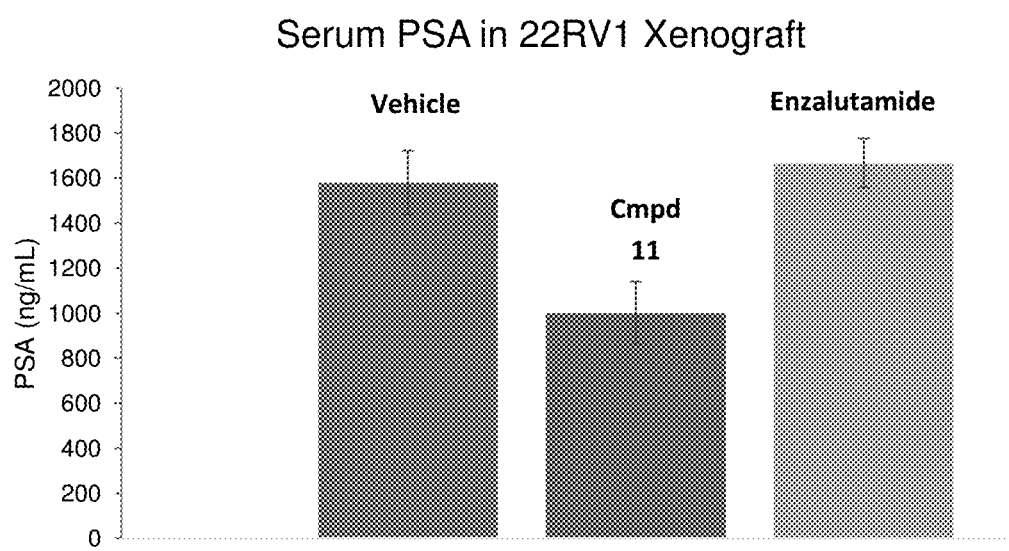

22RV-1 Xenograft Studies with Compound 11:

Since 11 degraded both AR-FL and AR-SV in LNCaP and 22RV-1 cells, the molecule was evaluated in 22RV-1 and LNCaP xenograft studies. FIG. 9A-FIG. 9B show that compound 11 inhibited tumor growth of an aggressive prostate cancer expressing AR splice variant. 22RV-1 is a highly aggressive tumor model that is unresponsive to any currently available treatments. A SARD compound of the present invention, 11, restricted its growth by approximately 50%. No side-effects were observed in the 3-4 weeks study. FIG. 9C demonstrated that 11 degraded both AR-FL and AR-V7 in the 22RV-1 xenografts whereas enzalutamide demonstrated no degradation of either AR in these xenografts. FIG. 9D demonstrated that 11 but not enzalutamide suppressed serum PSA in xenograft bearing animals, demonstrating that 11 suppressed AR gene expression in these tumors. This demonstrated that 11 but not enzalutamide can overcome the antiandrogen resistance present in 22CV-1 cells (e.g., AR-V7 dependent growth) by degrading the AR-V7, resulting in significantly suppressing androgenic tone in these tumors. This provide a proof-of-concept that SARDs such as 11 would be of clinical benefit to CRPC patients, particularly if systemic exposures could be improved.

Figure 10A:
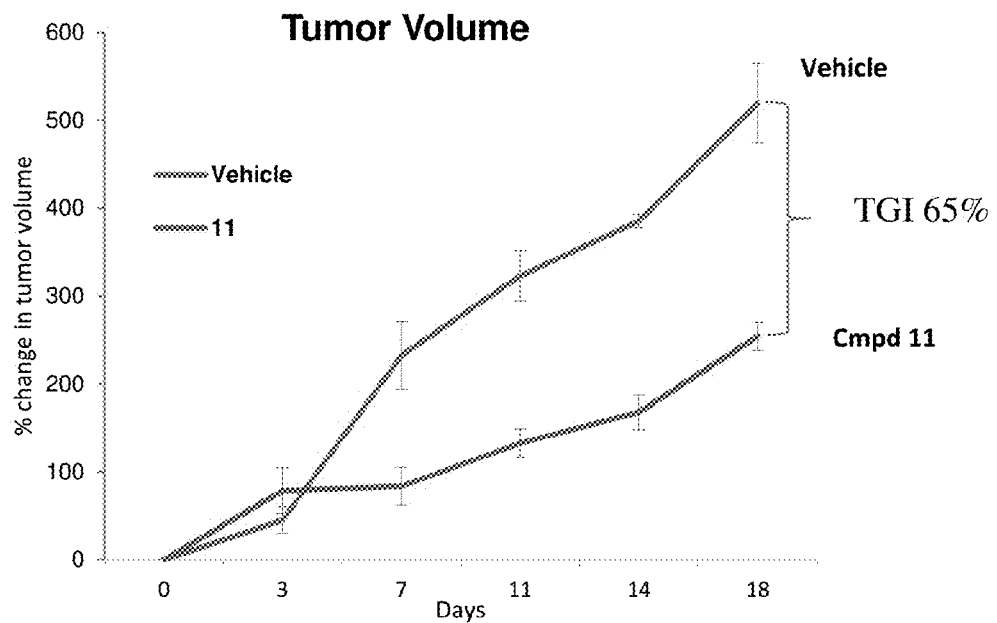
FIG. 10A-FIG. 10C demonstrates that 11 inhibited LNCaP tumor xenograft growth via (FIG. 10A) decreased tumor volume and (FIG. 10B) weights, and (FIG. 10C) serum PSA levels in animals treated with 11 when compared to vehicle.
Figure 10B:
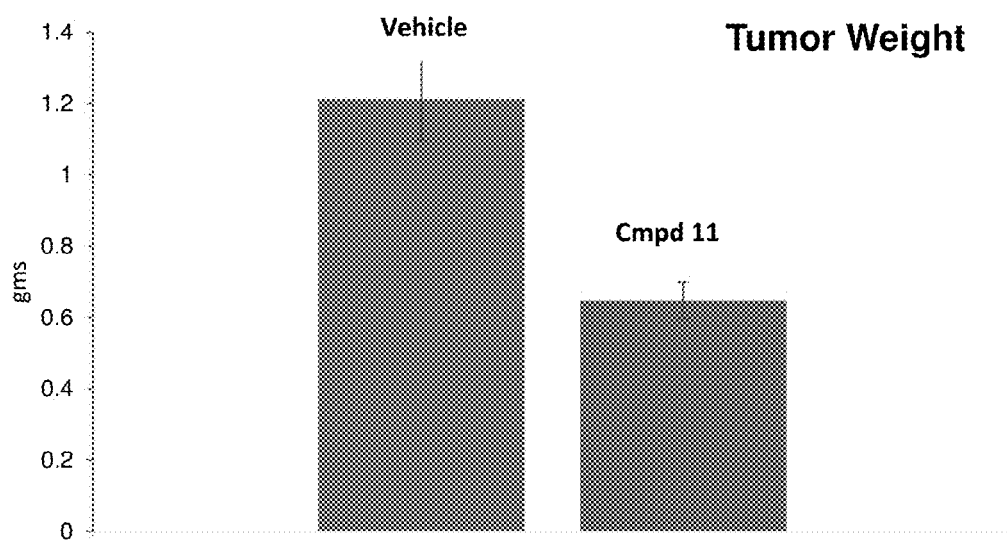
Figure 10C:
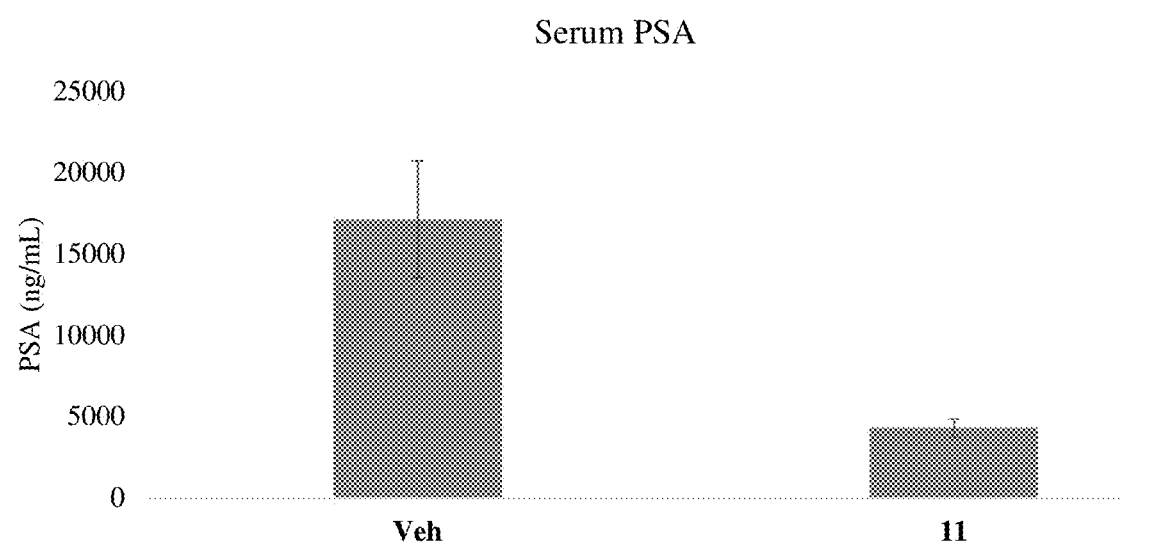

FIG. 10A-FIG. 10C show that 11 inhibited LNCaP tumor xenograft growth. As shown in FIG. 10C, the serum PSA level was inhibited by >75%.

Example 12

SARDs Bind to the AR-AF1

Figure 17A:
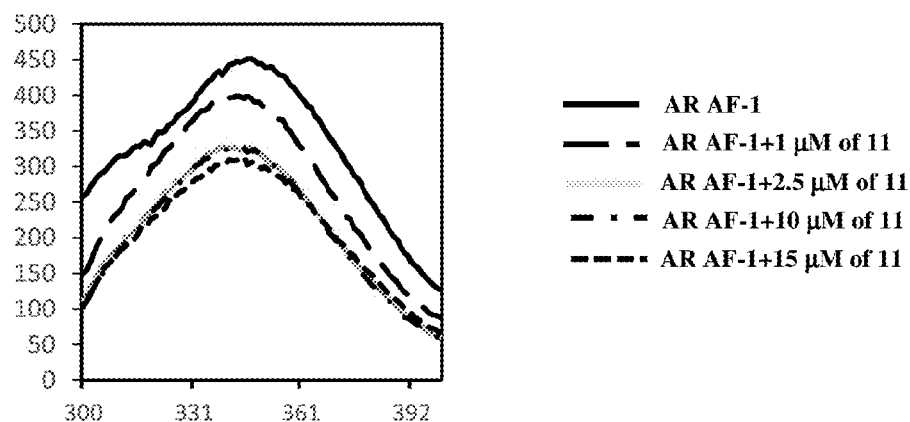
FIG. 17A-FIG. 17C presents biophysical data that suggests that SARDs bind to the N-terminal domain of the AR (in addition to the LBD in the C-terminus).
Figure 17B:
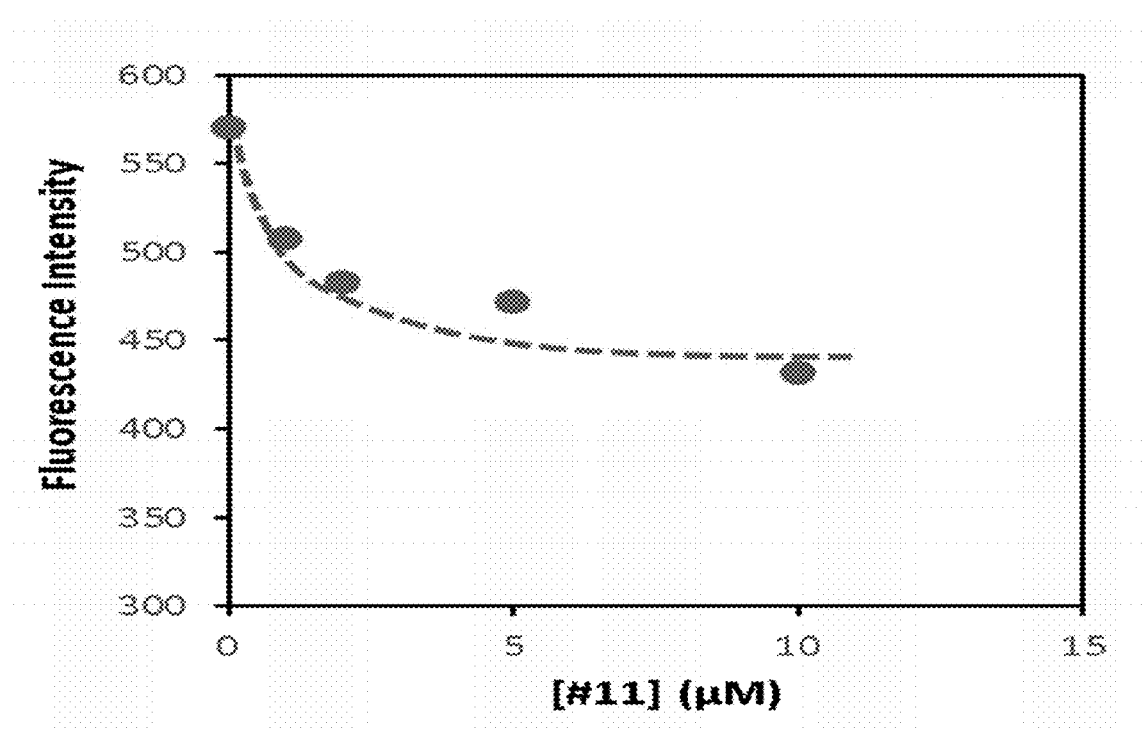
Figure 17C:
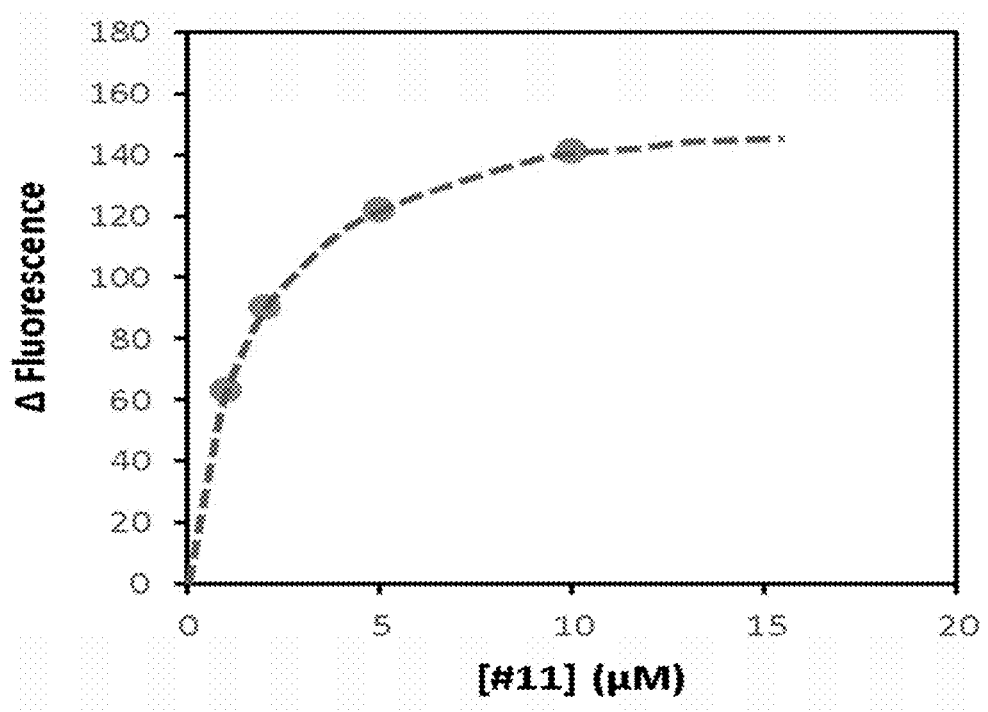

There are two tryptophan residues and up to 12 tyrosine residues in the AF1 of the AR. This has allowed the study of the folding properties of this domain using intrinsic steady state fluorescence emission spectra. Excitation at 287 nm excites both tyrosine and tryptophan residues. The emission maximum (λmax) for the tryptophan is sensitive to the exposure to solvent. In the presence of the natural osmolyte TMAO there is a characteristic 'blue shift' consistent with the tryptophan residues being less solvent exposed and a loss of the shoulder (~307 nm) for tyrosine as there is increased energy transfer to tryptophan as the polypeptide folds. To test if the compounds (enobosarm (negative control), and 17) interact with AF-1 and/or alter the folding of this domain the steady state fluorescence was measured for each compound with AR-AF1 alone or the presence of TMAO (3 M) or urea (4 or 6 M). 1 μM of AR-AF1 and 5 μM of the individual compounds were used, and preincubated for at least 30 minutes prior to measuring the emission spectra. The emission spectra were all corrected for buffer alone or buffer with TMAO/urea/compounds as necessary. FIG. 17A-FIG. 17C presents biophysical data that suggests that SARDs bind to the N-terminal domain of the AR (in addition to the LBD in the C-terminus). FIG. 17A: Dose-dependent shift in the fluorescence intensity by 11 when incubated with AR AF-1. The fluorescence shoulder observed at 307 nm, which corresponds to tyrosine residues in the AF-1, is shifted by 11. The overall fluorescence is also markedly altered by 11. FIG. 17C: Data shown in the left panel was plotted as difference in fluorescence between control and 11 treated samples (fluorescence in the absence of compound—fluorescence in the presence of compound), a dose dependent increase was observed in the presence of 11.

Based on half-maximum saturation for the change in fluorescence signal (at λmax 242 nm), the binding constant to AR-AF1 was calculated to be of $K_D=1.34\pm0.32$ μM (n=3, mean±SEM).

1 μM AR-AF1 was pre-incubated without or with increasing concentrations of compound 11 (up to 15 μM) and steady-state fluorescence emission, after excitation at 287 nm, measured from 300 to 400 nm. Data was analysed as described by Epps et al (1999) *J. Pharm* 51, 41-48, Rawel et al (2006) *Mol. Nutr. Food Res.* 50, 705-713 and Wang et al (2011) *Mol. Endcor.* 25, 2041-2053 which are hereby incorporated by reference.

Example 13

Androgen Receptor Binding and Transactivation of Carbazole Based SARDs

Ligand Binding Assay

Objective:
To determine SARDs binding affinity to the AR-LBD.
Method:
hAR-LBD (633-919) was cloned into pGex4t.1. Large scale GST-tagged AR-LBD was prepared and purified using a GST column. Recombinant ARLBD was combined with [$^3$H]mibolerone (PerkinElmer, Waltham, Mass.) in buffer A (10 mM Tris, pH 7.4, 1.5 mM disodium EDTA, 0.25 M sucrose, 10 mM sodium molybdate, 1 mM PMSF) to determine the equilibrium dissociation constant (Kd) of [$^3$H] mibolerone. Protein was incubated with increasing concentrations of [$^3$H]mibolerone with and without a high concentration of unlabeled mibolerone at 4° C. for 18 h in order to determine total and non-specific binding. Non-specific binding was then subtracted from total binding to determine specific binding and non-linear regression for ligand binding curve with one site saturation to determine the Kd of mibolerone.

Increasing concentrations of SARDs or DHT (range: $10^{-12}$ to $10^{-2}$ M) were incubated with [$^3$H]mibolerone and AR LBD using the conditions described above. Following incubation, the ligand bound AR-LBD complex was isolated using BiogelHT® hydroxyapatite, washed and counted in a scintillation counter after adding scintillation cocktail. Values are expressed as Ki (Table 1).

Transactivation Assay for Wt and Mutant AR

Objective:
To determine the effect of SARDs on androgen-induced transactivation of AR wildtype (wt) or AR carrying known AR-LB mutants (i.e., W741L or T877A).
Method:
HEK-293 cells were plated at 125,000 cells/well of a 24 well plate in DME+5% csFBS without phenol red. Cells were transfected with 0.25 ug GRE-LUC, 10 ng CMV-renilla LUC, and 50 ng CMV-hAR(wt) or CMV-hAR (W741L) or CMV-hAR(T877A) using lipofectamine transfection reagent in optiMEM medium. Medium was changed 24 h after transfection to DME+5% csFBS without phenol red and treated with a dose response of various drugs (Table 11: compounds 200-205) (1 pM to 10 uM). SARDs and antagonists were treated in combination with 0.1 nM R1881. Luciferase assay was performed 24 h after treatment on a Biotek synergy 4 plate reader. Firefly luciferase values were normalized to renilla luciferase values.

Transactivation Assay-Wt and Mutant AR

Objective:
To determine the effect of SARDs on androgen-induced transactivation of AR carrying known AR-LBD mutants.
Method:
HEK-293 cells were plated at 125,000 cells/well of a 24 well plate in DME+5% csFBS without phenol red. Cells were transfected with 0.25 ug GRE-LUC, 10 ng CMV-renilla LUC, and 50 ng CMV-hAR/W741L-AR/T877A-AR using lipofectamine transfection reagent in optiMEM medium. Medium was changed 24 h after transfection to DME+5% csFBS without phenol red and treated with a dose response of various drugs (1 pM to 10 uM). SARDs and antagonists were treated in combination with 0.1 nM R1881. Luciferase assay was performed 24 h after treatment on a Biotek synergy 4 plate reader. Firefly luciferase values were normalized to renilla luciferase values. (Table 11)

AR Degradation Using Compounds of this Invention

Determination of metabolic stability (in vitro $CL_{int}$) of test compounds:
Phase I Metabolism
The assay was done in a final volume of 0.5 ml in duplicates (n=2). Test compound (1 μM) was pre-incubated for 10 minutes at 37° C. in 100 mM Tris-HCl, pH 7.5 containing 0.5 mg/ml liver microsomal protein. After pre-incubation, reaction was started by addition of 1 mM NADPH (pre-incubated at 37° C.). Incubations were carried out in triplicate and at various time-points (0, 5, 10, 15, 30 and 60 minutes) 100 μl aliquots were removed and quenched with 100 μl of acetonitrile containing internal standard. Samples were vortex mixed and centrifuged at 4000 rpm for 10 minutes. The supernatants were transferred to 96 well plates and submitted for LC-MS/MS analysis. As control, sample incubations done in absence of NADPH were included. From % PCR (% Parent Compound Remaining), rate of compound disappearance is determined (slope) and in vitro $CL_{int}$ (μl/min/mg protein) was calculated.

Metabolic Stability in Phase I & Phase II Pathways

In this assay, test compound was incubated with liver microsomes and disappearance of drug was determined using discovery grade LC-MS/MS. To stimulate Phase II metabolic pathway (glucuronidation), UDPGA and alamethicin was included in the assay.

LC-MS/MS Analysis:

The analysis of the compounds under investigation was performed using LC-MS/MS system consisting of Agilent 1100 HPLC with an MDS/Sciex 4000 Q-Trap™ mass spectrometer. The separation was achieved using a $C_{18}$ analytical column (Alltima™, 2.1×100 mm, 3 μm) protected by a $C_{18}$ guard cartridge system (SecurityGuard™ ULTRA Cartridges UHPLC for 4.6 mm ID columns, Phenomenex). Mobile phase was consisting of channel A (95% acetonitrile+5% water+0.1% formic acid) and channel C (95% water+5% acetonitrile+0.1% formic acid) and was delivered at a flow rate of 0.4 mL/min. The volume ratio of acetonitrile and water was optimized for each of the analytes. Multiple reaction monitoring (MRM) scans were made with curtain gas, collision gas, nebulizer gas, and auxiliary gas optimized for each compound, and source temperature at 550° C. Molecular ions were formed using an ion spray voltage (IS) of −4200 V (negative mode). Declustering potential (DP), entrance potential (EP), collision energy (CE), product ion mass, and cell exit potential (CXP) were optimized for each compound.

TABLE 11

AR Binding, Inhibition of AR Transactivation, AR degradation and in vitro metabolic stability of SARDs:

| Compound | Binding $K_i$ (nM) | Transcriptional Activation (+0.1 nM R1881; R1881 $EC_{50}$ = 0.11 nM) | | | $T_{1/2}$ (min) $CL_{int}$ (μl/min/mg) |
|---|---|---|---|---|---|
| | | Wt. $IC_{50}$ (nM) | W741L $IC_{50}$ (nM) | T877A $IC_{50}$ (nM) | |
| DHT | 1 | — | — | — | |
| R-Bicalutamide | 545.5 | 248.2 | — | 557 | |
| Enzalutamide | 205.2 | 216.3 | 939 | 331.94 | |
| ARN-509 | — | 297.0 | 1939.41 | 390.50 | |
| ASC-J9 | — | 1008.0 | 3487.68 | 2288.16 | |
| 200 | 728.59 | 871.21 | | | 41.77 min 16.6 mL/min/kg |
| 201 | 506.94 | 237.91 | | | 89.68 min 7.729 mL/min/kg |
| 202 | | | | | |

The relatively long half-lives ($t_{1/2}$) and low metabolic clearance ($CL_{int}$) value in vitro compounds 200-202 of this invention suggest the possibilities oral bioavailability and stability in serum which would be favorable for systemic treatment of diseases of this invention such as prostate cancer, breast cancer, Kennedy's disease, and various androgen-dependent diseases.

TABLE 12

AR Binding, Inhibition of AR Transactivation, AR Degradation and in vitro Metabolic Stability of SARDs

| Compd ID | Structure | Log P (−0.4 to +5.6) | Binding/Wt. $K_i$ (nM) (DHT = 1 nM) | $IC_{50}$ (nM) | SARD Activity Full Length % inhibition at 1, 10 uM | S.V. (22RV1) % inhibition at 10 uM | DMPK (MLM) $T_{1/2}$ Clint |
|---|---|---|---|---|---|---|---|
| Enobosarm | [structure: NC, CF3-substituted phenyl-NH-C(O)-C(CH3)(OH)-CH2-O-phenyl-CN] | 3.44 | 20.21 | ~20 | | | |
| R-Bicalutamide | [structure: NC, CF3-substituted phenyl-NH-C(O)-C(CH3)(OH)-CH2-S(O)2-phenyl-F] | 2.57 | 508.84 | 248.2 | | | |

TABLE 12-continued

AR Binding, Inhibition of AR Transactivation, AR Degradation and in vitro Metabolic Stability of SARDs

| Compd ID | Structure | Log P (−0.4 to +5.6) | Binding/Wt. Ki (nM) (DHT = 1 nM) | IC$_{50}$ (nM) | SARD Activity Full Length % inhibition at 1, 10 uM | S.V. (22RV1) % inhibition at 10 uM | DMPK (MLM) T$_{1/2}$ Clint |
|---|---|---|---|---|---|---|---|
| Enzalut-amide | | 4.56 | 3641.29 | 216.3 | | | |
| ARN-509 | 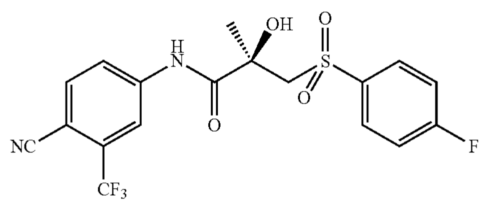 [SMILES: C[C@](O)(CS(=O)(=O)c1ccc(F)cc1)C(=O)Nc1ccc(C#N)c(C(F)(F)F)c1] | 3.47 | 1452.29 | | 0 | 0 | |
| | | 2.57 | 87.67 | — | | | |
| | | 1.86 | 407.08 | | | | |
| 200 | 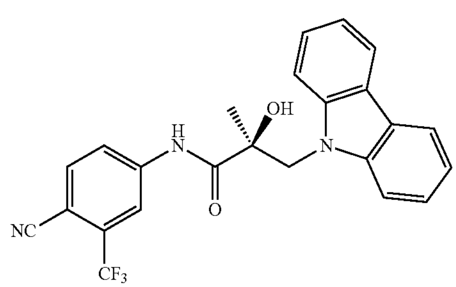 [SMILES: C[C@](O)(Cn1c2ccccc2c2ccccc21)C(=O)Nc1ccc(C#N)c(C(F)(F)F)c1] | 4.36 | 728.59 | 871.21 | 48 | 60 | 41.77 16.6 |
| 201 | 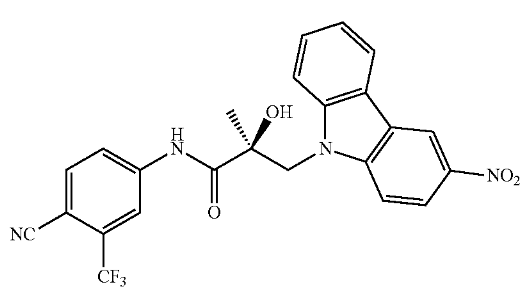 [SMILES: C[C@](O)(Cn1c2ccccc2c2cc([N+](=O)[O-])ccc21)C(=O)Nc1ccc(C#N)c(C(F)(F)F)c1] | 4.40 | 506.94 | 237.91 | 33 | | 89.68 7.729 |

TABLE 12-continued

AR Binding, Inhibition of AR Transactivation, AR Degradation and in vitro Metabolic Stability of SARDs

Figure 29A:
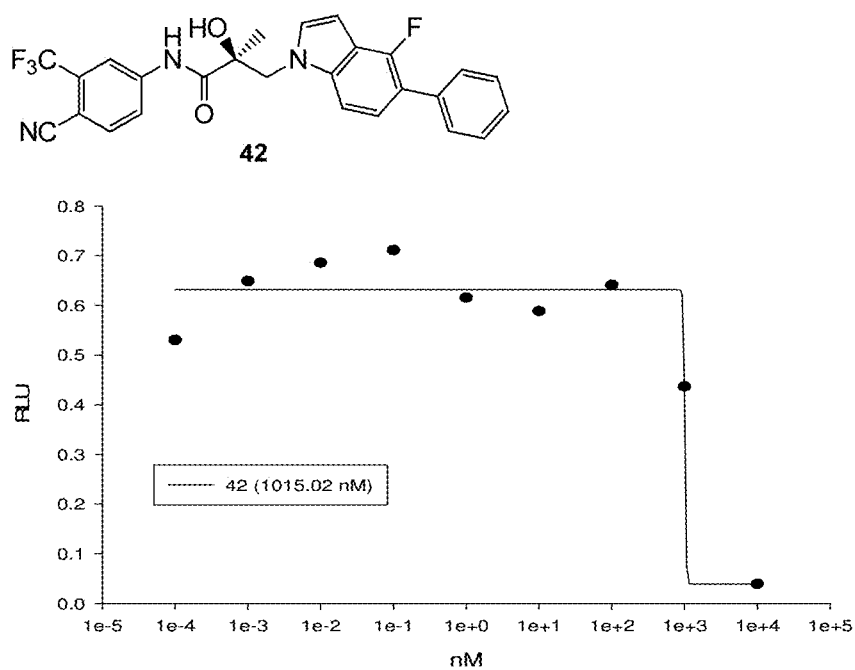
FIG. 29A-FIG. 29O depicts transactivation data, binding, and AR-FL and AR-SV degradation for SARDs compounds of this invention.
Figure 29B:
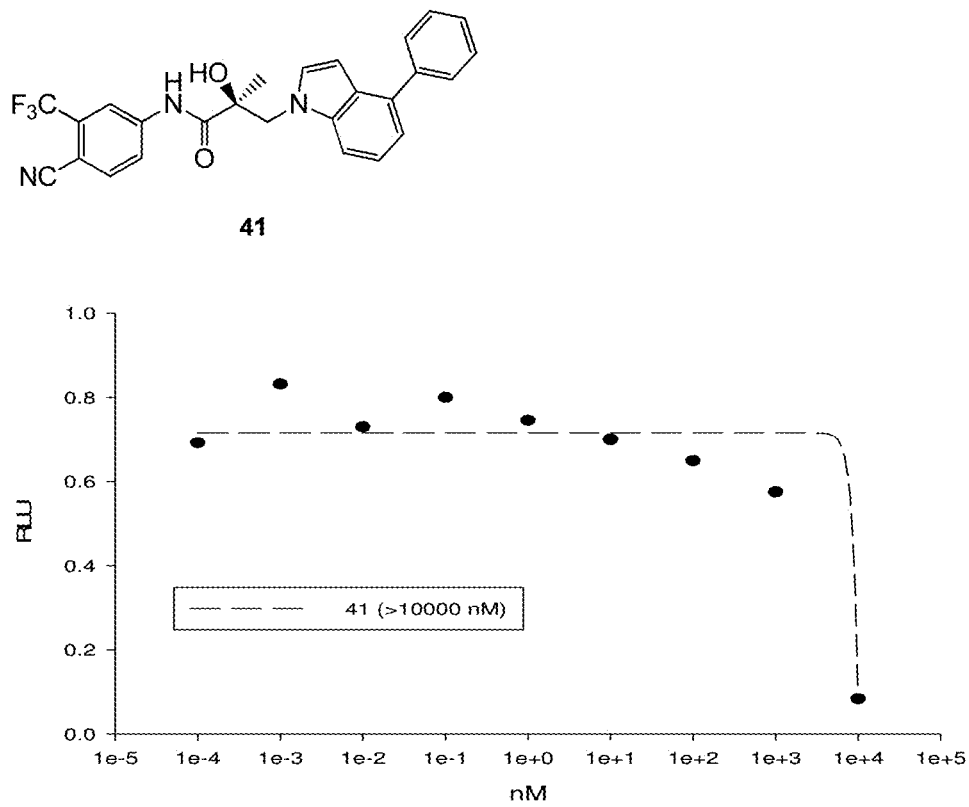
(FIG. 29B) presents transactivation data for 41 ($IC_{50}$=>10,000 nM) and binding (Ki=84.3 nM).
Figure 29C:
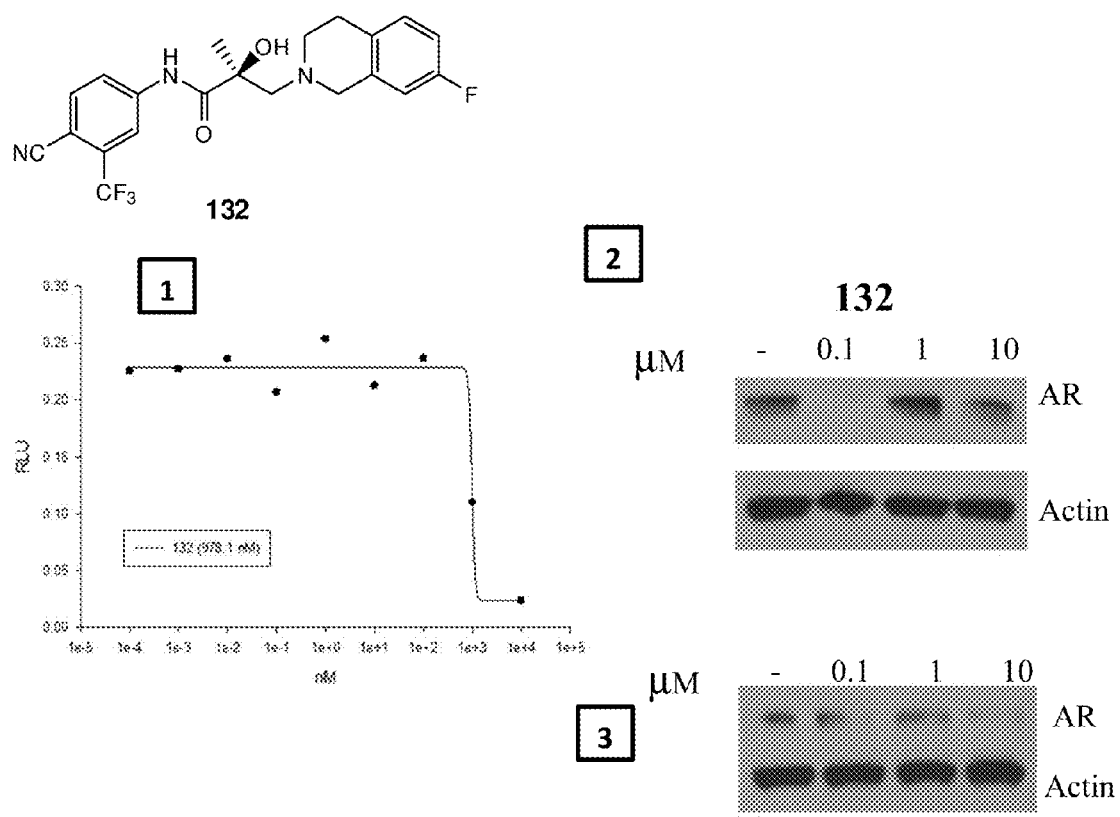
(FIG. 29C) presents (1) transactivation data for 132 ($IC_{50}$=978.1 nM) and binding (Ki=353.2 nM); (2) AR full length degradation; and (3) AR splice variant degradation.
Figure 29D:
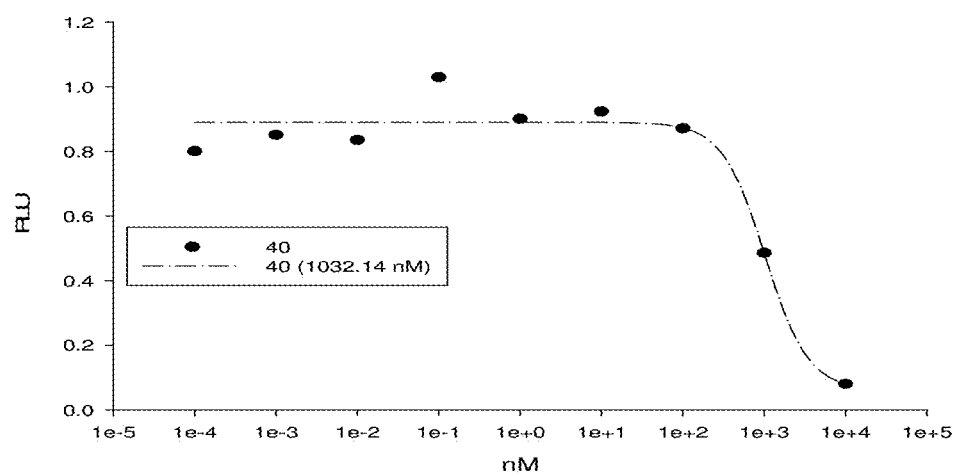
(FIG. 29D) presents (1) transactivation data for 40 ($IC_{50}$=1032.1 nM) and binding (Ki=134.9 nM).
Figure 29D:
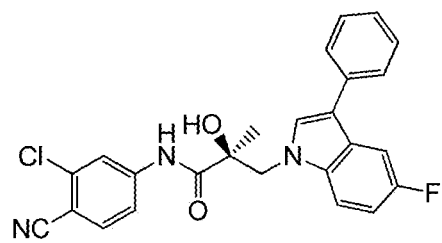
Figure 29E:
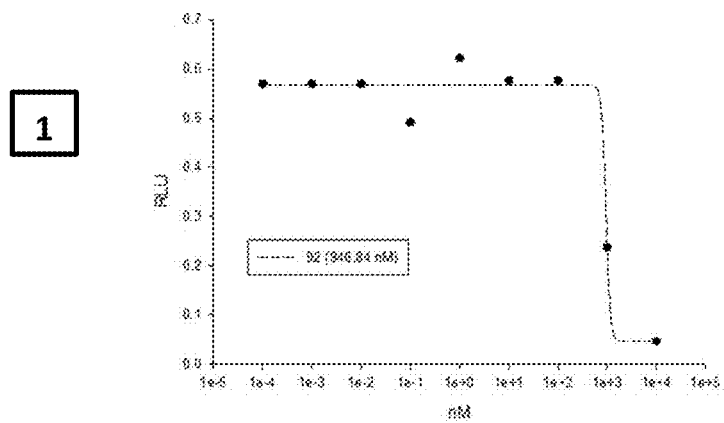
(FIG. 29E) presents (1) transactivation data for 92 ($IC_{50}$=946.8 nM) and binding (Ki=nM); (2) AR full length degradation; and (3) AR splice variant D567es degradation.
Figure 29E:
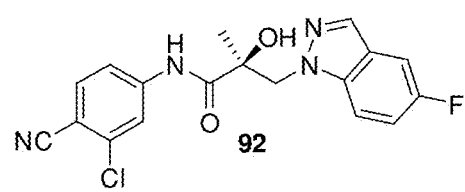
Figure 29E:
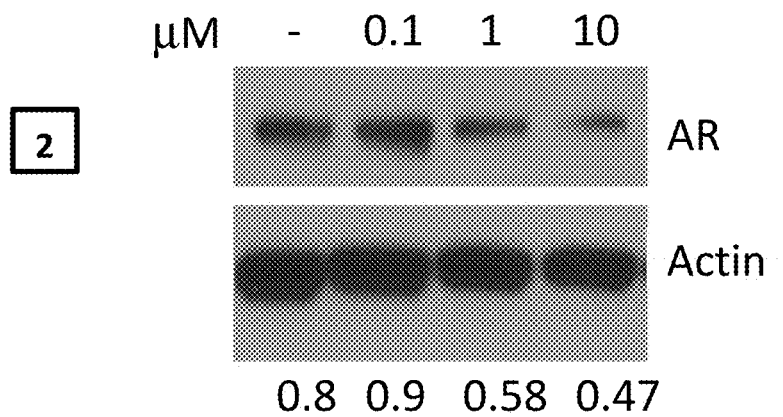
Figure 29E:
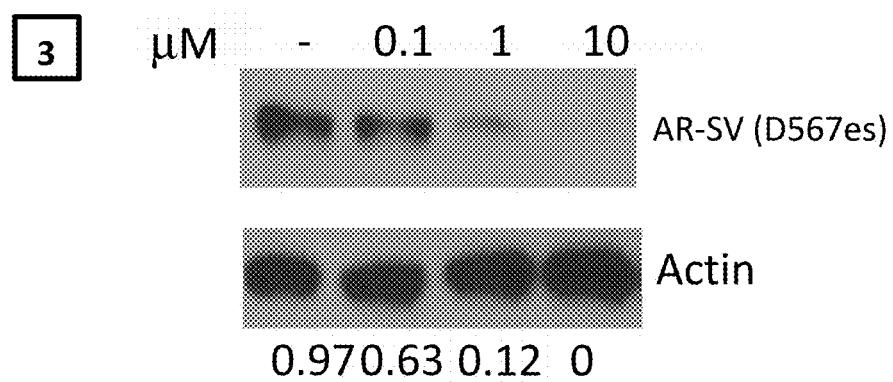
Figure 29F:
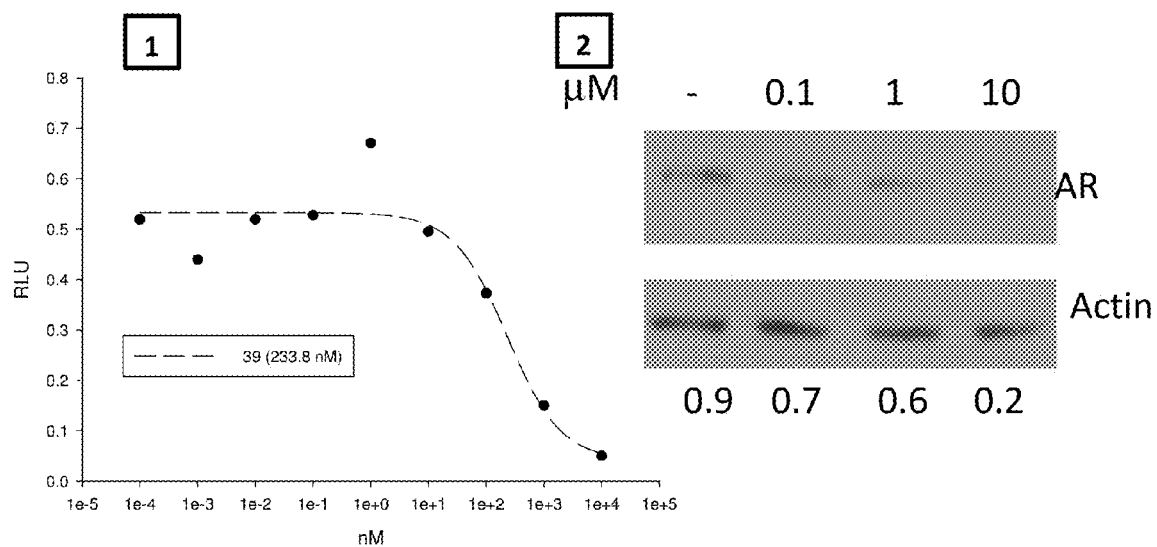
(FIG. 29F) presents (1) transactivation data for 39 ($IC_{50}$=233.8 nM) and binding (Ki=719.9 nM); (2) AR full length degradation.
Figure 29G:
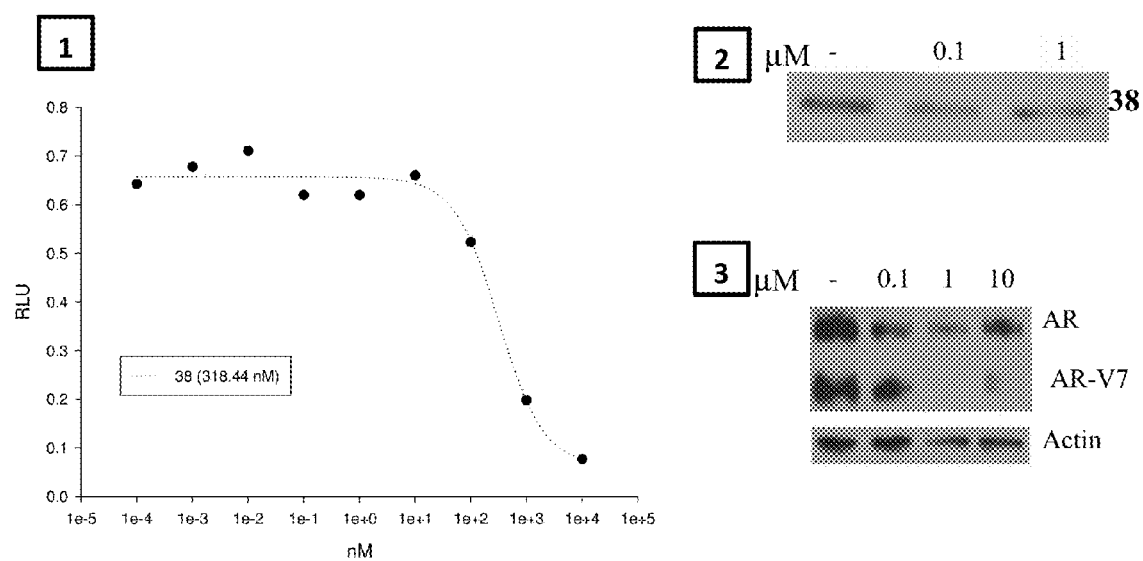
(FIG. 29G) presents (1) transactivation data for 38 ($IC_{50}$=318.4 nM) and binding (Ki=331.8 nM); (2) AR full length degradation; and (3) AR splice variant AR-V7 degradation.
Figure 29G:
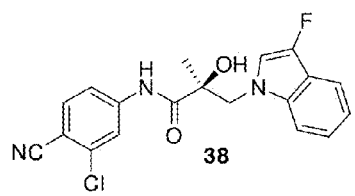
Figure 29H:
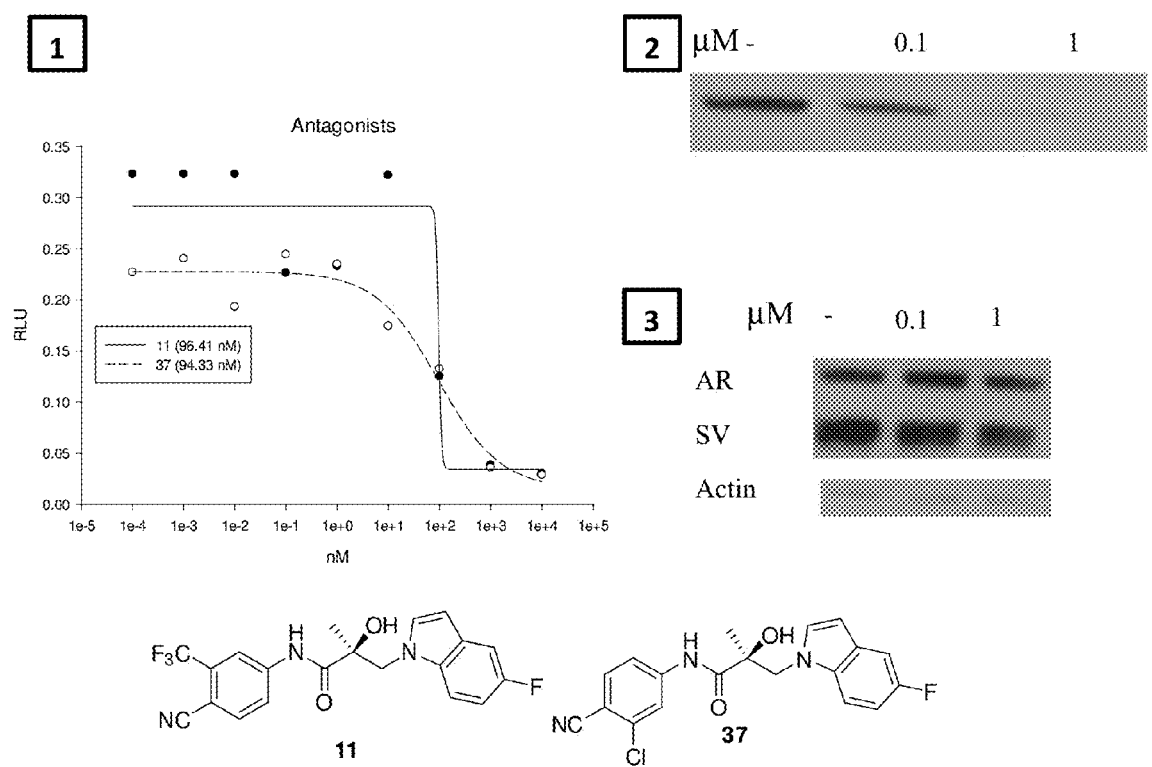
(FIG. 29H) presents (1) transactivation data for 11 ($IC_{50}$=96.4 nM) and 37 ($IC_{50}$=94.0 nM) and binding (Ki=252.6 nM); (2) AR full length degradation; and (3) AR splice variant degradation.
Figure 29I:
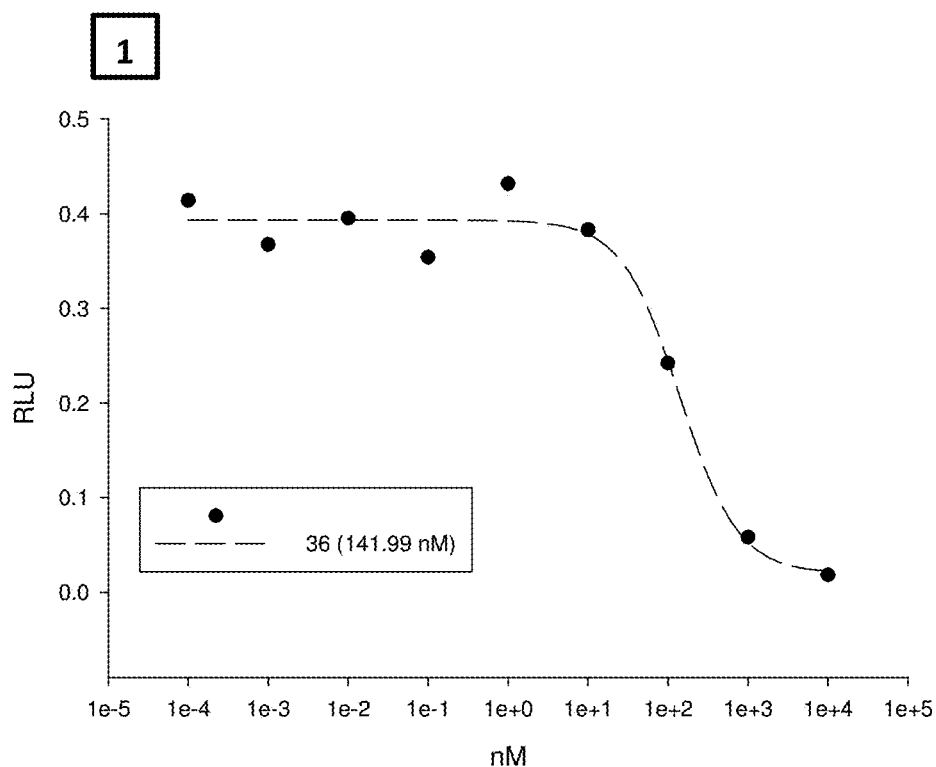
(FIG. 29I) presents (1) transactivation data for 36 ($IC_{50}$=1142.0 nM) and binding (Ki=315.3 nM); (2) AR full length degradation.
Figure 29I:
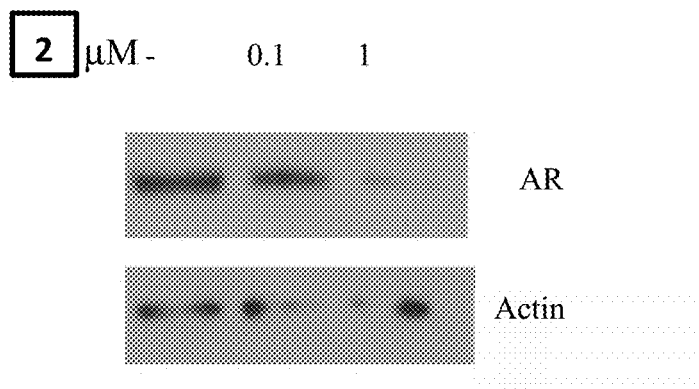
Figure 29I:
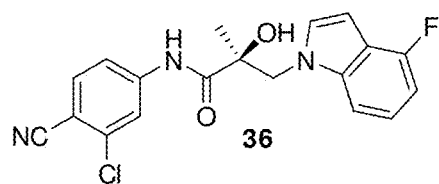
Figure 29J:
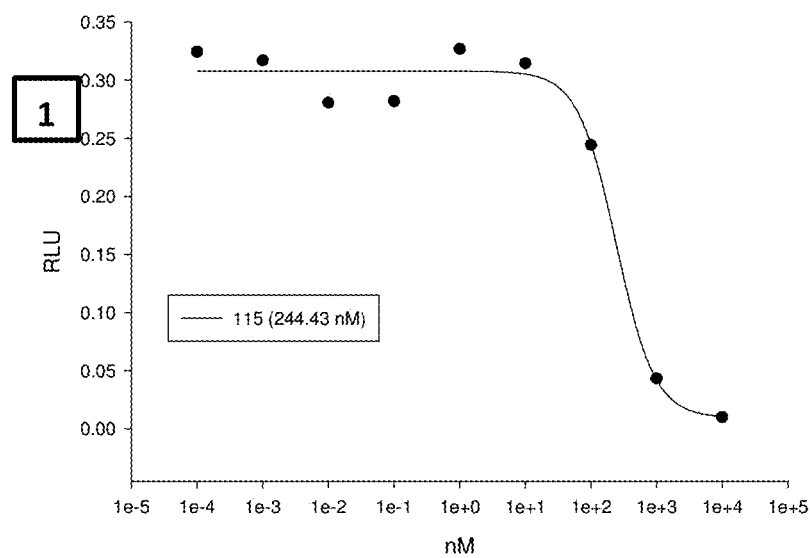
(FIG. 29J) presents (1) transactivation data for 115 (ICso=244.4 nM) and binding (Ki=71.5 nM); (2) AR full length degradation; and (3) AR splice variant AR-V7 degradation.
Figure 29J:
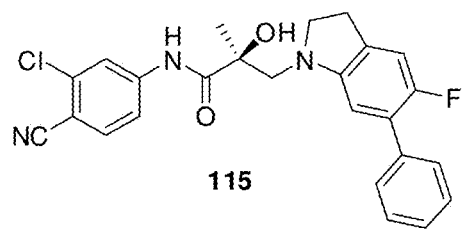
Figure 29J:
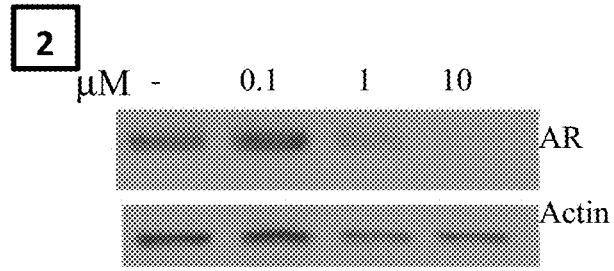
Figure 29J:
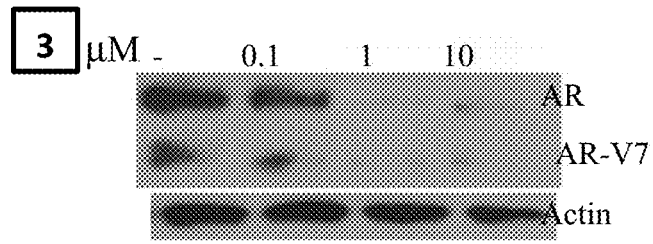
Figure 29K:
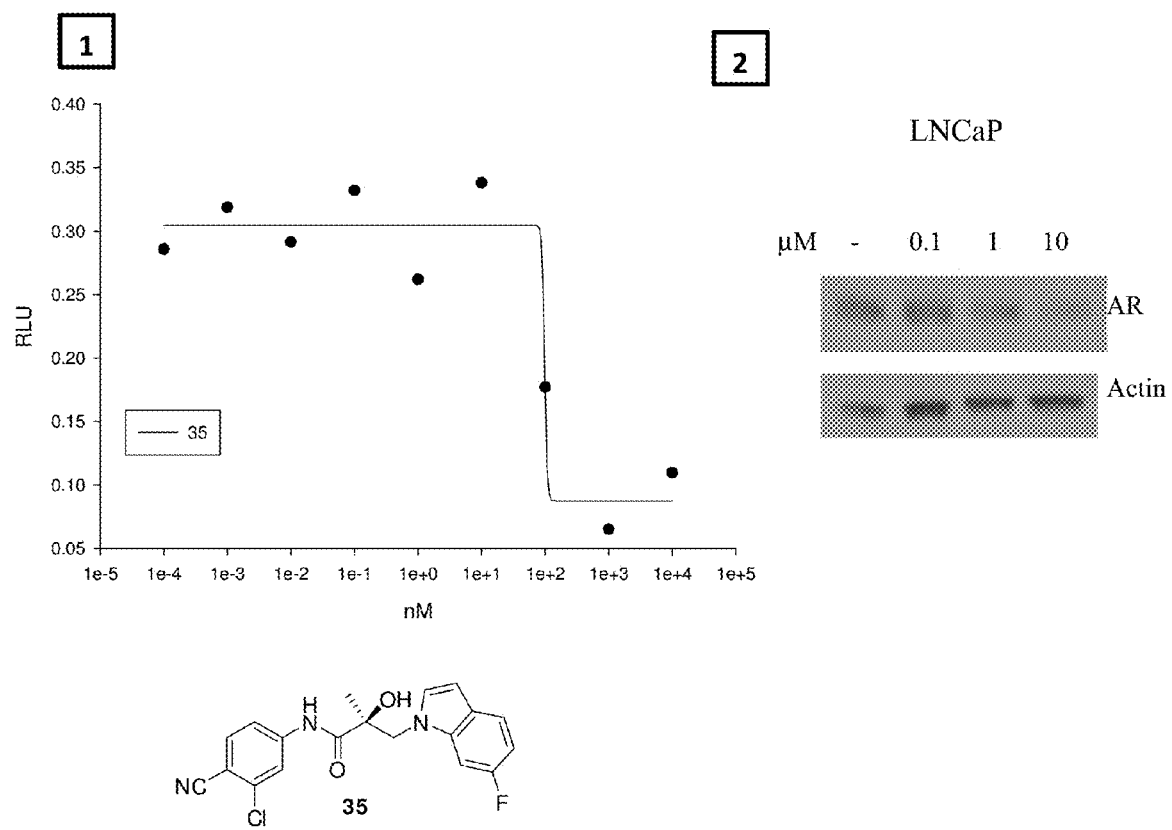
(FIG. 29K) presents (1) transactivation data for 35 (ICso=98.47 nM (data not shown)) and binding (Ki=155.7 nM); (2) AR full length degradation.
Figure 29L:
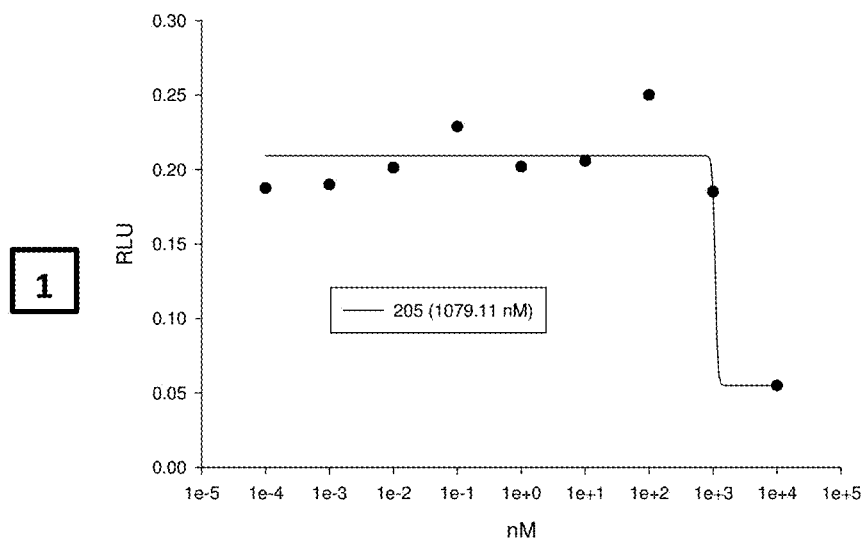
(FIG. 29L) presents (1) transactivation data for 205 ($IC_{50}$=1079.1 nM) and binding (Ki=90.7 nM), (2) AR full length degradation; and (3) AR splice variant AR-V7 degradation.
Figure 29L:
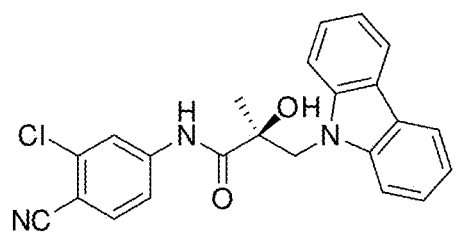
Figure 29L:
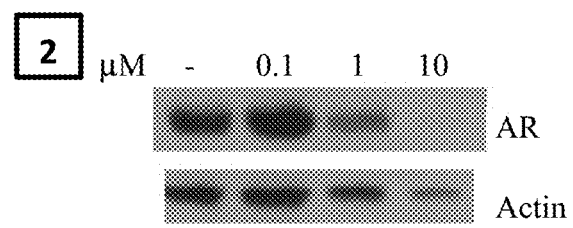
Figure 29L:
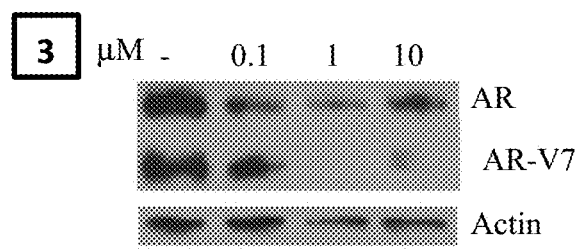
Figure 29M:
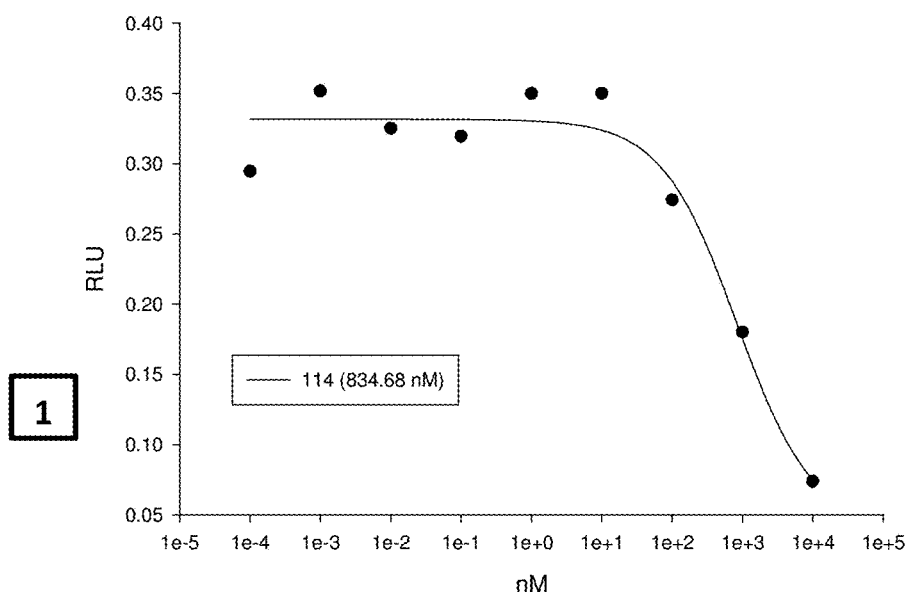
(FIG. 29M) presents (1) transactivation data for 114 ($IC_{50}$=834.7 nM) and binding (Ki=204.4 nM); (2) AR full length degradation; and (3) AR splice variant AR-V7 degradation.
Figure 29M:
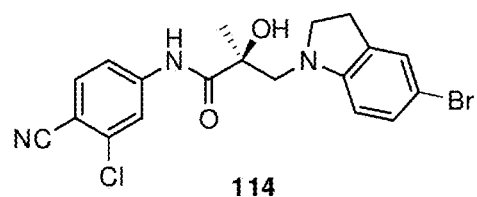
Figure 29M:
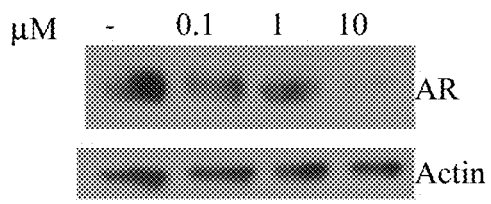
Figure 29M:
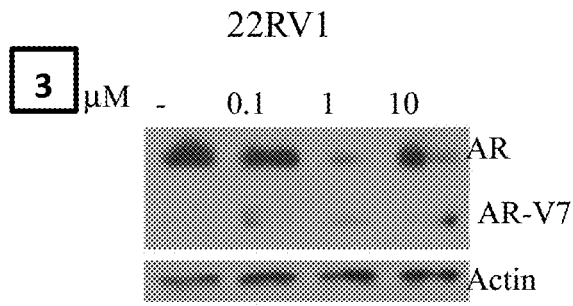
Figure 29N:
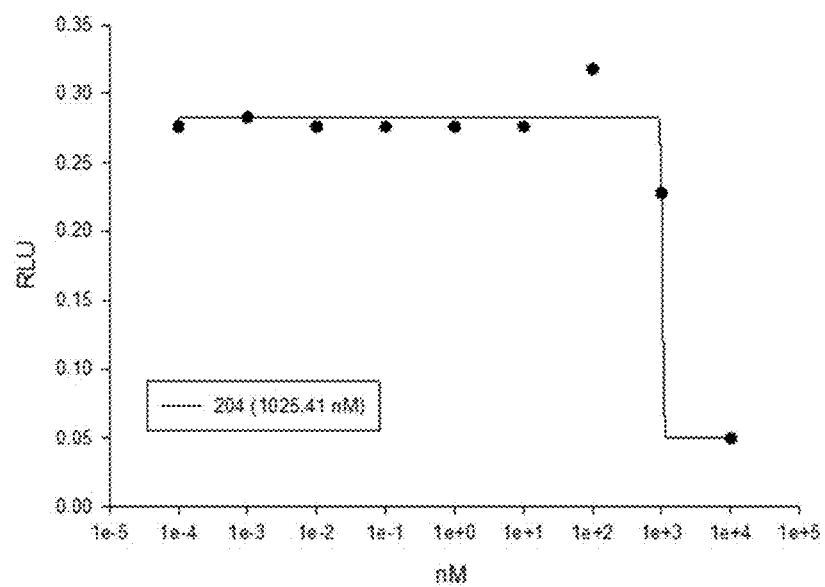
(FIG. 29N) presents (1) transactivation data for 204 ($IC_{50}$=1025.4 nM) and binding (Ki=809.6 nM).
Figure 29N:
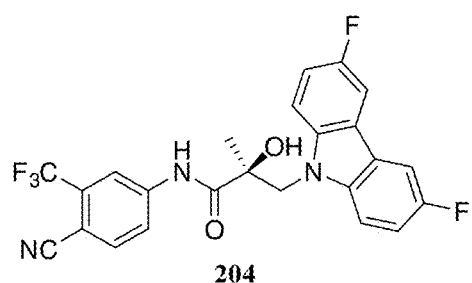
Figure 29O:
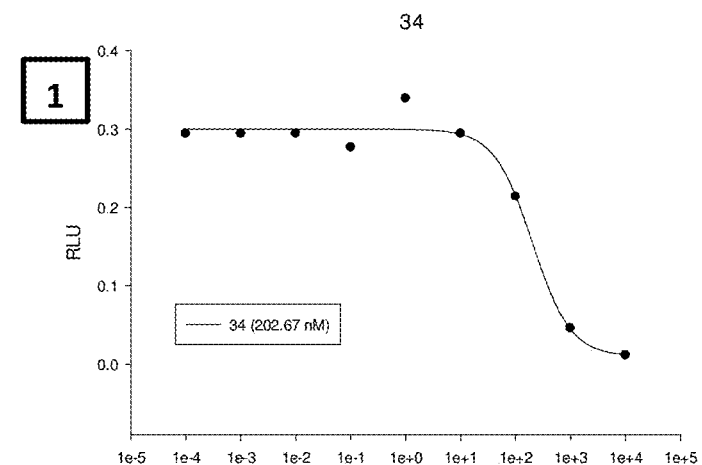
Figure 29O:
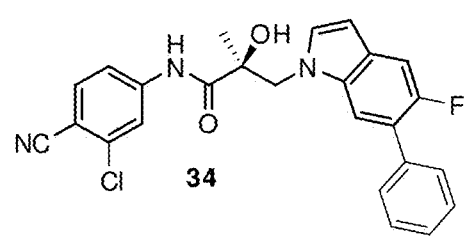
Figure 29O:
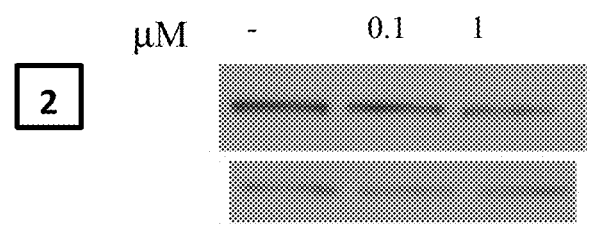
Figure 29O:
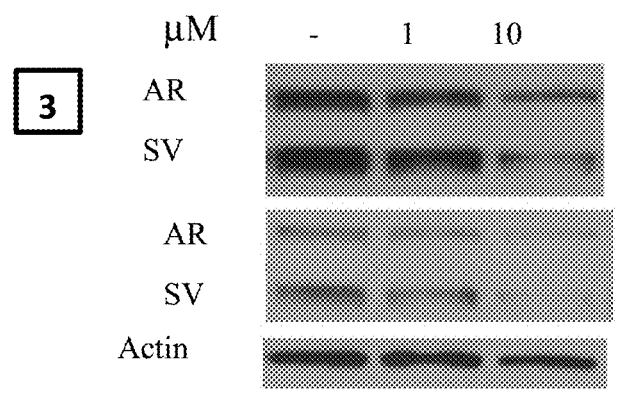

| Compd ID | Structure | Log P (−0.4 to +5.6) | Binding/Wt. Ki (nM) (DHT = 1 nM) | IC$_{50}$ (nM) | SARD Activity Full Length % inhibition at 1, 10 uM | S.V. (22RV1) % inhibition at 10 uM | DMPK (MLM) T$_{1/2}$ ClInt |
|---|---|---|---|---|---|---|---|
| 202 | 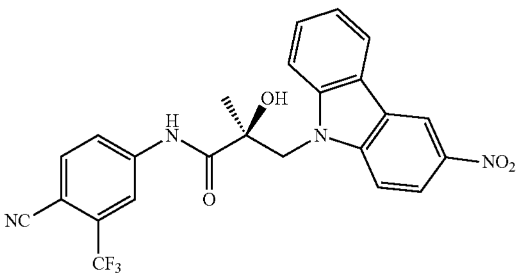 [SMILES: C[C@](O)(Cn1c2ccccc2c2cc([N+](=O)[O-])ccc21)C(=O)Nc1ccc(C#N)c(C(F)(F)F)c1] | 4.52 | 193.80 | 991.15 | 20 | 29 | 39.94 17.35 |
| 203 | 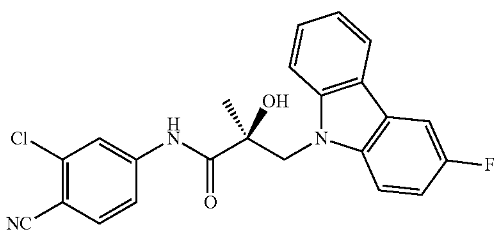 [SMILES: C[C@](O)(Cn1c2ccccc2c2cc(F)ccc21)C(=O)Nc1ccc(C#N)c(Cl)c1] | 4.16 | 248.54 | 1242.96 | 38 | 0 | |
| 204 | 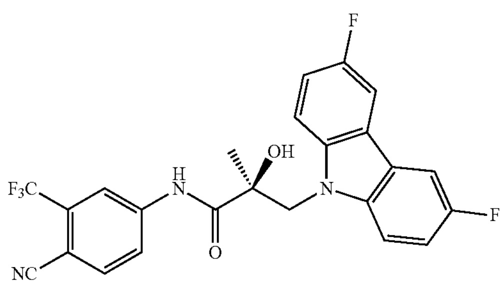 [SMILES: C[C@](O)(Cn1c2ccc(F)cc2c2cc(F)ccc21)C(=O)Nc1ccc(C#N)c(C(F)(F)F)c1] | 4.68 | 809.64 See FIG. 29M | 1025.41 See FIG. 29M | 51 | | |
| 205 | 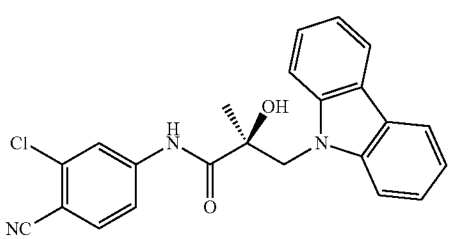 [SMILES: C[C@](O)(Cn1c2ccccc2c2ccccc21)C(=O)Nc1ccc(C#N)c(Cl)c1] | 4.00 | 90.68 See FIG 29K | 1079.11 See FIG 29K | 19, 87 | 87 | |

TABLE 13

Liver Microsome Data.

| Compd ID | MLM T1/2 | MLM ClInt | HLM T1/2 | HLM ClInt | RLM T1/2 | RLM ClInt | DLM T1/2 | DLM ClInt |
|---|---|---|---|---|---|---|---|---|
| 200 (5-carbazole) | 95.9 | 0.72 | | | | | | |
| 201 | 89.68 | 7.729 | 61.38 | 0.01129 | | | | |
| 202 | 39.94 | 17.35 | 14.28 | 48.54 | | | | |

Example 14

AR Degradation Using Compounds of this Invention

LNCaP Degradation Assay

Objective:

To determine the effect of SARDs on AR expression in LNCaP cells. Plasmid constructs and transient transfection. Human AR cloned into CMV vector backbone was used for the transactivation study. HEK-293 cells were plated at 120,000 cells per well of a 24 well plate in DME+5% csFBS. The cells were transfected using Lipofectamine (Invitrogen, Carlsbad, Calif.) with 0.25 µg GRE-LUC, 0.01 µg CMV-LUC (renilla luciferase) and 25 ng of the AR. The cells were treated 24 hrs after transfection as indicated in the figures and the luciferase assay performed 48 hrs after transfection. Data are represented as $IC_{50}$ obtained from four parameter logistics curve.

Ligand Binding Assay.

hAR-LBD (633-919) was cloned into pGex4t.1. Large scale GST-tagged AR-LBD was prepared and purified using a GST column. Recombinant ARLBD was combined with [$^3$H]mibolerone (PerkinElmer, Waltham, Mass.) in buffer A (10 mM Tris, pH 7.4, 1.5 mM disodium EDTA, 0.25 M sucrose, 10 mM sodium molybdate, 1 mM PMSF) to determine the equilibrium dissociation constant ($K_d$) of [$^3$H]mibolerone. Protein was incubated with increasing concentrations of [$^3$H]mibolerone with and without a high concentration of unlabeled mibolerone at 4° C. for 18 h in order to determine total and non-specific binding. Non-specific binding was then subtracted from total binding to determine specific binding and non-linear regression for ligand binding curve with one site saturation to determine the $K_d$ of mibolerone.

Increasing concentrations of SARDs or DHT (range: $10^{-12}$ to $10^{-4}$ M) were incubated with [$^3$H]mibolerone and AR LBD using the conditions described above. Following incubation, the ligand bound AR-LBD complex was isolated using biogelHT hydroxyapatite, washed and counted in a scintillation counter after adding scintillation cocktail. Values are expressed as $K_i$.

LNCaP Gene Expression Assay.

Method:

LNCaP cells were plated at 15,000 cells/well of a 96 well plate in RPMI+1% csFBS without phenol red. Forty-eight hours after plating, cells were treated with a dose response of SARDs. Twenty four hours after treatment, RNA was isolated using cells-to-ct reagent, cDNA synthesized, and expression of various genes was measured by realtime rtPCR (ABI 7900) using taqman primers and probes. Gene expression results were normalized to GAPDH.

LNCaP Growth Assay.

Method:

LNCaP cells were plated at 10,000 cells/well of a 96 well plate in RPMI+1% csFBS without phenol red. Cells were treated with a dose response of SARDs. Three days after treatment, cells were treated again. Six days after treatment, cells were fixed and cell viability was measured by SRB assay.

LNCaP or AD1 Degradation.

Method:

LNCaP or AD1 cells expressing full length AR were plated at 750,000-1,000,000 cells/well of a 6 well plate in growth medium (RPMI+10% FBS). Twenty four hours after plating, medium was changed to RPMI+1% csFBS without phenol red and maintained in this medium for 2 days. Medium was again changed to RPMI+1% csFBS without phenol red and cells were treated with SARDs (1 nM to 10 uM) in combination with 0.1 nM R1881. After 24 h of treatment, cells were washed with cold PBS and harvested. Protein was extracted using salt-containing lysis buffer with three free-thaw cycles. Protein concentration was estimated and five microgram of total protein was loaded on a SDS-PAGE, fractionated, and transferred to a PVDF membrane. The membrane was probed with AR N-20 antibody from SantaCruz and actin antibody from Sigma.

22RV1 and D567es Degradation.

Method: 22RV1 and D567es cells expressing AR splice variants were plated at 750,000-1,000,000 cells/well of a 6 well plate in growth medium (RPMI+10% FBS). Twenty four hours after plating, medium was changed and treated. After 24-30 h of treatment, cells were washed with cold PBS and harvested. Protein was extracted using salt-containing lysis buffer with three free-thaw cycles. Protein concentration was estimated and five microgram of total protein was loaded on a SDS-PAGE, fractionated, and transferred to a PVDF membrane. The membrane was probed with AR N-20 antibody from SantaCruz and actin antibody from Sigma.

22RV1 Growth and Gene Expression.

Methods:

Cell growth was evaluated as described before by SRB assay. Cells were plated in 96 well plate in full serum and treated for 6 days with medium change after day 3. Gene expression studies were performed in 22RV1 cells plated in 96 well plate at 10,000 cells/well in RPMI+10% FBS. Twenty four hours after plating, cells were treated for 3 days and gene expression studies were performed as described before.

Figure 26:
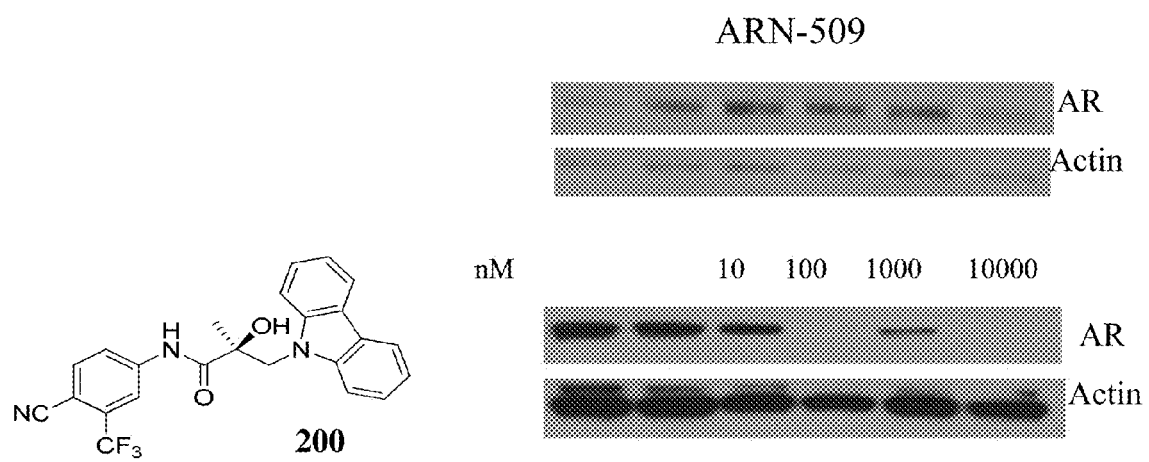
FIG. 26 depicts degradation in LNCaP cells using 200 and ARN-509. LNCaP cells treated with 200 were lyzed and subjected to Western blot analysis, as described above.

Results:

FIG. 26 presents AR degradation by 1 vs. ARN-509 in LNCaP cells. Western blot analysis by the method described above demonstrated the ability of 200 to degrade a mutant AR (i.e., T877A) at 100 nM and 10 µM in LNCaP cells whereas ARN-509 only degraded at 10 µM, suggesting that SARDs such as 200 will have clinical utility in prostate cancers including those whose growth is driven by antiandrogen resistance-conferring mutant AR's (i.e., advanced prostate cancers and CRPC).

Figure 27:
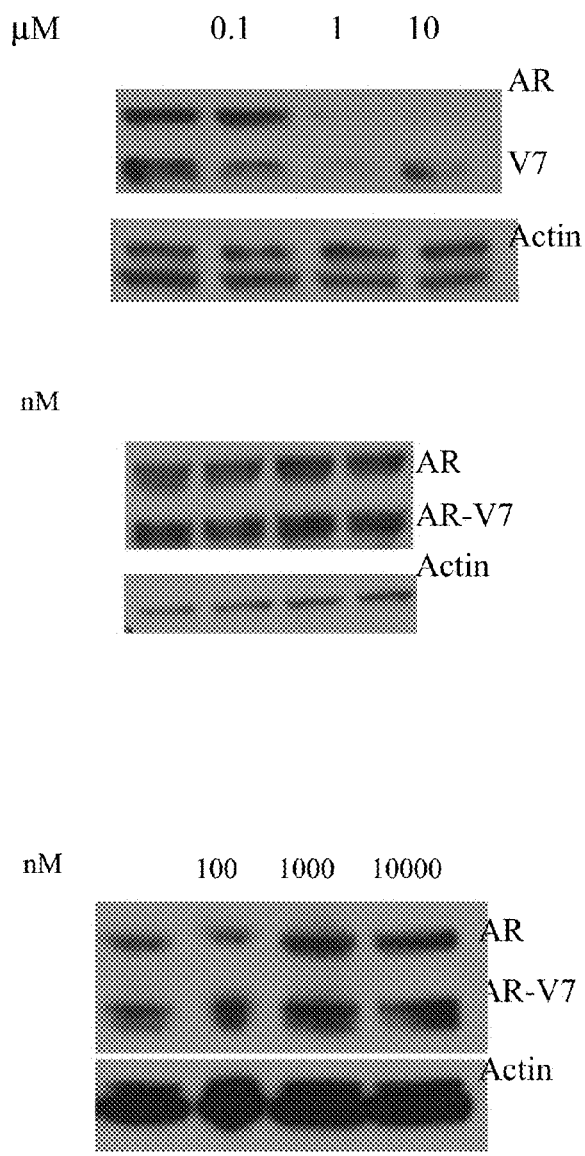
FIG. 27 depicts degradation in 22RV-1 cells using 200 and 202. 22RV-1 cells treated with 200 or 202 were lyzed and subjected to Western blot analysis, as described above.
Figure 28:
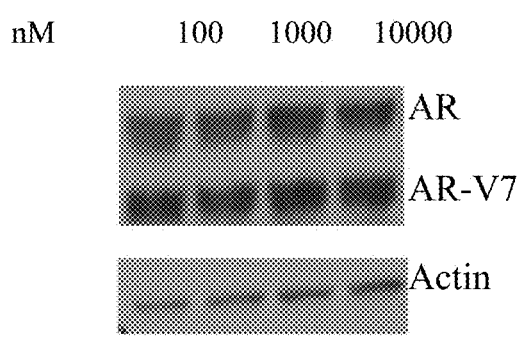
FIG. 28 depicts degradation in 22RV-1 cells using 202. 22RV-1 cells treated with 202 were lyzed and subjected to Western blot analysis, as described above.
Figure 28:
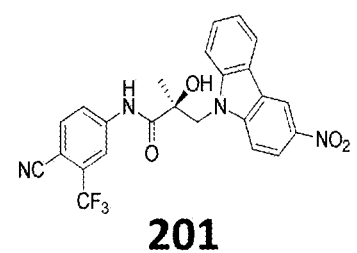

FIG. 27 and FIG. 28 present AR and AR-V7 degradation by 200 and 201 in 22RV-1 cells. 200 was capable of degrading full length androgen receptor (AR-FL) and truncated AR (AR-V7) in 22RV-1 cells, suggesting that SARDs may be able to overcome AR-V7 dependent prostate cancers (i.e., CRPC). By comparison, 201 demonstrated low levels of degradation in 22RV-1 cells.

These SARD activity demonstrations suggest the compounds of this invention are able to degrade a variety of AR variants, and hence should provide the ability to inhibit the AR-axis activity whether it is androgen-dependent or androgen-independent. Degradation of the AR removes the possibility of promiscuous activation of mutant ARs, activation by intracellular processes such as signal transduction and kinase activation, etc.; and suggests that the SARDs should also degrade the polyQ polymorphism in hyperandrogenic dermatologic disorders (shortened polyQ) or Kennedy's disease (extended polyQ), providing a rationale for treating either type of diseases by destroying the AR in the affected tissues (skin and neuromuscular system, respectively).

Example 15

Further Studies with SARDs

PCa Gene Expression and Cell Growth:

PCa cells (LNCaP and 22RV1) will be plated at 10,000 cells per well of a 96 well plate in respective medium supplemented with 1% csFBS or in full serum. The cells will be maintained for 3 days and will be treated with SARDs or controls alone or in combination with 0.1 nM R1881 (1% csFBS). RNA will be isolated and cDNA prepared using cells-to-ct kits (Life Technologies). Expression of various androgen-regulated genes will be measured using TaqMan primer probe mix on an ABI 7900 realtime PCR machine. The expression of individual genes will be normalized to 18S rRNA levels.

PCa cells will be plated at 10,000 cells per well of a 96 well plate in respective medium supplemented with 1% csFBS or in full serum. The cells will be treated with SARDs alone or in combination with 0.1 nM R1881. The cell viability will be measured using Sulforhodamine blue reagent. As negative control, AR-negative PC3 cells will be treated similarly to ensure the absence of any non-specific growth inhibitory properties of SARDs.

Preclinical Rodent Pharmacokinetic (PK) Studies:

The PK parameters of SARDs in various formulations will be determined in rats and mice as appropriate. Approximately 250 gram Sprague-Dawley rats will be randomized into groups of 5 and a catheter surgically implanted into the jugular vein. After a recovery period the rats will be administered test compound and 250 μL of venous blood will be serially sampled from the catheter at 0, 10, 20, 30, 60, 120, 240, 480, 720, 1440 and 2880 minutes post administration for an intravenous dose or 0, 20, 40, 60, 90, 120, 150, 180, 210, 240, 480, 720, 1440, and 2880 minutes post administration for a non-intravenous dose. For mice, approximately 20 gram C57BL/6 mice will be grouped into three per time point per route of administration. Following administration of an intravenous dose mice will be sacrificed and blood collected by cardiac puncture at 0, 10, 20, 30, 60, 120, 240, 480, 720, 1440 and 2880 minutes after intravenous dosing or 0, 30, 60, 90, 120, 150, 180, 210, 240, 480, 720, 1440, 2880 minutes after dosing for a non-intravenous dose. Samples will be collected in appropriate anti-coagulant containing tubes and plasma prepared for LC-MS-MS analyses. Relevant PK parameters will be estimated via non-compartmental analyses using Phoenix WinNonlin.

PCa Xenograft Studies:

Nod Scid γ (NSG)/nude mice (6-8 weeks in age) will be used in the xenograft experiments. Briefly, a mixture of 1:1 LNCaP or 22RV-1 cells in medium (10% FBS supplemented medium):matrigel mixture will be implanted subcutaneously in male NSG mice. Cell number to be implanted will depend on the cell type. Tumors will be implanted in male nude mice that have high circulating androgens or in castrated animals supplemented with DHT to streamline the hormone circulation and to reduce variability between animals. For CRPC model, animals will be castrated when VCaP tumors reach 100 mm³ and the tumors will be allowed to re-grow as CRPC. Animals will be randomized into groups once the tumors reach 200 mm³ and will be treated daily with vehicle or respective SARD. Tumor volume will be measured thrice weekly and the animals will be sacrificed at the end of the study. At sacrifice, tumors will be weighed and stored for further histological and molecular biological analysis. Tumor volume will be calculated using the formula length×width×width×0.5236.

Example 16

In Vivo Studies of SARDs

Hershberger Assay:

Mice (6-7 weeks old) were treated with vehicle or indicated SARDs (100 mg/kg/day twice daily) for 14 days orally. Animals were sacrificed and seminal vesicles weights were recorded and represented.

Figure 30A:
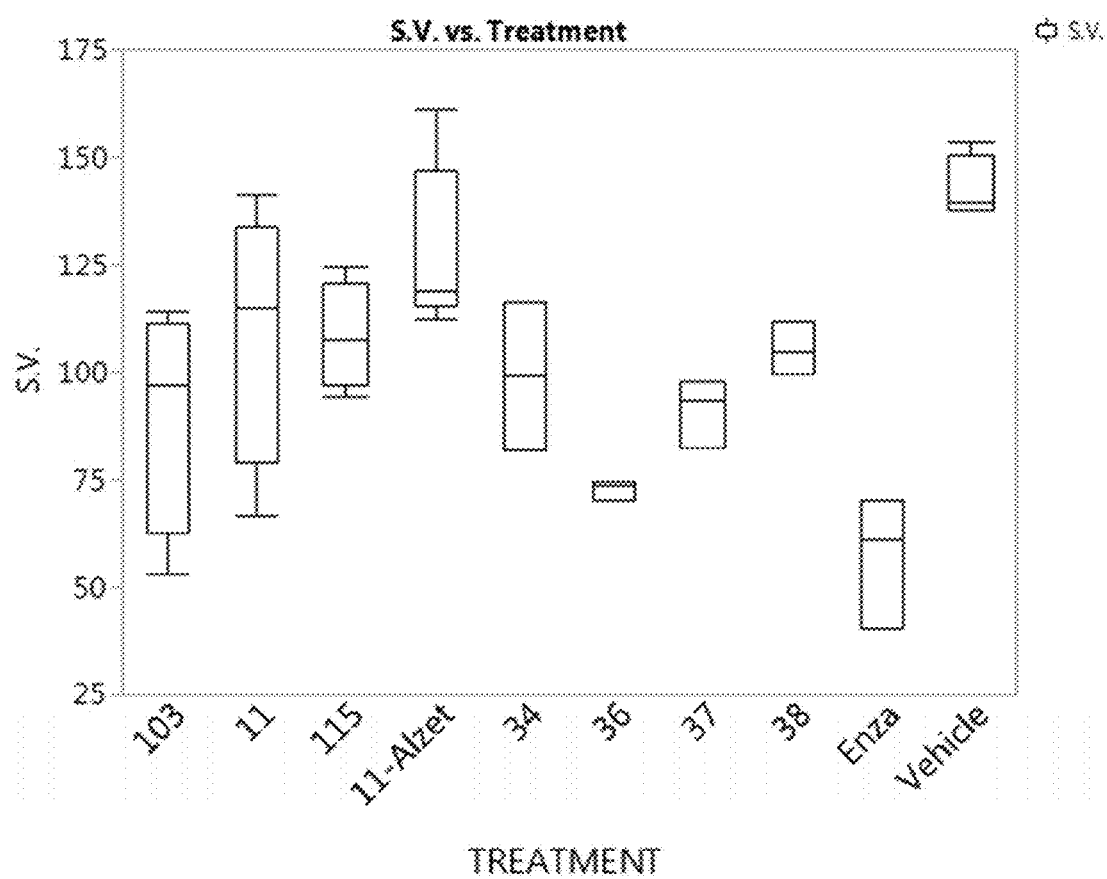
FIG. 30A-FIG. 30D presents Hershberger assay: Mice (6-7 weeks old) were treated with vehicle or indicated SARDs (100 mg/kg/day twice daily) for 14 days orally. Animals were sacrificed and seminal vesicles weights were recorded and represented. Results.
Figure 30B:
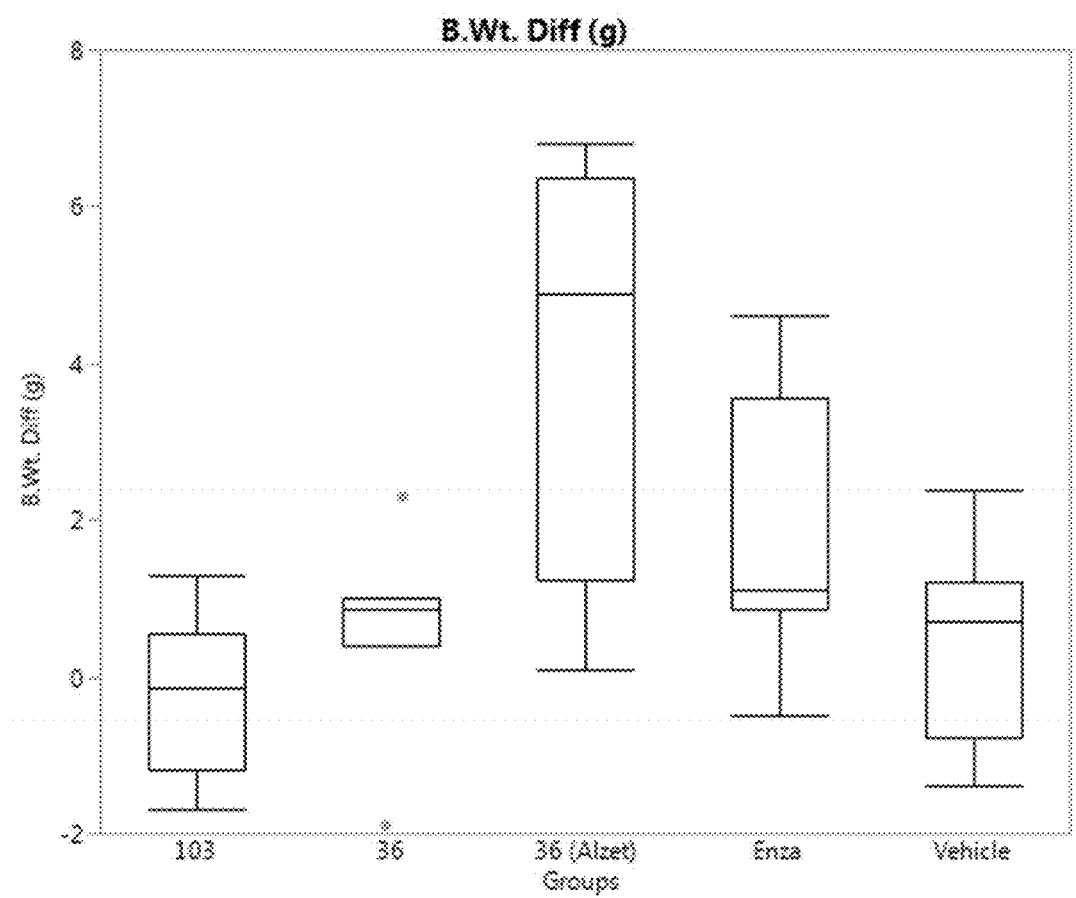
Figure 30C:
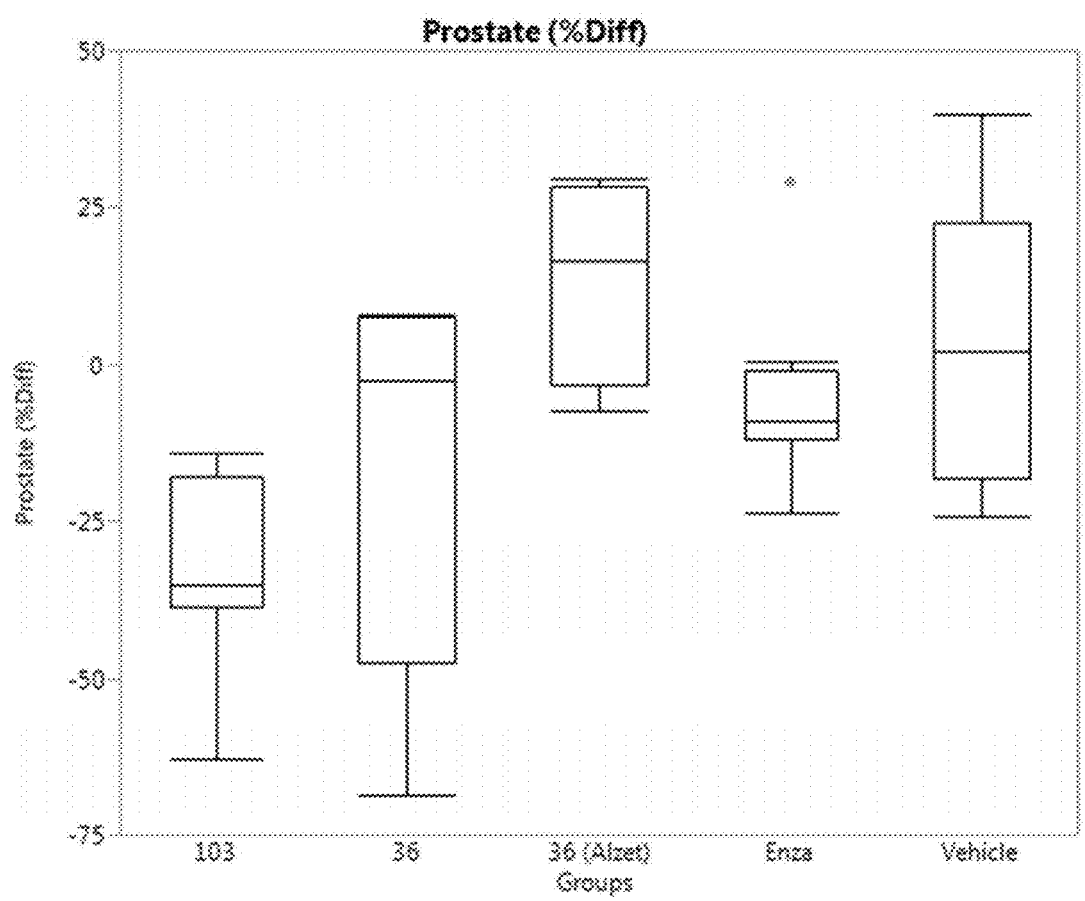
Figure 30D:
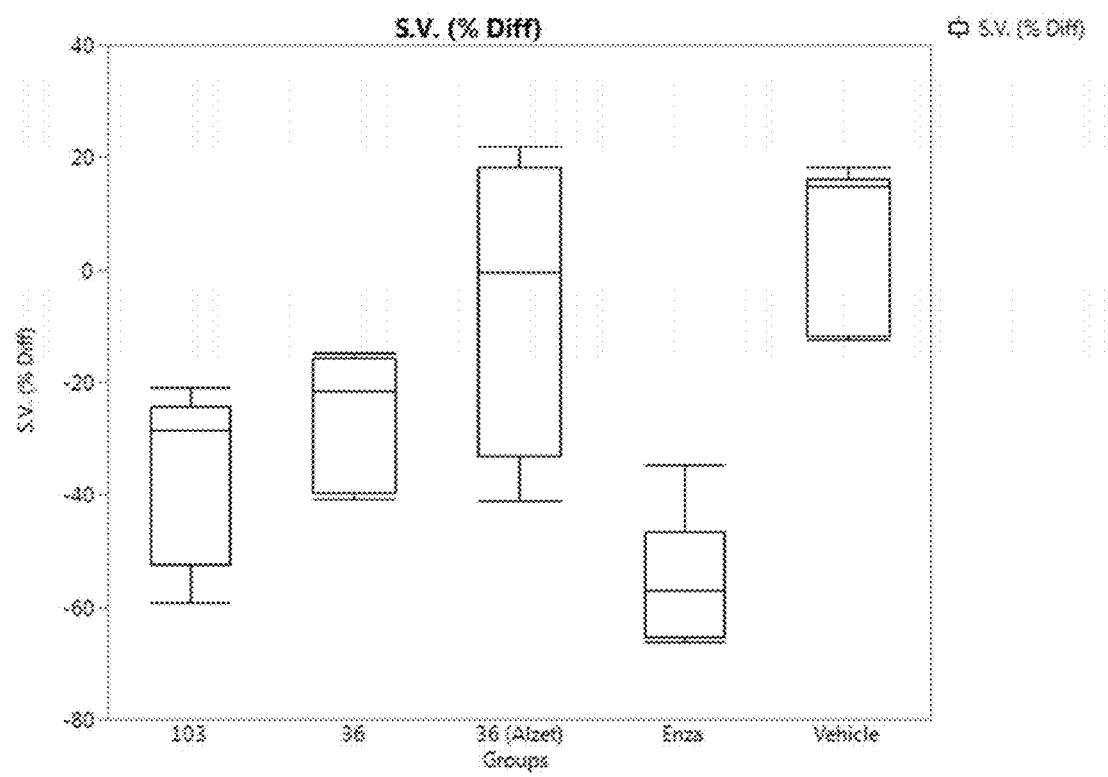

Results:

SARDs 11, 34, 37, 38, 103, and 115 demonstrated varying levels of inhibition of seminal vesicles growth. 103 had the greatest effect of SV (FIG. 30A and FIG. 30D), prostate (FIG. 30C), and also had an effect of body weight (FIG. 30B).

SARDs were also investigated in xenograft studies. 103 demonstrated low levels of efficacy in patient derived (FIG. 31) and mouse (FIG. 32) xenografts despite very low levels in the plasma.

TABLE 14

SARDs are detected in plasma and tumor.

| | Conc of 103 (nM) |
|---|---|
| Plasma Sample #768 | 3.81 |
| Plasma Sample #769 | 18.4 |
| Tumor Sample #768 | 142 |
| Tumor Sample #769 | 282 |
| Calibration Curve | |
| Range | 1.95-2000 Nm |
| $R^2$ | 0.9957 |
| Regression | Quadratic |
| Weighting | $1/x^2$ |

However, unexpectedly 103 was found to accumulate in the tumor, possibly explaining it activity (see chart above). SARDs selectively accumulate in tumor: NSG mice were implanted with patient-derived prostate cancer xenograft. Animals were treated for 14 days and tumor volumes were measured twice weekly. Animals were sacrificed, 103 extracted from serum and tumor and measured using LC-MS/MS method.

Figure 31:
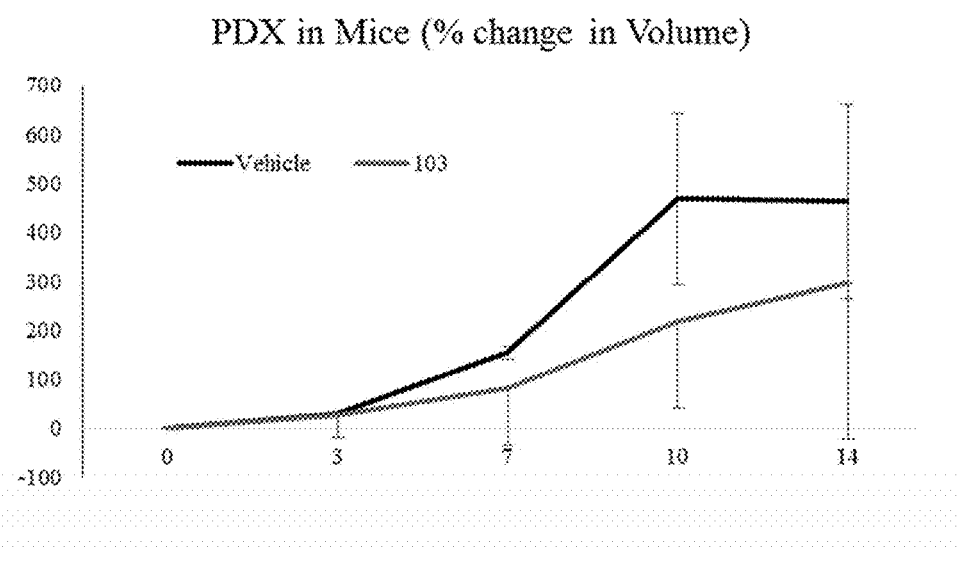
FIG. 31 demonstrates that 103 slowed prostate cancer tumor growth despite low levels in the plasma. SARD 103 selectively accumulated in tumor. NSG mice were implanted with patient-derived prostate cancer xenografts. Animals were treated for 14 days and tumor volumes were measured twice weekly. Animals were sacrificed, 103 was extracted from the serum and tumor and measured using LC-MS/MS method. 103 selectively accumulated in tumor with almost 10 times more tumor accumulation than in plasma, possibly providing an explanation for anti-tumor activity despite low levels of SARD in the plasma.
Figure 32:
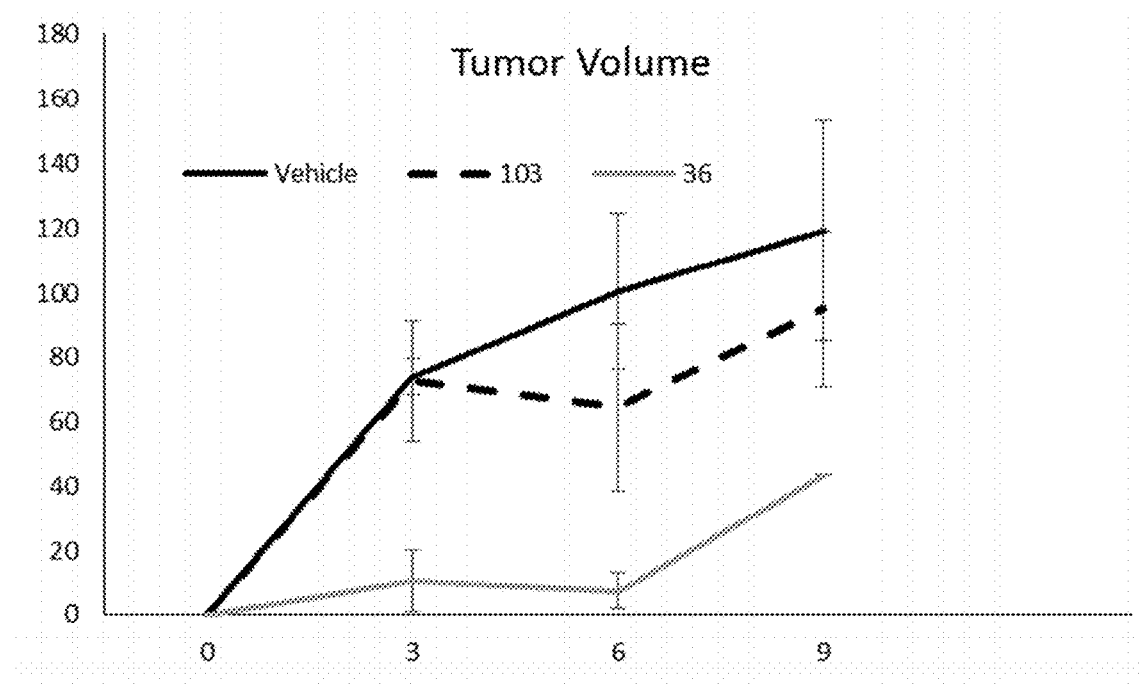
FIG. 32 presents data in a mouse xenograft model treated with 103 and 36. The % change in tumor volume is presented using 103 and 36. LNCaP cells were implanted (5 million cells/mouse) in NSG mice. Once tumors reach 70-200 $mm^3$, animals were randomized and treated with SARDs (100 mg/kg/twice daily). Tumor volume was measured at regular intervals and represented as % change from baseline.36 significantly inhibited tumor growth.

103 selectively accumulates in tumor with almost 10 times more tumor accumulation than in plasma. (FIG. 31). While 103 had weak activity in tumor xenografts, 36 demonstrated promising inhibition of tumor growth.

What is claimed is:

1. A selective androgen receptor degrader (SARD) compound represented by the structure of formula I:

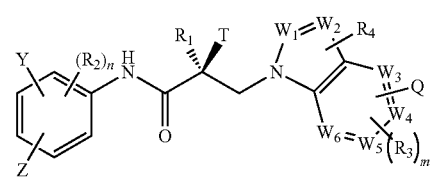

wherein
$W_1$ and $W_2$ are each independently selected from N or CH;
$W_3$, $W_4$, $W_5$ and $W_6$ are each CH;
wherein if any one of $W_1$, $W_2$, $W_3$, $W_4$, $W_5$, and $W_6$ is CH, then the H is optionally replaced with $R_4$, Q or $R_3$ in the respective position, and if any one of $W_1$, $W_2$, $W_3$, $W_4$, $W_5$, and $W_6$ is not CH, then the respective position is unsubstituted;

T is OH, OR, —NHCOCH$_3$, NHCOR or

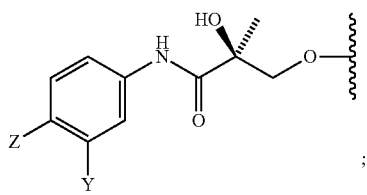
;

Z is CN at the para-position;
Y is CF$_3$, F, I, Br, Cl, CN or C(R)$_3$;
R is alkyl, haloalkyl, dihaloalkyl, trihaloalkyl, CH$_2$F, CHF$_2$, CF$_3$, CF$_2$CF$_3$, aryl, phenyl, F, Cl, Br, I, alkenyl or OH;
$R_1$ is CH$_3$, CH$_2$F, CHF$_2$, CF$_3$, CH$_2$CH$_3$, or CF$_2$CF$_3$;
$R_2$ is hydrogen, halogen, CN, NO$_2$, COOH, COOR, COR, NHCOR, CONHR, OH, OR, SH, SR, NH$_2$, NHR, NR$_2$, $C_1$-$C_{12}$-alkyl, $C_1$-$C_{12}$-haloalkyl, O—$C_1$-$C_{12}$-alkyl, O—$C_1$-$C_{12}$-haloalkyl, —SO$_2$-aryl, —SO$_2$-phenyl, —CO-aryl, arylalkyl, benzyl, aryl, or $C_3$-$C_7$-cycloalkyl;
Q is hydrogen, F, Cl, Br, I, CF$_3$, CN, NO$_2$, COOH, COOR, alkoxy, haloalkyl, optionally substituted linear or branched alkyl, optionally substituted linear or branched heteroalkyl, optionally substituted aryl, optionally substituted phenyl, optionally substituted cycloalkyl, optionally substituted heterocycloalkyl, optionally substituted arylalkyl, C(R)$_3$, N(R)$_2$, NHCOCH$_3$, NHCOCF$_3$, NHCOR, NHCONHR, NHCOOR, OCONHR, CONHR, NHCSCH$_3$, NHCSCF$_3$, NHCSR, NHSO$_2$CH$_3$, NHSO$_2$R, OR, COR, OCOR, OSO$_2$R, SO$_2$R, SR, NCS, SCN, NCO or OCN;
$R_3$ is hydrogen, F, Cl, Br, I, CF$_3$, CN, NO$_2$, NH$_2$, SH, COOH, COOR, alkoxy, haloalkyl, optionally substituted linear or branched alkyl, optionally substituted linear or branched heteroalkyl, optionally substituted aryl, optionally substituted phenyl, optionally substituted cycloalkyl, optionally substituted heterocycloalkyl, optionally substituted arylalkyl, C(R)$_3$, N(R)$_2$, NHCOCH$_3$, NHCOCF$_3$, NHCOR, NHCONHR, NHCOOR, OCONHR, CONHR, NHCSCH$_3$, NHCSCF$_3$, NHCSR, NHSO$_2$CH$_3$, NHSO$_2$R, OR, COR, OCOR, OSO$_2$R, SO$_2$R, SR, NCS, SCN, NCO or OCN;
$R_4$ is hydrogen, F, Cl, Br, I, CF$_3$, CN, NO$_2$, NH$_2$, SH, COOH, COOR, alkoxy, haloalkyl, optionally substituted linear or branched alkyl, optionally substituted linear or branched heteroalkyl, optionally substituted aryl, optionally substituted phenyl, optionally substituted cycloalkyl, optionally substituted heterocycloalkyl, optionally substituted arylalkyl, C(R)$_3$, N(R)$_2$, NHCOCH$_3$, NHCOCF$_3$, NHCOR, NHCONHR, NHCOOR, OCONHR, CONHR, NHCSCH$_3$, NHCSCF$_3$, NHCSR, NHSO$_2$CH$_3$, NHSO$_2$R, OR, COR, OCOR, OSO$_2$R, SO$_2$R, SR, NCS, SCN, NCO or OCN;
n is an integer between 1-3; and
m is an integer between 1-3.

2. The SARD compound according to claim 1, wherein $W_2$ is N and $W_1$, $W_3$, $W_4$, $W_5$, and $W_6$ are CH.

3. The SARD compound according to claim 1, wherein $W_1$ is N and $W_2$, $W_3$, $W_4$, $W_5$, and $W_6$ are CH.

4. The SARD compound according to claim 1, represented by the structure of formula III:

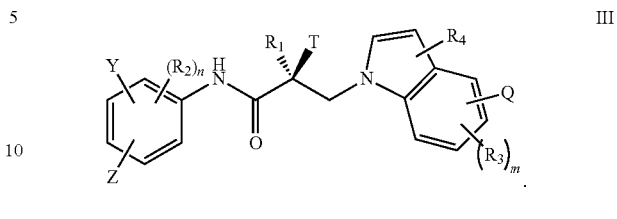

5. The SARD compound of claim 1, wherein Q is H, NO$_2$, COR, alkyl, alkoxy, aryl, CN, CF$_3$, F, Cl, Br or I.

6. The SARD compound of claim 1, wherein Z is CN.

7. The SARD compound of claim 1, wherein Y is Cl or CF$_3$.

8. The SARD compound of claim 1, represented by the structure of the following compounds:

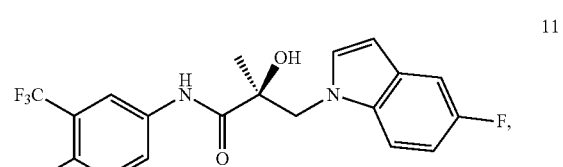
11

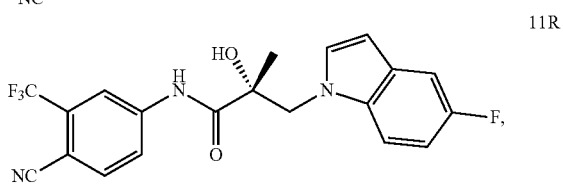
11R

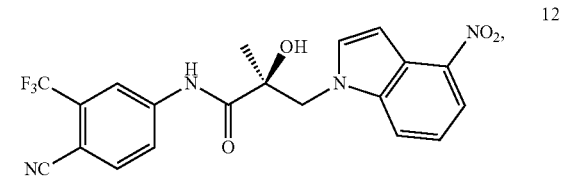
12

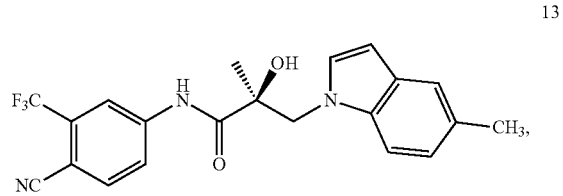
13

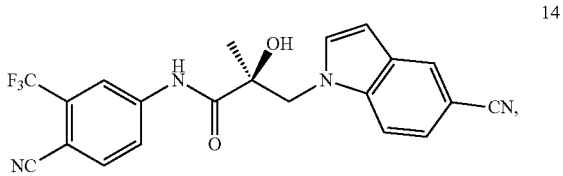
14

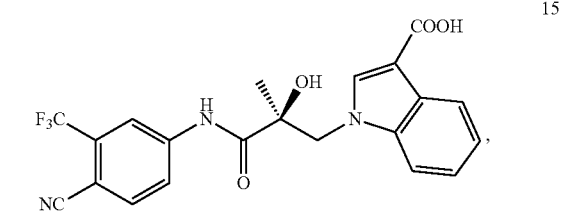
15
,

16
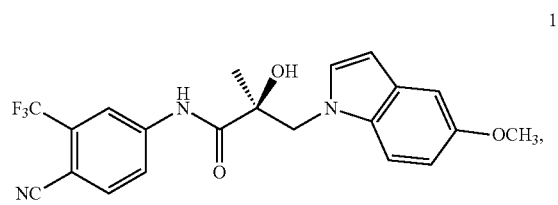
17
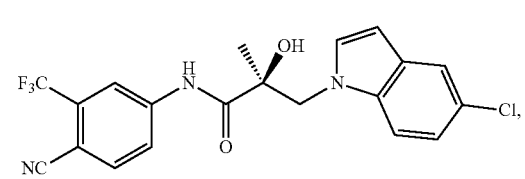
18
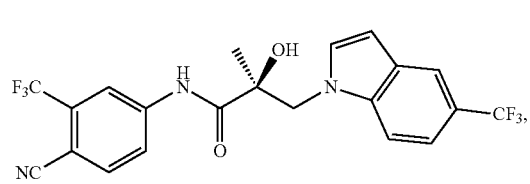
19
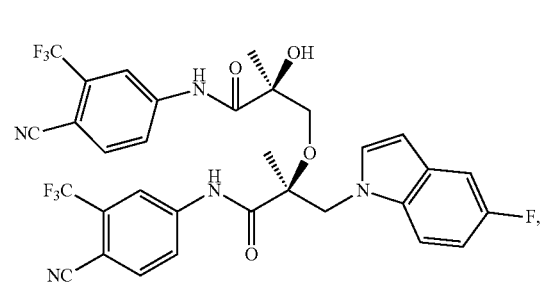
20
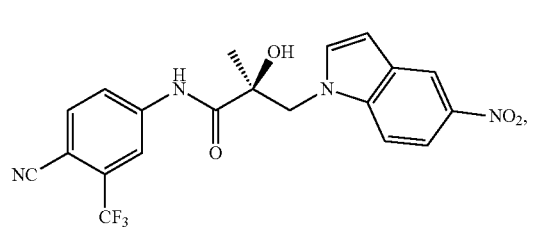
21
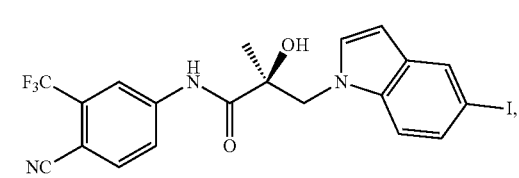
22
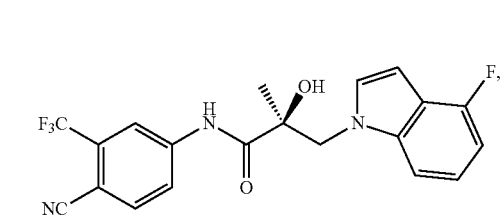
23
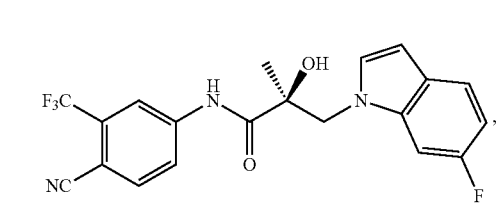
24
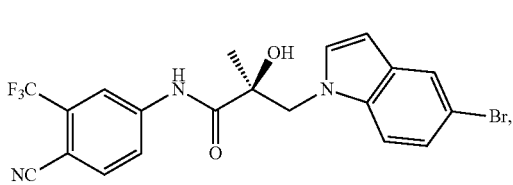
25
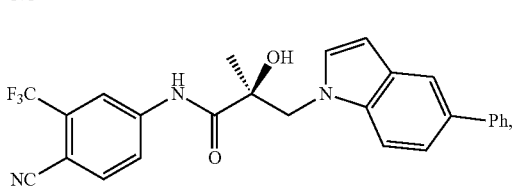
26
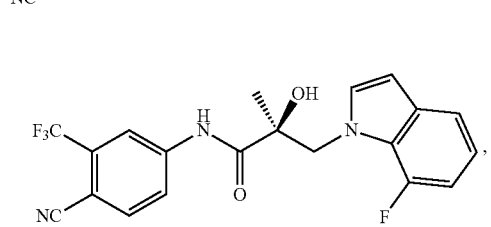
27
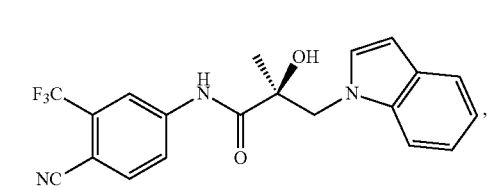
30
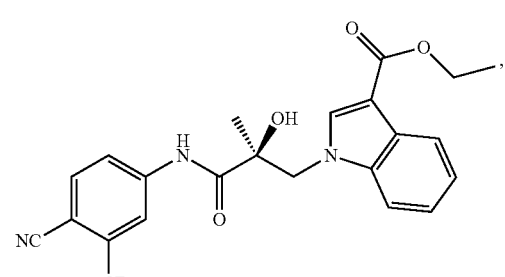
31
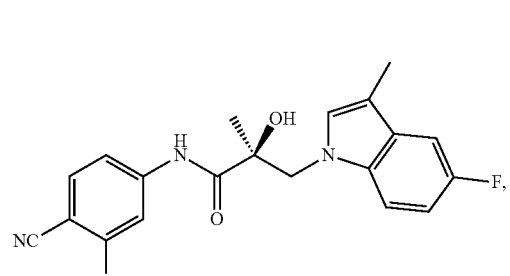
32
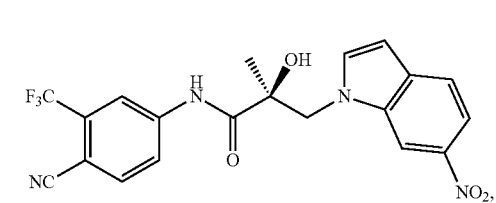

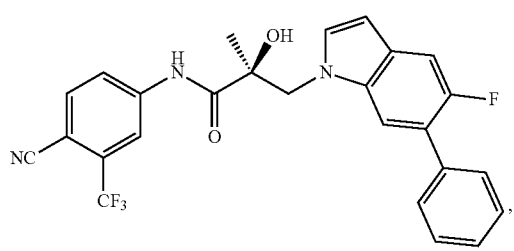
33
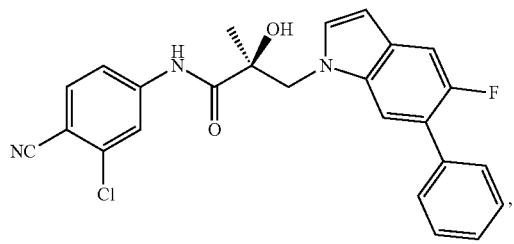
34
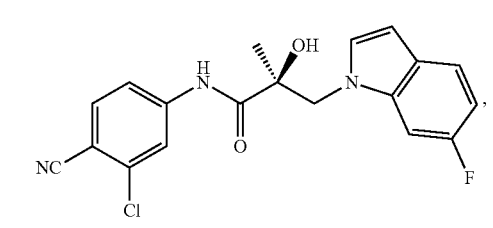
35
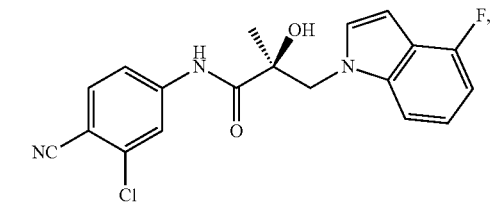
36
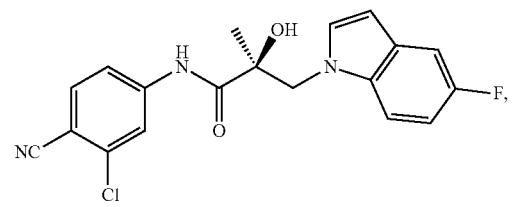
37
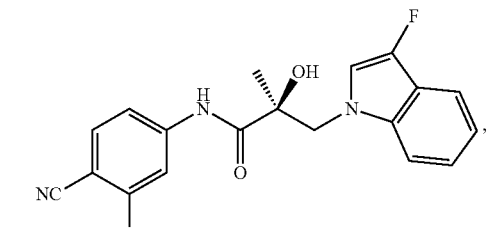
38
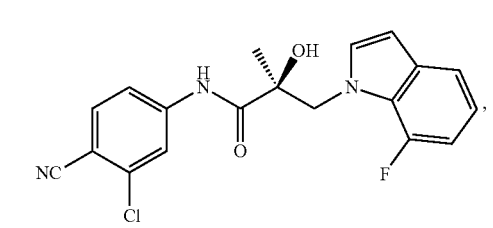
39
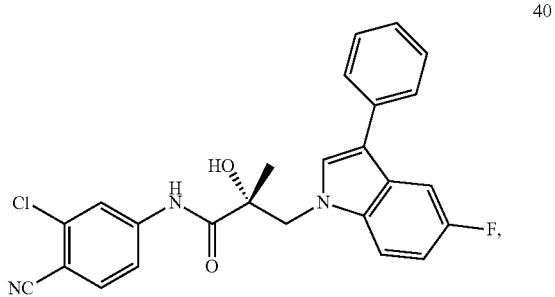
40
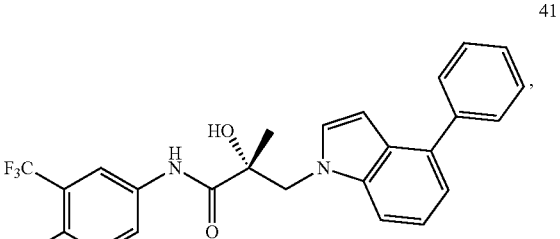
41
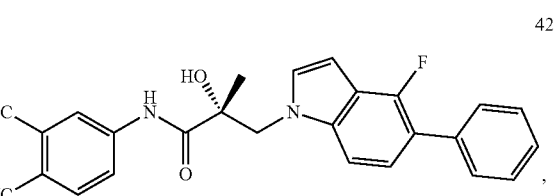
42
Benzimidazoles:
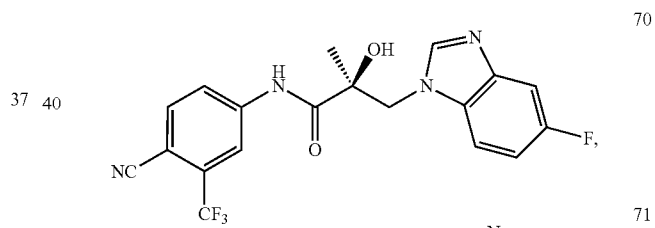
70
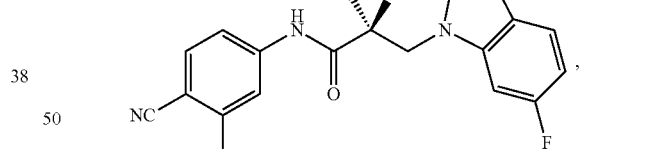
71
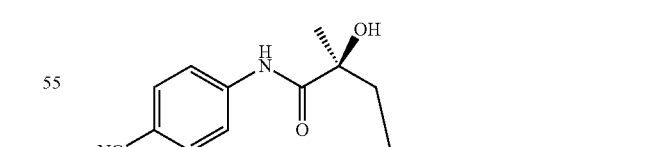
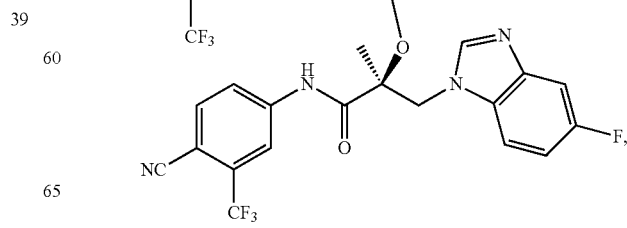
72

-continued

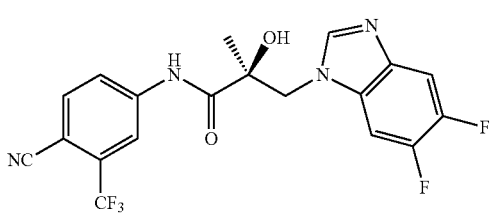
73

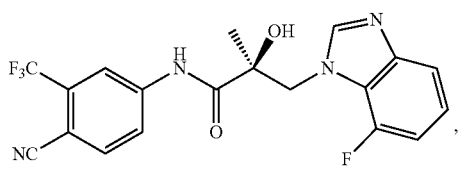
75

Indazoles:

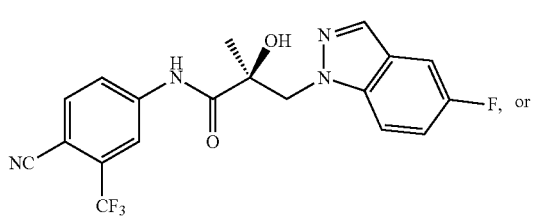
90

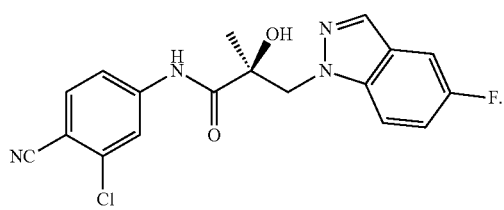
92

9. A pharmaceutical composition comprising a SARD compound according to claim 1, or its isomer, pharmaceutically acceptable salt, pharmaceutical product, polymorph, hydrate or any combination thereof, and a pharmaceutically acceptable carrier.

10. The pharmaceutical composition of claim 9, wherein said composition is formulated for topical use.

11. The pharmaceutical composition of claim 9, wherein said composition is in the form of a solution, lotion, salve, cream, ointment, liposome, spray, gel, foam, roller stick, cleansing soap or bar, emulsion, mousse, aerosol, shampoo, or any combination thereof.

12. A method of treating, suppressing, reducing the incidence, reducing the severity, or inhibiting the progression of prostate cancer (PCa) and its symptoms, or increasing the survival of a male subject suffering from prostate cancer comprising administering to said subject a therapeutically effective amount of a compound according to claim 1, or its isomer, pharmaceutically acceptable salt, pharmaceutical product, polymorph, hydrate or any combination thereof.

13. The method of claim 12, wherein the prostate cancer is advanced prostate cancer, castration resistant prostate cancer (CRPC), metastatic CRPC (mCRPC), non-metastatic CRPC (nmCRPC), high-risk nmCRPC or any combination thereof.

14. The method of claim 12, wherein said subject further receives androgen deprivation therapy (ADT).

15. The method of claim 12, wherein said subject has failed androgen deprivation therapy (ADT).

16. The method of claim 12, wherein said cancer is resistant to treatment with an androgen receptor antagonist or lyase inhibitor.

17. The method of claim 12, wherein said administering reduces the levels of AR, AR-full length (AR-FL), AR-FL with anti-androgen resistance-conferring AR-LBD mutations, AR-splice variant (AR-SV), or any combination thereof, in said subject.

18. A method of treating, suppressing, reducing the incidence, reducing the severity, or inhibiting the progression of acne in a subject, comprising administering to said subject a therapeutically effective amount of the compound of claim 1, or its isomer, pharmaceutically acceptable salt, pharmaceutical product, polymorph, hydrate or any combination thereof.

19. A method of treating, suppressing, reducing the incidence, reducing the severity, or inhibiting the progression of hirsutism in a subject, comprising administering to said subject a therapeutically effective amount of the compound of claim 1, or its isomer, pharmaceutically acceptable salt, pharmaceutical product, polymorph, hydrate or any combination thereof.

20. A method of treating, suppressing, reducing the incidence, reducing the severity, or inhibiting the progression of alopecia in a subject, comprising administering to said subject a therapeutically effective amount of the compound of claim 1, or its isomer, pharmaceutically acceptable salt, pharmaceutical product, polymorph, hydrate or any combination thereof.

21. The method of claim 20, wherein said alopecia is androgenic alopecia, alopecia areata, alopecia secondary to chemotherapy, alopecia secondary to radiation therapy, alopecia induced by scarring, alopecia induced by stress or any combination thereof.

22. A method of treating, suppressing, reducing the incidence, reducing the severity, or inhibiting the progression of androgen insensitivity syndrome in a subject, comprising administering to said subject a therapeutically effective amount of the compound of claim 1, or its isomer, pharmaceutically acceptable salt, pharmaceutical product, polymorph, hydrate or any combination thereof.

23. A method of treating, suppressing, reducing the incidence, reducing the severity, or inhibiting the progression of cancer in a subject, comprising administering to said subject a therapeutically effective amount of the compound of 1, or its isomer, pharmaceutically acceptable salt, pharmaceutical product, polymorph, hydrate or any combination thereof.

24. The method of claim 23, wherein said cancer is breast cancer, testicular cancer, uterine cancer, ovarian cancer, urogenital cancer, brain cancer, skin cancer, lymphoma, liver cancer, renal cancer, osteosarcoma, pancreatic cancer, endometrial cancer, lung cancer, non-small cell lung cancer (NSCLC), colon cancer, perianal adenomas, central nervous system cancer, or any combination thereof.

25. A selective androgen receptor degrader (SARD) compound represented by the structure of formula V:

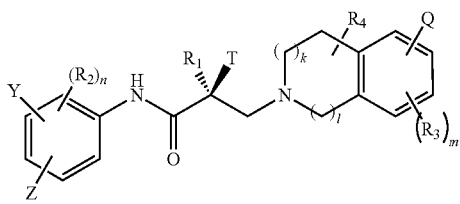

V wherein
T is OH, OR, —NHCOCH$_3$, NHCOR or

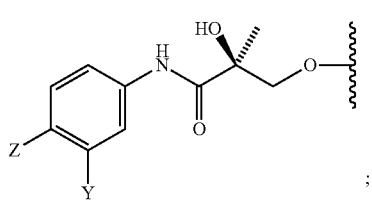
;

Z is CN and at the para-position;
Y is CF$_3$, F, I, Br, Cl, CN or C(R)$_3$;
R is alkyl, haloalkyl, dihaloalkyl, trihaloalkyl, CH$_2$F, CHF$_2$, CF$_3$, CF$_2$CF$_3$, aryl, phenyl, F, Cl, Br, I, alkenyl or OH;
R$_1$ is CH$_3$, CH$_2$F, CHF$_2$, CF$_3$, CH$_2$CH$_3$, or CF$_2$CF$_3$;
R$_2$ is hydrogen, halogen, CN, NO$_2$, COOH, COOR, COR, NHCOR, CONHR, OH, OR, SH, SR, NH$_2$, NHR, NR$_2$, C$_1$-C$_{12}$-alkyl, C$_1$-C$_{12}$-haloalkyl, O—C$_1$-C$_{12}$-alkyl, O—C$_1$-C$_{12}$-haloalkyl, —SO$_2$-aryl, —SO$_2$-phenyl, —CO-aryl, arylalkyl, benzyl, aryl, or C$_3$-C$_7$-cycloalkyl;
Q is hydrogen, F, Cl, Br, I, CF$_3$, CN, NO$_2$, COOH, COOR, alkoxy, haloalkyl, optionally substituted linear or branched alkyl, optionally substituted linear or branched heteroalkyl, optionally substituted aryl, optionally substituted phenyl, optionally substituted cycloalkyl, optionally substituted heterocycloalkyl, optionally substituted arylalkyl, C(R)$_3$, N(R)$_2$, NHCOCH$_3$, NHCOCF$_3$, NHCOR, NHCONHR, NHCOOR, OCONHR, CONHR, NHCSCH$_3$, NHCSCF$_3$, NHCSR, NHSO$_2$CH$_3$, NHSO$_2$R, OR, COR, OCOR, OSO$_2$R, SO$_2$R, SR, NCS, SCN, NCO or OCN;
R$_3$ is hydrogen, F, Cl, Br, I, CF$_3$, CN, NO$_2$, NH$_2$, SH, COOH, COOR, alkoxy, haloalkyl, optionally substituted linear or branched alkyl, optionally substituted linear or branched heteroalkyl, optionally substituted aryl, optionally substituted phenyl, optionally substituted cycloalkyl, optionally substituted heterocycloalkyl, optionally substituted arylalkyl, C(R)$_3$, N(R)$_2$, NHCOCH$_3$, NHCOCF$_3$, NHCOR, NHCONHR, NHCOOR, OCONHR, CONHR, NHCSCH$_3$, NHCSCF$_3$, NHCSR, NHSO$_2$CH$_3$, NHSO$_2$R, OR, COR, OCOR, OSO$_2$R, SO$_2$R, SR, NCS, SCN, NCO or OCN;
R$_4$ is hydrogen, F, Cl, Br, I, CF$_3$, CN, NO$_2$, NH$_2$, SH, COOH, COOR, keto (=O), alkoxy, haloalkyl, optionally substituted linear or branched alkyl, optionally substituted linear or branched heteroalkyl, optionally substituted aryl, optionally substituted phenyl, optionally substituted cycloalkyl, optionally substituted heterocycloalkyl, optionally substituted arylalkyl, C(R)$_3$, N(R)$_2$, NHCOCH$_3$, NHCOCF$_3$, NHCOR, NHCONHR, NHCOOR, OCONHR, CONHR, NHCSCH$_3$, NHCSCF$_3$, NHCSR, NHSO$_2$CH$_3$, NHSO$_2$R, OR, COR, OCOR, OSO$_2$R, SO$_2$R, SR, NCS, SCN, NCO or OCN;
n is an integer between 1-3;
m is an integer between 1-3;
l is 0 or 1; and
k is 0, 1 or 2.

26. The SARD compound of claim 25, wherein said compound is represented by the structure of formula VI:

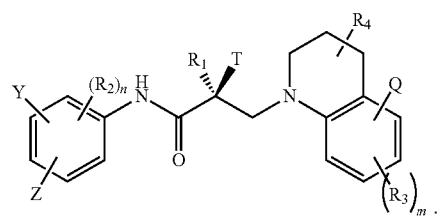

VI

27. The SARD compound of claim 25, wherein said compound is represented by the structure of formula VII:

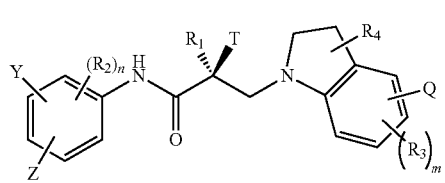

VII

28. The SARD compound of claim 25, wherein said compound is represented by the structure of formula IV:

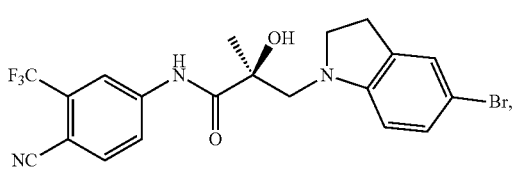

IV

29. The SARD compound of claim 25, wherein Q is hydrogen, F, Cl, Br, CN, NO$_2$, or phenyl.

30. The SARD compound of claim 25, wherein said compound is represented by the following structures:

Indolines

100

217
-continued
101
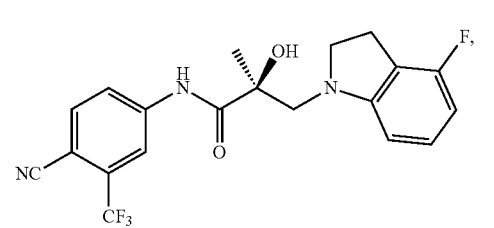
102
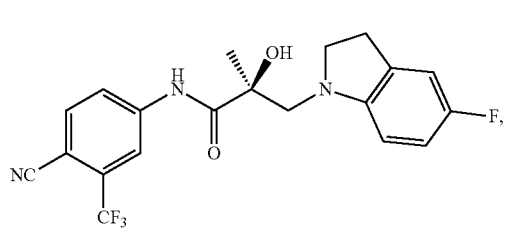
103
104
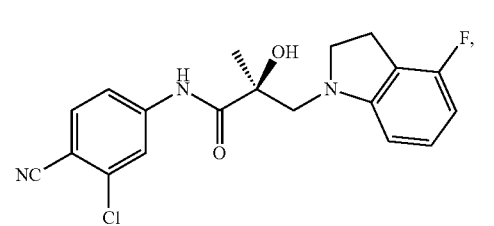
105
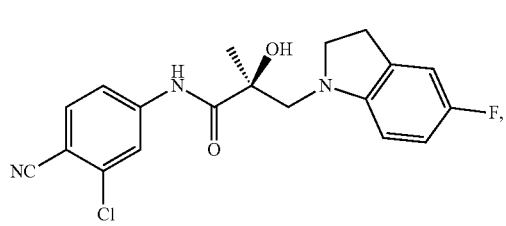
106
107
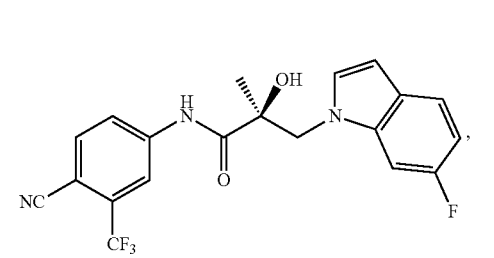
218
-continued
108
109
110
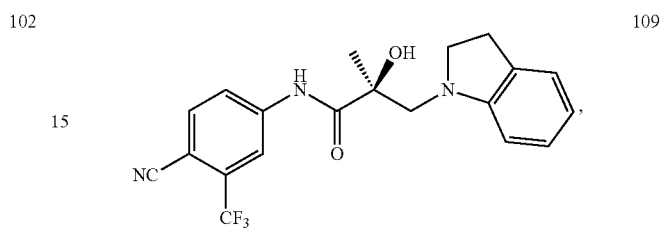
111
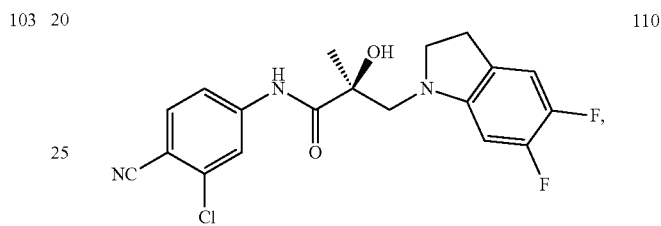
112
113
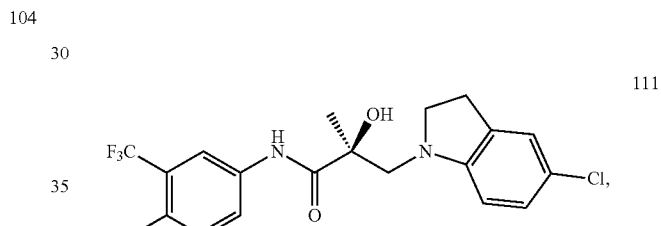
114
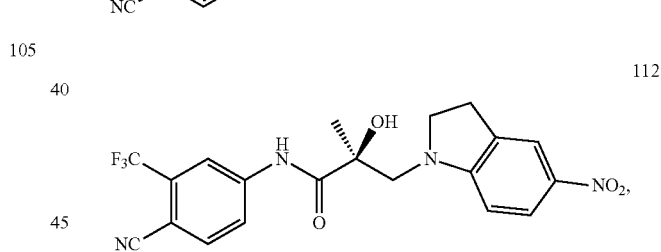

115

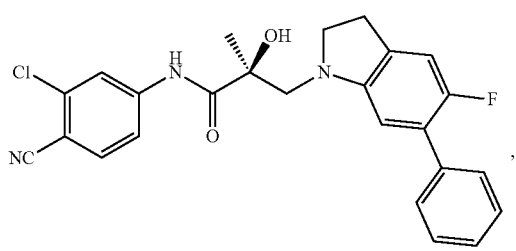

Isoquinolines and Quinolines

130

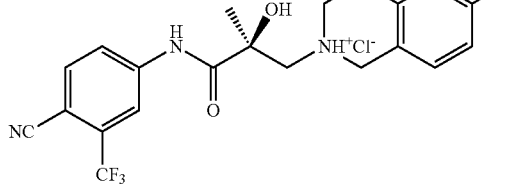

131

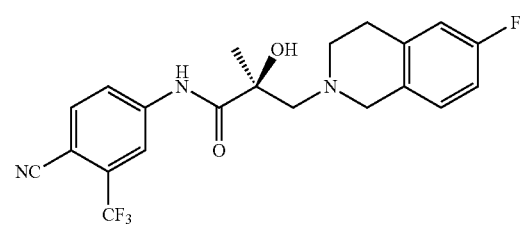

132

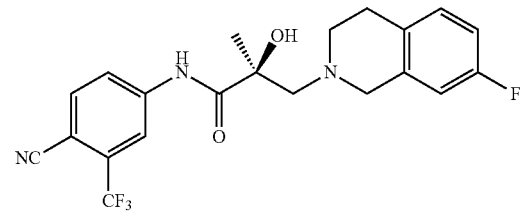

133

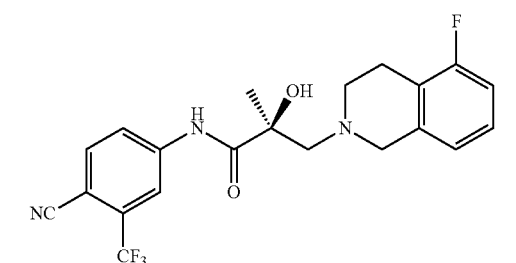

134

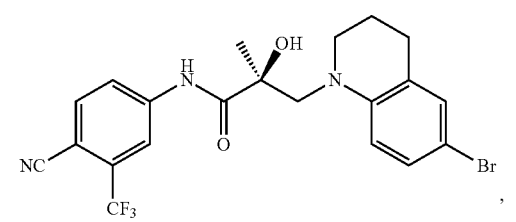

135

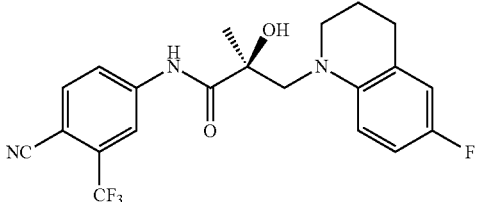

136

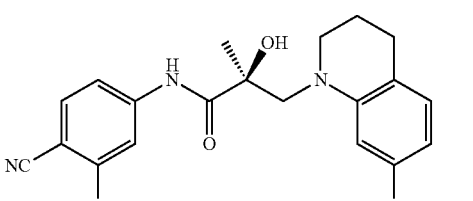

, or

137

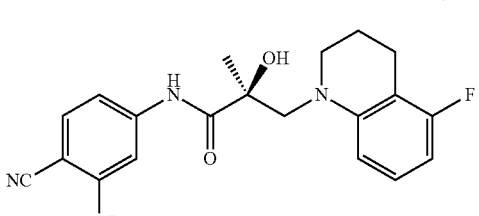

.

31. A pharmaceutical composition comprising a SARD compound according to claim 25, or its isomer, pharmaceutically acceptable salt, pharmaceutical product, polymorph, hydrate or any combination thereof, and a pharmaceutically acceptable carrier.

32. The pharmaceutical composition of claim 31, wherein said composition is formulated for topical use.

33. The pharmaceutical composition of claim 31, wherein said composition is in the form of a solution, lotion, salve, cream, ointment, liposome, spray, gel, foam, roller stick, cleansing soap or bar, emulsion, mousse, aerosol, shampoo, or any combination thereof.

34. A method of treating, suppressing, reducing the incidence, reducing the severity, or inhibiting the progression of prostate cancer (PCa) and its symptoms, or increasing the survival of a male subject suffering from prostate cancer comprising administering to said subject a therapeutically effective amount of a compound according to claim 25, or its isomer, pharmaceutically acceptable salt, pharmaceutical product, polymorph, hydrate or any combination thereof.

35. The method of claim 34, wherein the prostate cancer is advanced prostate cancer, castration resistant prostate cancer (CRPC), metastatic CRPC (mCRPC), non-metastatic CRPC (nmCRPC), high-risk nmCRPC or any combination thereof.

36. The method of claim 34 wherein said subject further receives androgen deprivation therapy (ADT).

37. The method of claim 34, wherein said subject has failed androgen deprivation therapy (ADT).

38. The method of claim 34, wherein said cancer is resistant to treatment with an androgen receptor antagonist or lyase inhibitor.

39. The method of claim 34, wherein said administering reduces the levels of AR, AR-full length (AR-FL), AR-FL with anti-androgen resistance-conferring AR-LBD mutations, AR-splice variant (AR-SV), or any combination thereof, in said subject.

40. A method of treating, suppressing, reducing the incidence, reducing the severity, or inhibiting the progression of acne in a subject, comprising administering to said subject a therapeutically effective amount of the compound of claim 25, or its isomer, pharmaceutically acceptable salt, pharmaceutical product, polymorph, hydrate or any combination thereof.

41. A method of treating, suppressing, reducing the incidence, reducing the severity, or inhibiting the progression of hirsutism in a subject, comprising administering to said subject a therapeutically effective amount of the compound of claim 25, or its isomer, pharmaceutically acceptable salt, pharmaceutical product, polymorph, hydrate or any combination thereof.

42. A method of treating, suppressing, reducing the incidence, reducing the severity, or inhibiting the progression of alopecia in a subject, comprising administering to said subject a therapeutically effective amount of the compound of claim 25, or its isomer, pharmaceutically acceptable salt, pharmaceutical product, polymorph, hydrate or any combination thereof.

43. The method of claim 42, wherein said alopecia is androgenic alopecia, alopecia areata, alopecia secondary to chemotherapy, alopecia secondary to radiation therapy, alopecia induced by scarring, alopecia induced by stress or any combination thereof.

44. A method of treating, suppressing, reducing the incidence, reducing the severity, or inhibiting the progression of androgen insensitivity syndrome in a subject, comprising administering to said subject a therapeutically effective amount of the compound of claim 25, or its isomer, pharmaceutically acceptable salt, pharmaceutical product, polymorph, hydrate or any combination thereof.

45. A method of treating, suppressing, reducing the incidence, reducing the severity, or inhibiting the progression of cancer in a subject, comprising administering to said subject a therapeutically effective amount of the compound of claim 25, or its isomer, pharmaceutically acceptable salt, pharmaceutical product, polymorph, hydrate or any combination thereof.

46. The method of claim 45, wherein said cancer is breast cancer, testicular cancer, uterine cancer, ovarian cancer, urogenital cancer, brain cancer, skin cancer, lymphoma, liver cancer, renal cancer, osteosarcoma, pancreatic cancer, endometrial cancer, lung cancer, non-small cell lung cancer (NSCLC), colon cancer, perianal adenoma, central nervous system cancer, or any combination thereof.

47. The SARD compound according to claim 1, wherein $W_1$, $W_2$, $W_3$, $W_4$, $W_5$, and $W_6$ are CH.

* * * * *